US012486280B2

(12) United States Patent
O'Boyle et al.

(10) Patent No.: US 12,486,280 B2
(45) Date of Patent: Dec. 2, 2025

(54) CDK INHIBITORS AND USES THEREOF

(71) Applicants: California Institute of Technology, Pasadena, CA (US); The Regents of the University of California, Oakland, CA (US); 1200 Pharma LLC, Culver City, CA (US)

(72) Inventors: Brendan M. O'Boyle, Monrovia, CA (US); Justin A. Hilf, Los Angeles, CA (US); Scott C. Virgil, Pasadena, CA (US); Alexander W. Sun, Irvine, CA (US); Brian M. Stoltz, San Marino, CA (US); Dylan Conklin, Woodland Hills, CA (US); Martina S. McDermott, Los Angeles, CA (US); Neil A. O'Brien, Los Angeles, CA (US); Michael J. Palazzolo, Los Angeles, CA (US); Dennis Slamon, Woodland Hills, CA (US); Michael D. Bartberger, Sherman Oaks, CA (US)

(73) Assignees: California Institute of Technology, Pasadena, CA (US); The Regents of the University of California, Oakland, CA (US); 1200 Pharma LLC, Culver City, CA (US)

(*) Notice: Subject to any disclaimer, the term of this patent is extended or adjusted under 35 U.S.C. 154(b) by 982 days.

(21) Appl. No.: 17/263,453

(22) PCT Filed: Jul. 26, 2019

(86) PCT No.: PCT/US2019/043754

§ 371 (c)(1),
(2) Date: Jan. 26, 2021

(87) PCT Pub. No.: WO2020/023917

PCT Pub. Date: Jan. 30, 2020

(65) Prior Publication Data

US 2022/0106325 A1 Apr. 7, 2022

Related U.S. Application Data

(60) Provisional application No. 62/711,192, filed on Jul. 27, 2018.

(51) Int. Cl.

| | |
|---|---|
| ***C07D 491/107*** | (2006.01) |
| ***A61P 35/00*** | (2006.01) |
| ***C07D 401/14*** | (2006.01) |
| ***C07D 413/14*** | (2006.01) |
| ***C07D 495/10*** | (2006.01) |
| ***C07D 498/10*** | (2006.01) |

(52) U.S. Cl.

CPC .......... *C07D 491/107* (2013.01); *A61P 35/00* (2018.01); *C07D 401/14* (2013.01); *C07D 413/14* (2013.01); *C07D 495/10* (2013.01); *C07D 498/10* (2013.01)

(58) Field of Classification Search

CPC ..... A61P 35/00; C07D 401/14; C07D 413/14; C07D 491/107; C07D 495/10; C07D 498/10

See application file for complete search history.

(56) References Cited

U.S. PATENT DOCUMENTS

| | | | |
|---|---|---|---|
| 7,855,211 | B2 | 12/2010 | Coates et al. |
| 9,259,399 | B2 | 2/2016 | Chen-Kiang et al. |
| 9,796,701 | B2 | 10/2017 | Wu et al. |
| 9,949,976 | B2 | 4/2018 | Wu et al. |
| 2006/0142312 | A1 | 6/2006 | Flamme et al. |
| 2010/0160340 | A1 | 6/2010 | Coates et al. |
| 2014/0057865 | A1 | 2/2014 | Fantl et al. |
| 2016/0265065 | A1 | 9/2016 | Bandla et al. |
| 2016/0332989 | A1 | 11/2016 | Wu et al. |
| 2018/0000819 | A1 | 1/2018 | Wu et al. |
| 2018/0045727 | A1 | 2/2018 | Spetzler et al. |
| 2019/0292605 | A1 | 9/2019 | Slamon et al. |
| 2020/0155550 | A1 | 5/2020 | Zhang et al. |

FOREIGN PATENT DOCUMENTS

| | | | |
|---|---|---|---|
| CN | 103864770 | A | 6/2014 |
| CN | 103910736 | A | 7/2014 |
| CN | 104177363 | A | 12/2014 |
| CN | 104610254 | A | 5/2015 |
| CN | 104892580 | A | 9/2015 |
| CN | 104910137 | A | 9/2015 |
| CN | 105130986 | A | 12/2015 |
| CN | 105153119 | A | 12/2015 |
| CN | 105418603 | A | 3/2016 |
| CN | 105622638 | A | 6/2016 |
| CN | 105732615 | A | 7/2016 |
| CN | 106083823 | A | 11/2016 |
| CN | 107266421 | A | 10/2017 |
| CN | 105294683 | B | 1/2018 |
| CN | 108602799 | A | 9/2018 |
| CN | 105294655 | B | 3/2019 |
| CN | 109963842 | B | 11/2020 |
| CN | 109952295 | B | 4/2021 |
| EP | 2379528 | B1 | 9/2013 |
| WO | WO-2003/062236 | A1 | 7/2003 |

(Continued)

OTHER PUBLICATIONS

Frederick et al., "A synthesis of abemaciclib utilizing a Leuckart-Wallach reaction," Tetrahedron Letters, 56(7): 949-951 (2015).

(Continued)

*Primary Examiner* — Kortney L. Klinkel
*Assistant Examiner* — Richard Grant Peckham
(74) *Attorney, Agent, or Firm* — Foley Hoag LLP; Janine S. Ladislaw

(57) ABSTRACT

The present disclosure provides compounds and compositions that are CDK inhibitors selective for CDK4 and/or CDK6, and methods of use thereof.

23 Claims, 38 Drawing Sheets

(56) References Cited

FOREIGN PATENT DOCUMENTS

WO WO-2007/140222 A2 12/2007
WO WO-2008/032157 A2 3/2008
WO WO-2010/020675 A1 2/2010
WO WO-2010/075074 A1 7/2010
WO WO-2012/063085 A2 5/2012
WO WO-2013/170671 A1 11/2013
WO WO-2014/109858 A1 7/2014
WO WO-2014/134308 A1 9/2014
WO WO-2014/144326 A1 9/2014
WO WO-2014/150925 A2 9/2014
WO WO-2014/183520 A1 11/2014
WO WO-2015/101293 A1 7/2015
WO WO-2015/196072 A2 12/2015
WO WO-2016/015597 A1 2/2016
WO WO-2016/015598 A1 2/2016
WO WO-2016/015604 A1 2/2016
WO WO-2016015605 A1 * 2/2016 ........... A61K 31/506
WO WO-2016/058501 A1 4/2016
WO WO-2016/139534 A2 9/2016
WO WO-2016/160617 A2 10/2016
WO WO-2016/173557 A1 11/2016
WO WO-2016/192630 A1 12/2016
WO WO-2017/041535 A1 3/2017
WO WO-2017/133701 A1 8/2017
WO WO-2018/045956 A1 3/2018
WO WO-2018/045957 A1 3/2018
WO WO-2018/202202 A1 11/2018
WO WO-2019/043504 A1 3/2019
WO WO-2020/023917 A1 1/2020

OTHER PUBLICATIONS

Extended European Search Report for EP Application No. 19841123.3 dated Apr. 8, 2022.

International Search Report and Written Opinion for International Application No. PCT/US2019/043754 dated Oct. 31, 2019.

* cited by examiner

| Group | 0 | 2 | 5 | 7 | 9 | 12 | 14 | 16 | 19 | 23 |
|---|---|---|---|---|---|---|---|---|---|---|
| Vehicle control (PO & IP) | 0.00% | -3.20% | -2.77% | 0.36% | -2.88% | -1.15% | -1.40% | -1.97% | -1.71% | -1.83% |
| Abemaciclib 60mg/kg PO | 0.00% | -3.08% | -3.83% | -1.71% | -5.46% | -2.92% | -5.52% | -4.87% | -4.39% | -4.50% |
| Compound A2 120mg/kg PO | 0.00% | -3.87% | -0.82% | -4.22% | -4.89% | -0.98% | -4.03% | -3.34% | -3.47% | -3.60% |
| Compound A22 60mg/kg - 120mg/kg PO | 0.00% | 0.34% | -1.31% | -2.81% | -4.71% | -1.24% | -3.22% | -4.12% | -2.46% | -3.91% |

| Dose | Compound A2 AUC | Compound A1 AUC | Compound A23 AUC | Abemaciclib AUC | |
|---|---|---|---|---|---|
| 100 | 0.63 | 0.35 | 0.64 | 0.64 | |
| 178 | 1.10 | 0.55 | 1.08 | 1.02 | |
| 316 | 1.41 | 0.82 | 1.24 | 1.05 | ng/ml x mins (millions) |
| 564 | 1.79 | 1.09 | 1.80 | 1.63 | |
| 1000 | 2.72 | 1.54 | 3.68 | 2.01 | |

| Group | Dates/Study Days | | | | | | | | | | |
|---|---|---|---|---|---|---|---|---|---|---|---|
| | 7/18/2017 | 7/20/2017 | 7/24/2017 | 7/26/2017 | 7/28/2017 | 7/31/2017 | 8/2/2017 | 8/4/2017 | 8/7/2017 | 8/9/2017 | 8/11/2017 |
| | 0 | 2 | 6 | 8 | 10 | 13 | 15 | 17 | 20 | 22 | 24 |
| Vehicle | 0.00% | -0.34% | 1.86% | -0.33% | -0.32% | 3.72% | -0.12% | 1.83% | 1.09% | 0.07% | 2.51% |
| Abemaciclib 75 mg/kg | 0.00% | -2.77% | -1.94% | -2.43% | -1.70% | -0.49% | -3.47% | -3.59% | -2.52% | -4.40% | -2.01% |
| Compound A2 54mg/kg | 0.00% | -2.01% | -0.30% | -3.22% | -2.69% | -0.15% | -4.54% | -5.90% | -1.00% | -4.89% | -3.32% |
| Compound A2 75mg/kg | 0.00% | -0.80% | -1.18% | -1.84% | -2.09% | 0.06% | -2.85% | -1.19% | -1.07% | -3.93% | -1.96% |
| Compound A2 123mg/kg | 0.00% | -4.07% | -4.06% | -5.24% | -5.60% | -3.01% | -5.29% | -6.00% | -4.34% | -7.22% | -6.06% |
| Compound A2 185mg/kg | 0.00% | -1.81% | -0.67% | -3.15% | -2.36% | -1.91% | -4.14% | -5.18% | -4.23% | -6.83% | -6.29% |
| Compound A2 278mg/kg | 0.00% | -3.39% | -4.22% | -5.26% | -4.89% | -5.27% | -7.12% | -6.53% | -6.30% | -8.57% | -8.68% |
| Compound A23 100mg/kg | 0.00% | -0.84% | -0.59% | -2.53% | -2.52% | 0.38% | -3.36% | -1.16% | 0.43% | -3.62% | -3.07% |
| Compound A12 38mg/kg | 0.00% | -3.53% | -0.47% | -0.74% | -0.39% | 2.42% | -1.36% | 0.36% | 1.31% | -2.25% | 0.91% |
| Compound A12 57mg/kg | 0.00% | -2.83% | -1.74% | -2.35% | -2.14% | -0.05% | -2.81% | -0.78% | -0.13% | -3.23% | -0.50% |
| Compound A12 86mg/kg | 0.00% | 0.54% | 1.37% | 1.24% | 0.53% | 3.93% | 1.44% | 1.74% | 3.33% | 0.02% | 2.90% |

FIG. 34

| Compound | 0 | 1 | 2 | 3 | 4 | 6 | 7 | 8 | 9 | 10 | 13 |
|---|---|---|---|---|---|---|---|---|---|---|---|
| Vehicle Control | 0.00% | -0.51% | -2.21% | -0.04% | 0.58% | 0.58% | -1.00% | -0.38% | -2.69% | -2.83% | -1.56% |
| A2 MTD 325mg/kg | 0.00% | 0.76% | 0.76% | 0.76% | -0.21% | -0.49% | -1.09% | -0.40% | -2.68% | -0.84% | -7.02% |
| A2 280mg/kg | 0.00% | -0.98% | -2.87% | -0.69% | -1.85% | -0.46% | -2.93% | -2.05% | -2.12% | -2.36% | -7.06% |
| A2 185mg/kg | 0.00% | 0.14% | -0.80% | 1.16% | -0.31% | 1.11% | -0.05% | -0.35% | -1.03% | -0.74% | -4.07% |
| A1 280mg/kg | 0.00% | -0.08% | -0.66% | -0.04% | -0.66% | -0.40% | -1.57% | -0.51% | -1.84% | -2.48% | -7.35% |
| A23 200mg/kg | 0.00% | -0.40% | -1.87% | 0.81% | -0.92% | 0.92% | 1.30% | -0.81% | -2.18% | -1.62% | -7.95% |
| Abemaciclib 150 mg/kg | 0.00% | -0.57% | -1.24% | 0.47% | -0.51% | 1.20% | 0.74% | 0.64% | 0.23% | -0.44% | -6.20% |
| Abemaciclib 100 mg/kg | 0.00% | 0.00% | -2.21% | -0.78% | -1.59% | 0.46% | -0.77% | -1.56% | -2.08% | -2.94% | -6.80% |
| Abemaciclib 75 mg/kg | 0.00% | -0.39% | -2.25% | -0.32% | -0.12% | 0.27% | 1.20% | 0.71% | 0.29% | -2.40% | -2.35% |

FIG. 35A

| Compound | 14 | 15 | 16 | 17 | 18 | 19 | 20 | 21 | 22 | 23 | 24 | 25 |
|---|---|---|---|---|---|---|---|---|---|---|---|---|
| Vehicle Control | -1.80% | -3.38% | -2.19% | -2.81% | -3.49% | -2.20% | 0.66% | -0.04% | -2.67% | 0.09% | -0.17% | -3.05% |
| A2 MTD 325mg/kg | -6.03% | -6.54% | -6.57% | -8.78% | -6.93% | -7.33% | -5.96% | -9.58% | -5.98% | -6.02% | -7.17% | -8.78% |
| A2 280mg/kg | -6.41% | -6.73% | -8.00% | -7.32% | -8.34% | -8.45% | -6.65% | -7.54% | -7.21% | -8.11% | -9.27% | -10.39% |
| A2 185mg/kg | -3.22% | -4.63% | -3.71% | -4.54% | -4.84% | -5.97% | -1.25% | -4.06% | -5.12% | -3.25% | -3.44% | -6.47% |
| A1 280mg/kg | -6.26% | -6.39% | -4.98% | -5.27% | -4.95% | -6.10% | -3.63% | -3.98% | -4.12% | -4.21% | -4.20% | -6.96% |
| A23 200mg/kg | -7.11% | -7.69% | -5.40% | -6.23% | -6.81% | -7.76% | -5.71% | -5.50% | -6.88% | -6.00% | -5.73% | -8.74% |
| Abemaciclib 150 mg/kg | -7.37% | -7.03% | -8.30% | -8.03% | -8.03% | -9.79% | -8.59% | -10.20% | -7.43% | -6.60% | -7.14% | -6.75% |
| Abemaciclib 100 mg/kg | -8.58% | -8.37% | -7.52% | -8.40% | -6.50% | -7.91% | -5.62% | -5.28% | -6.86% | -5.47% | -4.95% | -7.55% |
| Abemaciclib 75 mg/kg | -4.05% | -2.81% | -2.58% | -4.39% | -3.79% | -3.26% | 1.41% | -2.00% | -2.74% | -0.49% | -2.47% | 5.98% |

FIG. 35B

| Xenograft Model/Group | No. Mice | Mean tumor volume $mm^3$ | | | T/C | Max Mean % Body Weight Loss | No. of mice to drop below 10% BWL | Deaths | |
|---|---|---|---|---|---|---|---|---|---|
| | | Day 1 | Day last | Change = DLast-D1 | | | | TR | NTR |
| ZR751 Vehicle Control | 8 | 196 | 417 | 221 | - | 3.5 | 0 | 0 | 0 |
| 325mg/kg Compound A2 | 8 | 203 | 234 | 30 | 0.561 | 9.6 | 5 | 2 | 0 |
| 280mg/kg Compound A2 | 8 | 198 | 249 | 51 | 0.597 | 10.4 | 5 | 0 | 0 |
| 185mg/kg Compound A2 | 8 | 197 | 281 | 85 | 0.675 | 6.5 | 0 | 0 | 0 |
| 280mg/kg Compound A1 | 8 | 200 | 213 | 13 | 0.510 | 7.0 | 2 | 0 | 0 |
| 200mg/kg Compound A23 | 8 | 206 | 267 | 62 | 0.642 | 8.7 | 3 | 1 | 0 |
| 150mg/kg Abemaciclib | 8 | 212 | 193 | -19 | 0.464 | 10.2 | 6 | 2 | 0 |
| 100mg/kg Abemaciclib | 8 | 203 | 182 | -21 | 0.436 | 8.6 | 3 | 0 | 0 |
| 75mg/kg Abemaciclib | 8 | 194 | 161 | -33 | 0.386 | 6.0 | 1 | 0 | 0 |

T/C: ratio of final tumor volume in treated vs control
TR: Treatment Related, NTR: Non-Treatment related

FIG. 36

CDK INHIBITORS AND USES THEREOF

CROSS-REFERENCE TO RELATED APPLICATIONS

This application is a 371(c) national stage of PCT/US2019/043754, filed Jul. 26, 2019, which claims the benefit of and priority to U.S. Provisional Patent Application Ser. No. 62/711,192, filed Jul. 27, 2018, the contents of each of which are hereby incorporated by reference in their entirety.

BACKGROUND

CDK4 and CDK6 are cyclin-dependent kinases that control the transition between the G1 and S phases of the cell cycle. The S phase is the period during which the cell synthesizes new DNA and prepares itself to divide during the process of mitosis. CDK4/6 activity is typically deregulated and overactive in cancer cells. There can be amplification or overexpression of the genes encoding cyclins or of the genes encoding the CDKs themselves. Additionally, loss of endogenous inhibitors of CDK4 (also known as INK4 inhibitors) by gene deletion, mutation, or promoter hypermethylation, can also lead to overactivity of CDK4 and CDK6.

Attempts have been made to prepare compounds that inhibit CDK4/6 activity, and a number of such compounds have been disclosed in the art. However, in view of the number of pathological responses that are mediated by CDK4/6, there remains a need for inhibitors of CDK4/6 that can be used in the treatment of a variety of conditions, including cancer.

SUMMARY OF THE INVENTION

In certain aspects, provided herein are compounds having the structure of Formula (I)

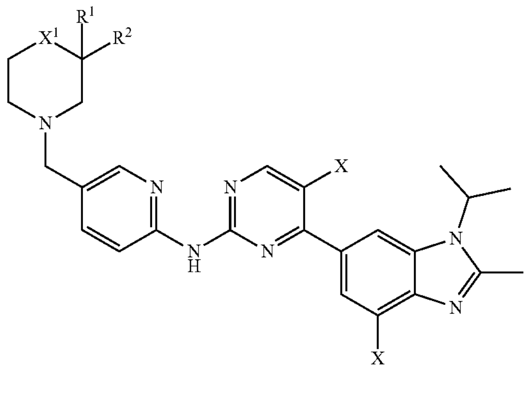

or a pharmaceutically acceptable salt thereof, wherein:

- X is, independently for each occurrence, halo, preferably fluoro;
- $X^1$ is O or $NR^{X1}$, preferably $X^1$ is O;
- $R^{X1}$ is H or alkyl, preferably lower alkyl;
- $R^1$ is alkyl, preferably lower alkyl; and
- $R^2$ is optionally substituted alkyl, optionally substituted haloalkyl, optionally substituted alkenyl, optionally substituted hydroxyalkyl, optionally substituted aminoalkyl, or optionally substituted amidoalkyl; or
- $R^1$ and $R^2$, together with the carbon atom through which they are joined, form an optionally substituted 5- or 6-membered heterocyclic ring (e.g., a pyrrolidine ring, a piperidine ring, a piperazine ring, a pyrrolidine ring, a tetrahydropyran ring, a tetrahydrofuran ring, or a morpholine ring, each of which may be optionally substituted).

In certain aspects, provided herein are compounds having the structure of Formula (Ia):

(Ia)

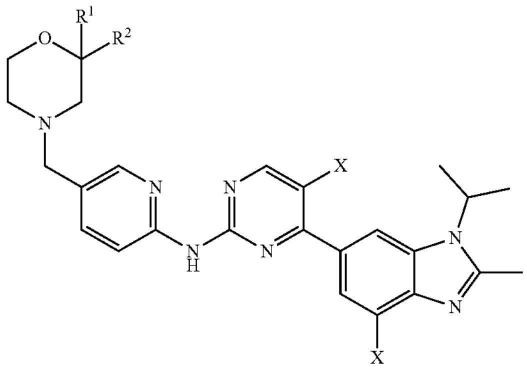

or a pharmaceutically acceptable salt thereof, wherein:

- X is, independently for each occurrence, halo, preferably fluoro;
- $R^1$ is alkyl, preferably lower alkyl; and
- $R^2$ is optionally substituted alkyl, optionally substituted haloalkyl, optionally substituted alkenyl, optionally substituted hydroxyalkyl, optionally substituted aminoalkyl, or optionally substituted amidoalkyl; or
- $R^1$ and $R^2$, together with the carbon atom through which they are joined, form an optionally substituted 5- or 6-membered heterocyclic ring.

In certain aspects, provided herein are compounds having the structure of Formula (Ib):

(Ib)

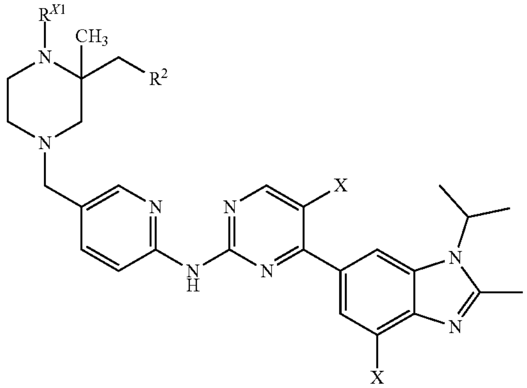

or a pharmaceutically acceptable salt thereof, wherein:

- X is, independently for each occurrence, halo, preferably fluoro;
- $R^{X1}$ is H or alkyl, preferably lower alkyl; and
- $R^2$ is optionally substituted alkyl, optionally substituted haloalkyl, optionally substituted alkenyl, optionally substituted hydroxyalkyl, optionally substituted aminoalkyl, or optionally substituted amidoalkyl.

In some embodiments, $R^1$ is $C_1$-$C_4$-alkyl (e.g., methyl, ethyl).

In some embodiments, $R^2$ is optionally substituted $C_1$-$C_4$-alkyl or $(CH_2)_nR^{2a}$, wherein:

$R^{2a}$ is optionally substituted $C_1$-$C_4$-alkyl, optionally substituted $C_1$-$C_4$-haloalkyl, optionally substituted $C_2$-$C_4$-alkenyl, or optionally substituted $C_1$-$C_4$-hydroxyalkyl, optionally substituted $C_1$-$C_4$-alkoxy-$C_1$-$C_4$-alkyl, optionally substituted $C_1$-$C_4$-alky 1 amino-$C_1$-$C_4$-alky 1, or optionally substituted $C_1$-$C_4$-alkylamino-$C_1$-$C_4$-haloalkyl; and n is an integer having a value of 1 or 2.

In certain aspects, $R^2$ is optionally substituted alkyl, optionally substituted haloalkyl, optionally substituted alkenyl, optionally substituted hydroxyalkyl, or optionally substituted aminoalkyl.

For example, in certain embodiments, $R^2$ is substituted $C_1$-$C_4$-alkyl. In other embodiments, $R^2$ is methyl, ethyl, propylenyl, n-propyl, isopropyl, n-butyl, sec-butyl, tert-butyl, $(CH_2)_2OH$, $—(CH_2CH(CH_3))OH$, $(CH_2)_2O(CH_2CH_3)$, $—(CH_2)_2OCH_2CH_3$, $—(CH_2)_2N(H)(CH_3)$, $—(CH_2)_2N(H)(C(CH_3)_3)$, $—(CH_2)_2N(H)(C(O)CH_3)$, $—(CH_2)_2N(H)(CH_2CH_2F)$, $—(CH_2)_2N(CH_3)(CH_2CH_2F)$, $—(CH_2)_2N(CH_3)_2$, $—(CH_2)_2N(CH_2CH_3)_2$, $—(CH_2)_2N(CH_2CH_3)_2$, $—(CH_2CH(CH_3))N(CH_3)_2$, $—CH_2C(O)—NHCH_3$, $—CH_2C(O)—N(CH_3)_2$, $—CH_2C(O)—N(CH_2CH_3)_2$, or $—CH_2C(O)$-heterocyclyl, such as $—CH_2C(O)$—N-linked heterocyclyl.

In some embodiments, $R^2$ is $(CH_2)_nC(O)NR^{2a}R^{2b}$ or $(CH_2)_nNR^{2a}R^{2b}$, wherein:

$R^{2a}$ and $R^{2b}$ are each independently H, alkyl, haloalkyl, alkenyl, $(CR^cR^d)_mOR^{2c}$, or —C(O)alkyl;

$R^c$, $R^d$, and $R^e$ are each independently H or alkyl, preferably lower alkyl;

n is an integer having a value of 1 or 2; and m is an integer having a value of 2 to 5.

Alternatively, in some embodiments, $R^2$ is $(CH_2)_nC(O)NR^{2a}R^{2b}$ or $(CH_2)_nNR^{2a}R^{2b}$, wherein:

$R^{2a}$ and $R^{2b}$, together with the nitrogen atom through which they are joined, form an optionally substituted 3- to 6-membered heterocyclic ring; and n is an integer having a value of 1 or 2.

For example, $R^{2a}$ and $R^{2b}$, together with the nitrogen atom through which they are joined, may form an optionally substituted heterocyclic ring selected from:

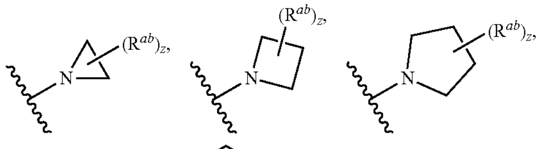

and

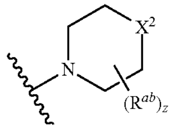

wherein:

each $R^{ab}$ is independently halo, hydroxyl, alkyl, haloalkyl, or alkoxy;

$X^2$ is O, $NR^{x1}$ or $CR^{x2}R^{x3}$;

$R^{x1}$, $R^{x2}$, and $R^{x3}$ are each independently H or alkyl, preferably lower alkyl; and z is an integer having a value of 0 to 2.

In certain embodiments of the compound of Formula (I) or Formula (Ia), $R^1$ and $R^2$, together with the carbon atom through which they are joined, form a heterocyclic ring having the structure:

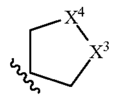

wherein:

$X^3$ is $NR^{Y1a}$ or $CR^{Y1b}R^{Y1c}$;

$X^4$ is O or $CR^{Y2a}R^{Y2b}$;

$R^{Y1a}$ is H, alkyl, $—C(O)R^{Y1aa}$; or $—S(O)_2$alkyl;

$R^{Y1aa}$ is alkyl or alkoxy; and $R^{Y1b}$, $R^{Y1c}$, $R^{Y2a}$, and $R^{Y2b}$ are each independently H or alkyl, preferably lower alkyl.

In some such embodiments, the heterocyclic ring is selected from:

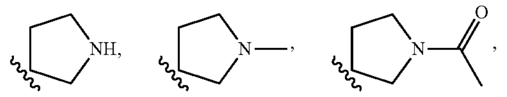

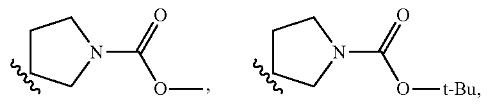

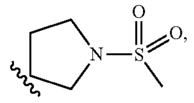

and

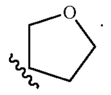

In some embodiments, the compound of Formula (I) is selected from:

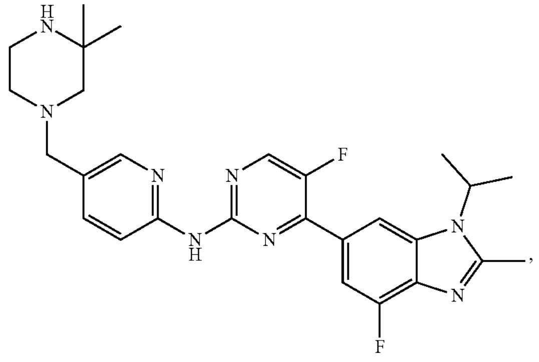

-continued

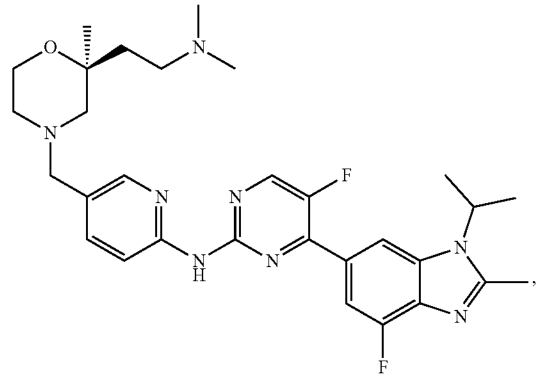

,

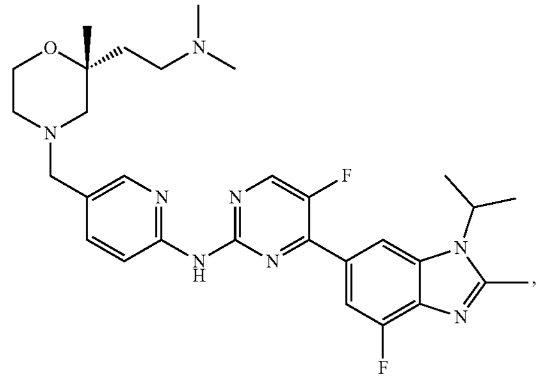

,

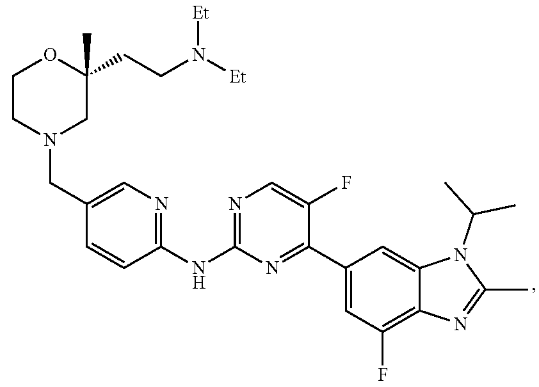

,

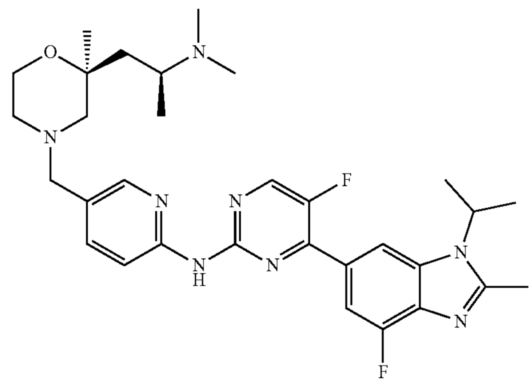

,

-continued and

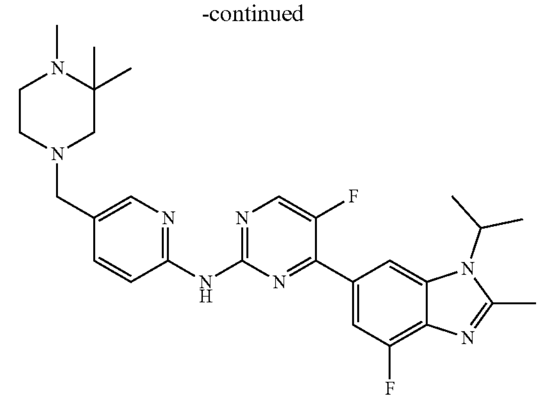

or a pharmaceutically acceptable salt thereof.

In certain embodiments, the disclosure relates to compounds having the structure of Formula (IVa) or (IVb):

(IVa)

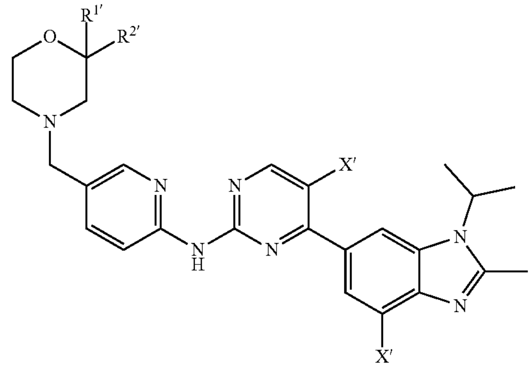

(IVb)

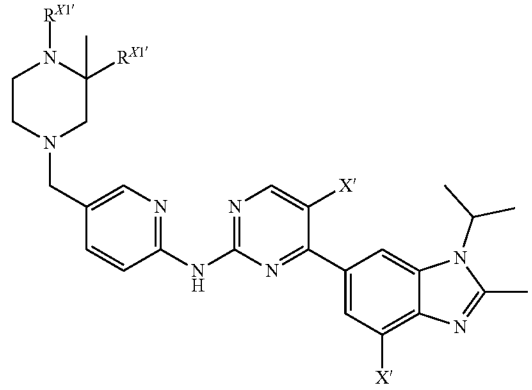

or a pharmaceutically acceptable salt thereof, wherein:

X' in each instance is independently halo, preferably F;

$R^{X1'}$ in each instance is independently H or lower alkyl;

$R^{1'}$ is $C_1$-$C_3$alkyl;

$R^{2'}$ is hydroxy alkyl or $(CR^{2c'}_2)_nNR^{2a'}R^{2b'}$;

$R^{2a'}$ is H, lower alkyl, acyl or haloalkyl;

$R^{2b'}$ is H, lower alkyl, acyl or haloalkyl; or $R^{2a'}$ and $R^{2b'}$ together through the N atom through which they are joined, form a 4-, 5- or 6-membered heterocyclic ring optionally substituted with $R^{ab'}_{z'}$; or $R^{1'}$ and $R^{2'}$ together through the C atom through which they are joined, form a 5- or 6-membered heterocyclic ring optionally substituted with acyloxy;

$R^{ab'}$, when present, in each instance is independently halo, hydroxy, lower alkyl or alkoxy;

each $R^{2c'}$ is independently H or alkyl, preferably methyl;

n' is an integer having a value of 1 or 2;

z' is an integer having a value of 0, 1 or 2; and wherein the compound has a CDK4 $K_i$ of about 0.960 nM or lower.

In some embodiments, the invention relates to a compound having the structure of Formula (V):

(V)

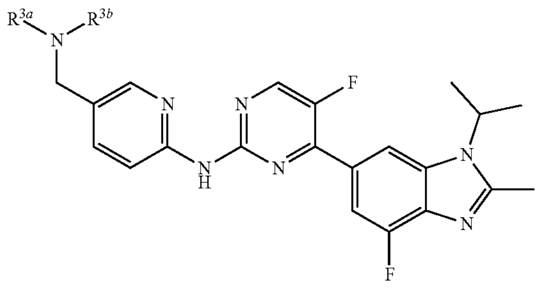

or a pharmaceutically acceptable salt thereof, wherein:

$R^{3a}$ and $R^{3b}$, taken together with the nitrogen atom to which they are attached, form an optionally substituted [3.3] spirocyclic moiety, wherein the optionally substituted [3.3] spirocyclic moiety optionally comprises at least one additional heteroatom selected from O, S, and SO2, provided that the compound is not

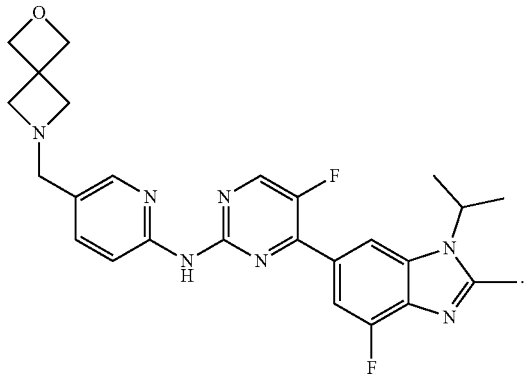 [SMILES: Cc1nc2c(F)cc(-c3nc(Nc4ccc(CN5CC6(COC6)C5)cn4)ncc3F)cc2n1C(C)C]

In some embodiments, the compound has the structure of Formula (Va):

(Va)

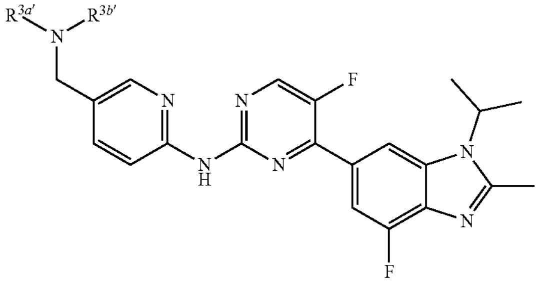

or a pharmaceutically acceptable salt thereof, wherein:

$R^{3a}$ and $R^{3b}$, taken together with the nitrogen atom to which they are attached, form a structure selected from:

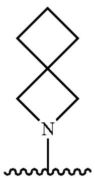 , 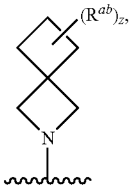 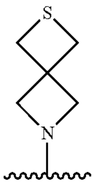 , 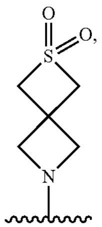

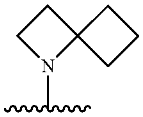 , 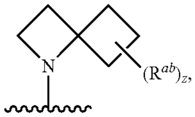 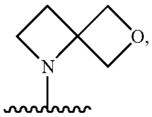

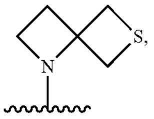 and 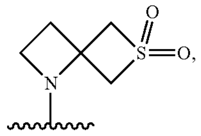

wherein each $R^{ab}$ is independently halo, hydroxyl, alkyl, haloalkyl, or alkoxy; and z is 0, 1, or 2.

In certain embodiments, $R^{3a}$ and $R^{3b}$, taken together with the nitrogen atom to which they are attached, form

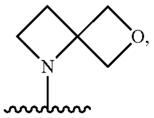 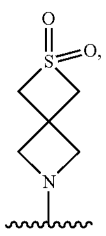 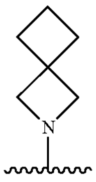 , or

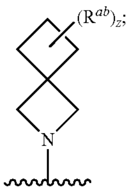

each $R^{ab}$ is independently halo; and z is 2.

In some embodiments, $R^{3a}$ and $R^{3b}$, taken together with the nitrogen atom to which they are attached, form

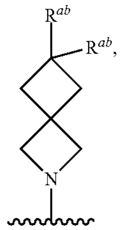

wherein $R^{ab}$ is fluoro.

The present disclosure also relates to compositions (e.g., pharmaceutical compositions) comprising a compound of Formula (I), Formula (IVa), Formula (IVb), Formula (V), or Formula (Va), and a carrier (e.g., a pharmaceutically acceptable carrier, such as a diluent or excipient).

In certain aspects, the present disclosure provides methods of treating a condition or disorder in a subject in need thereof comprising administering to the subject a compound of Formula (I), Formula (Ia), Formula (Ib), Formula (IVa), Formula (IVb), Formula (V), or Formula (Va), or a pharmaceutically acceptable salt thereof. Such conditions and disorders include, but are not limited to, cancers, viral infections, inflammatory diseases, cardiovascular diseases, neurodegenerative disorders, glomerulonephritis, myelodysplasia syndromes, ischemic injury associated myocardial infarctions, stroke and reperfusion injury, arrhythmia, atherosclerosis, toxin-induced or alcohol-related liver diseases, hematological diseases, degenerative diseases of the musculoskeletal system, and ophthalmic diseases.

In certain other aspects, provided herein are methods of sensitizing cancer and/or tumor cells in a subject in need thereof to a chemotherapeutic agent or to radiation comprising administering to the subject an inhibitor of CDK4 and/or CDK in an amount sufficient to arrest the cancer and/or tumor cell cycle, and thereby sensitize the cancer and/or tumor cells in the mammal to a chemotherapeutic agent or to radiation, wherein the inhibitor of CDK4 and/or CDK6 is a compound of Formula (I), Formula (Ia), Formula (Ib), Formula (IVa), Formula (IVb), Formula (V), or Formula (Va), or a pharmaceutically acceptable salt thereof.

In yet other aspects, provided herein are methods of inhibiting CDK4 and/or CDK6 in a cell comprising contacting said cell with a compound of Formula (I), Formula (Ia), Formula (Ib), Formula (IVa), Formula (IVb), Formula (V), or Formula (Va), or a pharmaceutically acceptable salt thereof, such that CDK4 and/or CDK6 enzymes are inhibited in said cell.

BRIEF DESCRIPTION OF THE DRAWINGS

FIG. 34 tabulates body weight data over the 25 days of dosing in the xenograft study.

FIGS. 35A and 35B tabulate the animal body weight data at day 26 (final day) of the xenograft study.

FIG. 36 shows a summary of the results from the xenograft efficacy study.

DETAILED DESCRIPTION OF THE INVENTION

Figure 1:
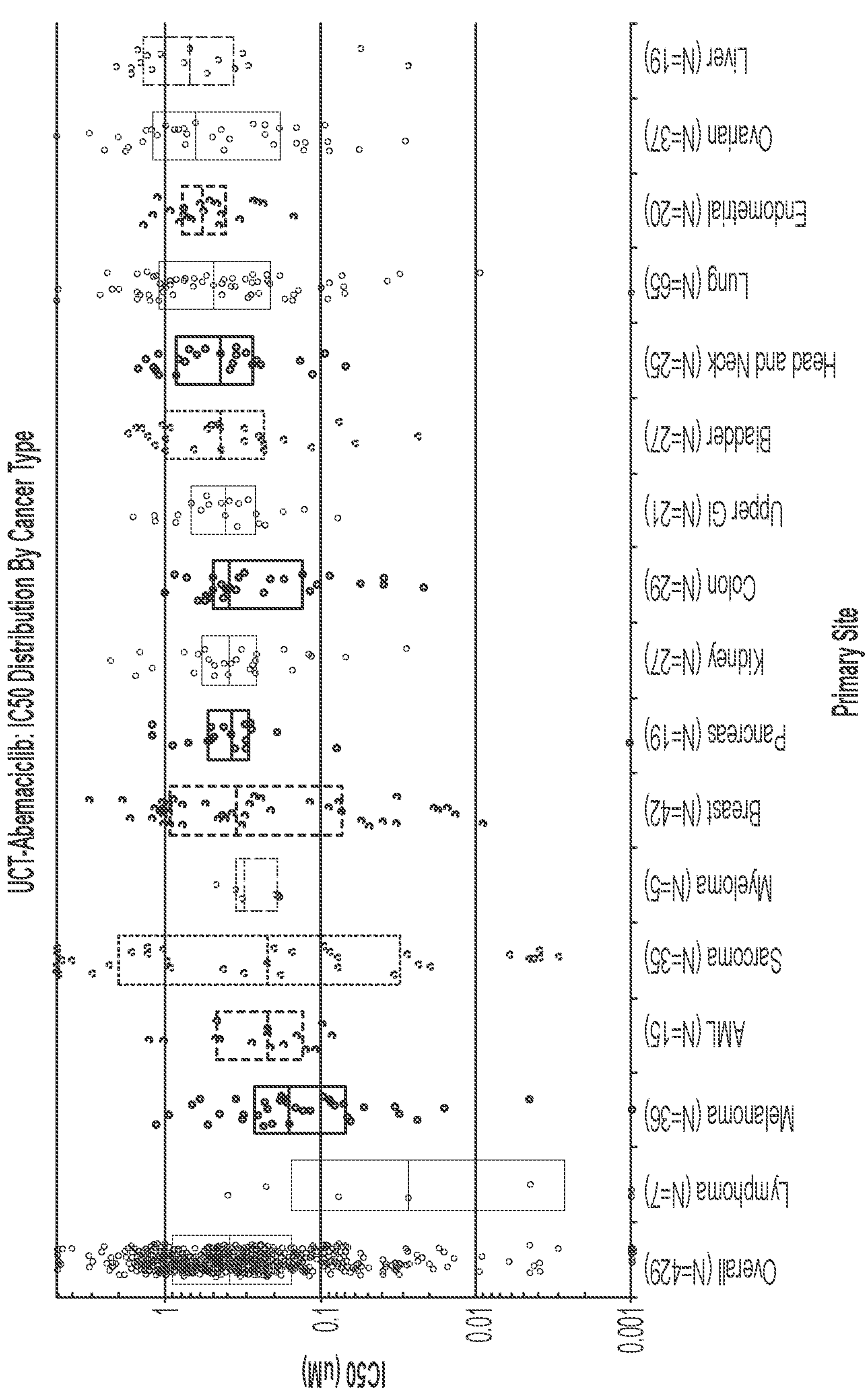
FIG. 1 shows Abemaciclib $IC_{50}$ distribution by cancer type.
Figure 2:
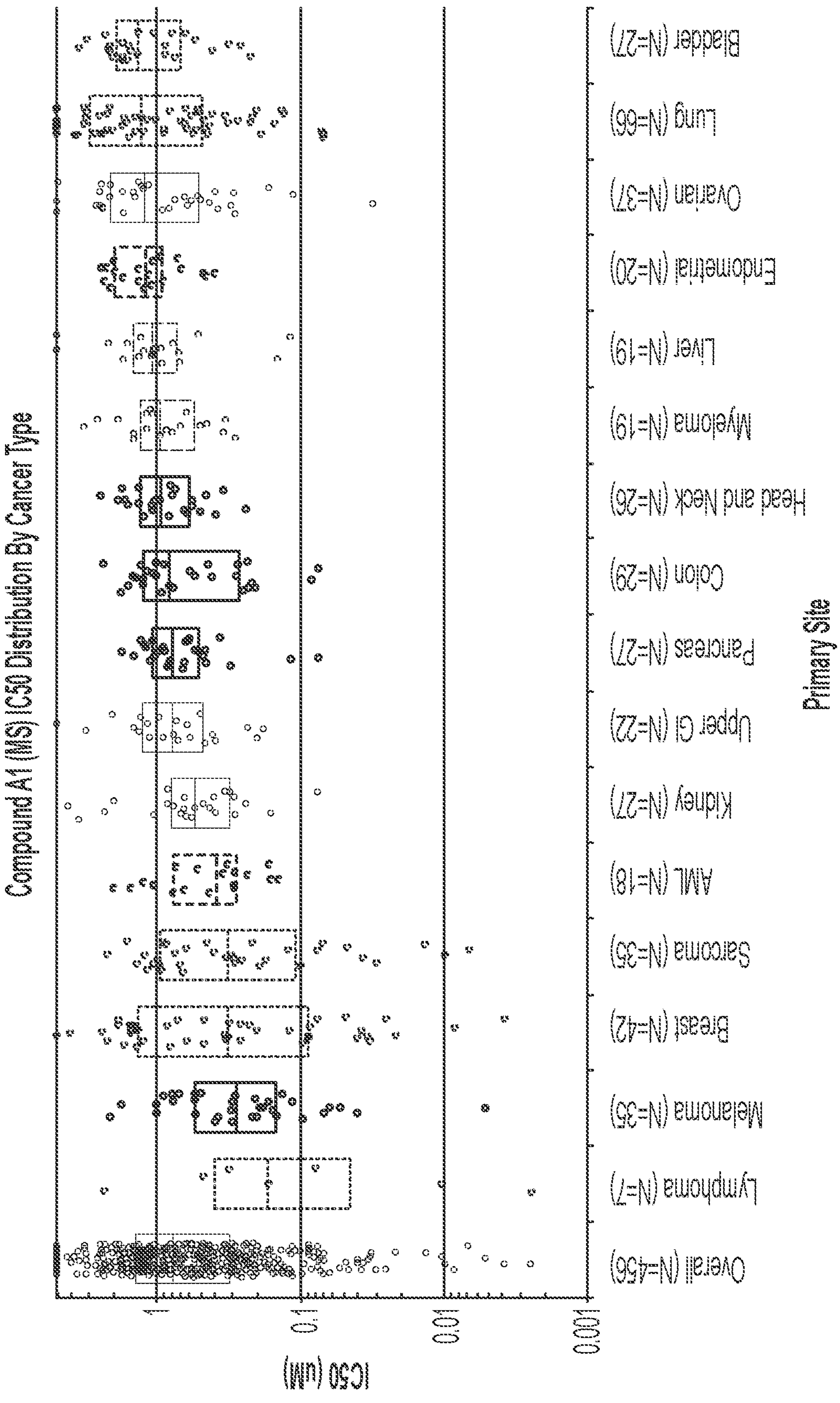
FIG. 2 shows compound A1 (mesylate salt) $IC_{50}$ distribution by cancer type.
Figure 3:
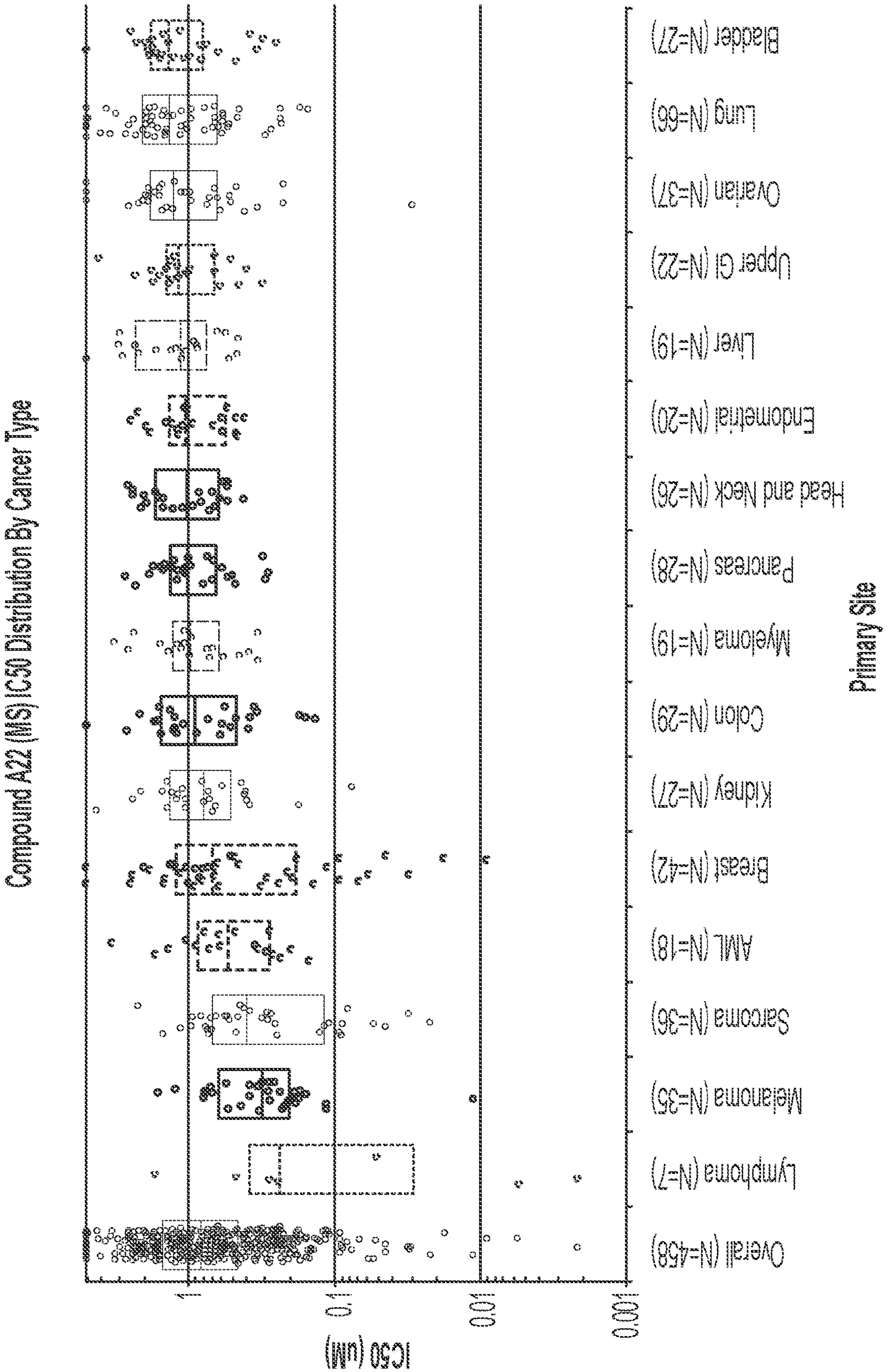
FIG. 3 shows compound A22 (mesylate salt) $IC_{50}$ distribution by cancer type.
Figure 4:
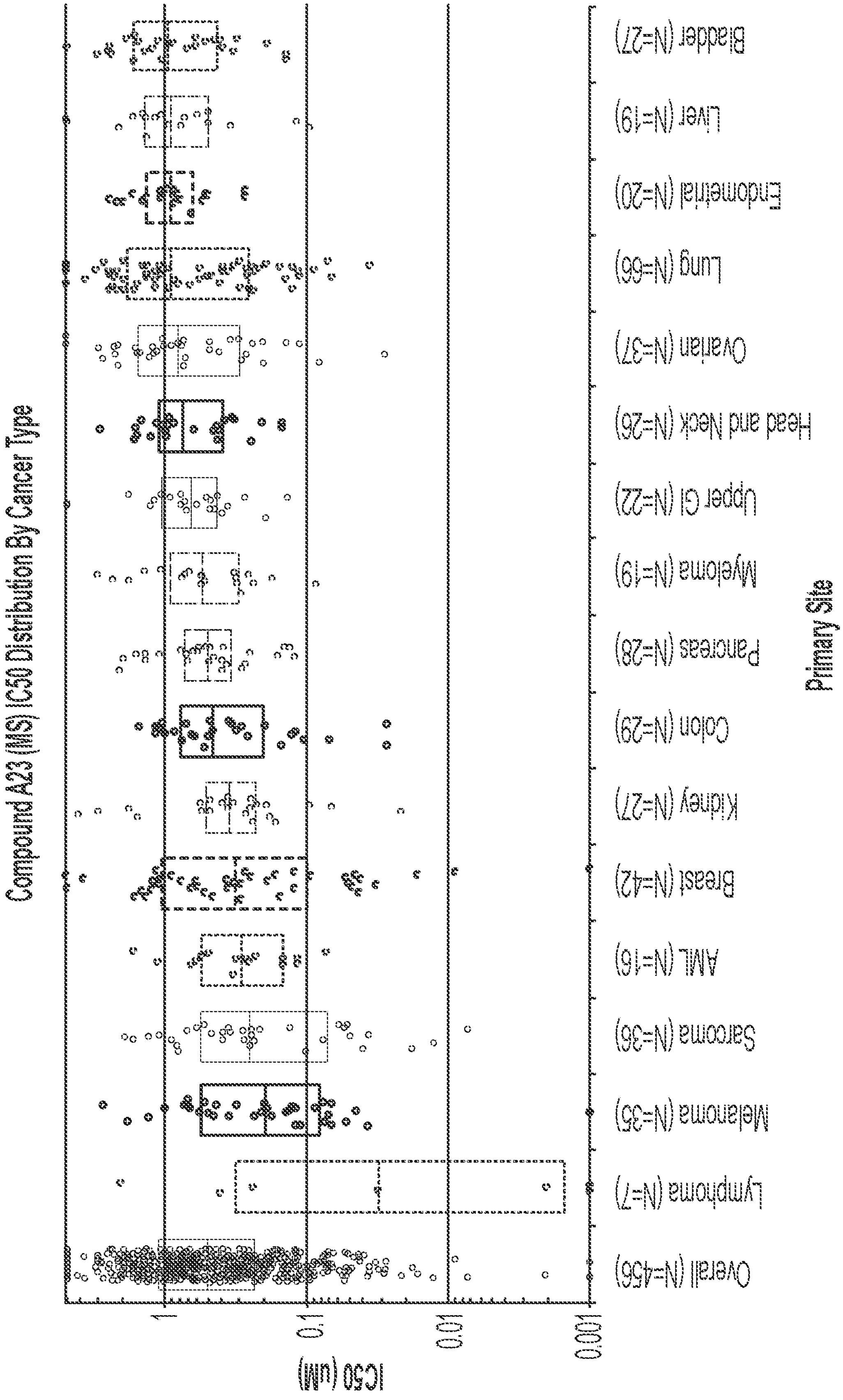
FIG. 4 shows compound A23 (mesylate salt) $IC_{50}$ distribution by cancer type.
Figure 5:
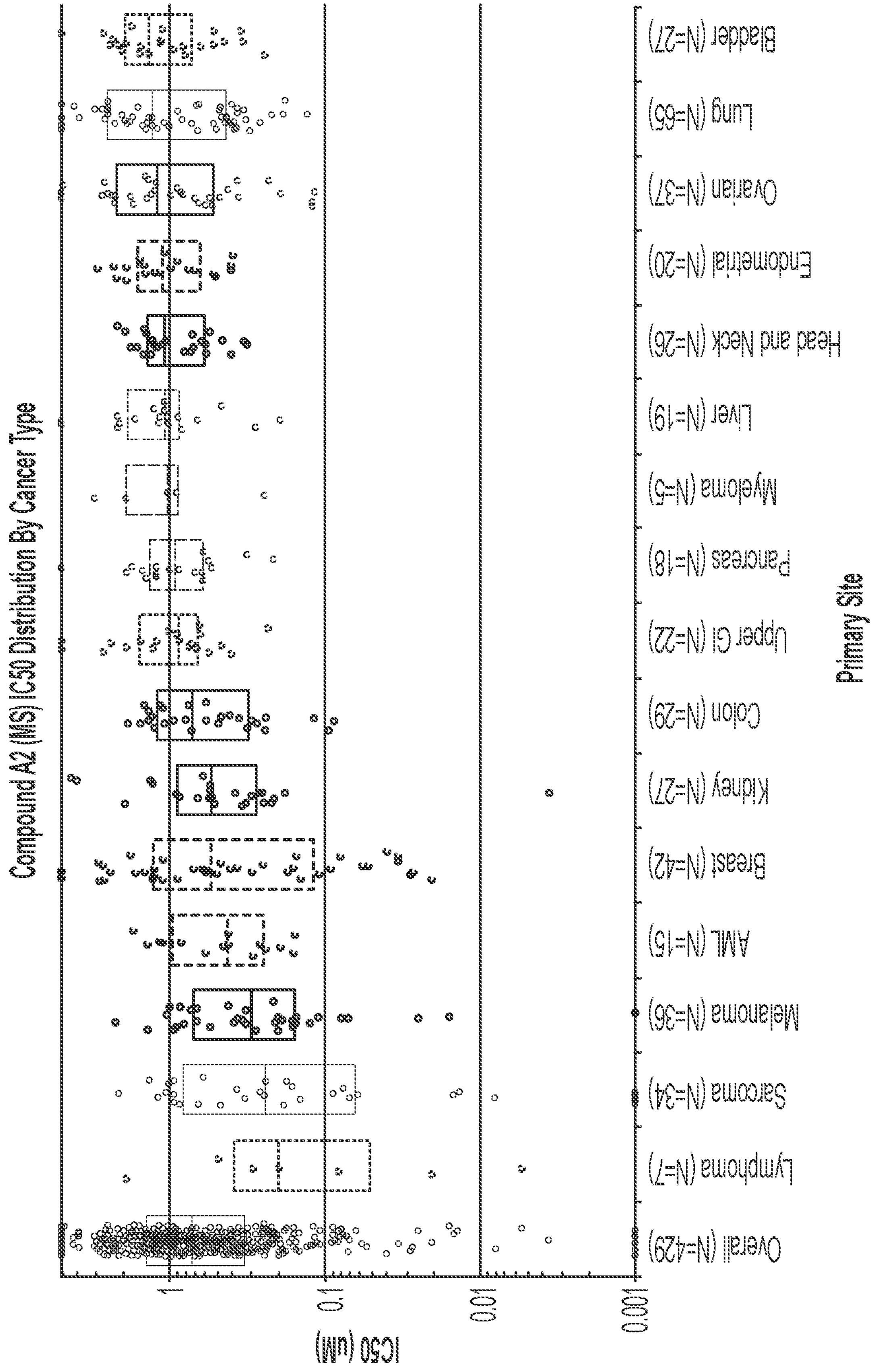
FIG. 5 shows compound A2 (mesylate salt) $IC_{50}$ distribution by cancer type.
Figure 6:
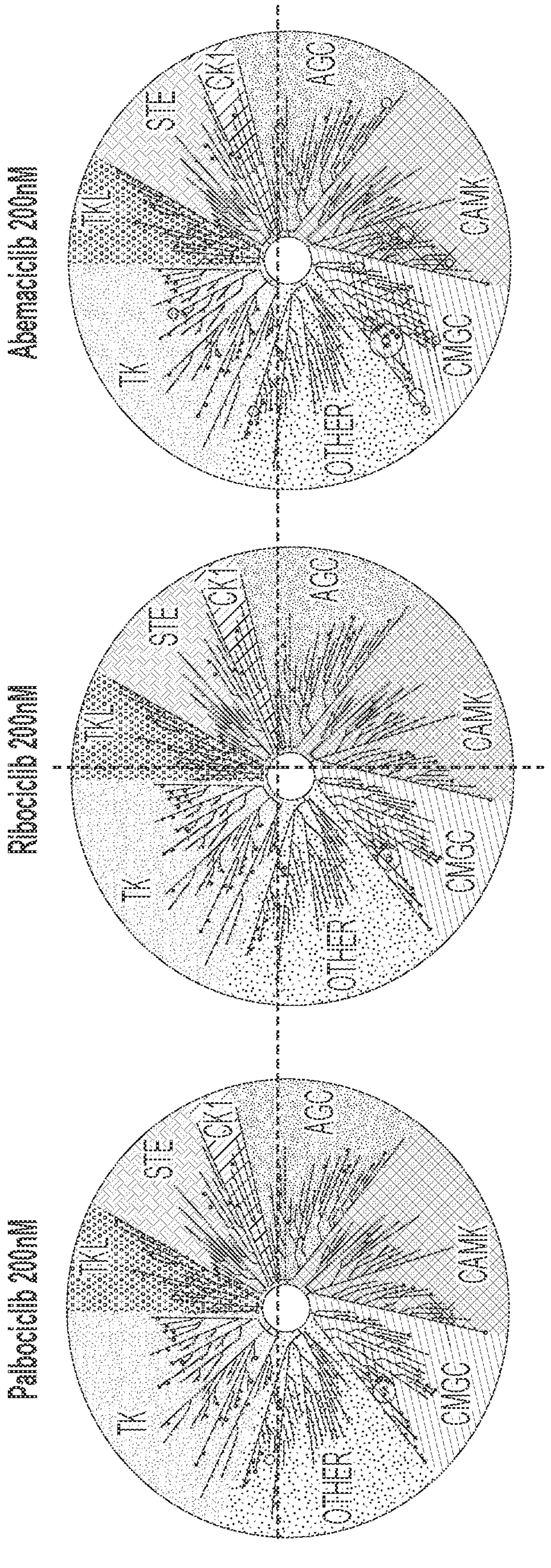
FIG. 6 shows the relative selectivity of CDK4/6 inhibitors palbociclib (200 nM), ribociclib (200 nM), and abemaciclib (200 nM). Compared to palbociclib and ribociclib, abemaciclib hits extra kinases: CDK16, CDK7, DYRK1B, GSK3B, JNK1/2/3, PIM1, ROCK2, PRKCE; ribociclib is the cleanest, but hits ULK2.
Figure 7:
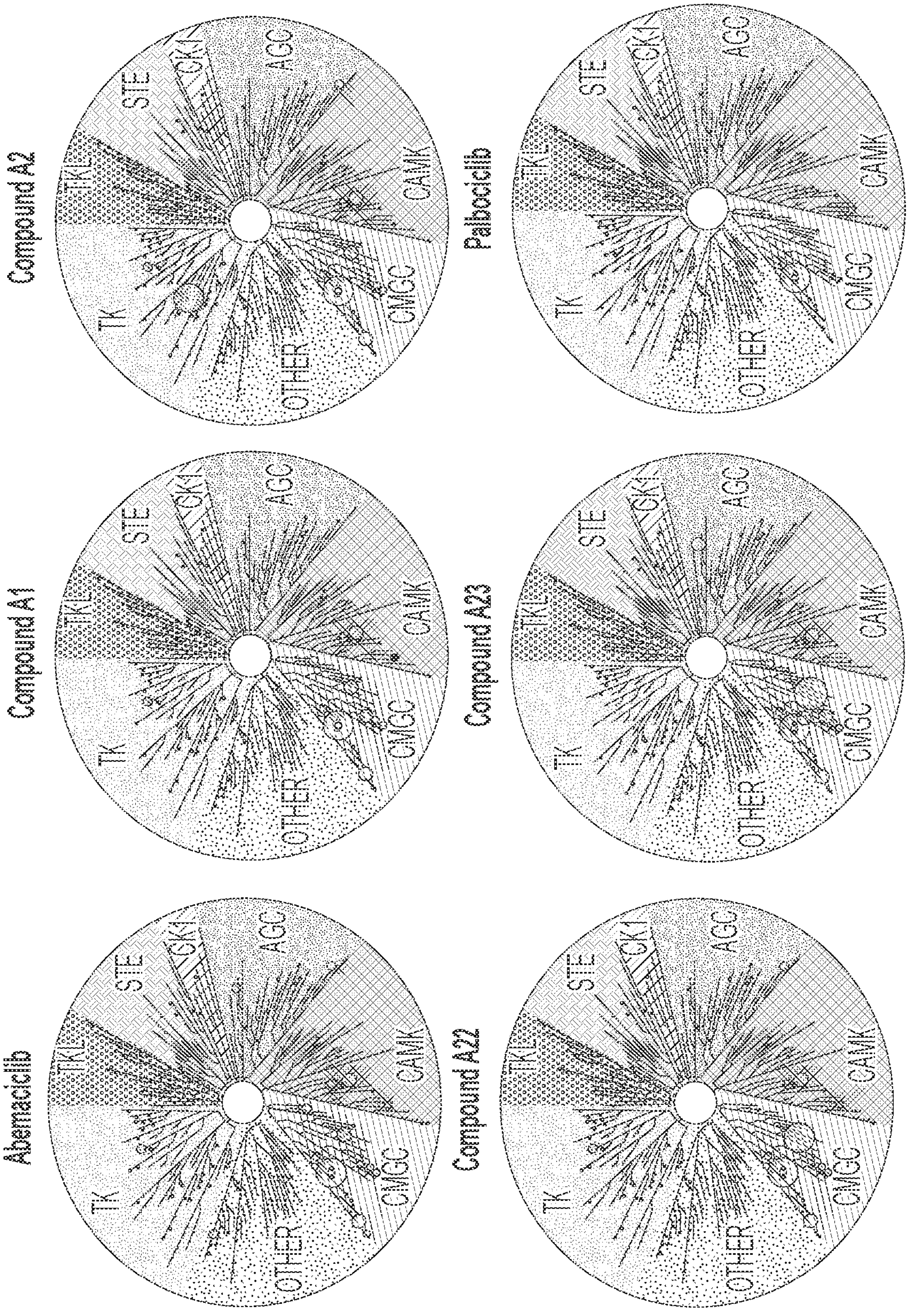
FIG. 7 shows a kinase inhibition screen of certain compounds at 200 nM compared to abemaciclib at 200 nM.
Figure 8:
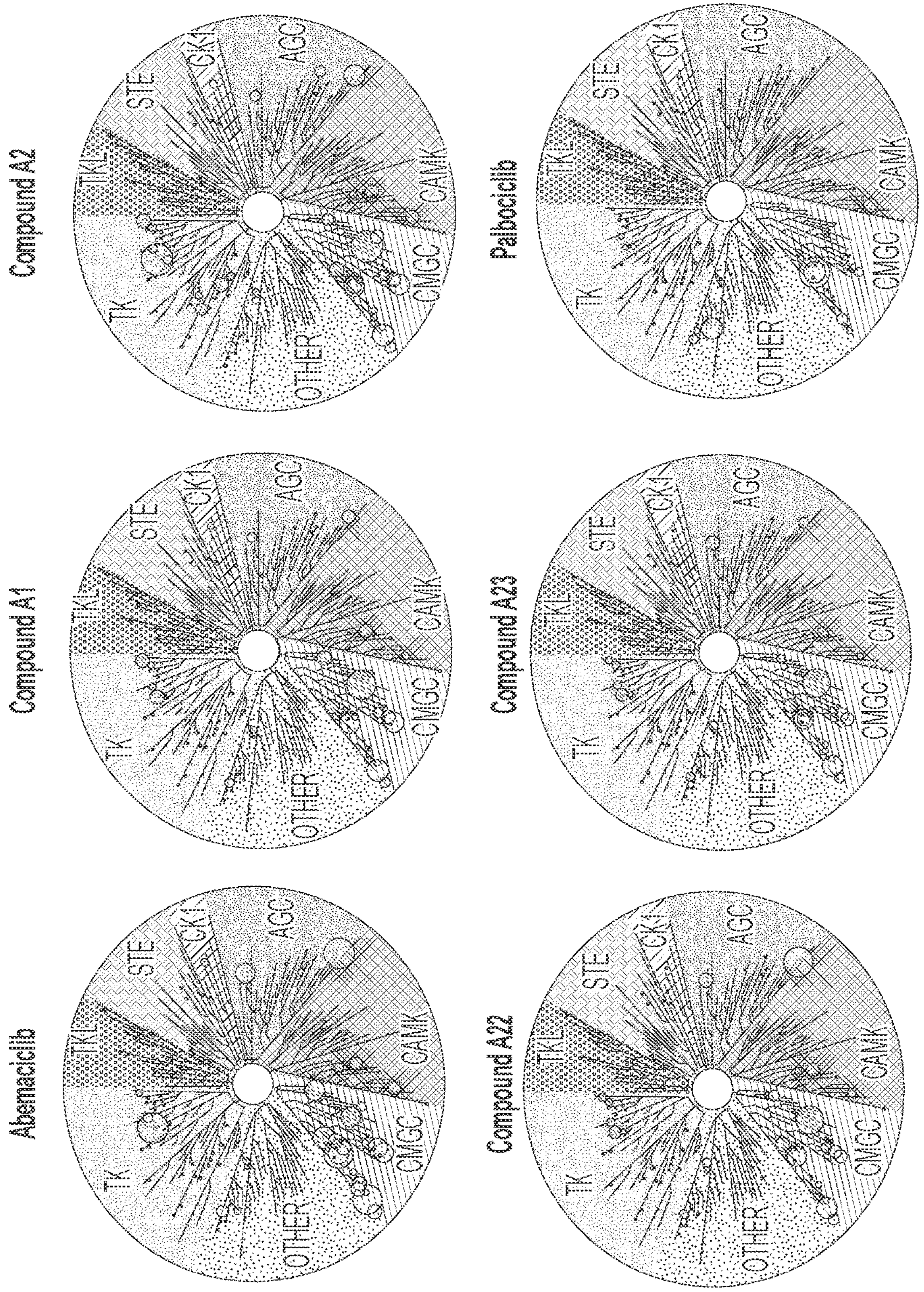
FIG. 8 shows a kinase inhibition screen of certain compounds at 2000 nM compared to abemaciclib at 2000 nM.
Figure 9:
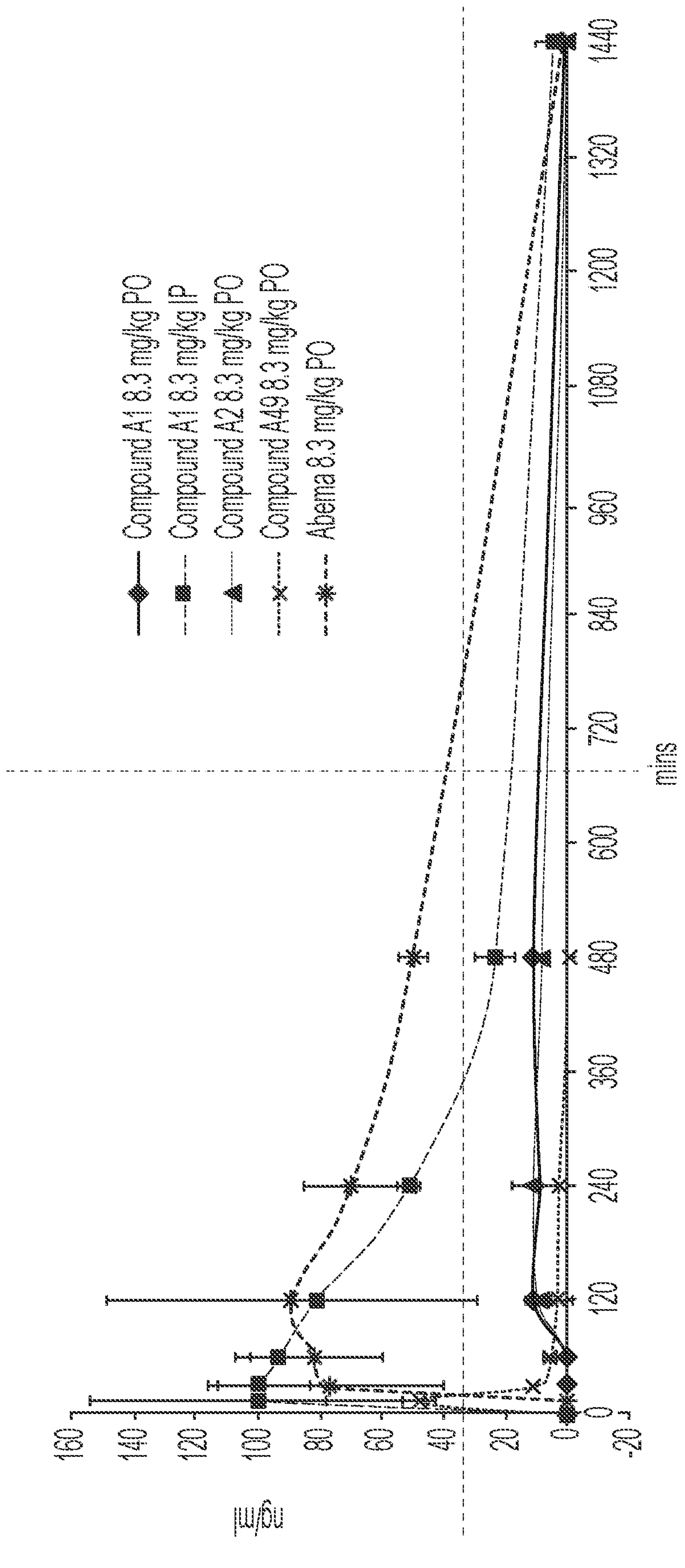
FIG. 9 shows a PK experiment with single doses at 8.3 mg/kg that explored PO vs IP and comparative exposure with Abemaciclib. This exploratory mouse PK study suggested variations in PK for the tested compounds. For example, compounds A1 and A2 administered by PO have a low $C_{max}$, with slow metabolism and a longer half-life as compared to abemaciclib. Compound A49 administered by PO has a high $C_{max}$, followed by rapid metabolism. Compounds A1 and A2 administered by IP achieved similar bioavailability as abemaciclib.
Figure 10:
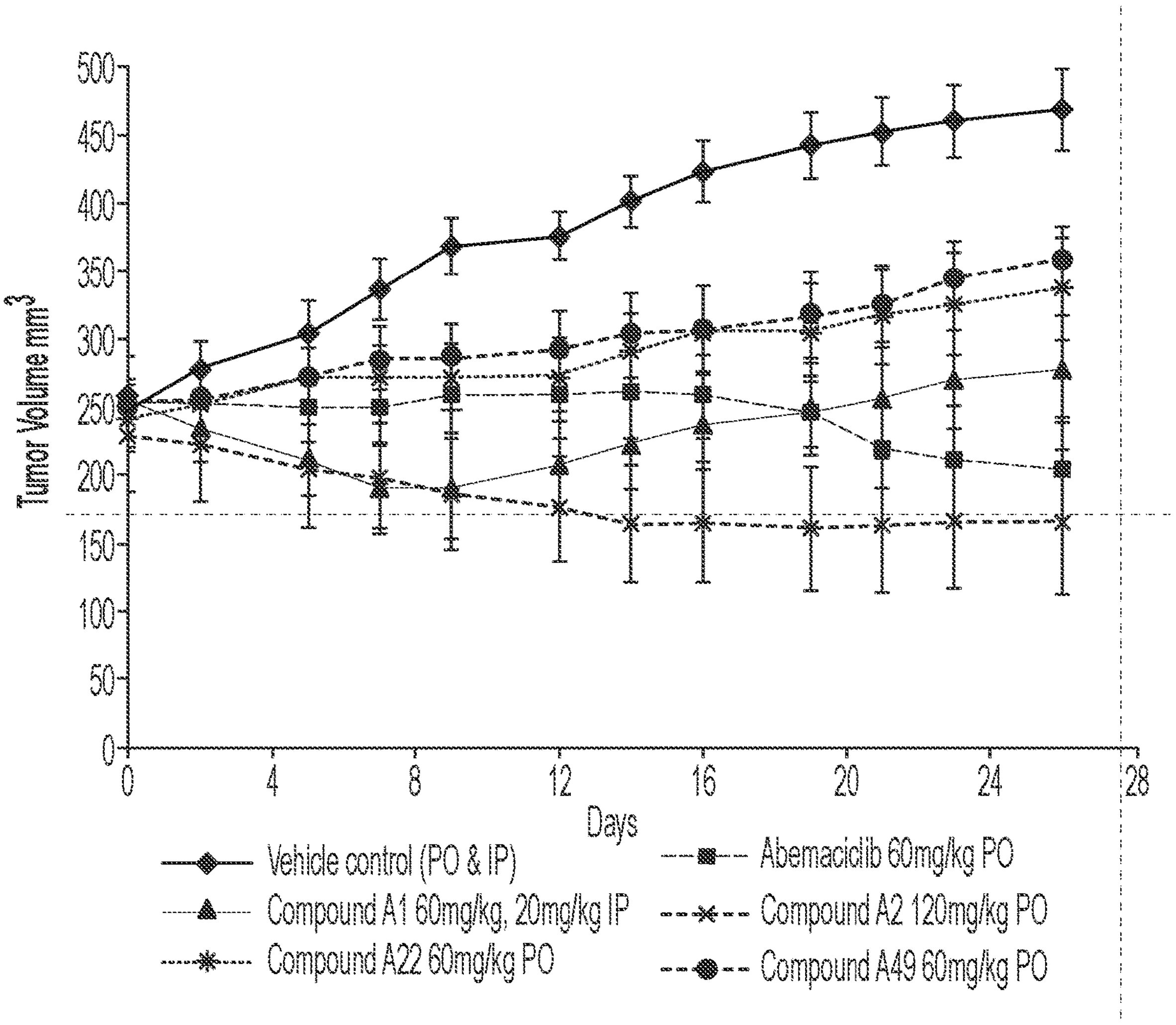
FIGS. 10 and 11 show efficacy data from the first ER+ breast cancer cell line xenograft study over 26 days of dosing of certain compounds of the invention. Compound A1 was administered by IP at 60 mg/kg, and given a 2 day break and re-started at 20 mg/kg QD from day 5 onward. Compound A22 was administered by PO and increased to 120 mg/kg from day 12 onward. Compound A49 was administered by PO and dosing was stopped on day 19. The ZR751 cell line was used for this study.
Figure 11:
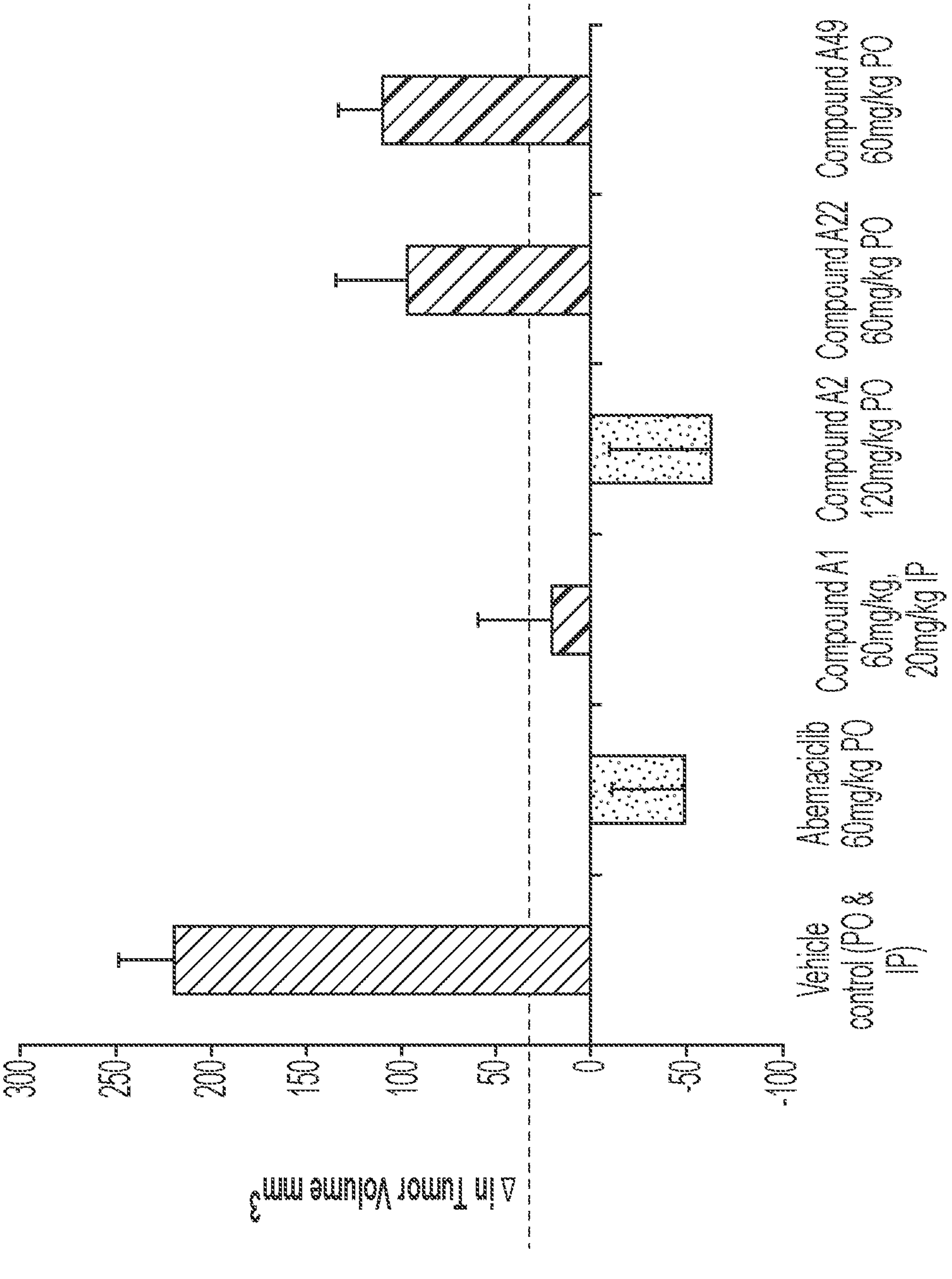
Figures 12A, 12B:
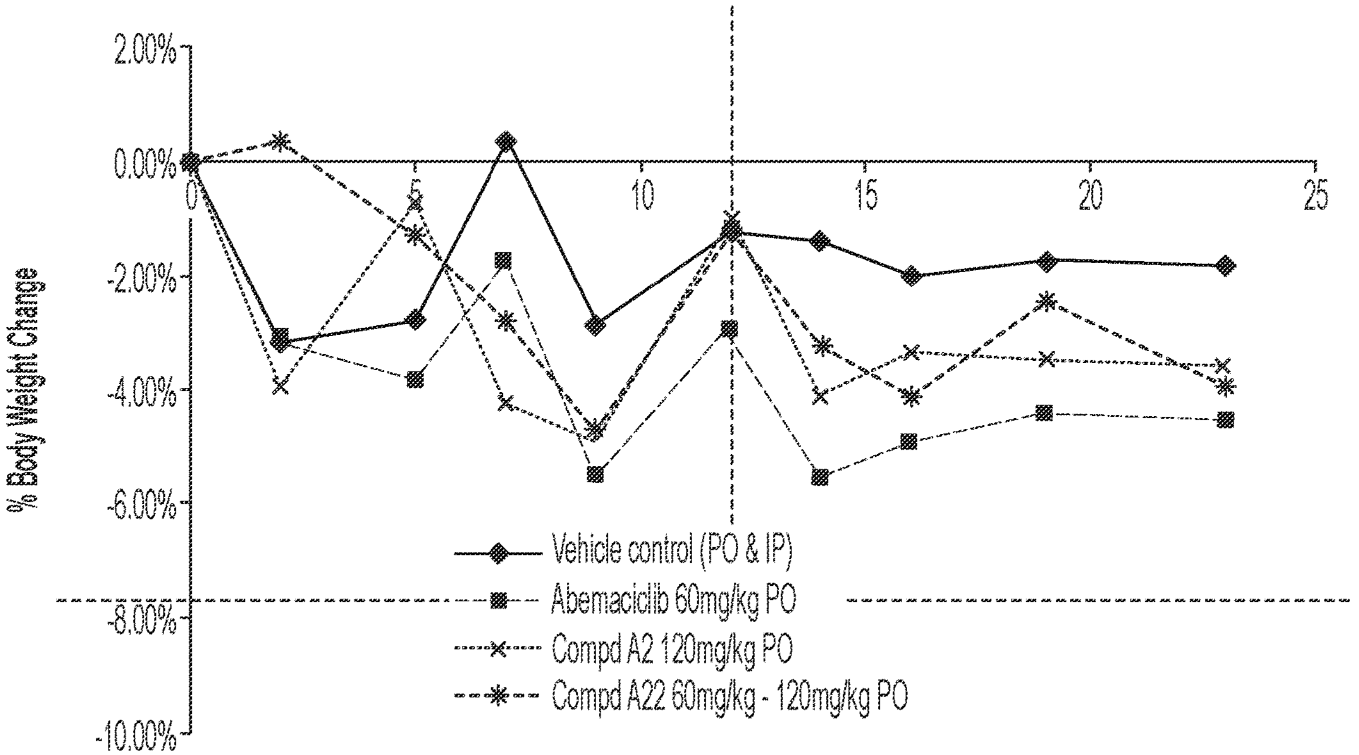
FIGS. 12A and 12B show the results from the first ER+ breast cancer cell line xenograft study.
Figure 13:
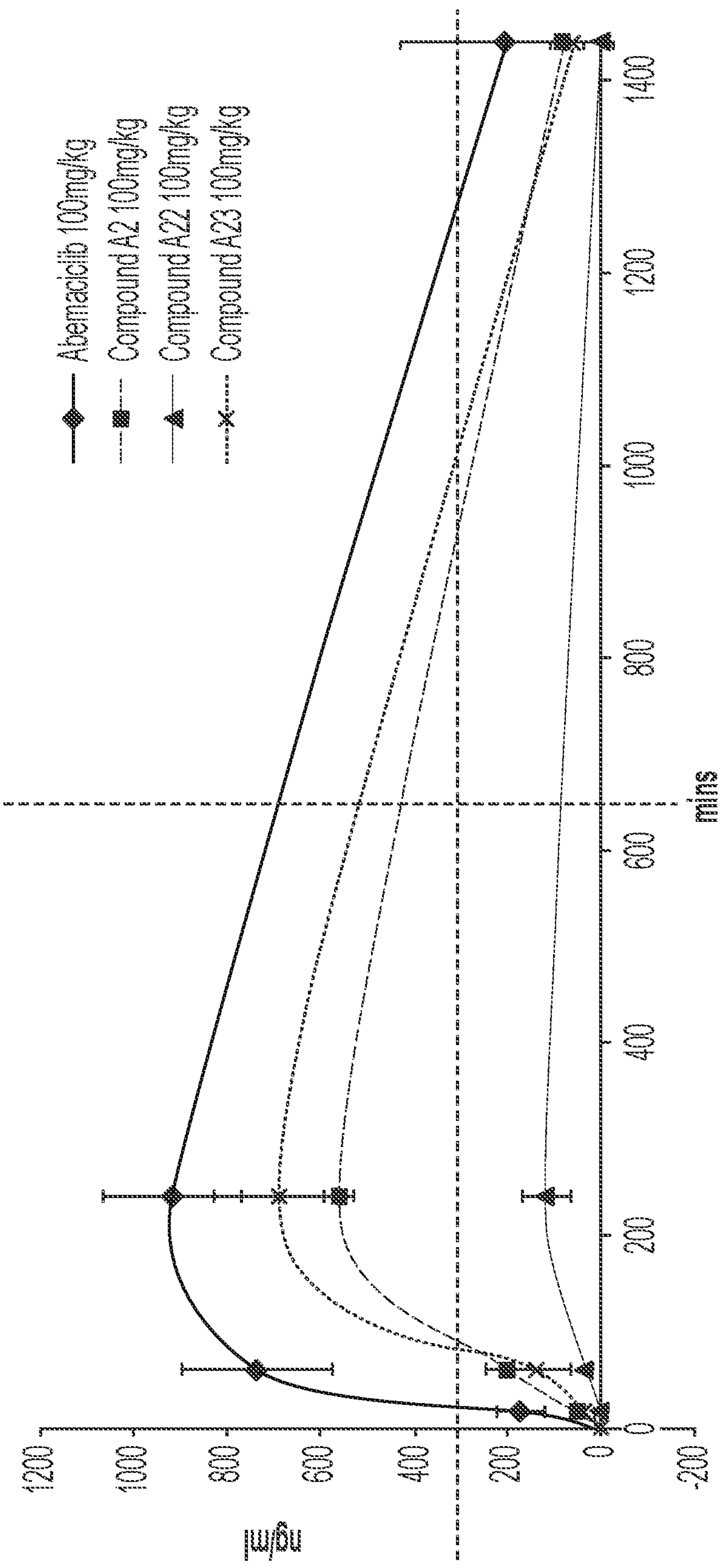
FIG. 13 shows the results of a follow up PK study for certain compounds of the invention, each dosed at 100 mg/kg by PO.
Figure 14:
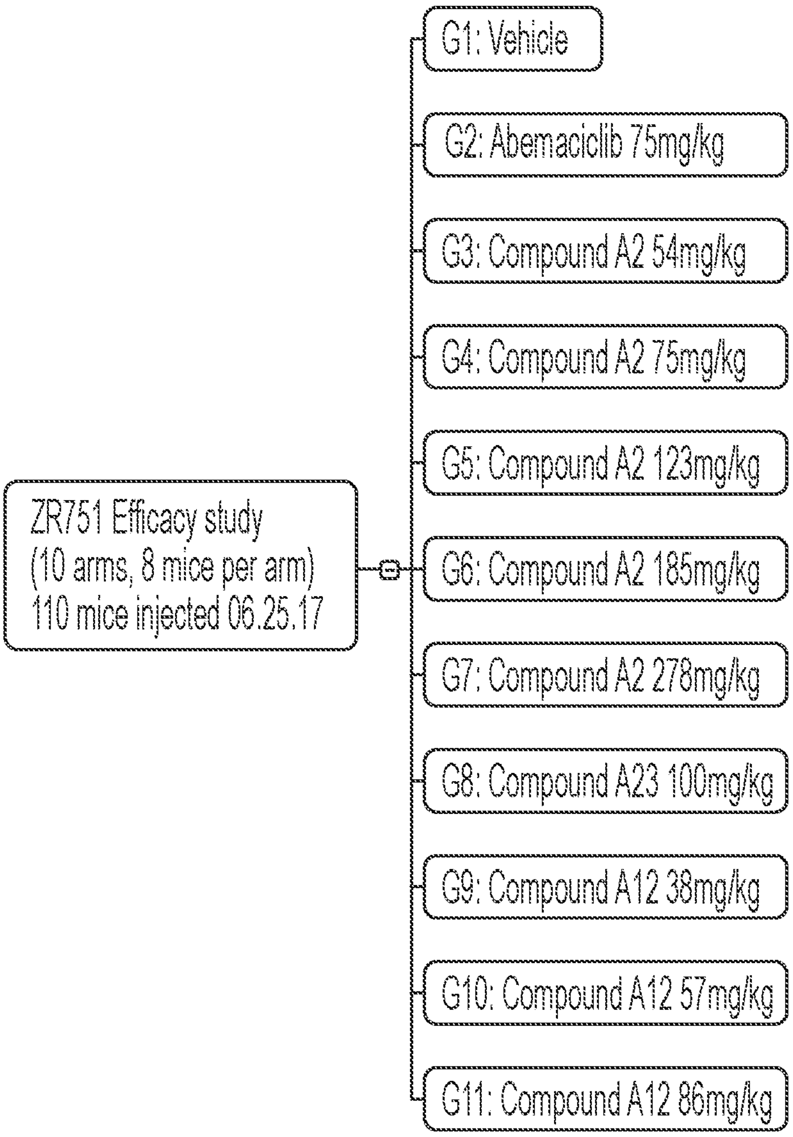
FIG. 14 shows an exemplary treatment plan for the $2^{nd}$ ER+ breast cancer cell line xenograft study. The ZR751 cell line was used for this study.
Figure 15:
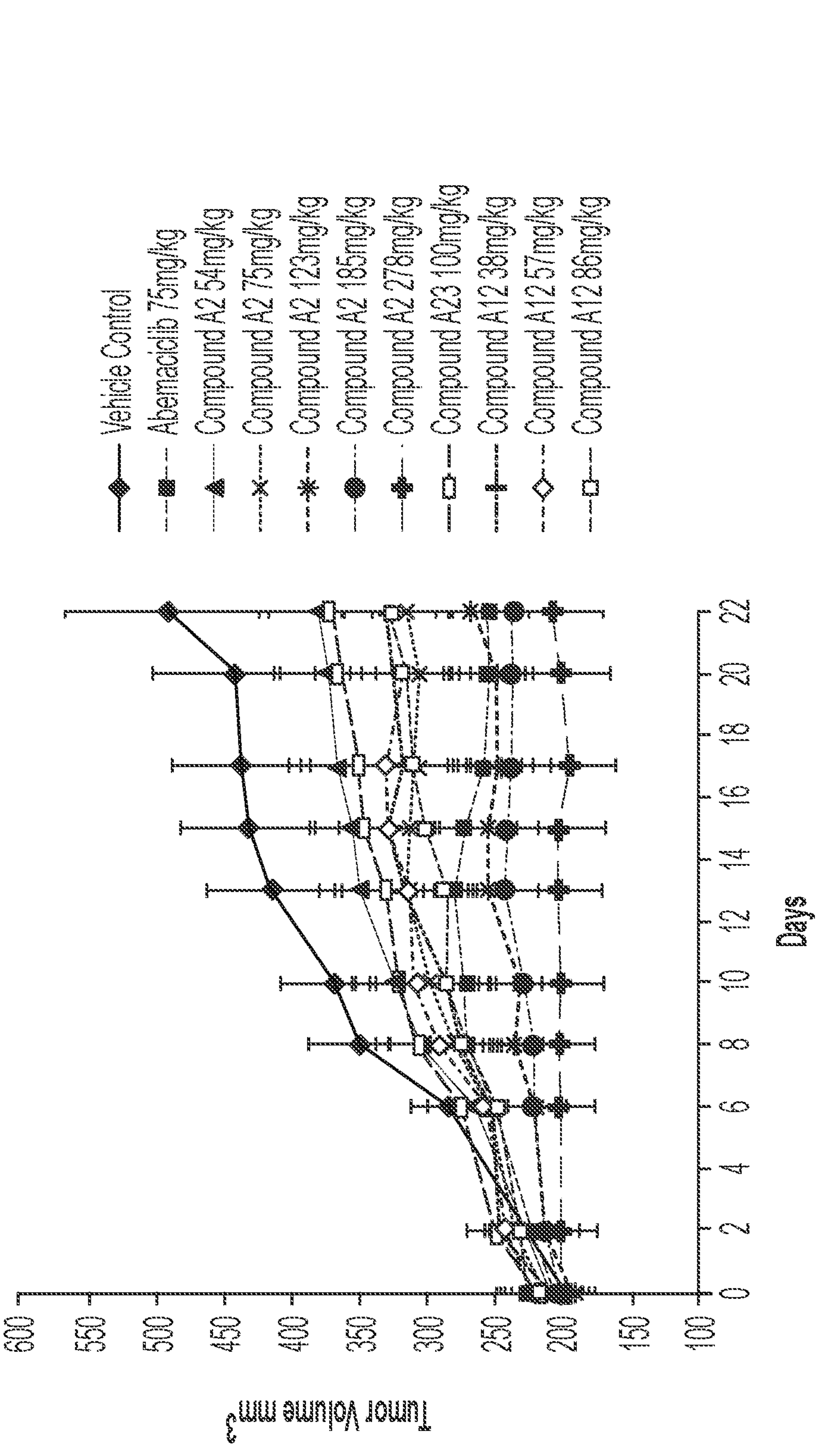
FIGS. 15 and 16 show the results of the second xenograft efficacy study at day 22.
Figure 16:
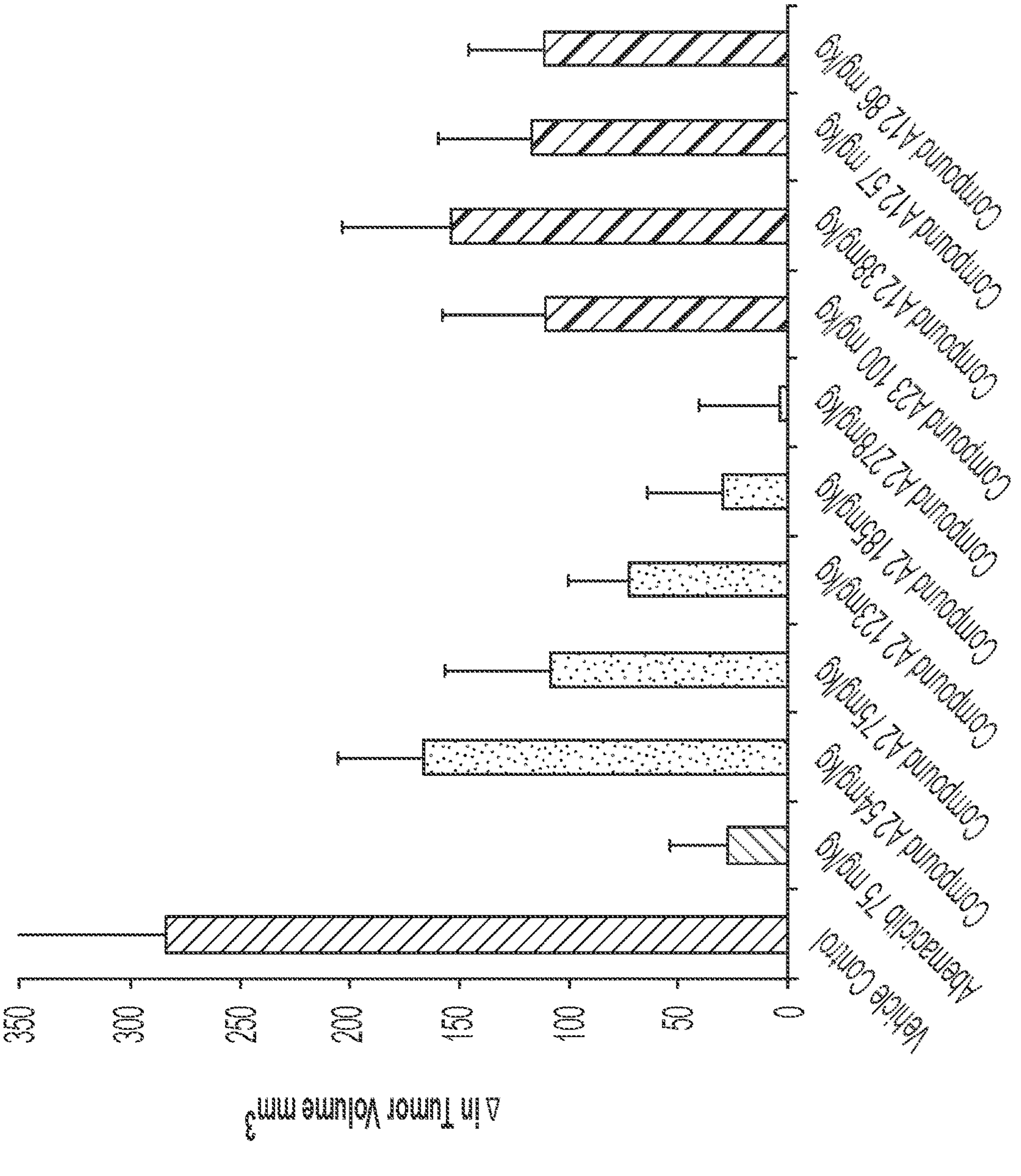
Figure 17:
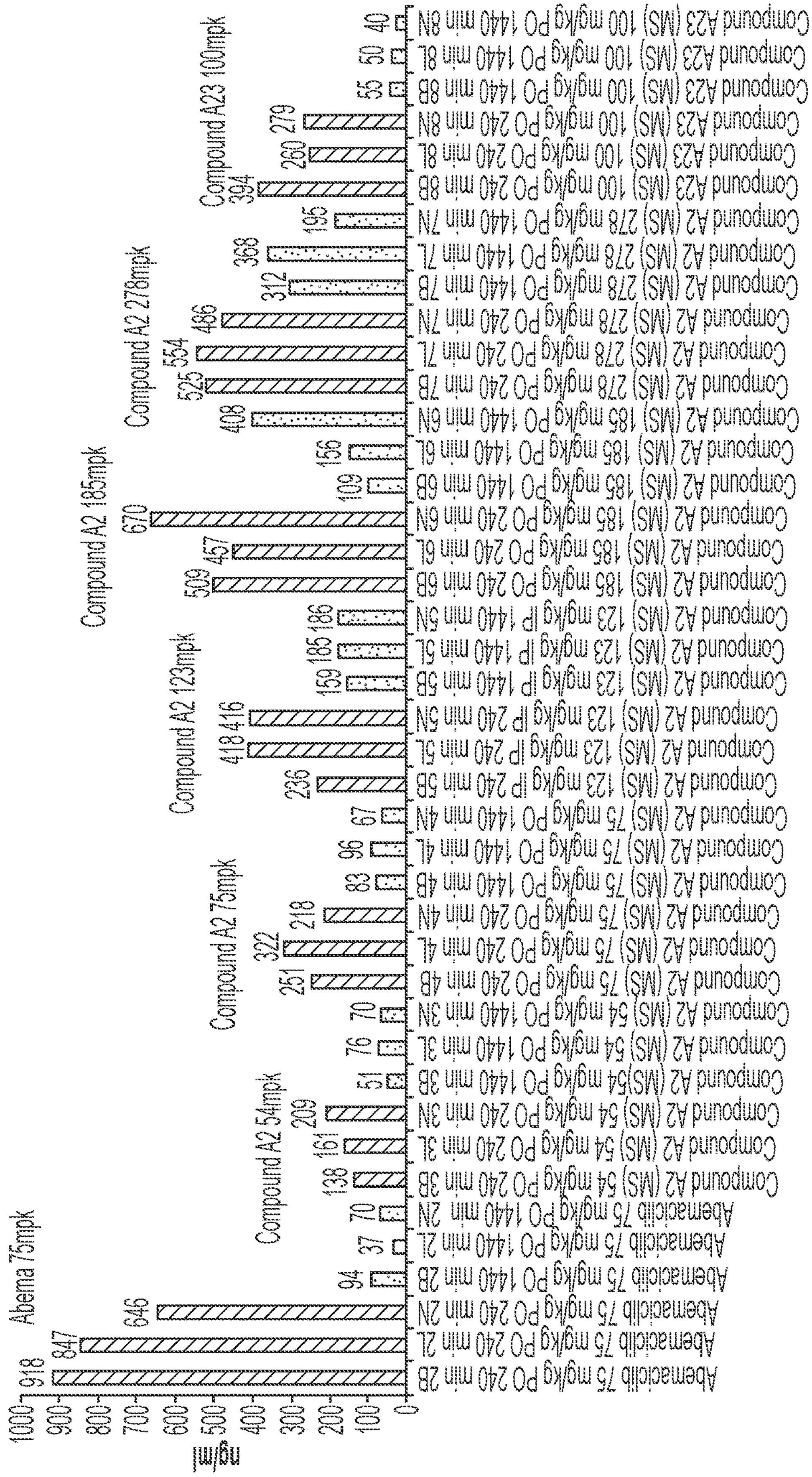
FIG. 17 shows the PK results from the second xenograft efficacy study, which were determined from plasma collected at 240 and 1,440 mins post dose on day 10 of the study.
Figure 18A:
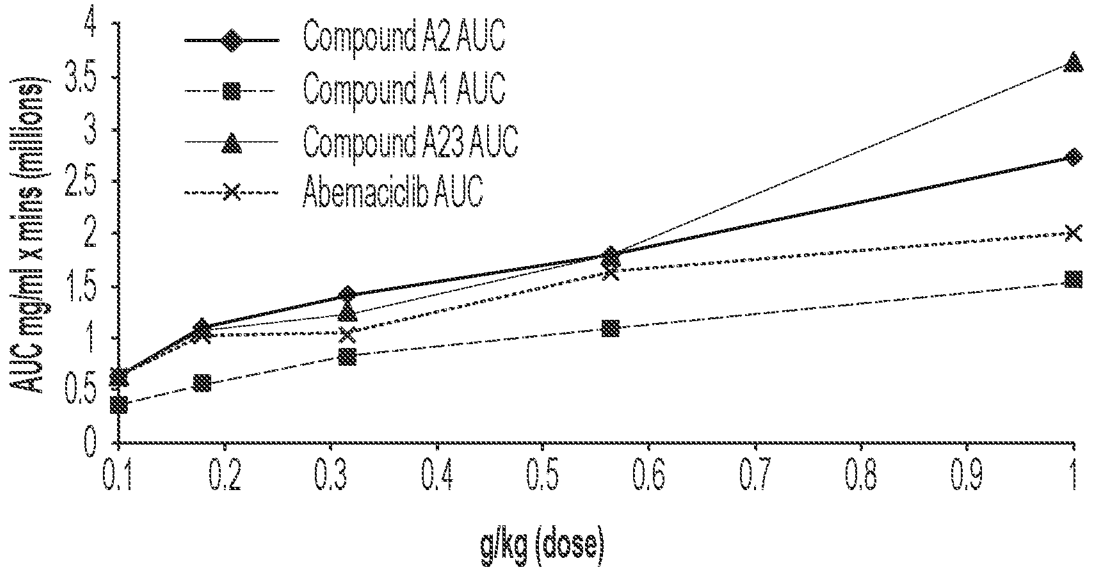
FIG. 18A shows comparative AUC measurements for Compounds A2, A1, A23, and abemaciclib from doses of 100 to 1000 mg/kg.
Figure 18B:
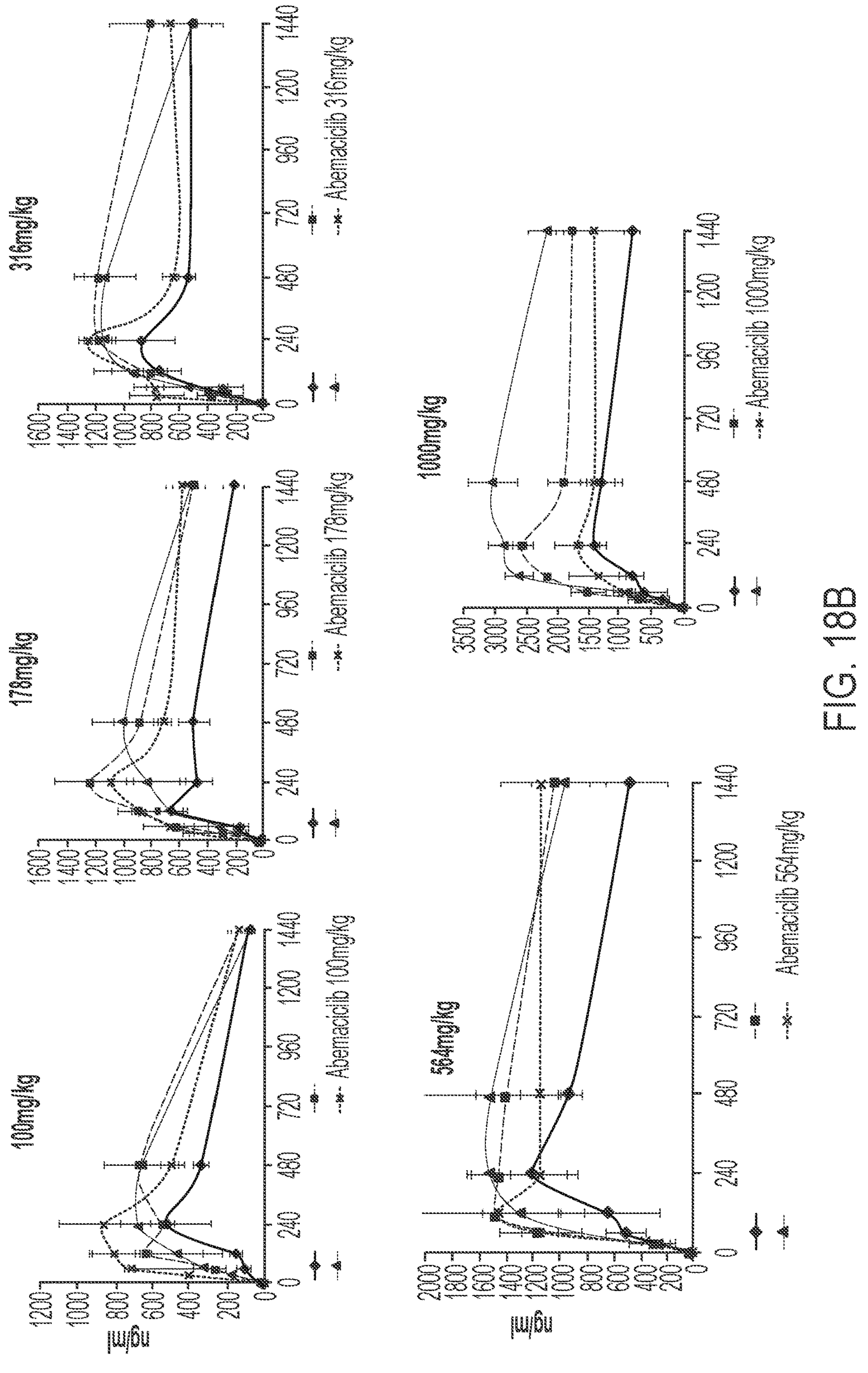
FIG. 18B shows comparative PK curves for Compounds A2, A1, A23, and abemaciclib from doses of 100 to 1000 mg/kg.
Figure 19:
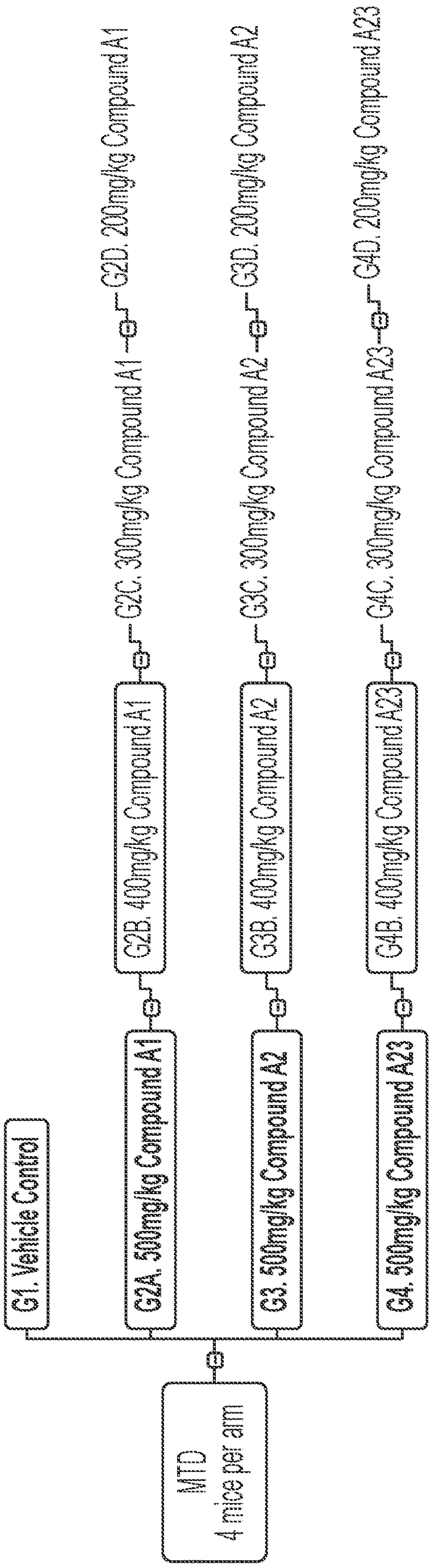
FIG. 19 shows an exemplary design of a 14-day dose de-escalation study.
Figure 20:
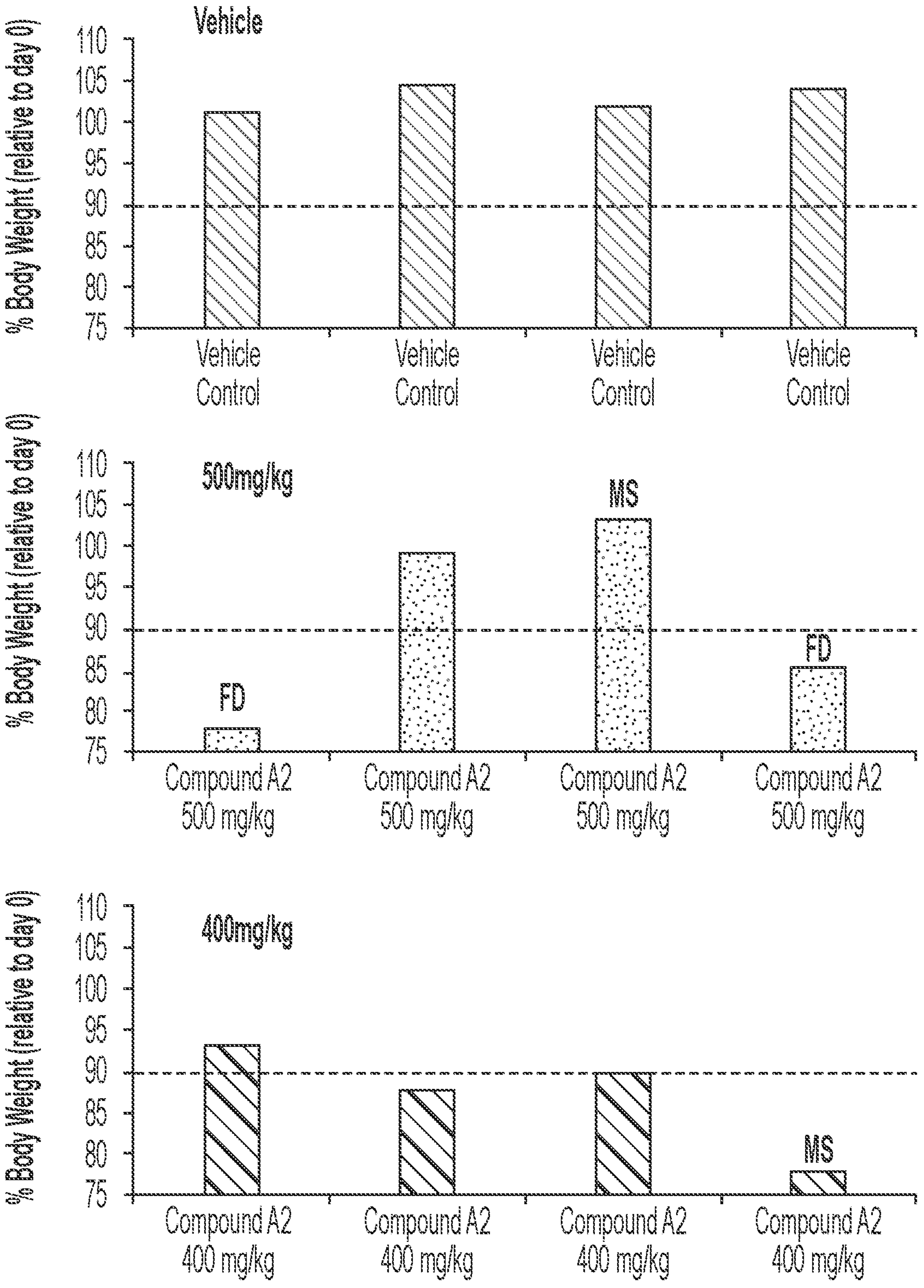
FIGS. 20 and 21 show results of a 14-day dose de-escalation study for Compound A2. The maximum tolerated dose for Compound A2 was between about 278 and about 399 mg/kg QD.
Figure 21:
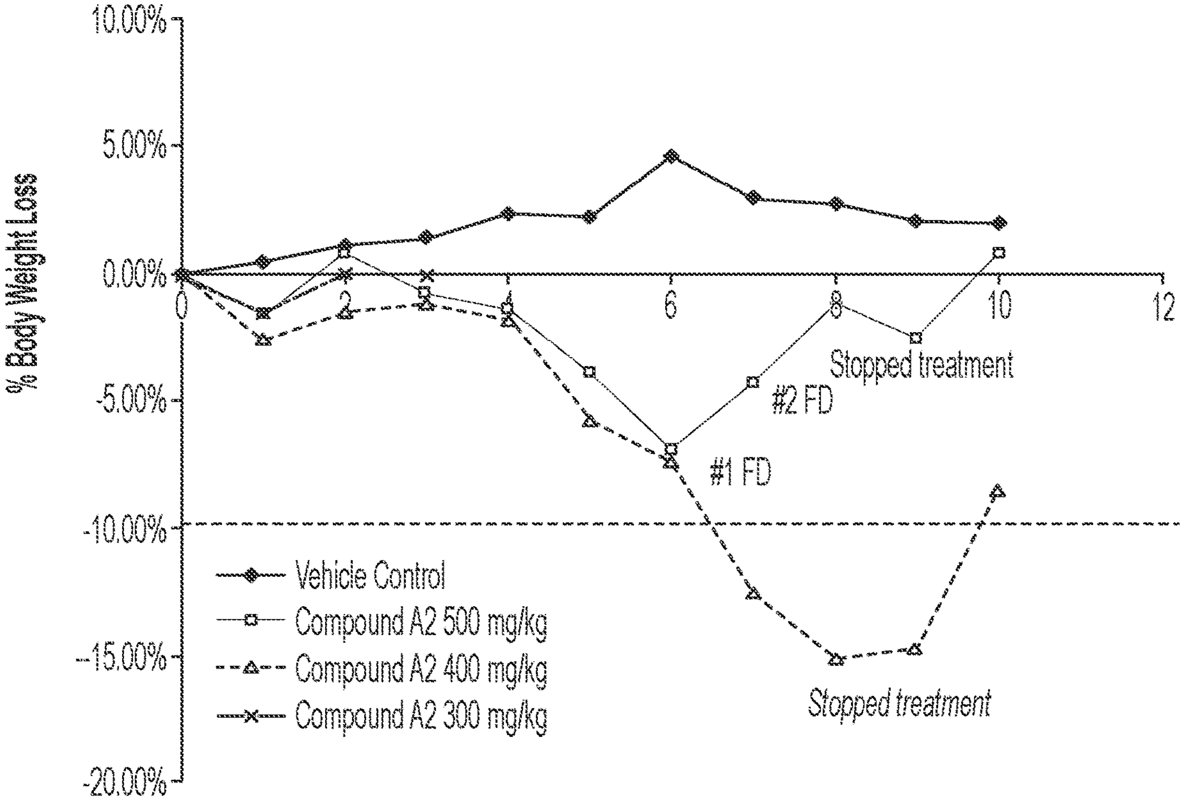
Figure 22:
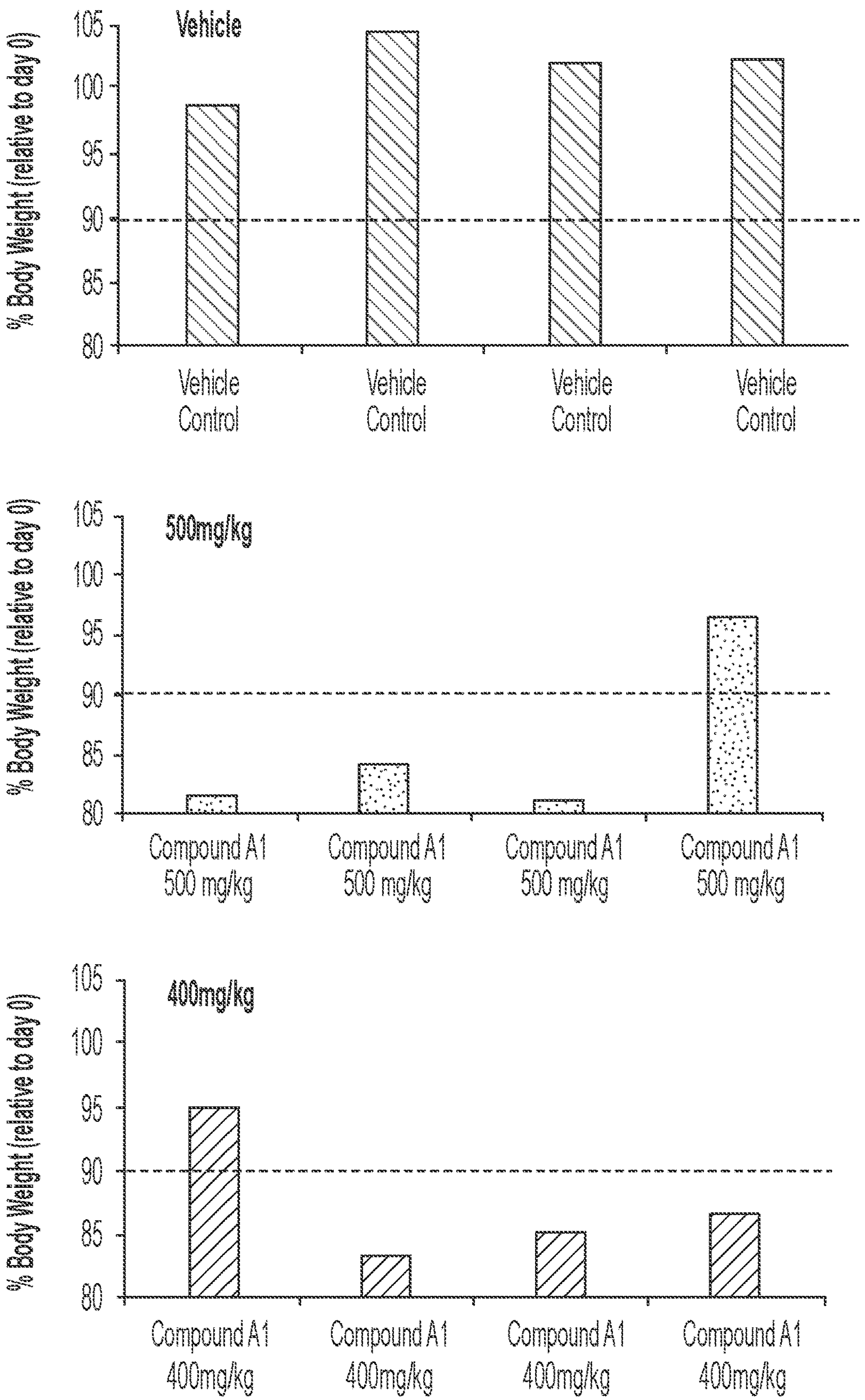
FIGS. 22 and 23 show results of a 14-day dose de-escalation study for Compound A1. The maximum tolerated dose for Compound A1 was less than about 400 mg/kg QD.
Figure 23:
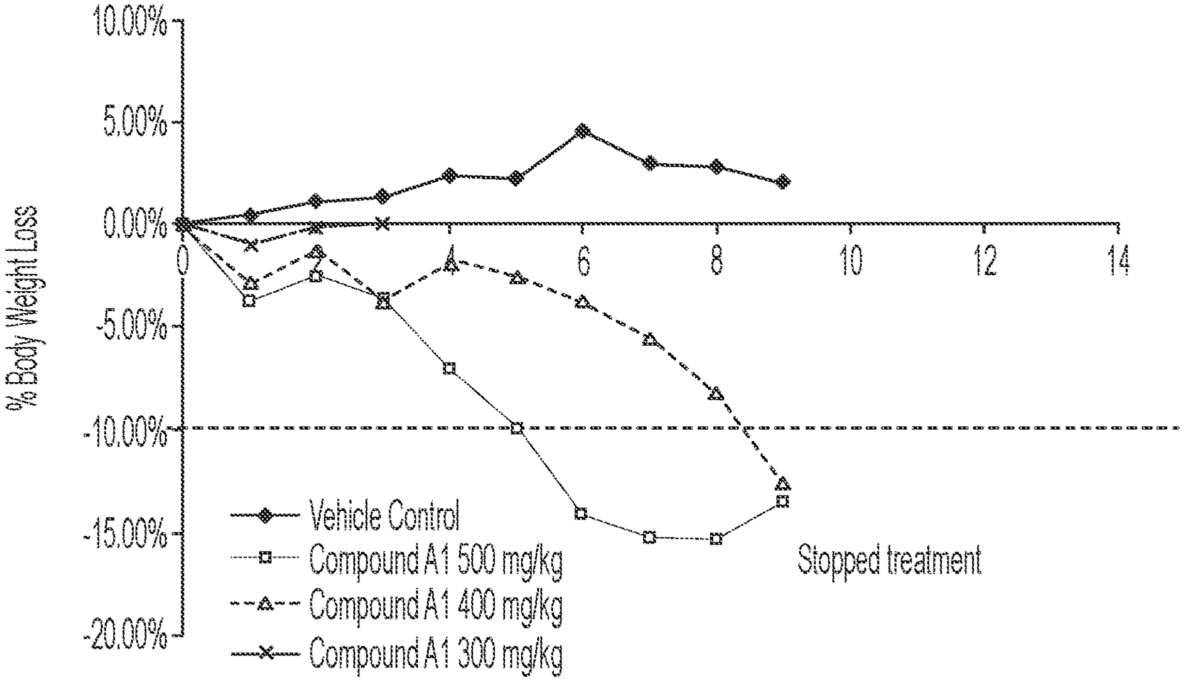
Figure 24:
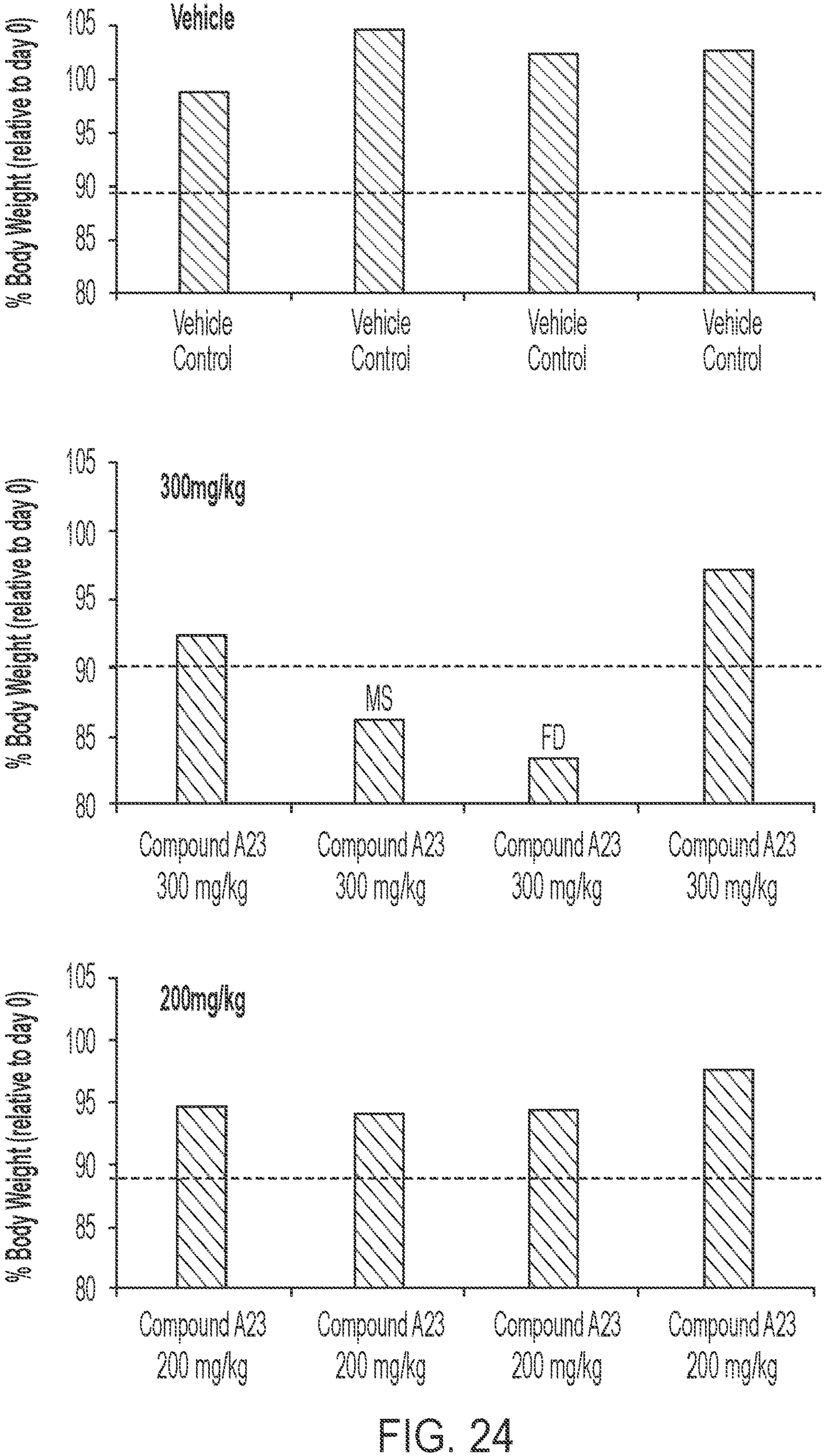
FIGS. 24 and 25 show results of a 14-day dose de-escalation study for Compound A23. The maximum tolerated dose for Compound A23 was about 200 mg/kg QD.
Figure 25:
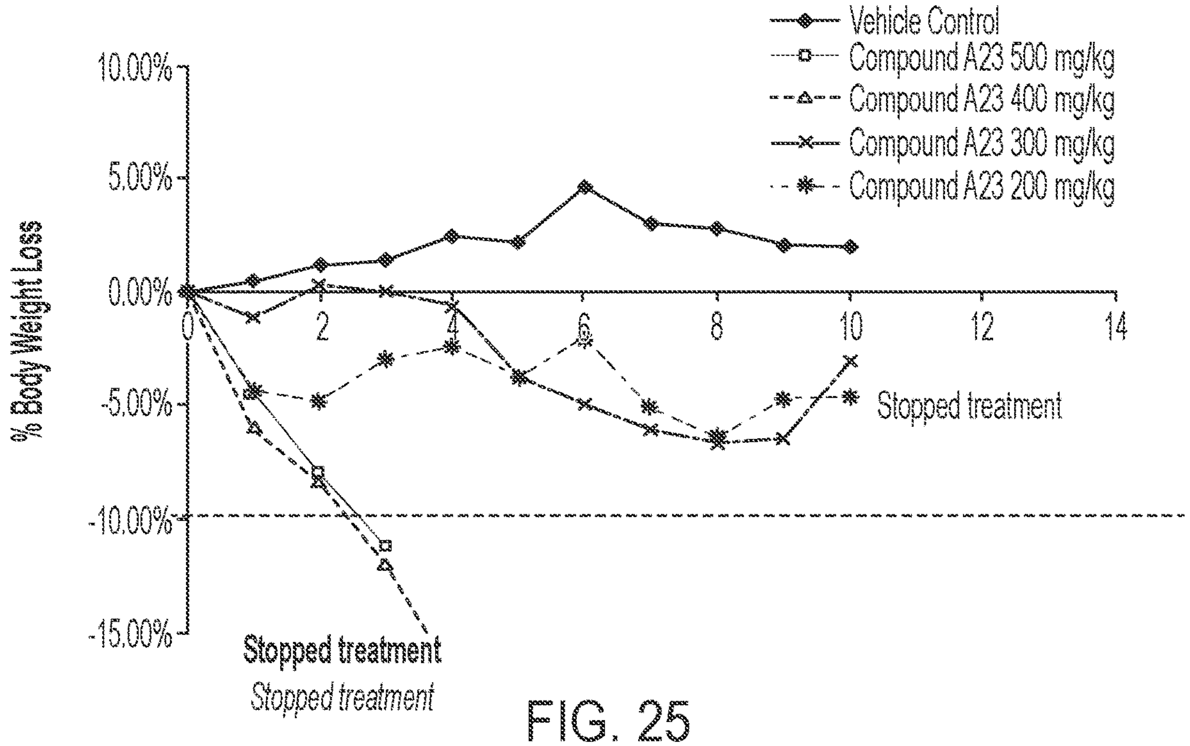
Figure 26:
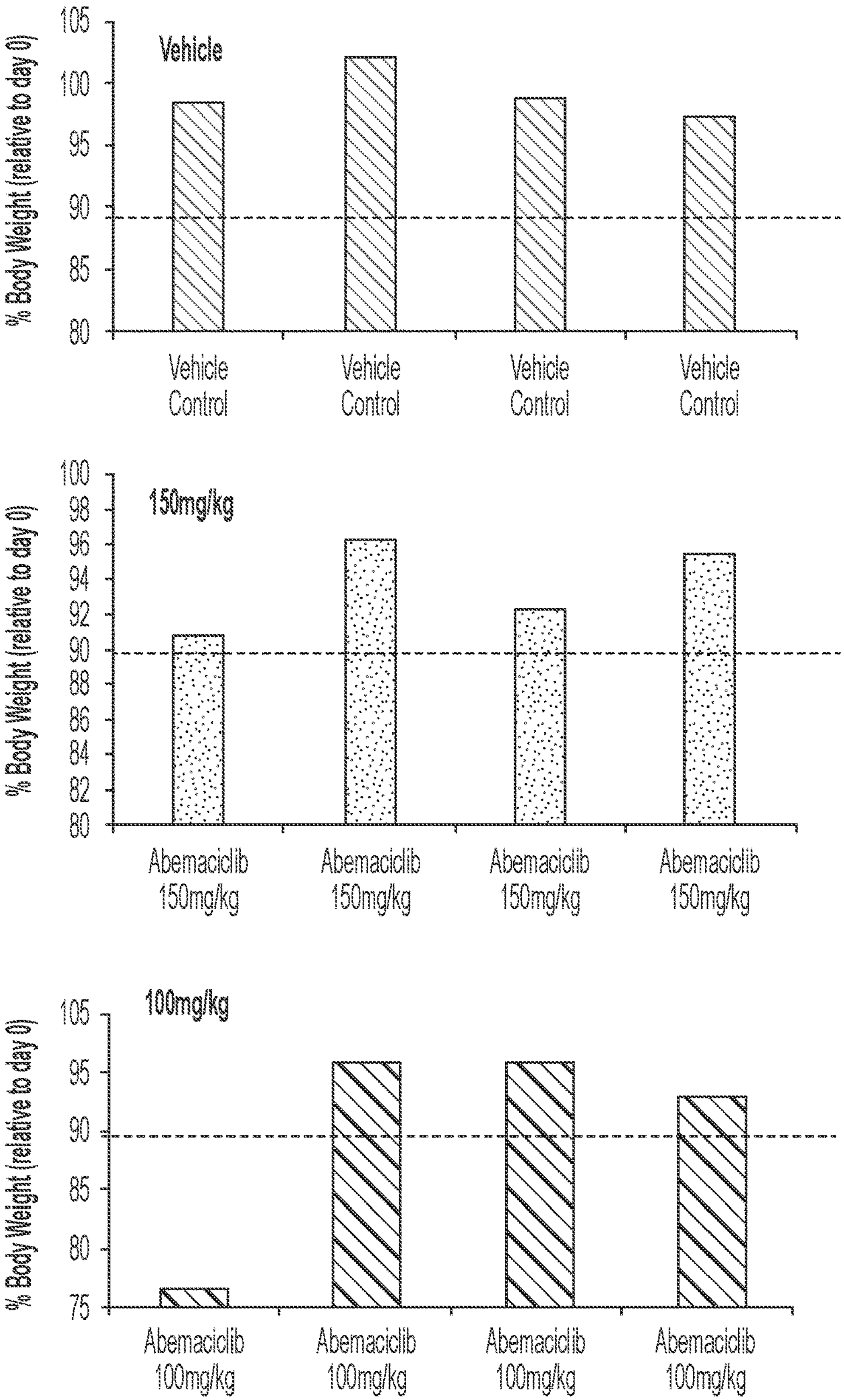
FIGS. 26 and 27 show results of a 14-day dose de-escalation study for abemaciclib. The maximum tolerated dose for abemaciclib was between about 100 and about 150 mg/kg QD.
Figure 27:
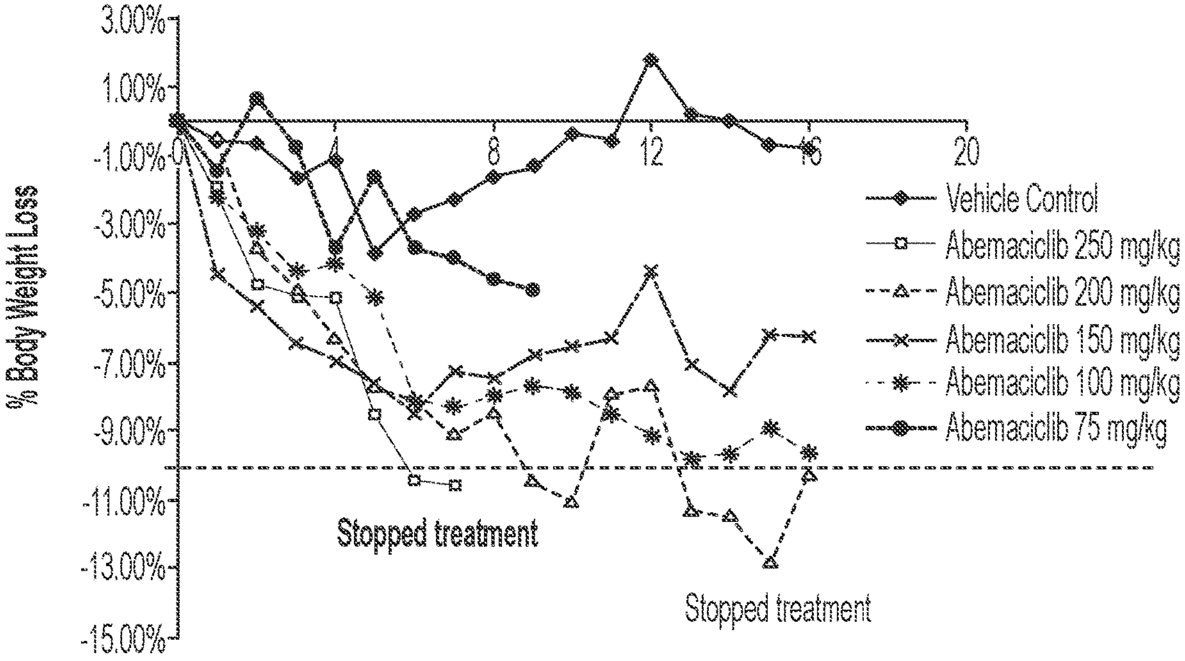
Figure 28:
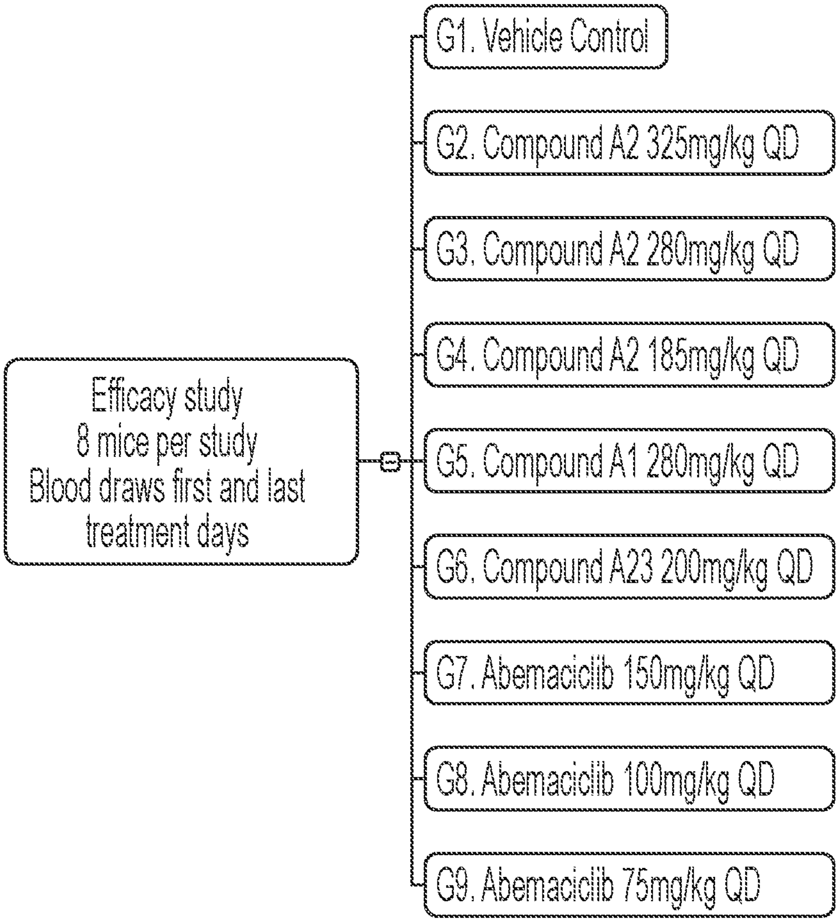
FIG. 28 shows an exemplary treatment plan for a xenograft study involving 8 mice per experimental group. Blood draws were taken on the first and last treatment days.
Figure 29:
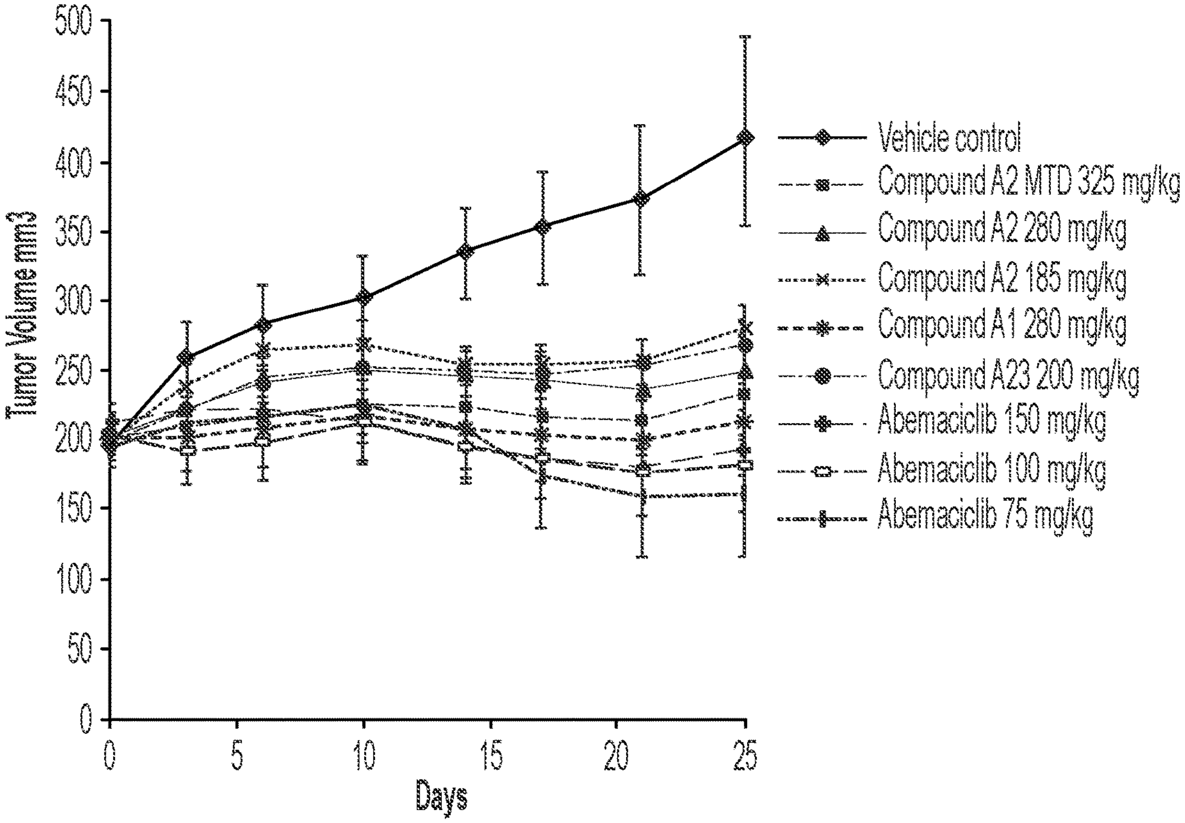
FIGS. 29 and 30 show the xenograft efficacy data over the 26-day study and on the final day (day 26), respectively.
Figure 30:
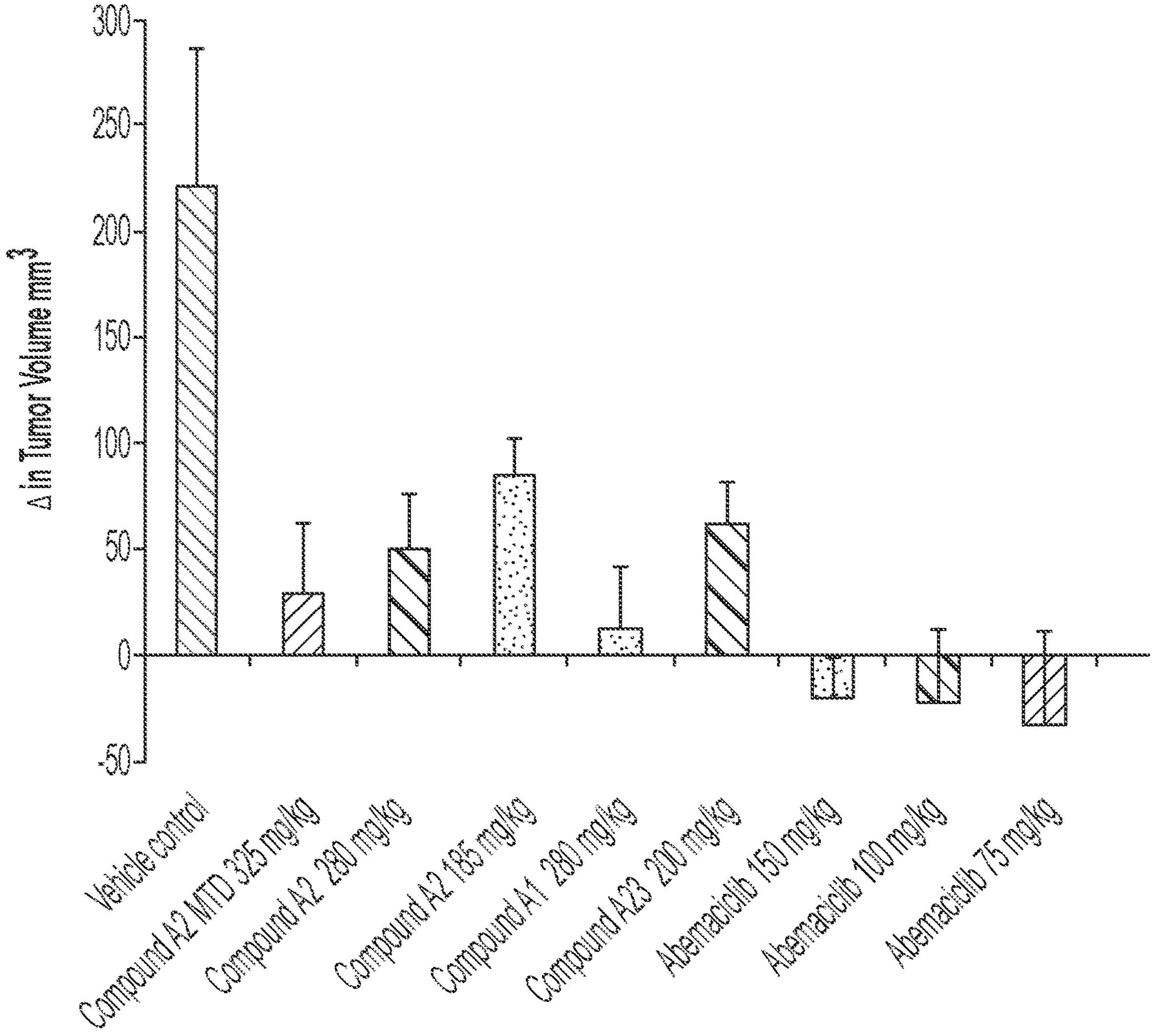
Figure 31:
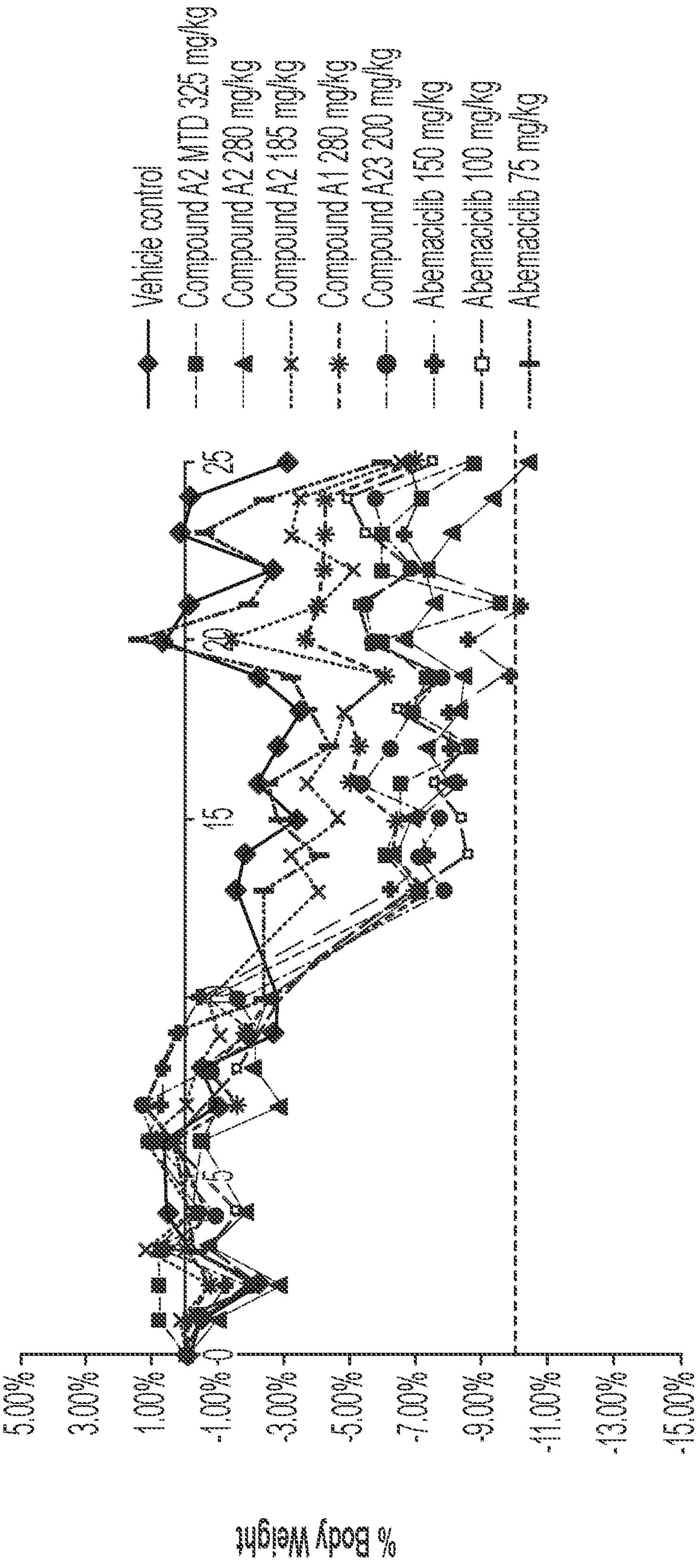
FIG. 31 is a graphical representation of the animal body weight data over the 26 days of the xenograft study.
Figure 32:
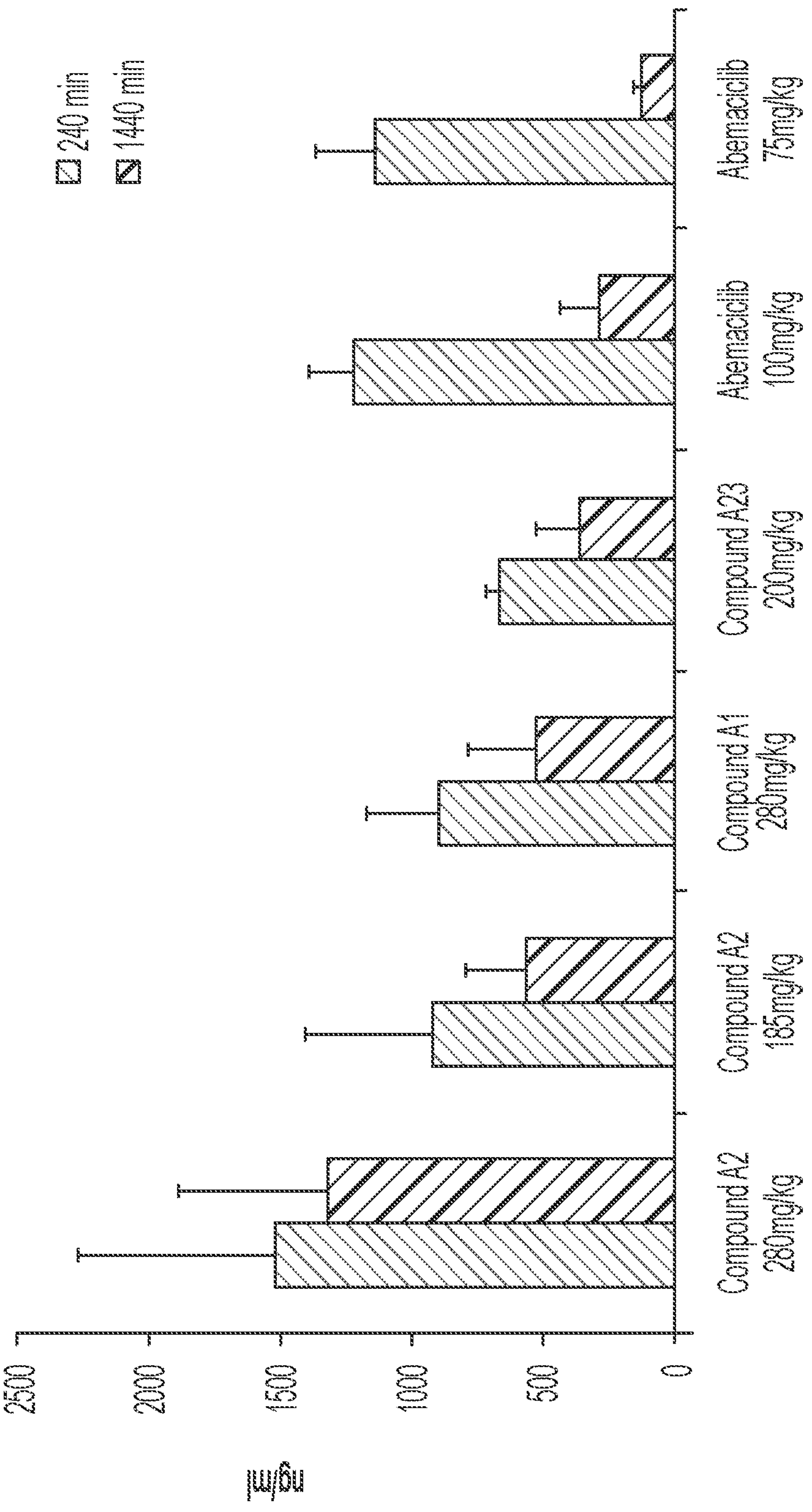
FIG. 32 shows the PK data for Compounds A1, A2, A23, and abemaciclib in blood draw on day 25 of the xenograft study.
Figure 33:
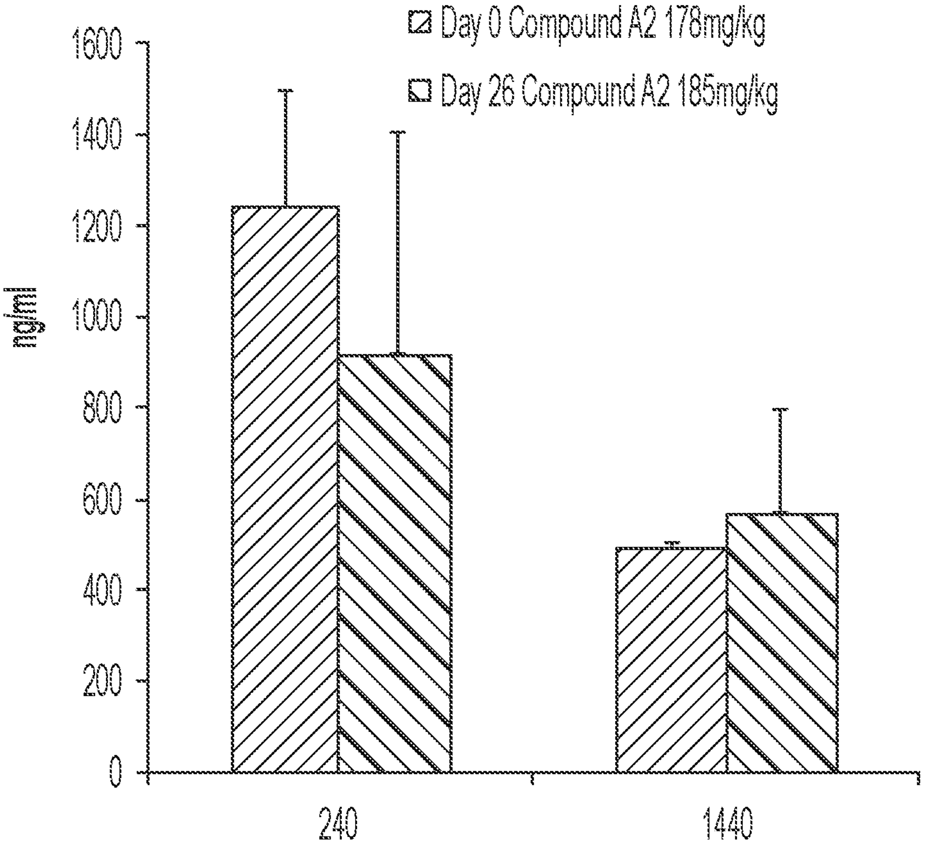
FIG. 33 shows accumulation of compounds of the invention versus abemaciclib over a 26-day xenograft study.

Abemaciclib (trade name Verzenio™):

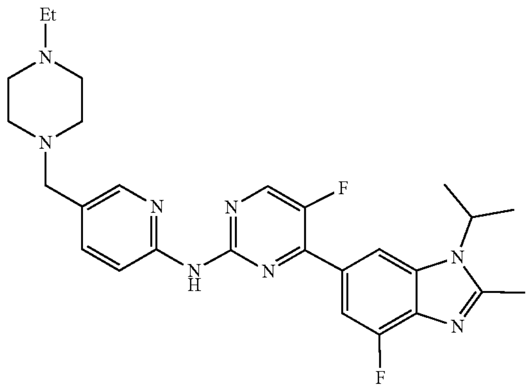 [SMILES: CCN1CCN(Cc2ccc(Nc3ncc(F)c(-c4cc(F)c5nc(C)n(C(C)C)c5c4)n3)nc2)CC1]

inhibits the enzymes cyclin-dependent kinase 4 (CDK4) and cyclin-dependent kinase 6 (CDK6). These enzymes are responsible for phosphorylating and thus activating the retinoblastoma protein, which plays a role in cell cycle progression from the G1 (first gap) to the S (synthesis) phase. Blocking this pathway prevents cells from progressing to the S phase, thereby inducing apoptosis (cell death). The compounds disclosed herein share certain structural features of abemaciclib, and also may act as CDK inhibitors selective for CDK4 and/or CDK6.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g., "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed", W. H. Freeman & Co., New York (2000); Griffiths et al., "Introduction to Genetic Analysis, 7th ed", W. H. Freeman & Co., N.Y. (1999); and Gilbert et ah, "Developmental Biology, 6th ed", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, trifluoromethoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl," as used herein, refers to an aliphatic group containing at least one double bond and is intended to include both "unsubstituted alkenyls" and "substituted alkenyls" the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen (e.g., fluoro), a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_1$-$C_6$ alkyl, $C_3$-$C_6$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_x$-$C_y$," when used in conjunction with a chemical moiety, such as, acyl, acyloxy, alkyl, alkenyl, alkynyl, or alkoxy is meant to include groups that contain from x to y carbons in the chain. For example, the term "$C_x$-$C_y$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. Co alkyl indicates a hydrogen where the group is in a terminal position, a bond if internal. The terms "$C_2$-$C_y$ alkenyl" and "$C_2$-$C_y$ alkynyl" refer to substituted or unsubstituted unsaturated aliphatic groups analogous in length and possible substitution to the alkyls described above, but that contain at least one double or triple bond respectively.

The term "alkylamino," as used herein, refers to an amino group substituted with at least one alkyl group.

The term "alkylthio," as used herein, refers to a thiol group substituted with an alkyl group and may be represented by the general formula alkylS—.

The term "alkynyl," as used herein, refers to an aliphatic group containing at least one triple bond and is intended to include both "unsubstituted alkynyls" and "substituted alkynyls," the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide," as used herein, refers to a group

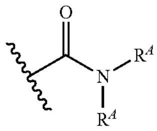

wherein each $R^A$ independently represent a hydrogen or hydrocarbyl group, or two $R^A$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

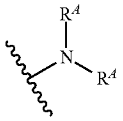

or

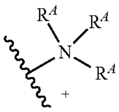

wherein each $R^A$ independently represents a hydrogen or a hydrocarbyl group, or two $R^A$ are taken together with the N atom to which they are attached complete a heterocycle having from 4 to 8 atoms in the ring structure.

The term "aminoalkyl," as used herein, refers to an alkyl group substituted with an amino group.

The term "aryl" as used herein include substituted or unsubstituted single-ring aromatic groups in which each atom of the ring is carbon. Preferably the ring is a 6- or 10-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

A "cycloalkyl" group is a cyclic hydrocarbon which is completely saturated. "Cycloalkyl" includes monocyclic and bicyclic rings. Typically, a monocyclic cycloalkyl group has from 3- to about 10-carbon atoms, more typically 3- to 8-carbon atoms unless otherwise defined. The second ring of a bicyclic cycloalkyl may be selected from saturated, unsaturated and aromatic rings. Cycloalkyl includes bicyclic molecules in which one, two, or three or more atoms are shared between the two rings (e.g., fused bicyclic compounds, bridged bicyclic compounds, and spirocyclic compounds).

The term "fused bicyclic compound" refers to a bicyclic molecule in which two rings share two adjacent atoms. In other words, the rings share one covalent bond, i.e., the so-called bridgehead atoms are directly connected (e.g., α-thujene and decalin). For example in a fused cycloalkyl each of the rings shares two adjacent atoms with the other ring, and the second ring of a fused bicyclic cycloalkyl may be selected from saturated, unsaturated and aromatic rings. A "cycloalkenyl" group is a cyclic hydrocarbon containing one or more double bonds.

The term "bridged bicyclic compound" refers to a bicyclic molecule in which the two rings share three or more atoms, separating the two bridgehead atoms by a bridge containing at least one atom. For example, norbomane, also known as bicyclo[2.2.1]heptane, can be thought of as a pair of cyclopentane rings each sharing three of their five carbon atoms.

The term "spirocyclic compound" refers to a bicyclic molecule in which the two rings have only one single atom, the spiro atom, in common.

The terms "halo" and "halogen" as used herein means halogen and includes chloro, fluoro, bromo, and iodo.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, pyrrolidine, piperidine, piperazine, pyrrolidine, tetrahydropyran, tetrahydrofuran, morpholine, lactones, lactams, and the like.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_1$-$C_6$ alkyl, $C_3$-$C_6$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry,* 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt that is suitable for or compatible with the treatment of patients.

The term "pharmaceutically acceptable acid addition salt" as used herein means any non-toxic organic or inorganic salt of any base compounds disclosed herein. Illustrative inorganic acids that form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds disclosed herein are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of the invention for laboratory use, or for subsequent conversion to a pharmaceutically acceptable acid addition salt.

The term "pharmaceutically acceptable basic addition salt" as used herein means any non-toxic organic or inorganic base addition salt of any acid compounds of the invention, or any of their intermediates. Illustrative inorganic bases that form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixtures and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of the invention). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of the invention, or a pharmaceutically acceptable salt thereof. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

As used herein "an inhibitor of CDK4/6" or "CDK4/6 inhibitor therapy" refers to a compound or composition that inhibits activity of CDK4/6, e.g., to phosphorylate a serine or threonine residue on proteins, or inhibits the interaction of CDK4/6 with other proteins that may be in the signal pathway.

As used herein "sensitive to cyclin dependent kinase 4/6 (CDK4/6) inhibitor" or "CDK4/6 i-sensitive cancer" refers to a cell or cancer that has reduced growth in the presence of a CDK4/6 inhibitor compared to in the absence of such an inhibitor. Sensitivity can refer to a cytotoxic or cytostatic effect of the CDK4/6 inhibitor on the cell. It is contemplated that a sensitive cell line can have a 1.5, 2, 3, 4, 5, 6, 7, 8, 9, 10, 15, 20, 25-fold or more change in growth rate in the presence of a CDK4/6 inhibitor. Sensitivity can also be measured by change in genome sequence or copy number of a gene, increase or reduction in particular protein expression or mRNA expression, or other measurement disclosed herein to be a measure of sensitivity.

The term "response to CDK4 and/or CDK6 inhibitors" relates to any response of the hyperproliferative disorder (e.g., cancer) to an agent that inhibits CDK4 or CDK6, preferably to a change in tumor mass and/or volume after initiation of chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months.

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

As used herein "resistant to a cyclin dependent kinase 4/6 (CDK4/6) inhibitor" or "CDK4/6 i-resistant cancer" refers to a cell or cancer that has normal (or baseline) growth in the presence of a CDK4/6 inhibitor and is substantially similar as in the absence of such an inhibitor. Resistance can be measured by a relative maintenance of cell growth rate in the presence of a CDK4/6 inhibitor, or by a change in genome sequence or copy number of a gene, increase or reduction in particular protein expression or mRNA expression, or other measurement disclosed herein to be a measure of resistance.

The term "sensitize" means to alter cancer cells or tumor cells in a way that allows for more effective treatment of the associated cancer with a cancer therapy (e.g., anti-immune checkpoint, chemotherapeutic, and/or radiation therapy). In some embodiments, normal cells are not affected to an extent that causes the normal cells to be unduly injured by the immune checkpoint therapy. An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), and cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in an animal by measuring the tumor size reduction over a period of time, for example, 6 months for a human and 4-6 weeks for a mouse. A composition or a method sensitizes response to a therapeutic treatment if the increase in treatment sensitivity or the reduction in resistance is 25% or more, for example, 30%, 540%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

Compounds of the Invention

The present disclosure provides compounds having the structure of Formula (I):

(I)

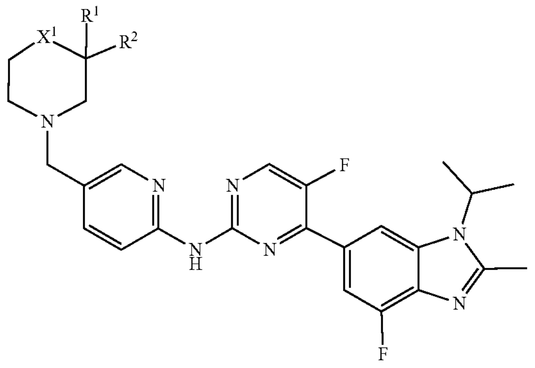

or a pharmaceutically acceptable salt thereof, wherein:

$X^1$ is O or $NR^{X1}$;

$R^{X1}$ is H or alkyl, preferably lower alkyl;

$R^1$ is alkyl, preferably lower alkyl; and $R^2$ is optionally substituted alkyl, optionally substituted haloalkyl, optionally substituted alkenyl, optionally substituted hydroxyalkyl, optionally substituted aminoalkyl, or optionally substituted amidoalkyl; or $R^1$ and $R^2$, together with the carbon atom through which they are joined, form an optionally substituted 5- or 6-membered heterocyclic ring.

In certain aspects, $R^2$ is optionally substituted alkyl, optionally substituted haloalkyl, optionally substituted alkenyl, optionally substituted hydroxyalkyl, or optionally substituted aminoalkyl. In certain aspects, provided herein are compounds having the structure of Formula (Ia):

(Ia)

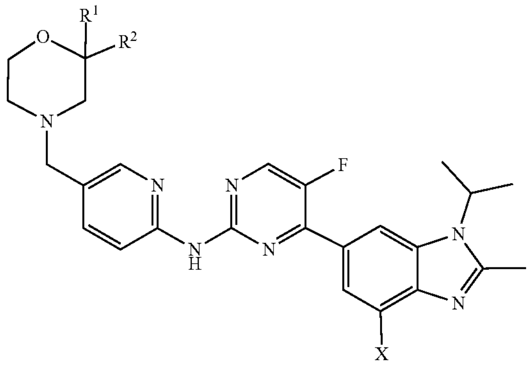

or a pharmaceutically acceptable salt thereof, wherein:

X is, independently for each occurrence, halo, preferably fluoro;

$R^1$ is alkyl, preferably lower alkyl; and $R^2$ is optionally substituted alkyl, optionally substituted haloalkyl, optionally substituted alkenyl, optionally substituted hydroxyalkyl, optionally substituted aminoalkyl, or optionally substituted amidoalkyl; or $R^1$ and $R^2$, together with the carbon atom through which they are joined, form an optionally substituted 5- or 6-membered heterocyclic ring.

In certain aspects, $R^2$ is optionally substituted alkyl, optionally substituted haloalkyl, optionally substituted alkenyl, optionally substituted hydroxyalkyl, or optionally substituted aminoalkyl.

In certain aspects, provided herein are compounds having the structure of Formula (Ib):

(Ib)

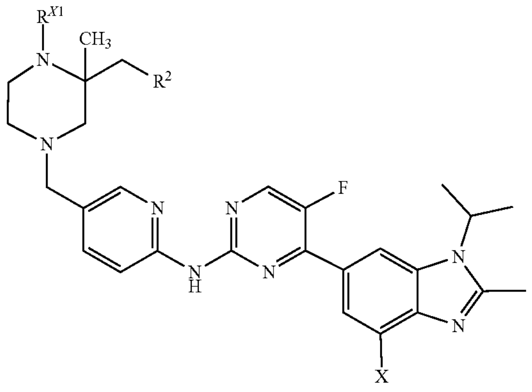

or a pharmaceutically acceptable salt thereof, wherein:

X is, independently for each occurrence, halo, preferably fluoro;

$R^{X1}$ is H or alkyl, preferably lower alkyl; and $R^2$ is optionally substituted alkyl, optionally substituted haloalkyl, optionally substituted alkenyl, optionally substituted hydroxyalkyl, optionally substituted aminoalkyl, or optionally substituted amidoalkyl.

In certain aspects, $R^2$ is optionally substituted alkyl, optionally substituted haloalkyl, optionally substituted alkenyl, optionally substituted hydroxyalkyl, or optionally substituted aminoalkyl.

In some embodiments, the compounds of Formula (I) have the structure of Formula (II):

(II)

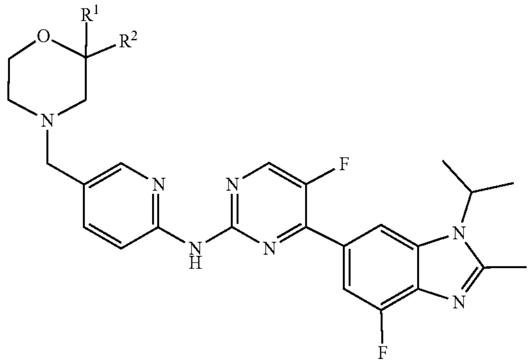

or a pharmaceutically acceptable salt thereof.

In some such embodiments, the compounds of Formula (II) have the structure of Formula (IIa):

(IIa)

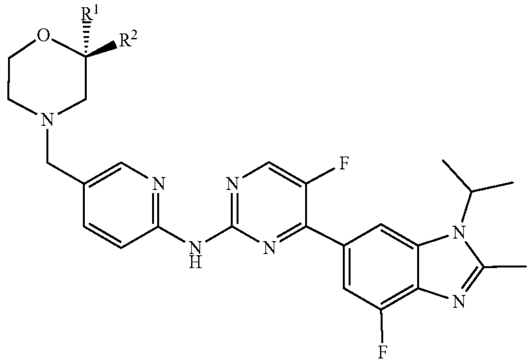

or a pharmaceutically acceptable salt thereof. Alternatively, the compounds of Formula (II) have the structure of Formula (IIb):

(IIb)

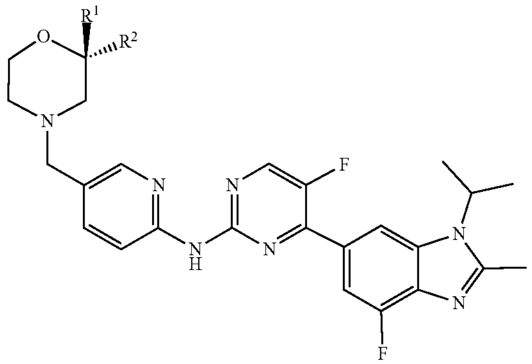

or a pharmaceutically acceptable salt thereof.

In some embodiments, the compounds of Formula (I) have the structure of Formula (III):

(III)

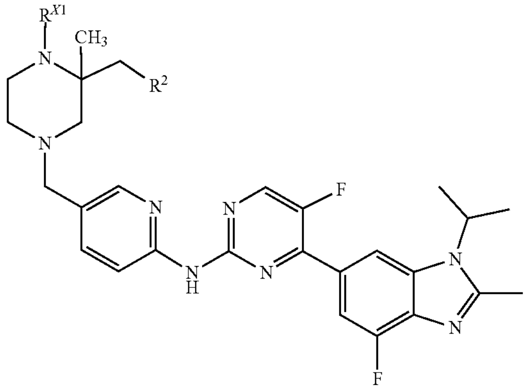

or a pharmaceutically acceptable salt thereof.

In some such embodiments, the compounds of Formula (III) have the structure of Formula (IIIa):

(IIIa)

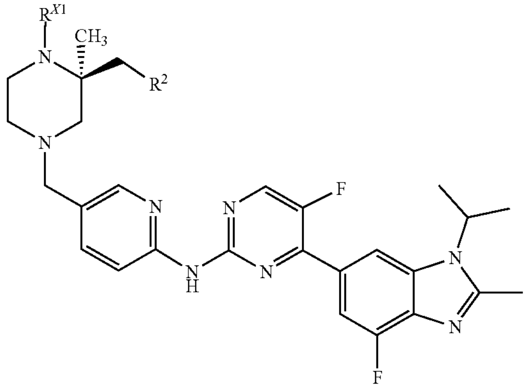

or a pharmaceutically acceptable salt thereof. Alternatively, the compounds of Formula (III) have the structure of Formula (IIIb):

(IIIb)

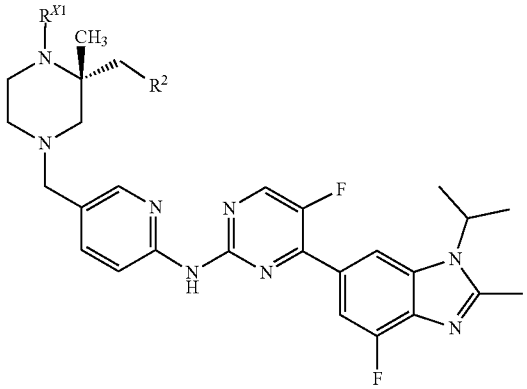

or a pharmaceutically acceptable salt thereof.

In certain embodiments of the compounds of Formulas (I), (Ia), (Ib), (III), (IIIa), and (IIIb), $R^{X1}$ is H or methyl. In preferred embodiments, wherein $R^{X1}$ is H.

In some embodiments of the disclosed compounds, $R^1$ is $C_1$-$C_4$-alkyl. In some such embodiments, $R^1$ is methyl or ethyl. In certain embodiments, $R^1$ is methyl.

In some embodiments of the disclosed compounds, $R^2$ is optionally substituted $C_1$-$C_4$-alkyl or $(CH_2)_nR^{2a}$, wherein $R^{2a}$ is optionally substituted $C_1$-$C_4$-alkyl, optionally substituted $C_1$-$C_4$-haloalkyl, optionally substituted $C_2$-$C_4$-alkenyl, or optionally substituted $C_1$-$C_4$-hydroxyalkyl, optionally substituted $C_1$-$C_4$-alkoxy-$C_1$-$C_4$-alkyl, optionally substituted $C_1$-$C_4$-alkylamino-$C_1$-$C_4$-alkyl, or optionally substituted $C_1$-$C_4$-alkylamino-$C_1$-$C_4$-haloalkyl; and n is an integer having a value of 1 or 2. In some such embodiments, $R^2$ is substituted $C_1$-$C_4$-alkyl. In other embodiments, $R^2$ is methyl, ethyl, propylenyl, n-propyl, isopropyl, n-butyl, sec-butyl, tert-butyl, $(CH_2)_2OH$, $—(CH_2CH(CH_3))OH$, $(CH_2)_2O(CH_2CH_3)$, $—(CH_2)_2OCH_2CH_3$, $—(CH_2)_2N(H)(CH_3)$, $—(CH_2)_2N(H)(C(CH_3)_3)$, $—(CH_2)_2N(H)(C(O)CH_3)$, $—(CH_2)_2N(H)(CH_2CH_2F)$, $—(CH_2)_2N(CH_3)(CH_2CH_2F)$, $—(CH_2)_2N(CH_3)_2$, $—(CH_2)_2N(CH_2CH_3)_2$, $—(CH_2)_2N(CH_2CH_3)_2$, $—(CH_2CH(CH_3))N(CH_3)_2$, $—CH_2C(O)—NHCH_3$, $—CH_2C(O)—N(CH_3)_2$, $—CH_2C(O)—N(CH_2CH_3)_2$, or $—CH_2C(O)$-heterocyclyl, such as $—CH_2C(O)—N$-linked heterocyclyl. In other embodiments, $R^2$ is methyl, ethyl, propylenyl, n-propyl, isopropyl, n-butyl, sec-butyl, tert-butyl, $(CH_2)_2OH$, $—(CH_2CH(CH_3))OH$, $(CH_2)_2O(CH_2CH_3)$, $—(CH_2)_2OCH_2CH_3$, $—(CH_2)_2N(H)(CH_3)$, $—(CH_2)_2N(H)(C(CH_3)_3)$, $—(CH_2)_2N(H)(C(O)CH_3)$, $—(CH_2)_2N(H)(CH_2CH_2F)$, $—(CH_2)_2N(CH_3)(CH_2CH_2F)$, $—(CH_2)_2N(CH_3)_2$, $—(CH_2)_2N(CH_2CH_3)_2$, $—(CH_2)_2N(CH_2CH_3)_2$, or $—(CH_2CH(CH_3))N(CH_3)_2$.

In other embodiments of the disclosed compounds, $R^2$ is $(CH_2)_nC(O)NR^{2a}R^{2b}$, wherein $R^{2a}$ and $R^{2b}$ are each independently H, alkyl, haloalkyl, alkenyl, $(CR^cR^d)_mOR^c$, or —C(O)alkyl; $R^c$, $R^d$, and $R^e$ are each independently H or alkyl, preferably lower alkyl; n is an integer having a value of 1 or 2; and m is an integer having a value of 2 to 5.

In other embodiments of the disclosed compounds, $R^2$ is $(CH_2)_nNR^{2a}R^{2b}$, wherein $R^{2a}$ and $R^{2b}$ are each independently H, alkyl, haloalkyl, alkenyl, $(CR^cR^d)_mOR^e$, or —C(O)alkyl; $R^c$, $R^d$, and $R^e$ are each independently H or alkyl, preferably lower alkyl; n is an integer having a value of 1 or 2; and m is an integer having a value of 2 to 5.

In yet other embodiments of the disclosed compounds, $R^2$ is $(CH_2)_nC(O)NR^{2a}R^{2b}$, wherein $R^{2a}$ and $R^{2b}$, together with the nitrogen atom through which they are joined, form an optionally substituted 3- to 6-membered heterocyclic ring; and n is an integer having a value of 1 or 2. In some such embodiments, $R^{2a}$ and $R^{2b}$, together with the nitrogen atom through which they are joined, form an optionally substituted heterocyclic ring selected from:

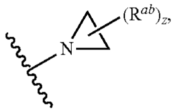, 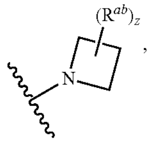,

-continued

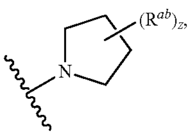, and 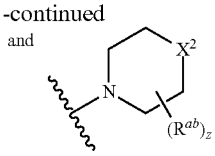

wherein:

each $R^{ab}$ is independently halo, hydroxyl, alkyl, haloalkyl, or alkoxy;

$X^2$ is O, $NR^{x1}$ or $CR^{x2}R^{x3}$;

$R^{x1}$, $R^{x2}$, and $R^{x3}$ are each independently H, halo, alkyl, preferably lower alkyl, or alkoxy; and z is an integer having a value of 0 to 2.

In yet other embodiments of the disclosed compounds, $R^2$ is $(CH_2)_nNR^{2a}R^{2b}$, wherein $R^{2a}$ and $R^{2b}$, together with the nitrogen atom through which they are joined, form an optionally substituted 3- to 6-membered heterocyclic ring; and n is an integer having a value of 1 or 2. In some such embodiments, $R^{2a}$ and $R^{2b}$, together with the nitrogen atom through which they are joined, form an optionally substituted heterocyclic ring selected from:

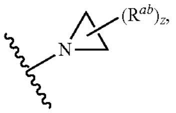, 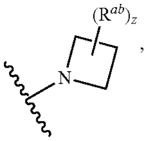,

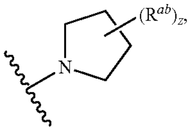, and 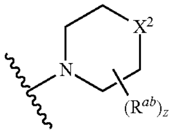

wherein:

each $R^{ab}$ is independently halo, hydroxyl, alkyl, haloalkyl, or alkoxy;

$X^2$ is O, $NR^{x1}$ or $CR^{x2}R^{x3}$;

$R^{x1}$, $R^{x2}$, and $R^{x3}$ are each independently H, halo, alkyl, preferably lower alkyl, or alkoxy; and z is an integer having a value of 0 to 2.

For example, the optionally substituted heterocyclic ring may be selected from:

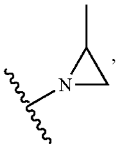, 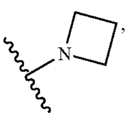, 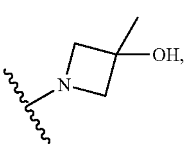,

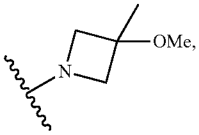, 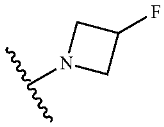,

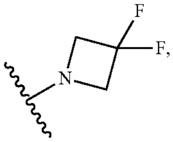, 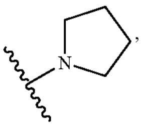,

-continued

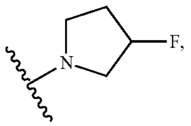, and 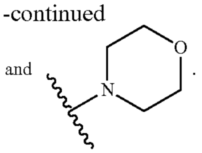.

In some embodiments of the disclosed compounds, $R^1$ and $R^2$, together with the carbon atom through which they are joined, form a heterocyclic ring having the structure:

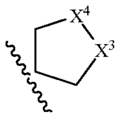

wherein:

$X^3$ is $NR^{Y1a}$ or $CR^{Y1b}R^{Y1c}$;

$X^4$ is O or $CR^{Y2a}R^{Y2b}$;

$R^{Y1a}$ is H, alkyl, —C(O)$R^{Y1aa}$; or —$S(O)_2$alkyl;

$R^{Y1aa}$ is alkyl or alkoxy; and $R^{Y1b}$, $R^{Y1c}$, $R^{Y2a}$, and $R^{Y2b}$ are each independently H or alkyl, preferably lower alkyl.

In some such embodiments, the heterocyclic ring is selected from:

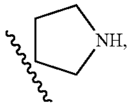, 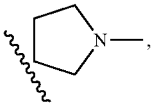, 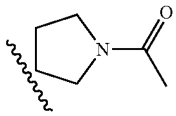,

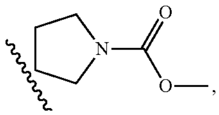, 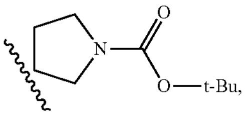,

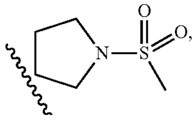, and 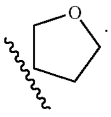.

In some embodiments of the disclosed compounds, $X^1$ is O or $NR^{X1}$;

$R^{X1}$ is H or alkyl, preferably lower alkyl;

$R^1$ is methyl; and $R^2$ is optionally substituted alkyl, optionally substituted hydroxyalkyl, or $(CR^{2c}{}_2)_nNR^{2a}R^{2b}$; or $R^1$ and $R^2$, together with the carbon atom through which they are joined, form a 5- or 6-membered heterocyclic ring having one N atom and the N atom is optionally substituted with lower alkyl;

$R^{2a}$ is H, methyl, or ethyl;

$R^{2b}$ is H, methyl, or ethyl;

each $R^{2c}$ is independently H or alkyl, preferably methyl; and n is an integer having a value of 1 to 4.

In some embodiments of the disclosed compounds, $X^1$ is O or $NR^{X1}$;

$R^{X1}$ is H, methyl or ethyl;

$R^1$ is methyl;

$R^2$ is $(CR^{2c}{}_2)_nNR^{2a}R^{2b}$;

$R^{2a}$ is H, methyl, or ethyl;

$R^{2b}$ is H, methyl, or ethyl;

each $R^{2c}$ is independently H or alkyl, preferably methyl; and n is an integer having a value of 1 to 4.

In some embodiments, each $R^{2c}$ is H. In other embodiments, at least one $R^{2c}$ is alkyl, preferably methyl, and the rest are H.

In certain embodiments of the disclosed compounds, $X^1$ is O. In some such embodiments, $(CR^{2c}{}_2)_nNR^{2a}R^{2b}$, wherein at least one $R^{2c}$ is optionally alkyl and the rest are H. In other embodiments, wherein $X^1$ is $NR^{X1}$. In some such embodiments, $(CR^{2c}{}_2)_nNR^{2a}R^{2b}$, wherein at least one $R^{2c}$ is optionally methyl and the rest are H.

In particular embodiments of the disclosed compounds, $R^{2a}$ and $R^{2b}$ are not both H.

In some embodiments of the disclosed compounds, $X^1$ is O;

$R^1$ is methyl;

$R^2$ is optionally substituted hydroxyalkyl or optionally substituted $C_1$-$C_4$ alkyl-$NHR^{2a}$, wherein $R^{2a}$ is methyl or ethyl; or $R^1$ and $R^2$, together with the carbon atom through which they are joined, form a 5- or 6-membered heterocyclic ring having one N atom optionally substituted with lower alkyl.

In some embodiments of the disclosed compounds, $X^1$ is O or $NR^{X1}$;

$R^{X1}$ is H or alkyl, preferably lower alkyl;

$R^1$ is methyl or ethyl;

$R^2$ is lower alkyl, $(CH_2)_nOH$ or $(CR^{2c}{}_2)_nNR^{2a}R^{2b}$; or $R^1$ and $R^2$, together with the carbon atom through which they are joined, form a 5- or 6-membered heterocyclic ring having one N atom substituted with —C(O)oxyalkyl;

$R^{2a}$ is H or lower alkyl optionally substituted with one or more halogen;

$R^{2b}$ is H or lower alkyl optionally substituted with one or more halogen; and $R^{2a}$ and $R^{2b}$ together through the N atom through which they are joined, form a 3-, 4-, or 5-membered heterocyclic ring optionally substituted with $R^{ab}{}_z$, wherein:

$R^{ab}$ is halogen, hydroxyl, lower alkyl, haloalkyl, oxyalkyl;

each $R^{2c}$ is independently H or alkyl, preferably methyl;

z is an integer having a value of 0 to 2; and n is an integer having a value of 2 to 4.

In some such embodiments, $R^{2a}$ and $R^{2b}$ are not both H.

In some embodiments of the disclosed compounds, $X^1$ is O or $NR^{X1}$;

$R^{X1}$ is H or alkyl, preferably lower alkyl;

$R^1$ is methyl;

$R^2$ is $C_1$-$C_2$ alkyl or $(CH_2)_nNR^{2a}R^{2b}$; or $R^1$ and $R^2$, together with the carbon atom through which they are joined, form a 5- or 6-membered heterocyclic ring having one N atom optionally substituted with —C(O)alkyl;

$R^{2a}$ is unsubstituted lower alkyl;

$R^{2b}$ is unsubstituted lower alkyl;

n is an integer having a value of 2 to 4.

In some embodiments of the disclosed compounds, $X^1$ is O or $NR^{X1}$;

$R^{X1}$ is H or alkyl, preferably lower alkyl;

$R^1$ is methyl;

$R^2$ is $C_1$-$C_2$ alkyl or $(CR^{2e}{}_2)_nNR^{2a}R^{2b}$;

$R^{2a}$ is unsubstituted lower alkyl;

$R^{2b}$ is unsubstituted lower alkyl;

each $R^{2c}$ is independently H or alkyl, preferably methyl; and n is an integer having a value of 2 to 4.

In some embodiments of the disclosed compounds, $X^1$ is O or $NR^{X1}$;

$R^{X1}$ is H or alkyl, preferably lower alkyl;

$R^1$ is alkyl, preferably lower alkyl;

$R^2$ is $C_1$-$C_3$ alkyl, is $C_1$-$C_3$ alkenyl, optionally substituted hydroxyalkyl, optionally substituted alkoxyalkyl, or $(CR^{2c}{}_2)_nNR^{2a}R^{2b}$; or $R^1$ and $R^2$, together with the carbon atom through which they are joined, form a 5- or 6-membered heterocyclic ring having one heteroatom selected from N and O and is optionally substituted with lower alkyl, carbonyl, tert-butyloxycarbonyl, —C(O)oxyalkyl, or —$S(O)_2$alkyl;

$R^{2a}$ and $R^{2b}$ are each independently H, alkyl, or —C(O) alkyl; or $R^{2a}$ and $R^{2b}$ together through the N atom through which they are joined, form a 3- to 6-membered heterocyclic ring optionally having one C replaced with O, wherein the heterocyclic ring is optionally substituted with $(R^{ab})_z$, each $R^{ab}$ is independently halogen, hydroxyl, or lower alkyl;

each $R^{2c}$ is independently H or alkyl, preferably methyl;

z is an integer having a value of 1 or 2;

n is an integer having a value of 2 to 4.

In certain embodiments, the compound of Formula (I) is selected from:

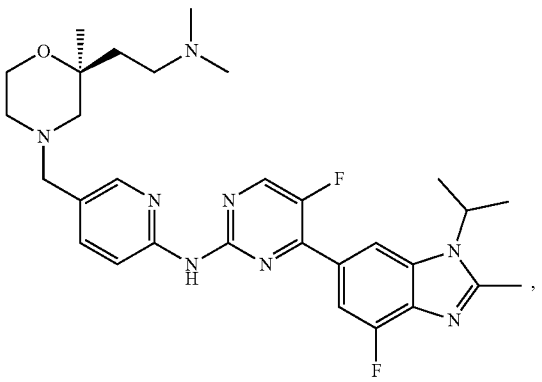

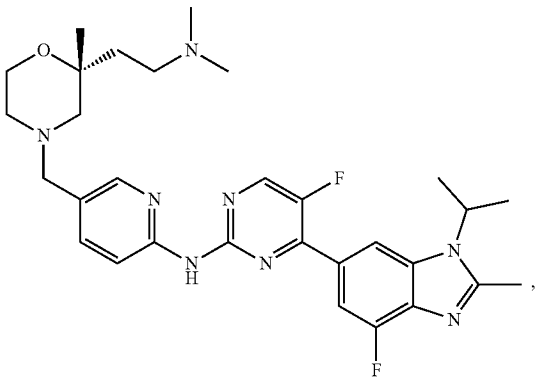

-continued

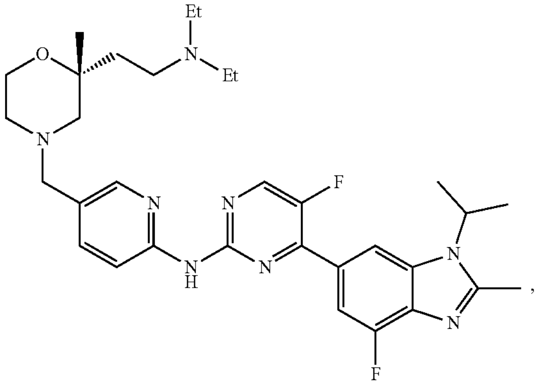

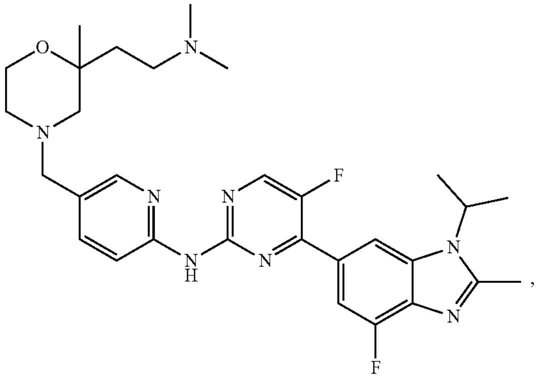

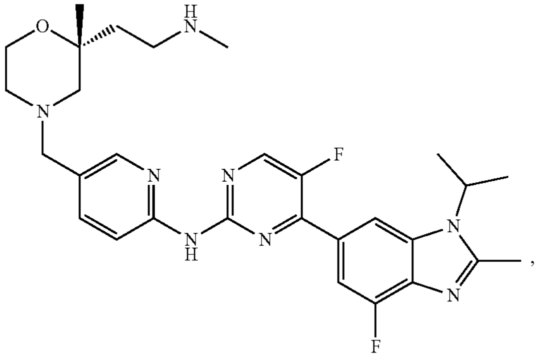

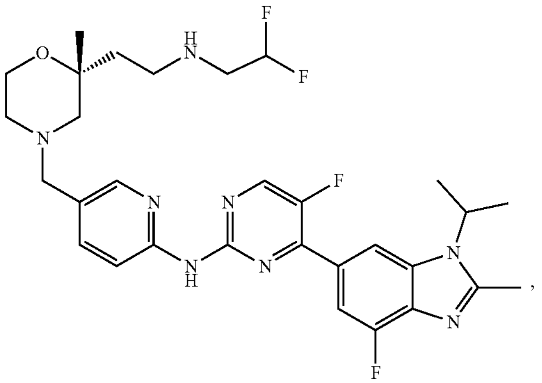

-continued
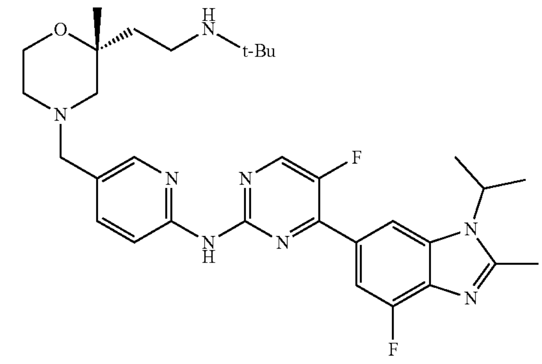
,
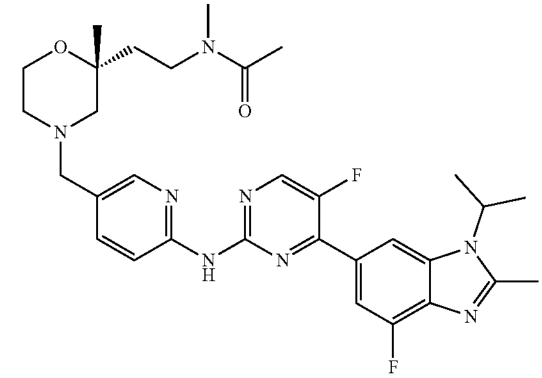
,
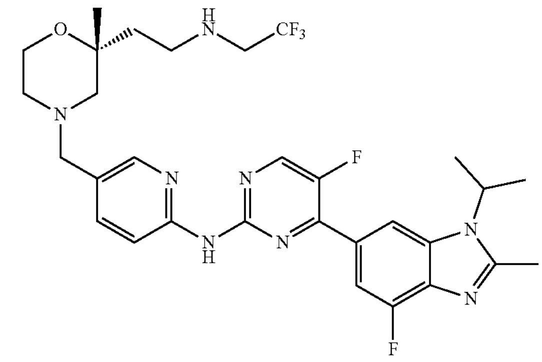
,
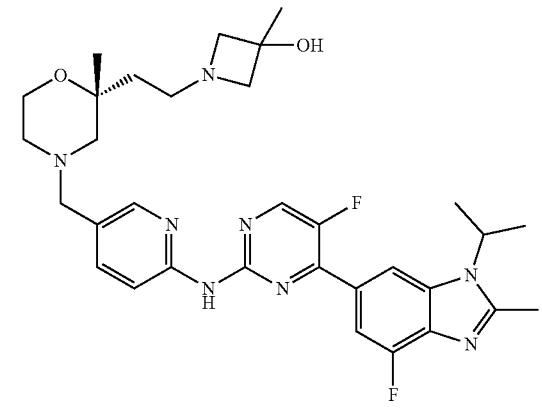
,
-continued
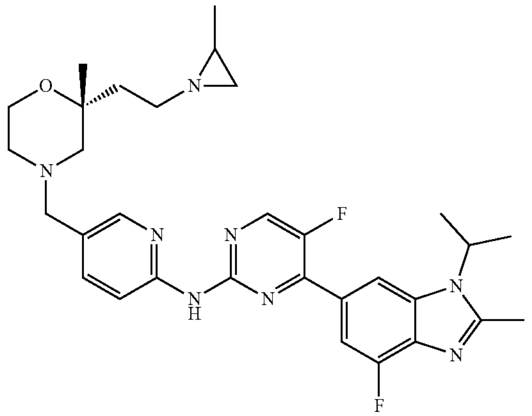
,
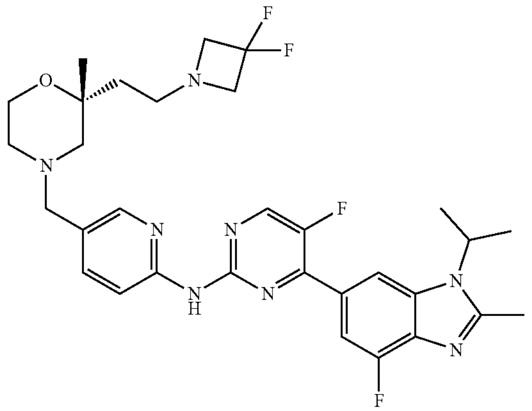
,
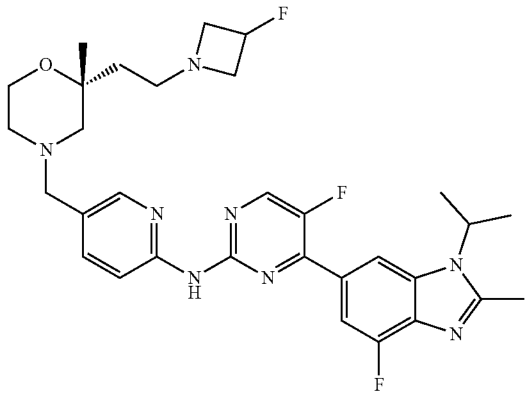
,
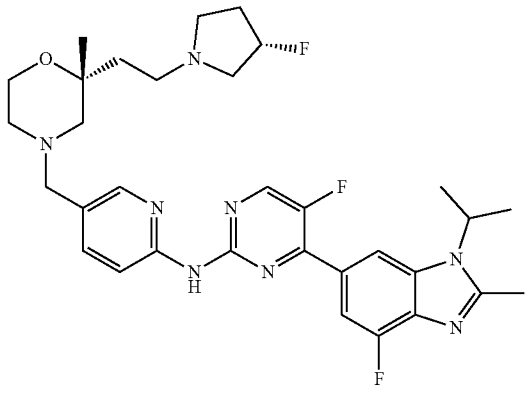
, -continued
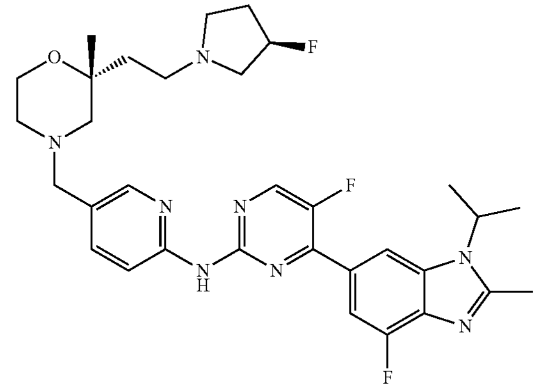
,
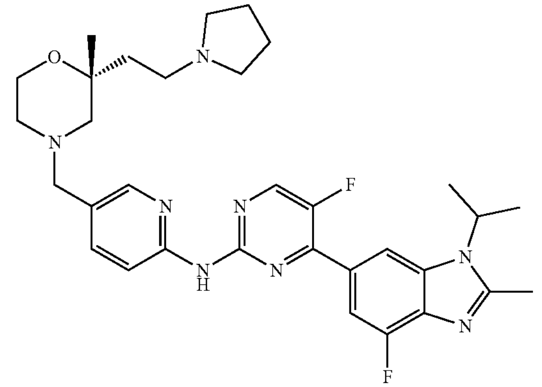
,
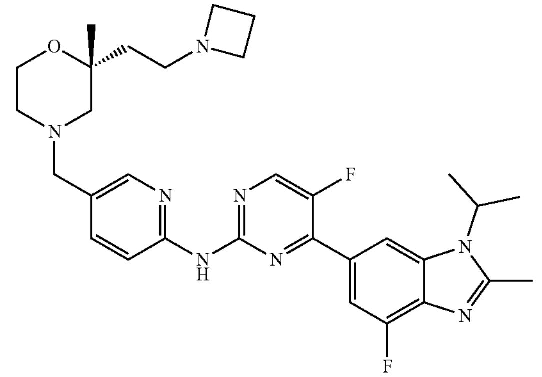
,
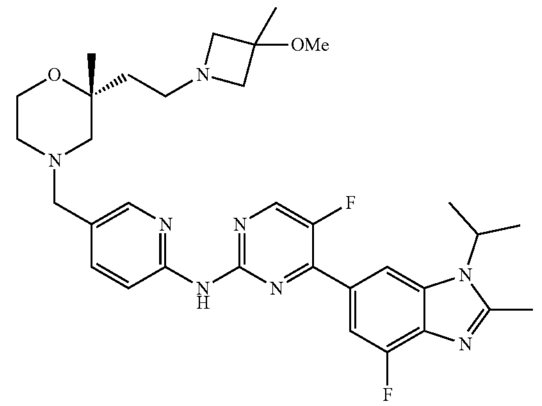
,
-continued
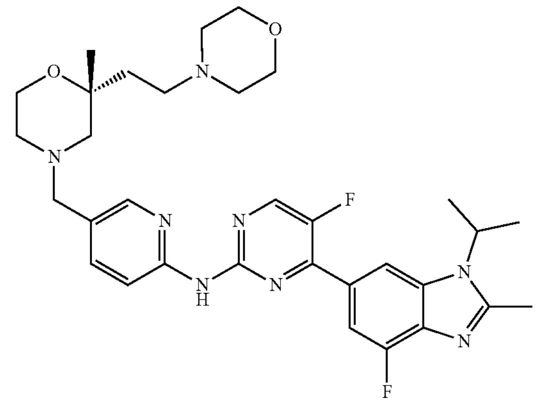
,
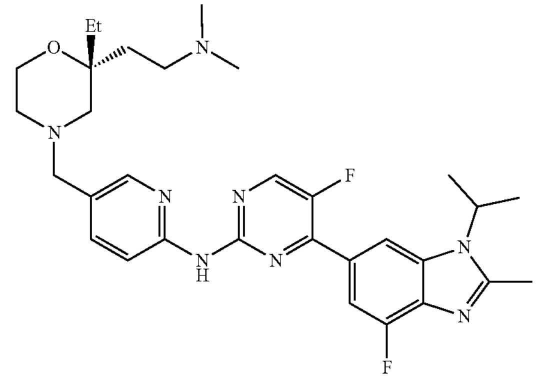
,
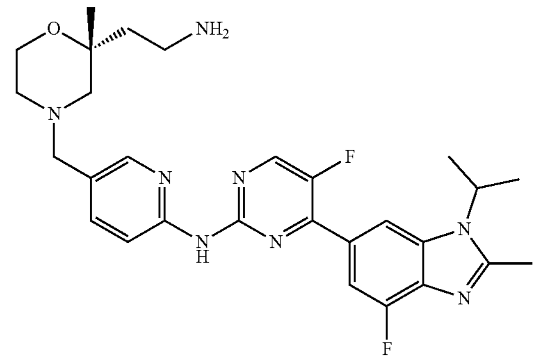
,
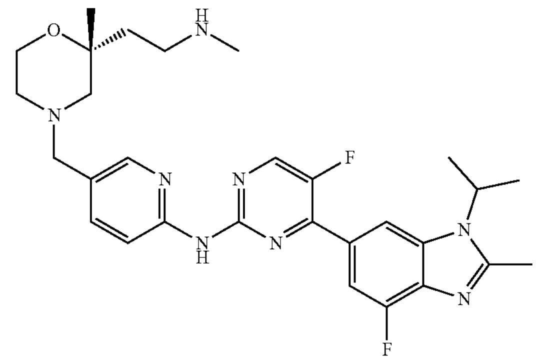
, -continued
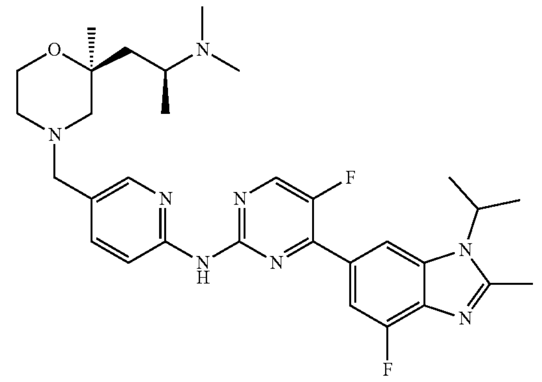
,
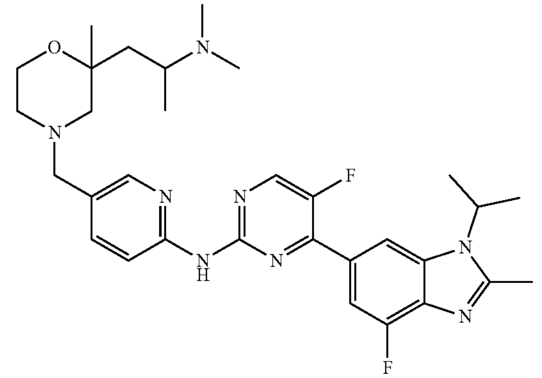
,
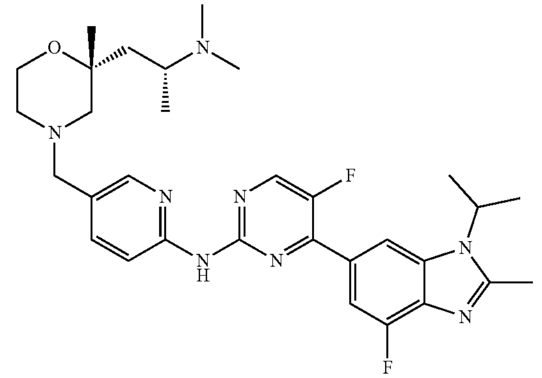
,
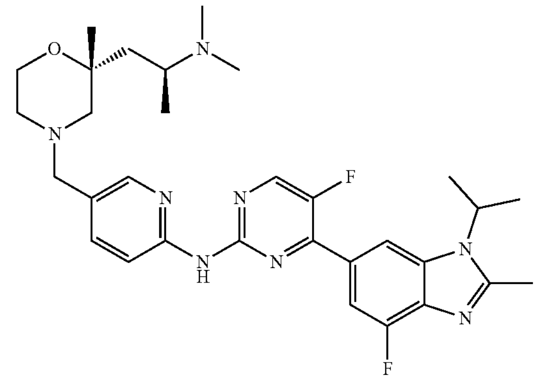
,
-continued
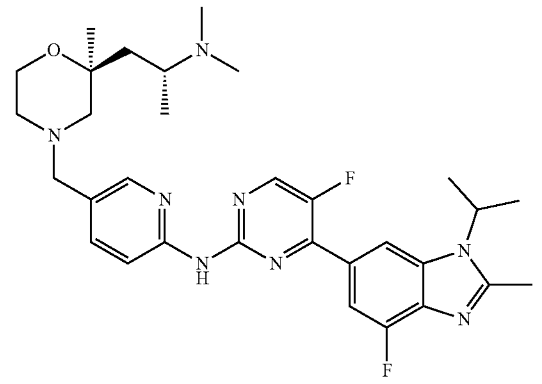
,
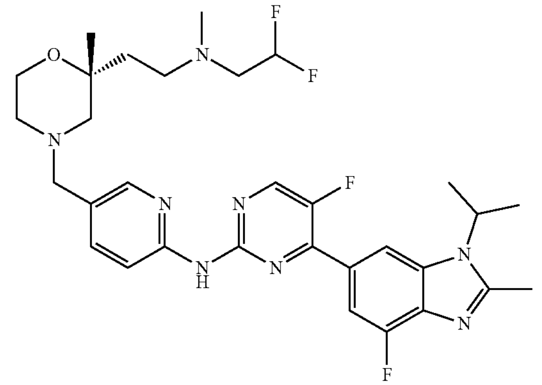
,
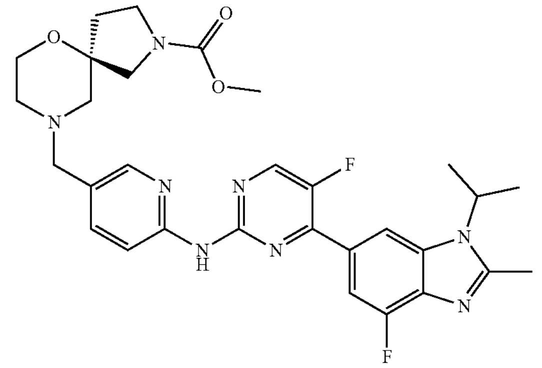
,
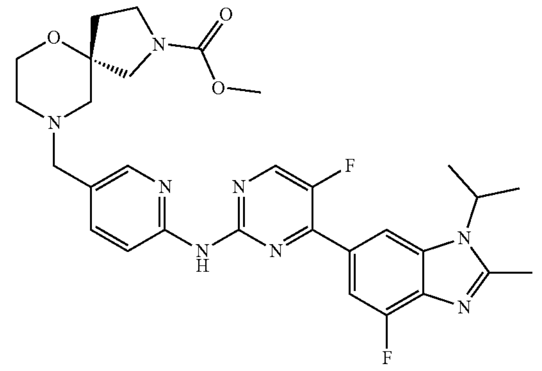
, -continued
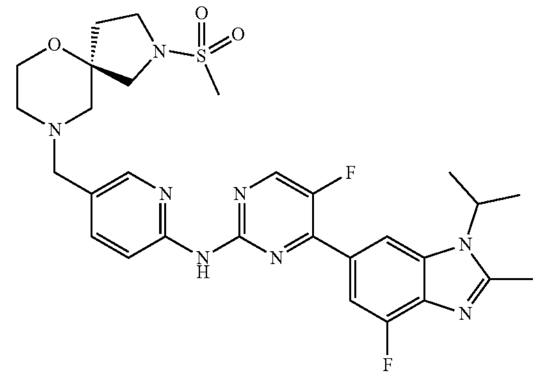
,
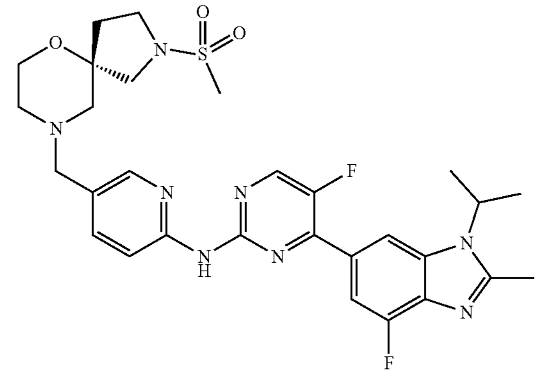
,
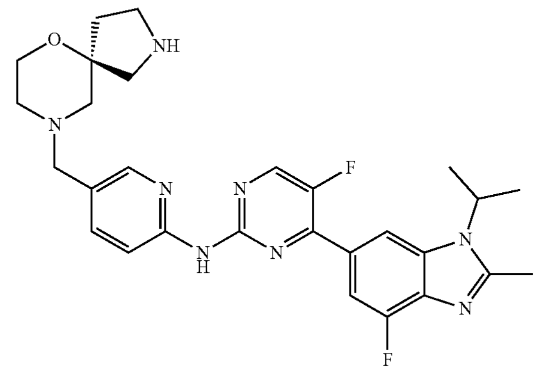
,
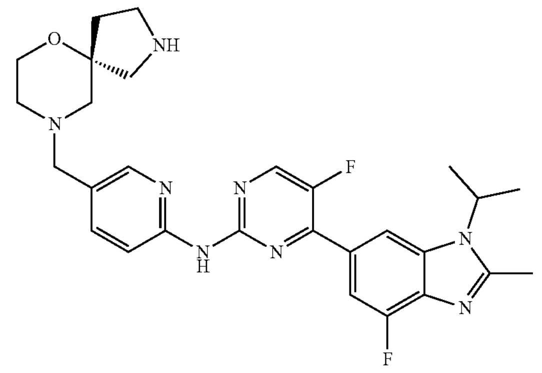
,
-continued
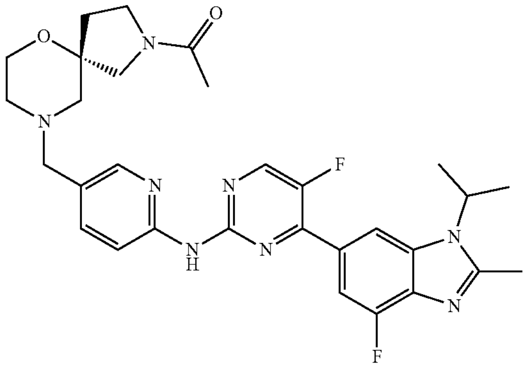
,
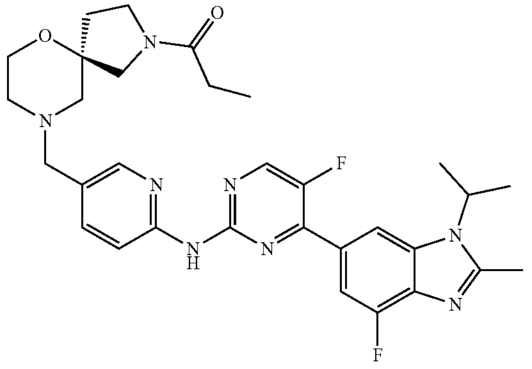
,
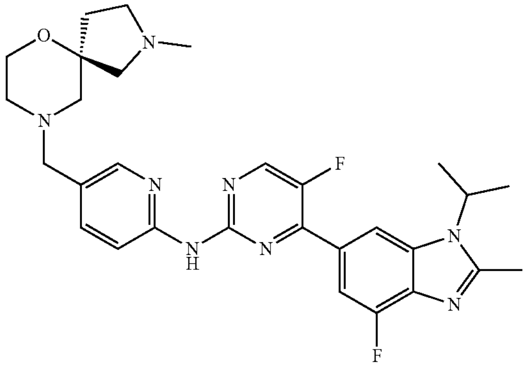
,
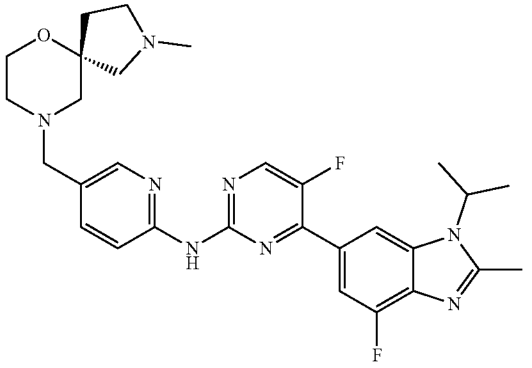
, -continued
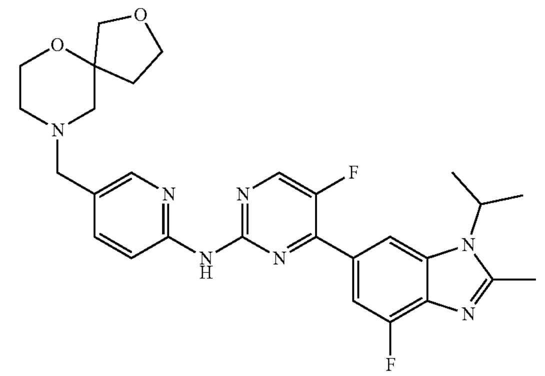
,
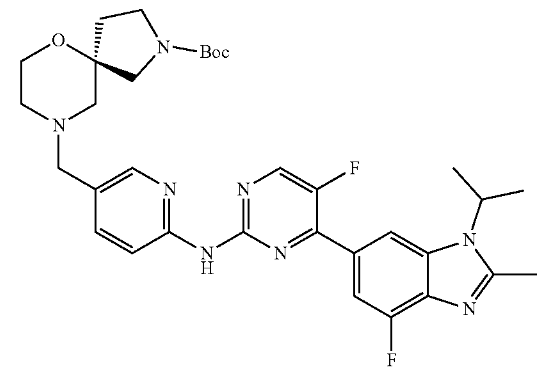
,
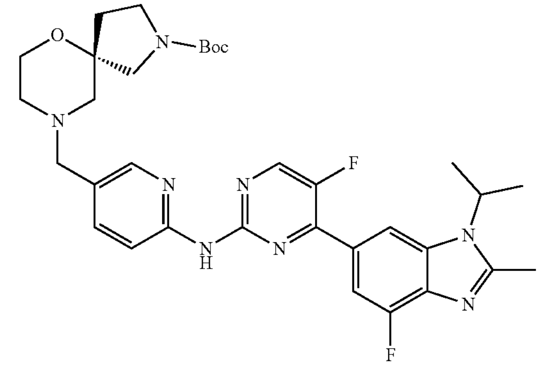
,
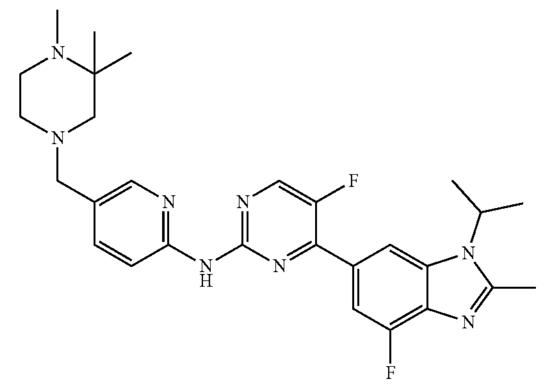
,
-continued
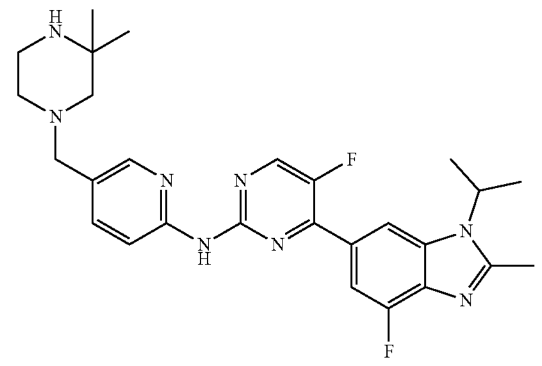
,
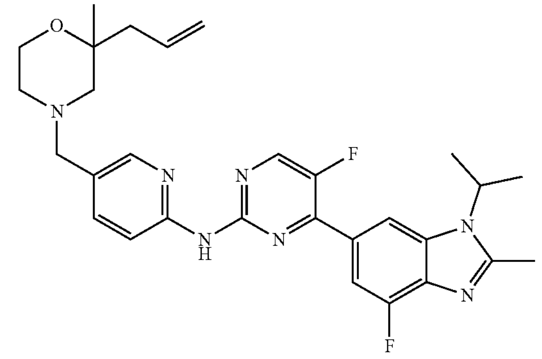
,
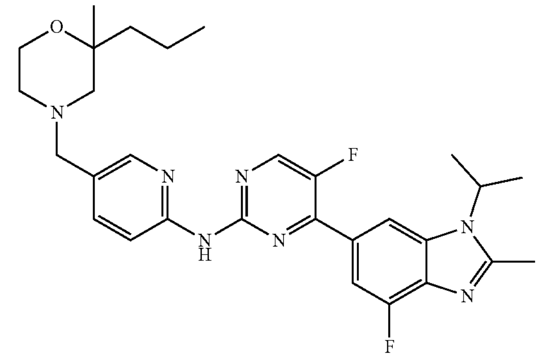
,
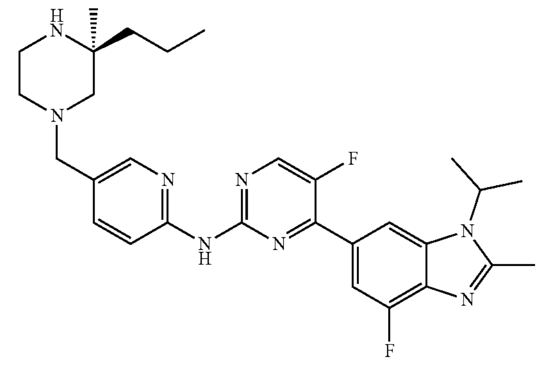
, -continued
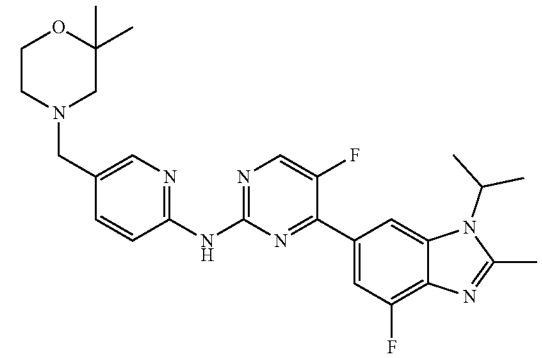
,
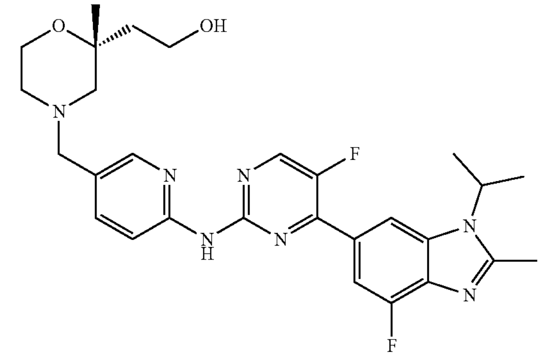
,
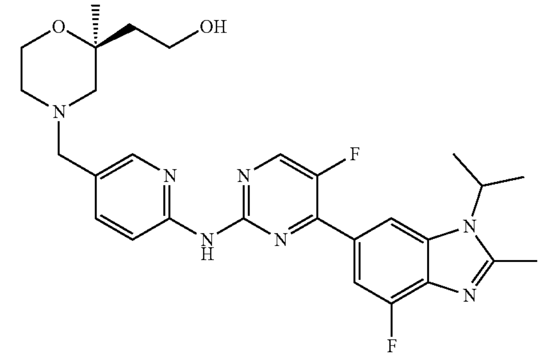
,
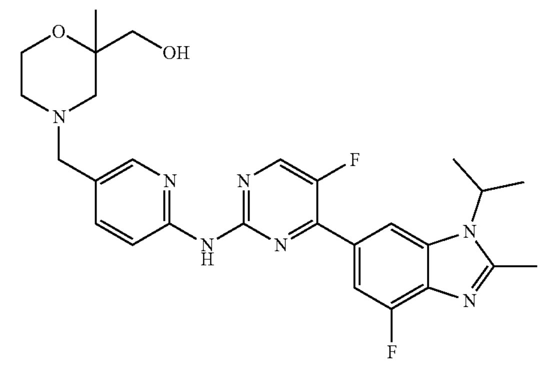
,
-continued
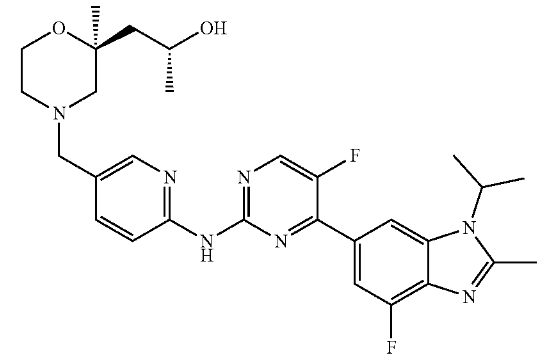
,
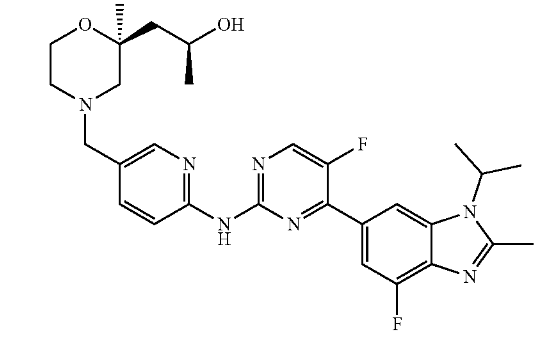
,
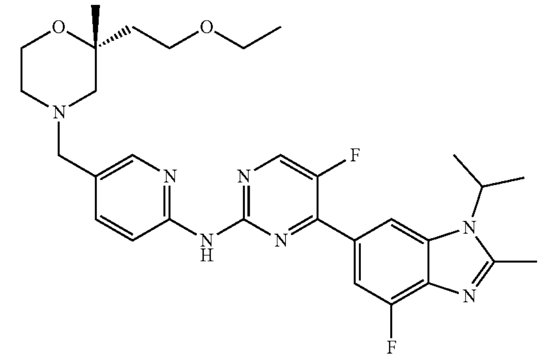
,
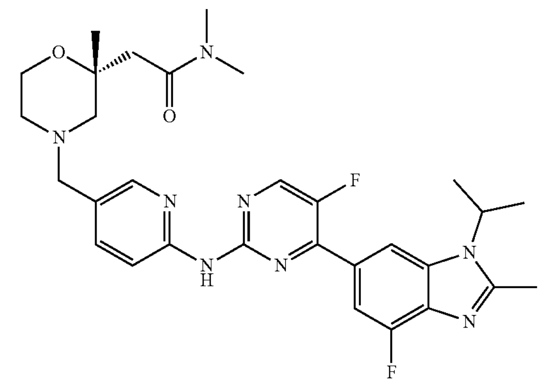
, -continued
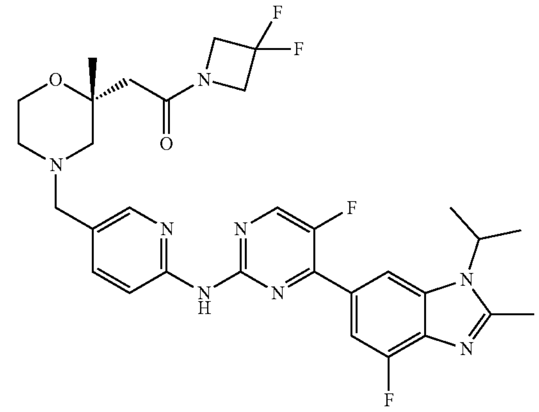
,
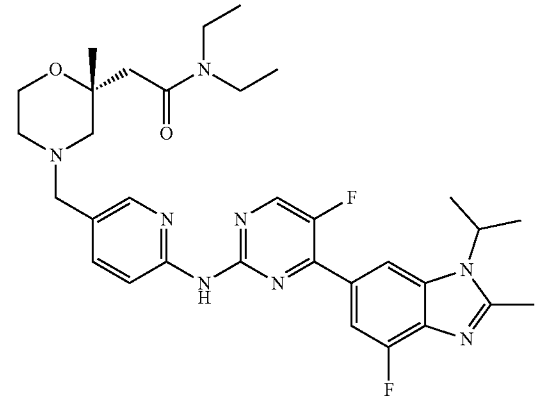
,
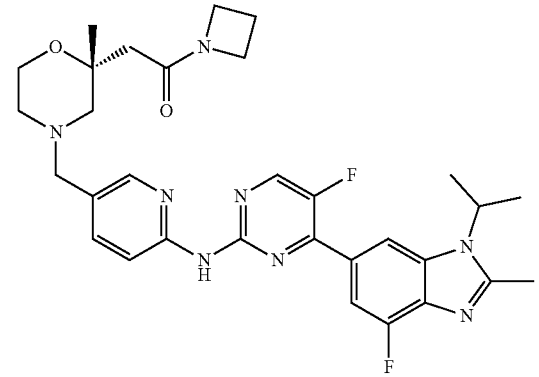
,
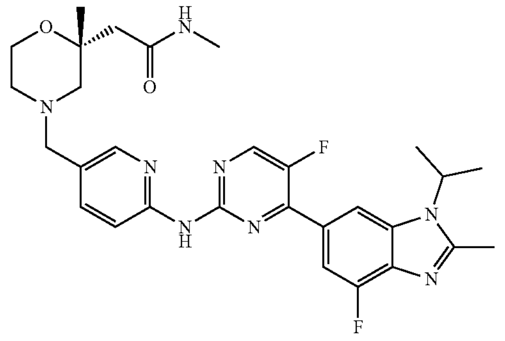
, and
-continued
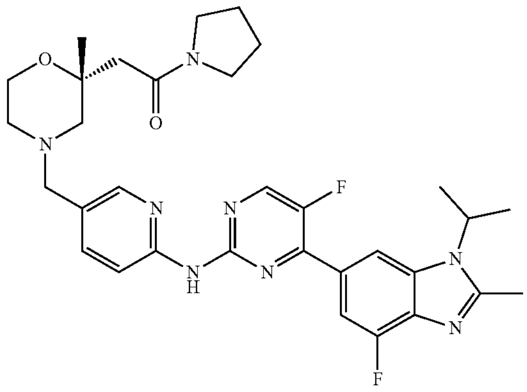
,
or a pharmaceutically acceptable salt thereof.
In certain embodiments, the compound of Formula (I) is selected from:
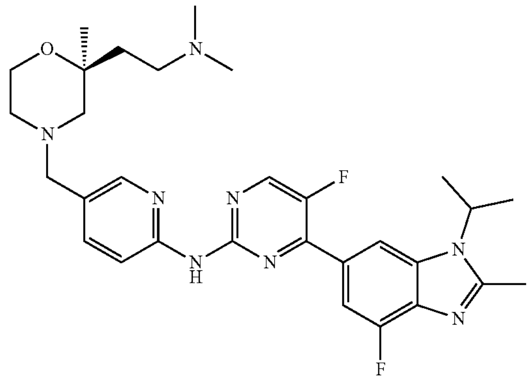
,
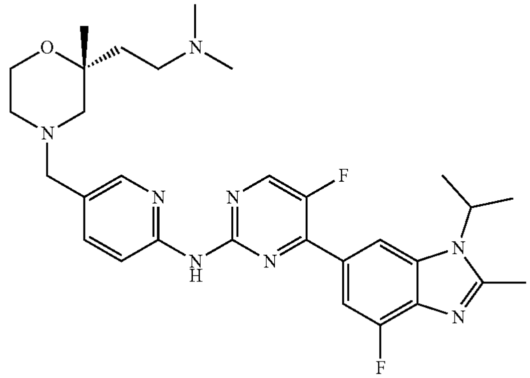
,
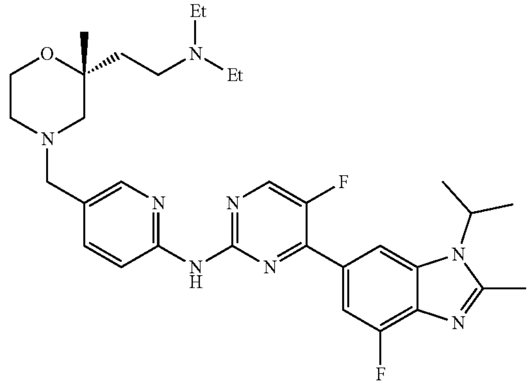
, -continued
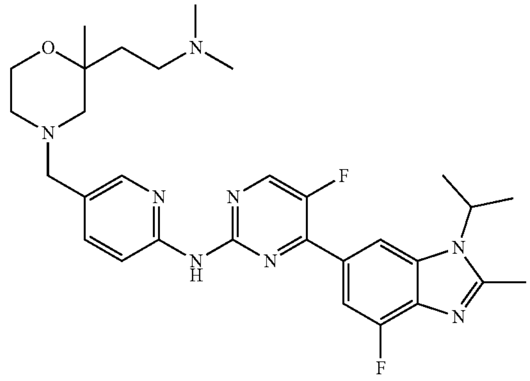
,
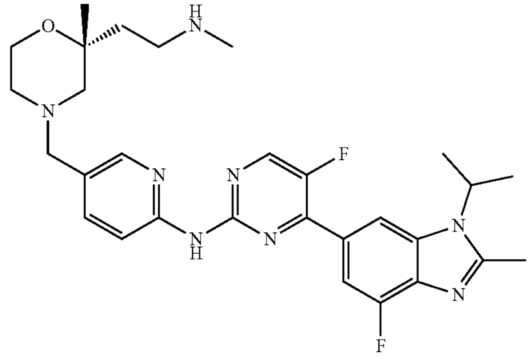
,
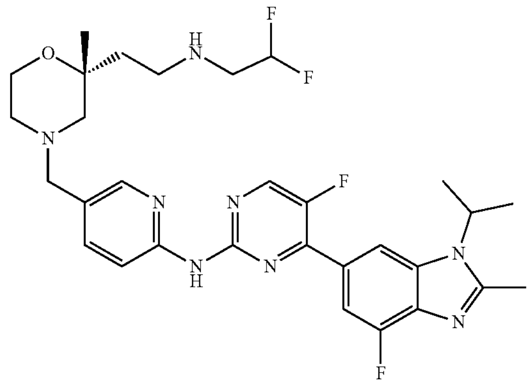
,
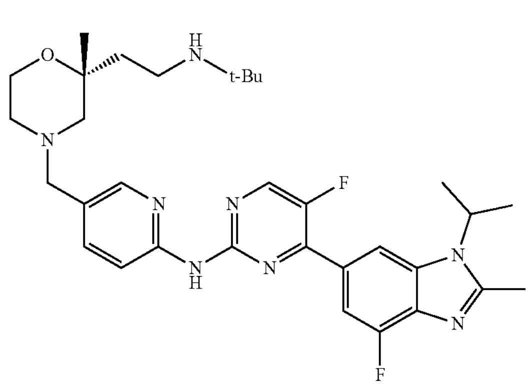
,
-continued
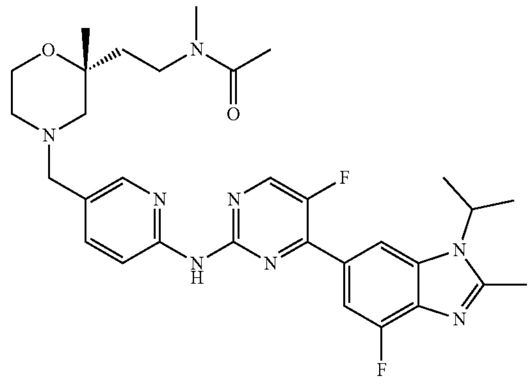
,
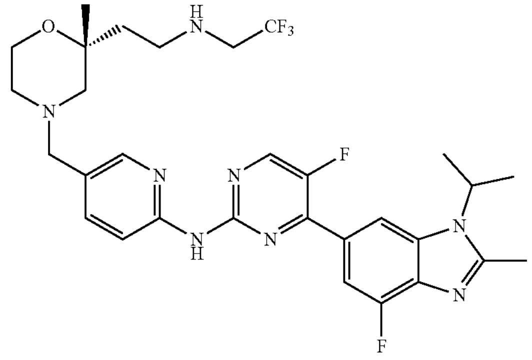
,
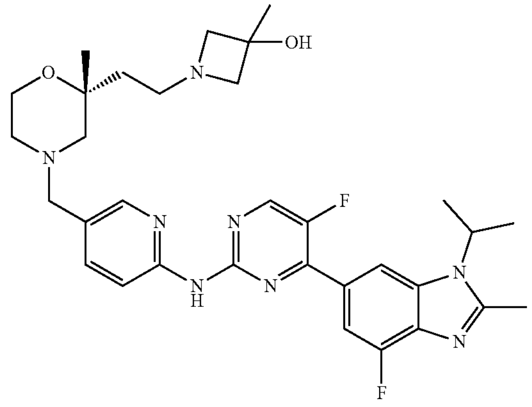
,
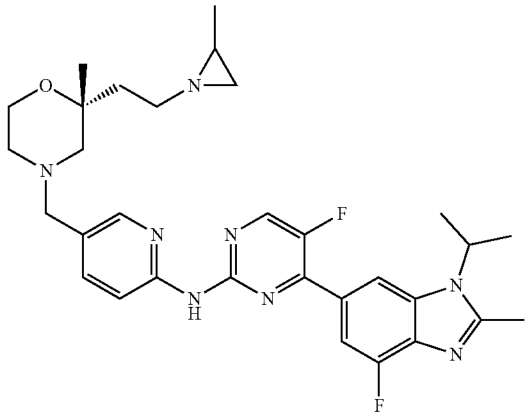
, -continued
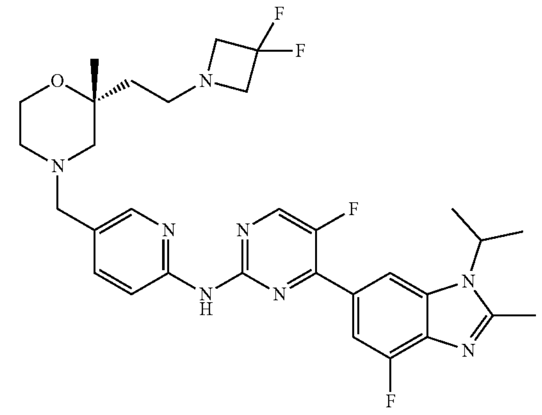
,
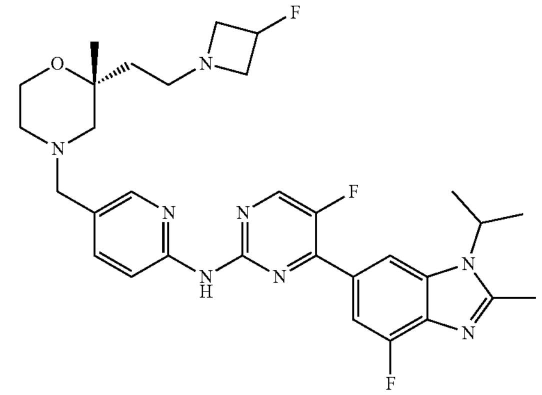
,
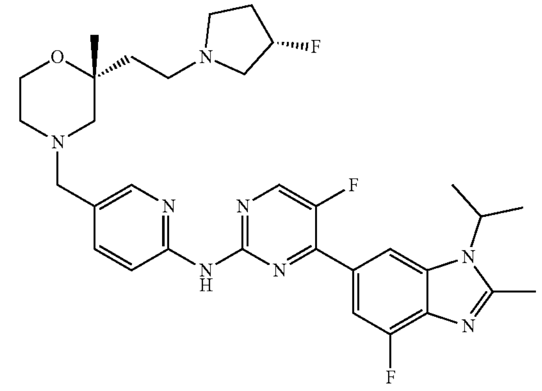
,
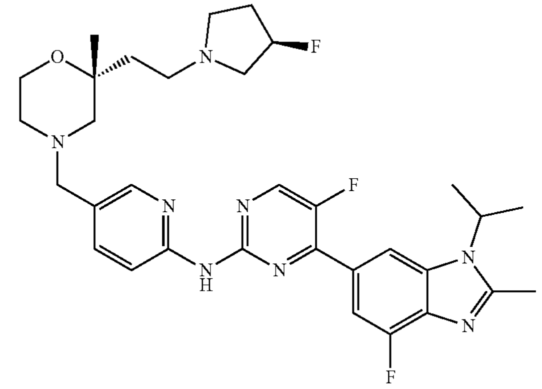
,
-continued
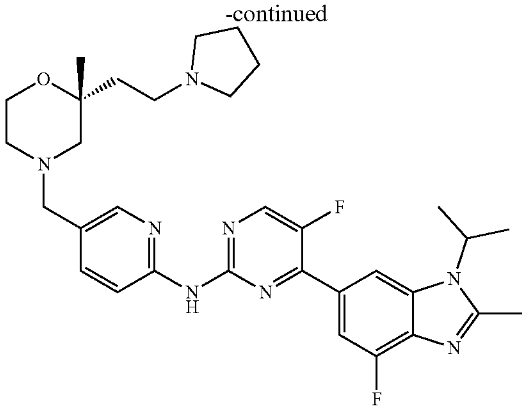
,
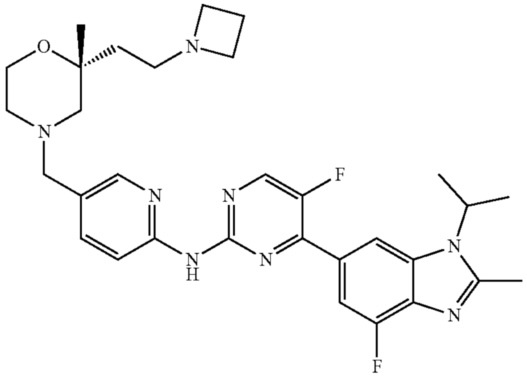
,
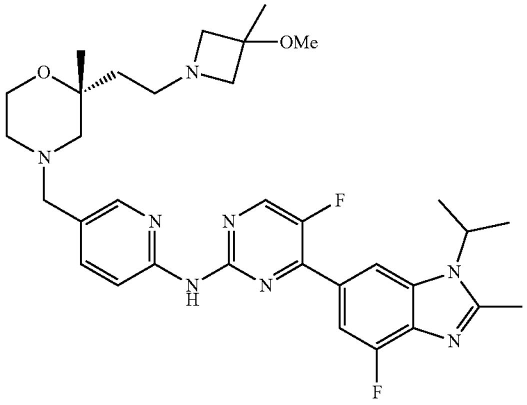
,
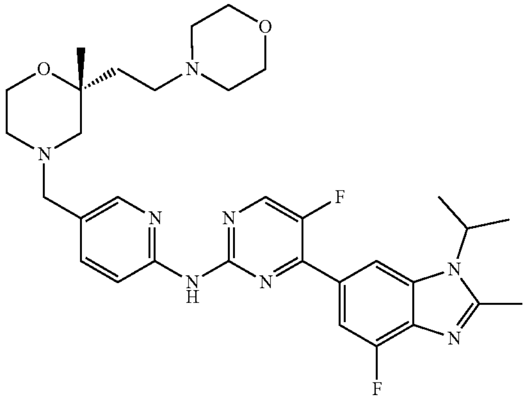
, -continued
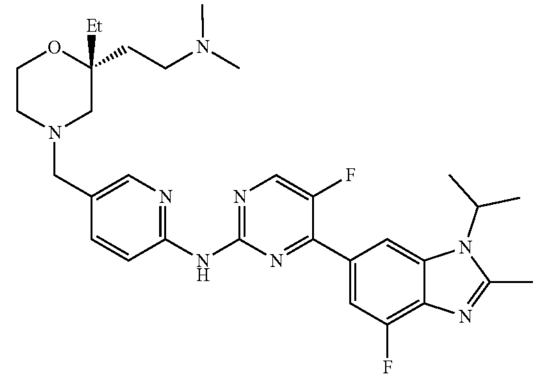
,
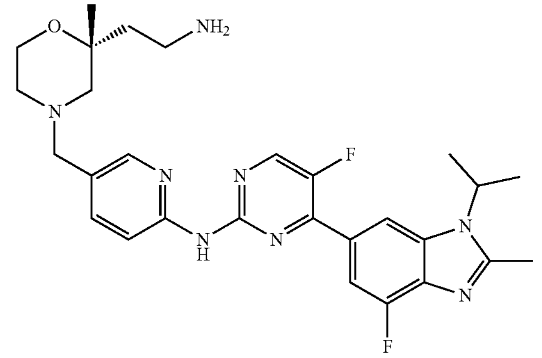
,
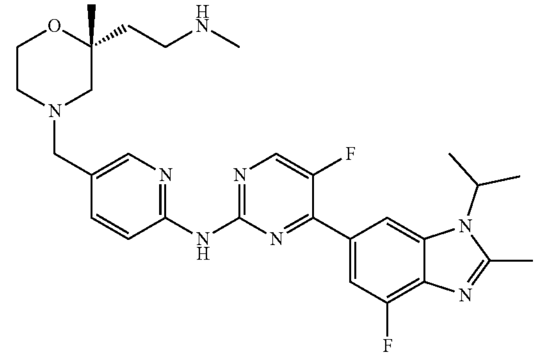
,
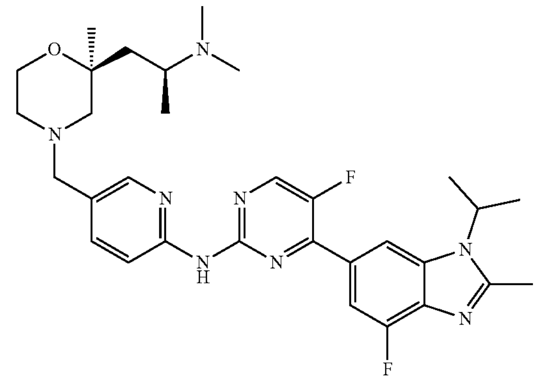
,
-continued
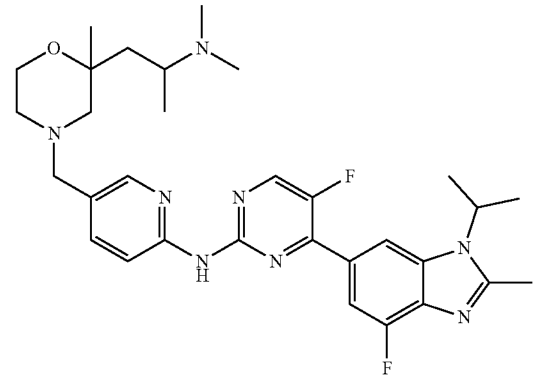
,
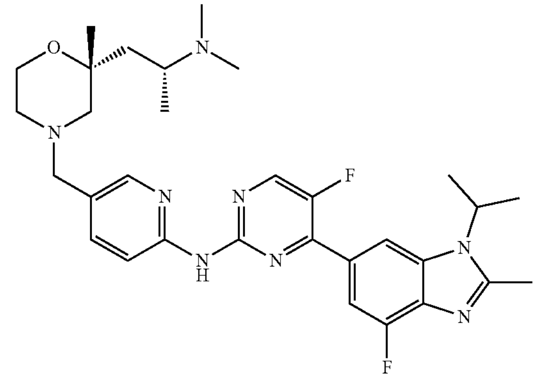
,
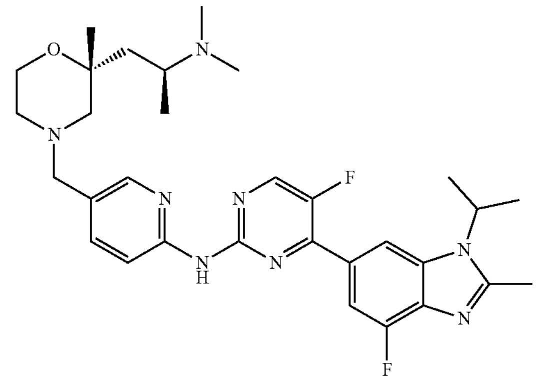
,
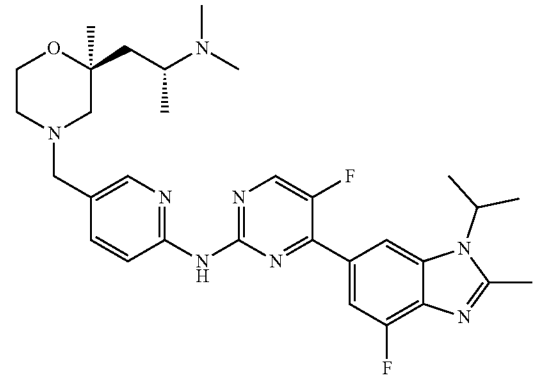
, -continued
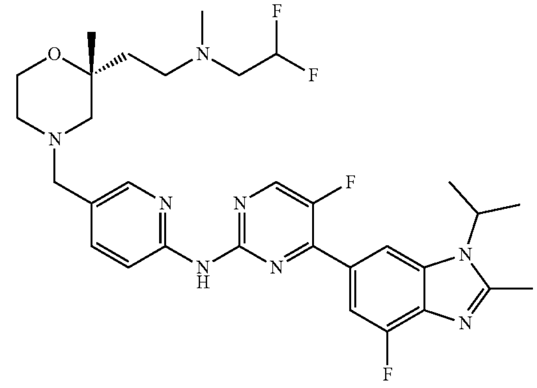
,
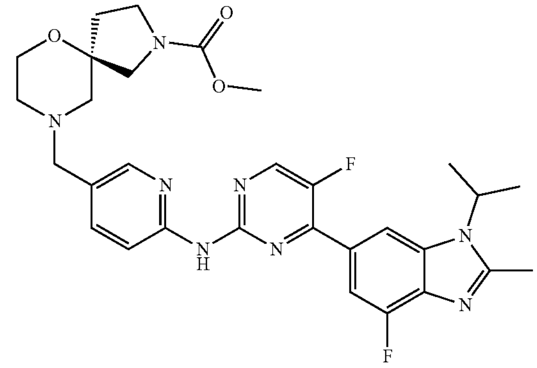
,
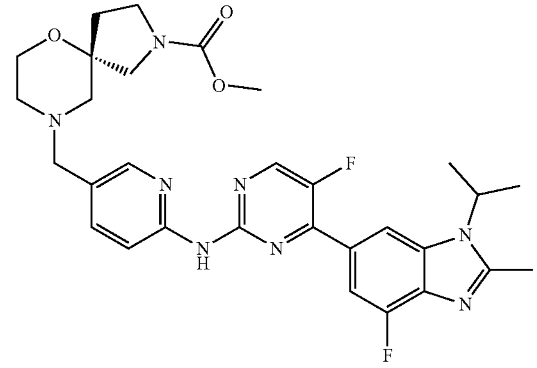
,
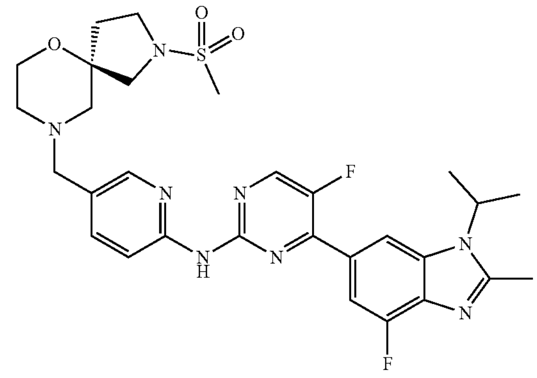
,
-continued
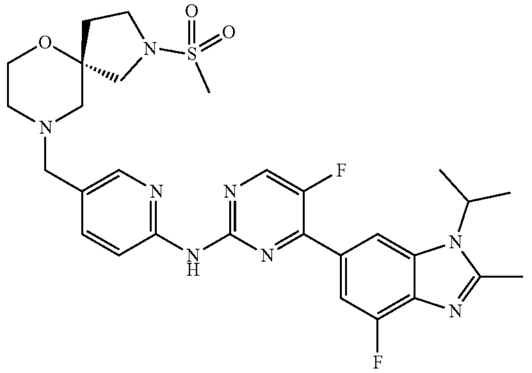
,
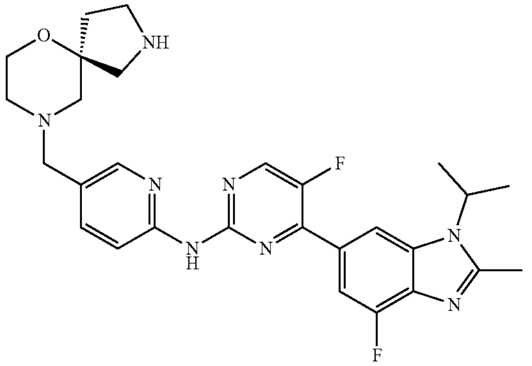
,
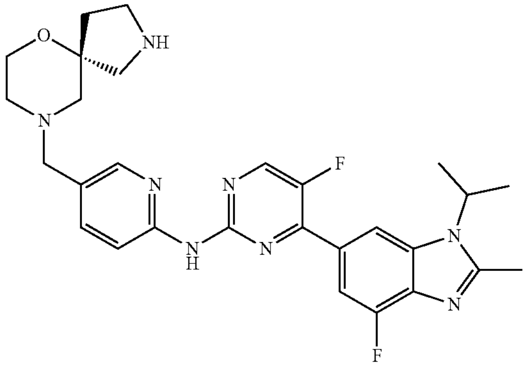
,
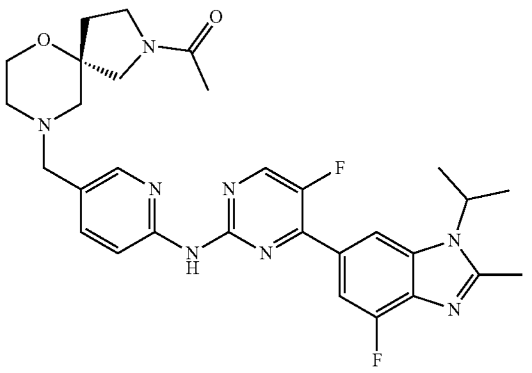
, -continued
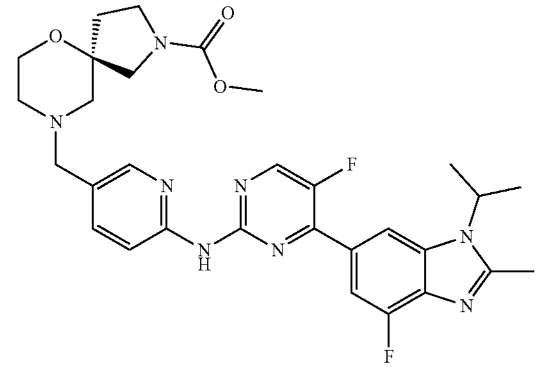
,
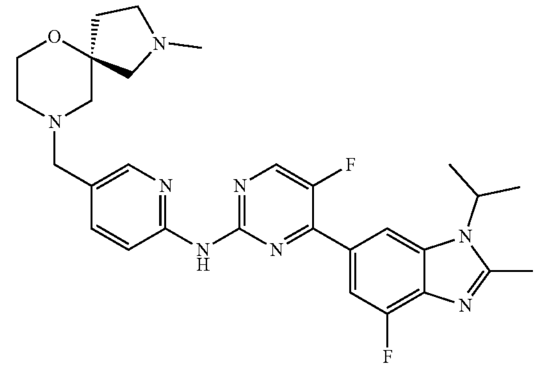
,
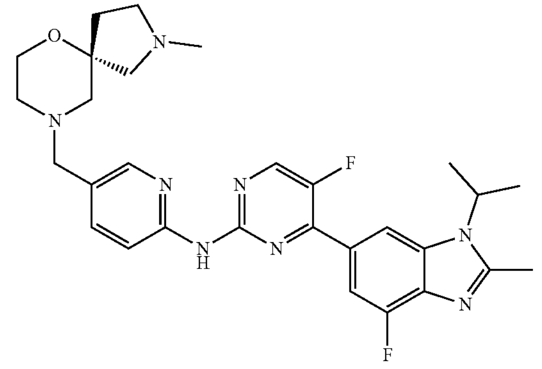
,
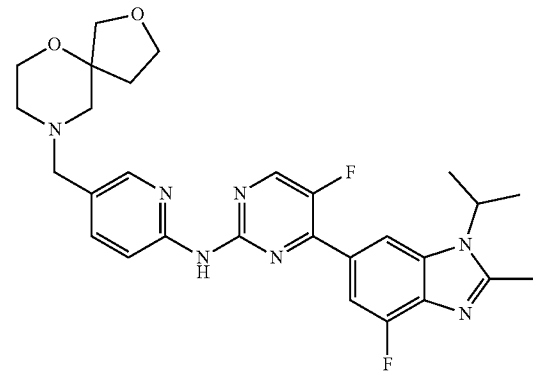
,
-continued
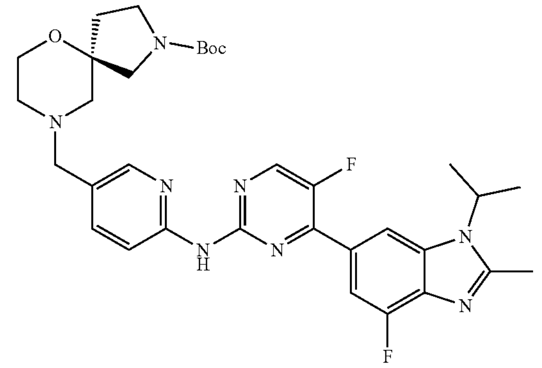
,
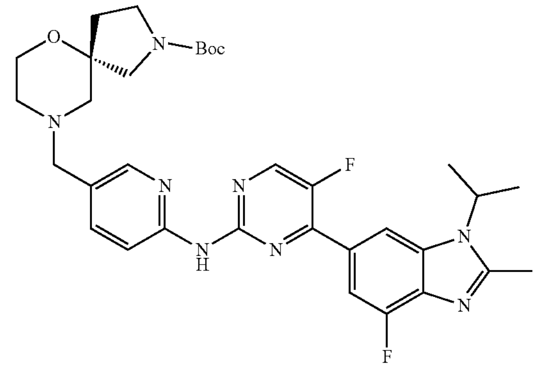
,
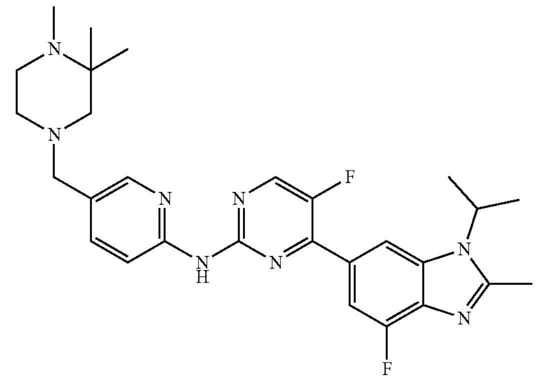
,
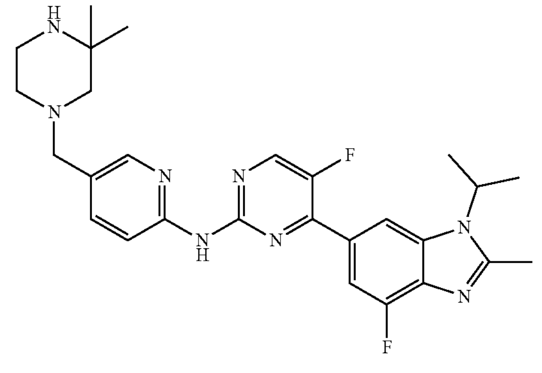
, -continued
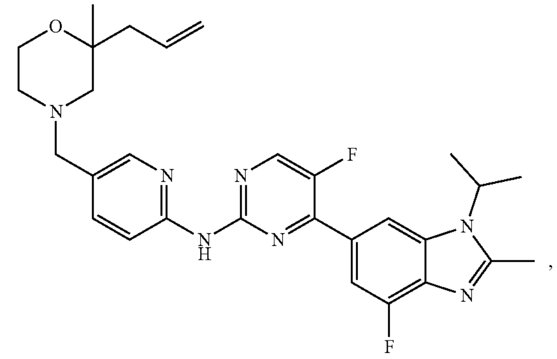
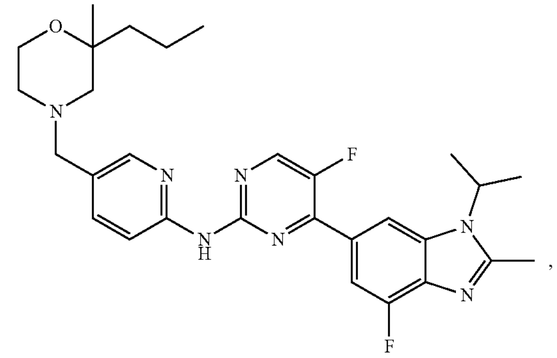
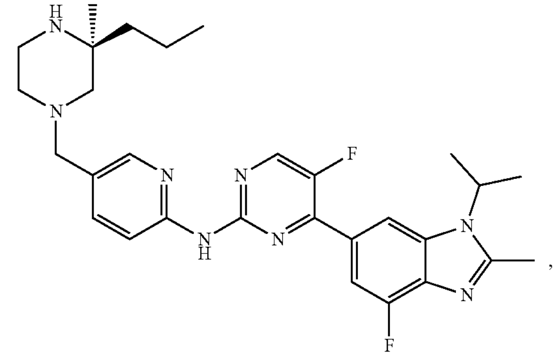
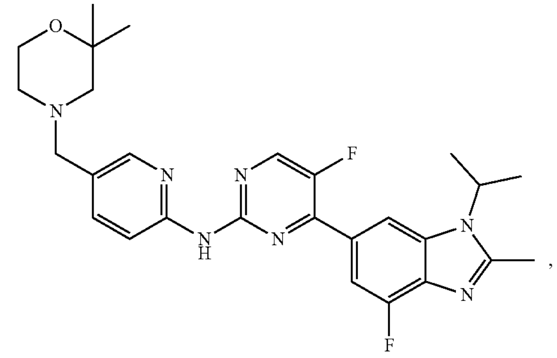
-continued
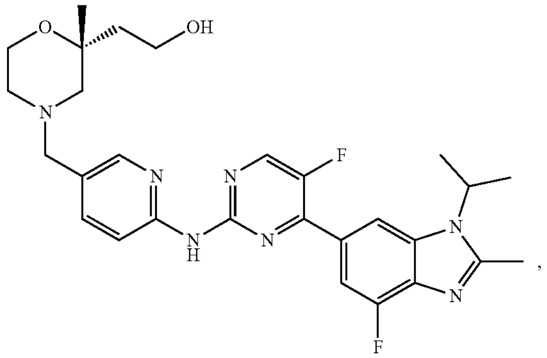 [SMILES: CCOCC[C@]1(C)CN(Cc2ccc(Nc3ncc(F)c(-c4cc(F)c5nc(C)n(C(C)C)c5c4)n3)nc2)CCO1]
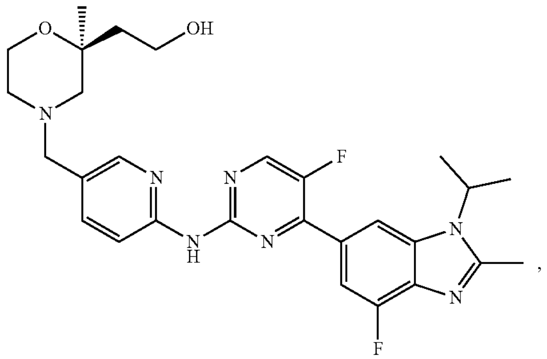
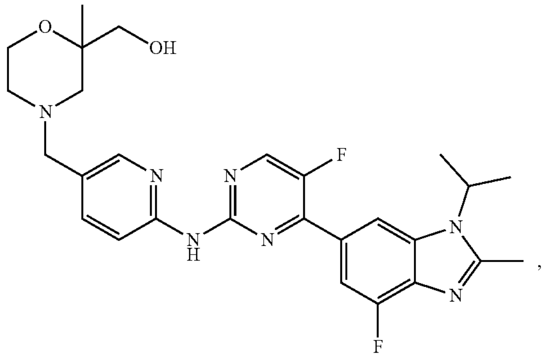
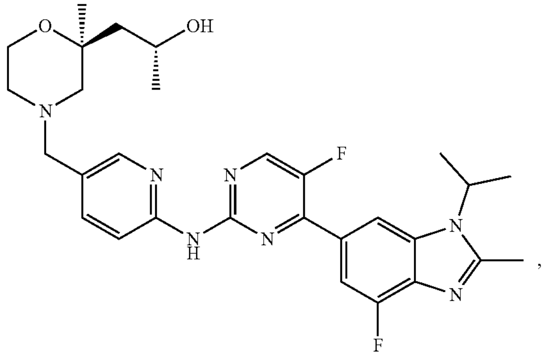

-continued
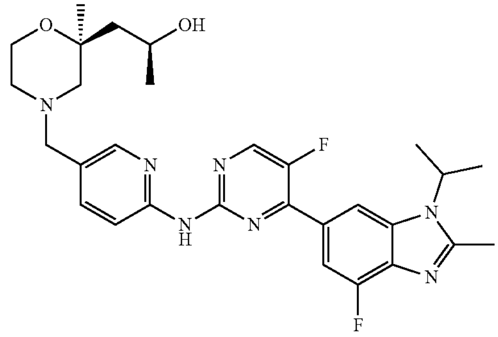
, and
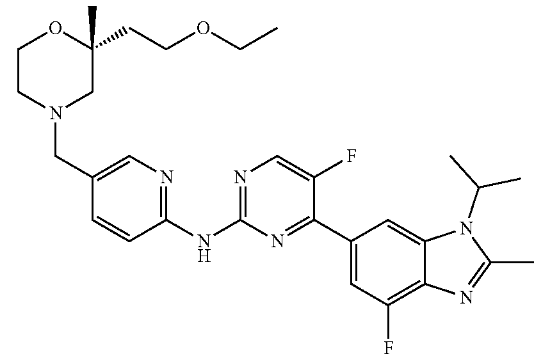
,
or a pharmaceutically acceptable salt thereof.
In some such embodiments, the compound of Formula (I) is selected from:
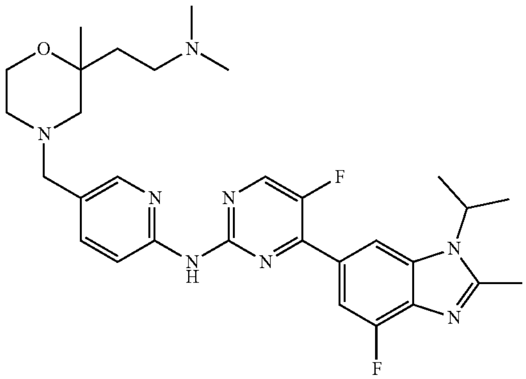
,
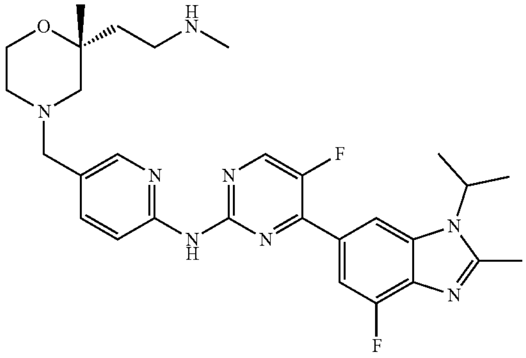
,
-continued
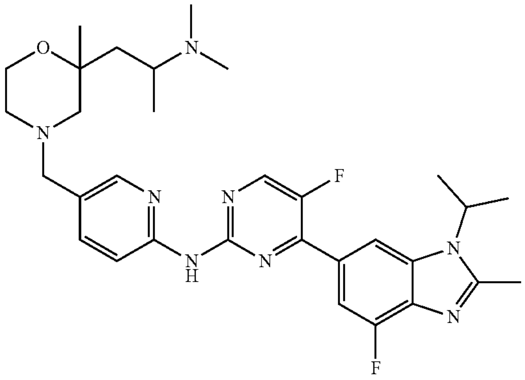
,
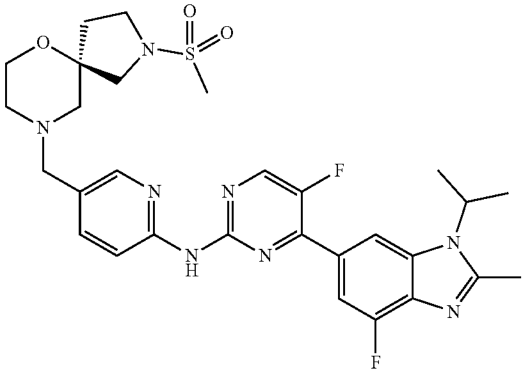
,
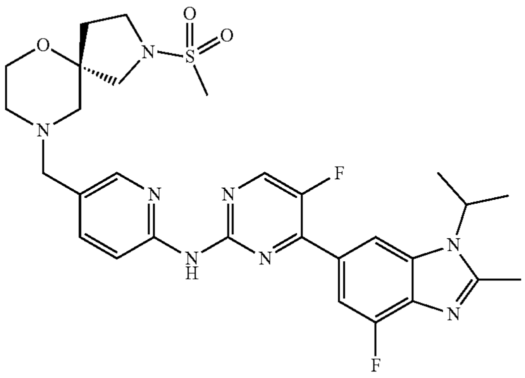
,
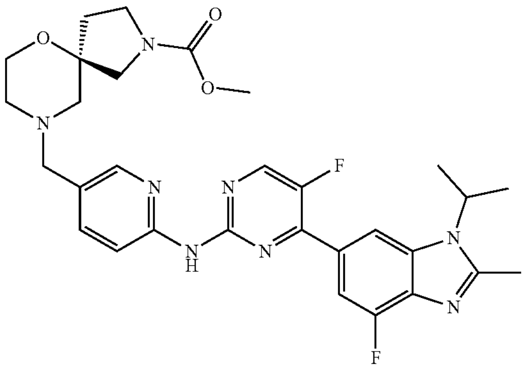
, -continued
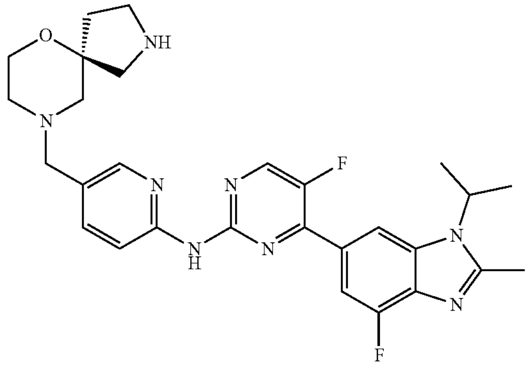
,
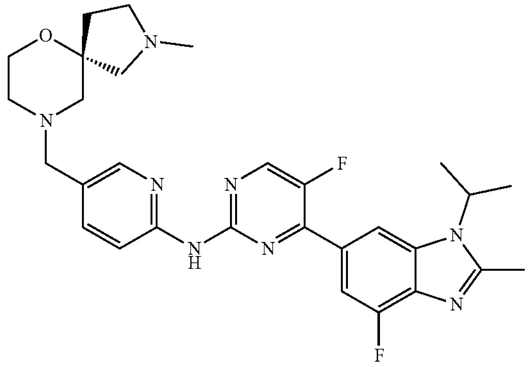
,
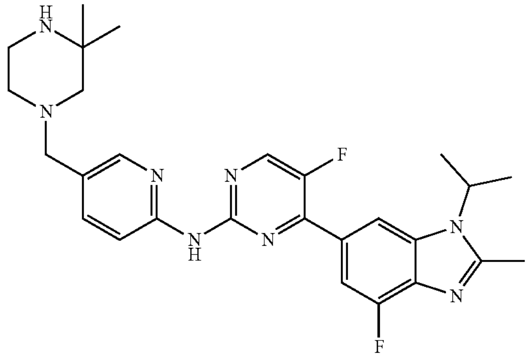
,
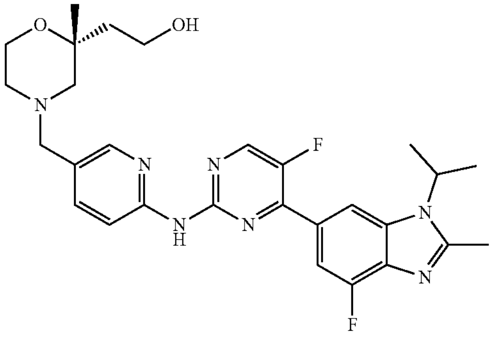
, and
-continued
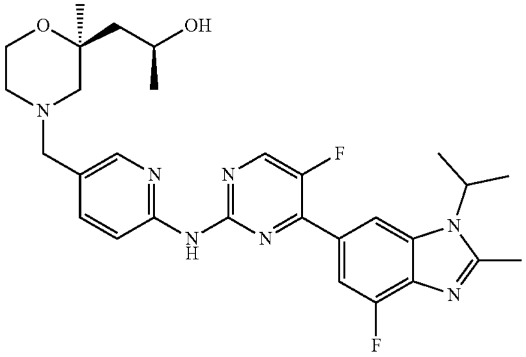
,
or a pharmaceutically acceptable salt thereof.
In preferred embodiments, the compound of Formula (I) is selected from:
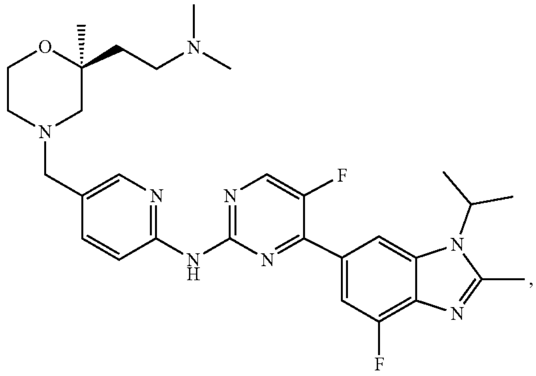
,
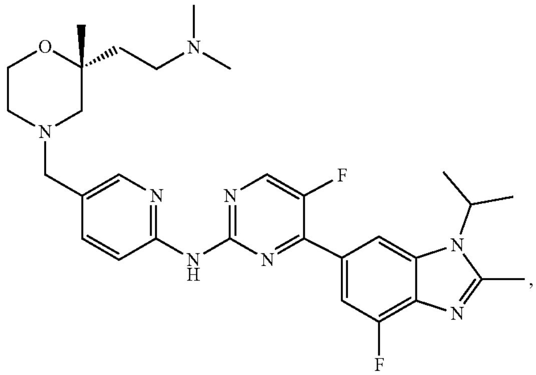
,
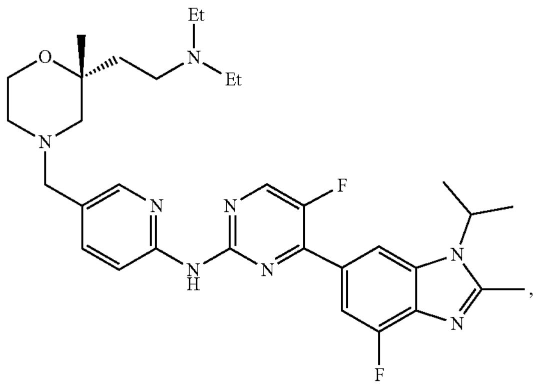
, -continued
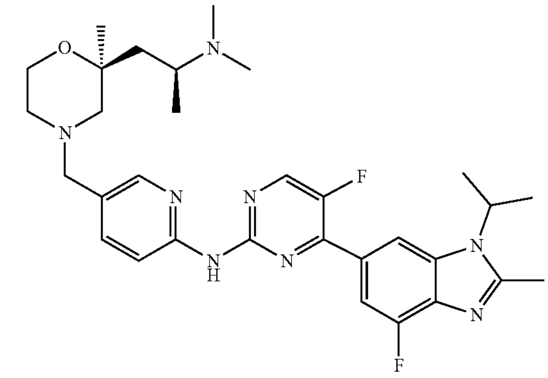
,
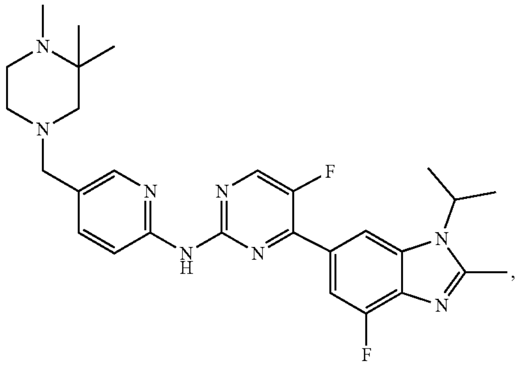
, and
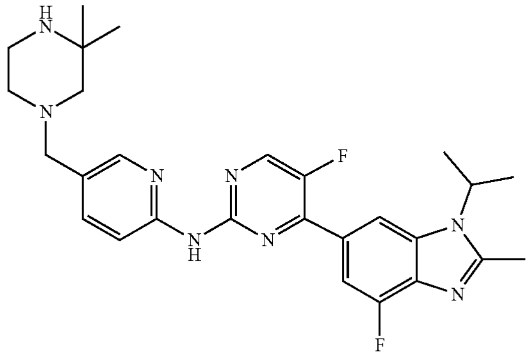
,
or a pharmaceutically acceptable salt thereof.
In other preferred embodiments, the compound of Formula (I) is selected from:
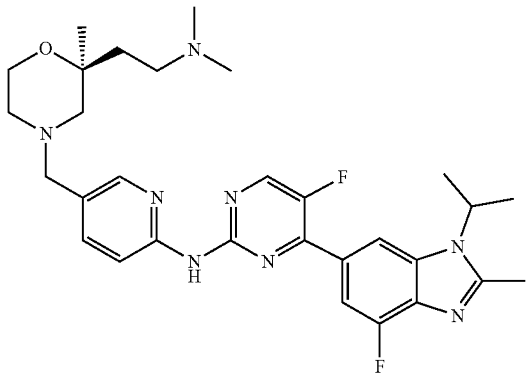
,
-continued
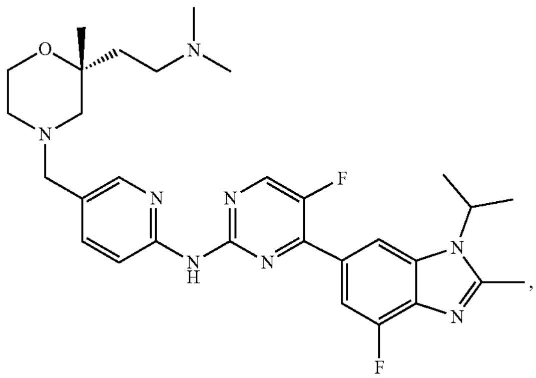
,
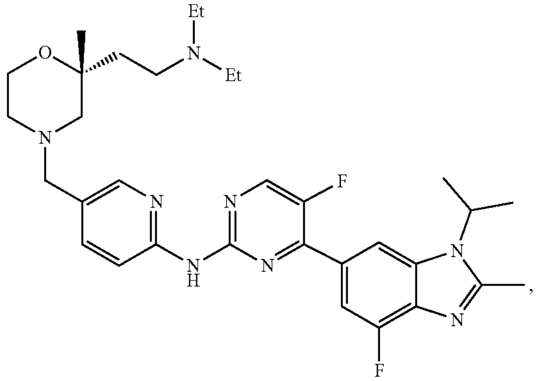
,
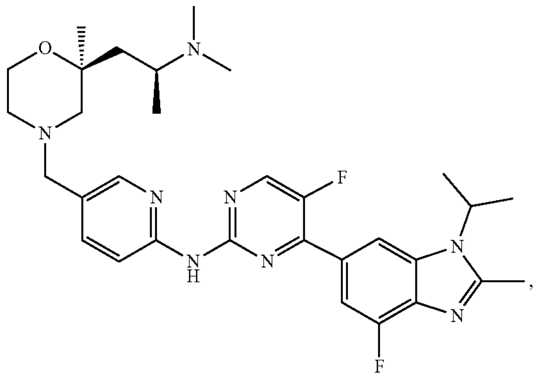
,
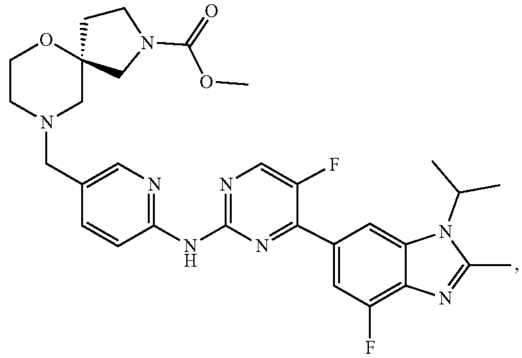
, and -continued
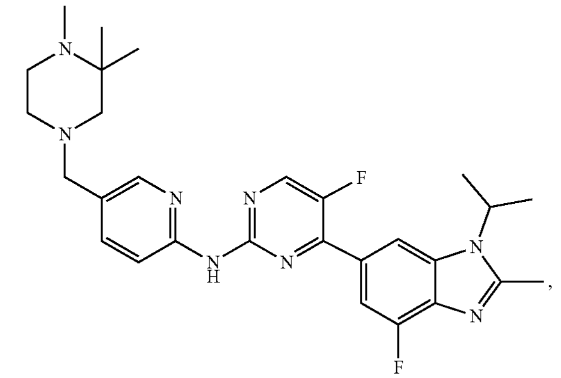
or a pharmaceutically acceptable salt thereof.
In yet other preferred embodiments, the compound of Formula (I) is selected from:
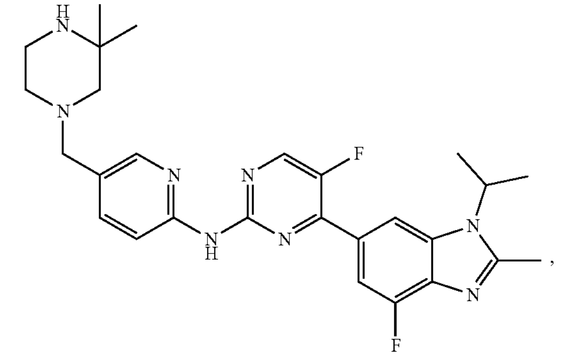
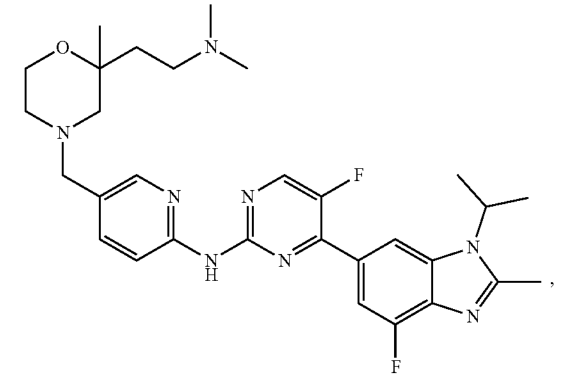
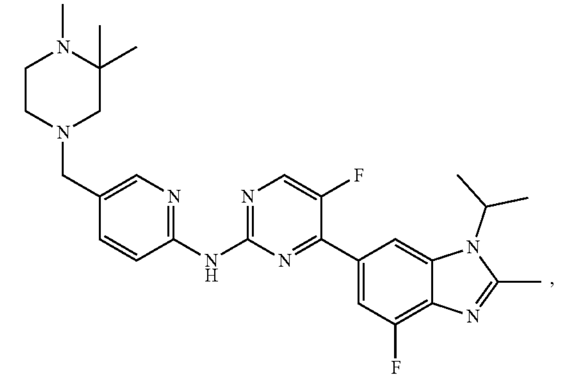
-continued
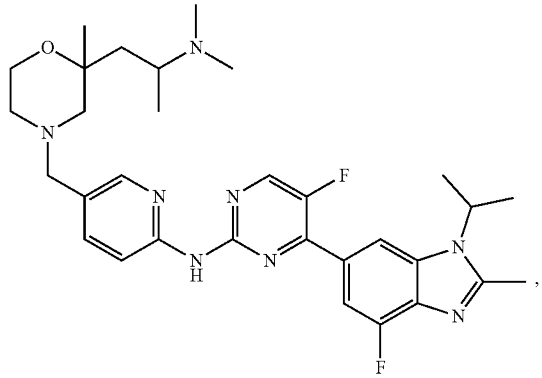
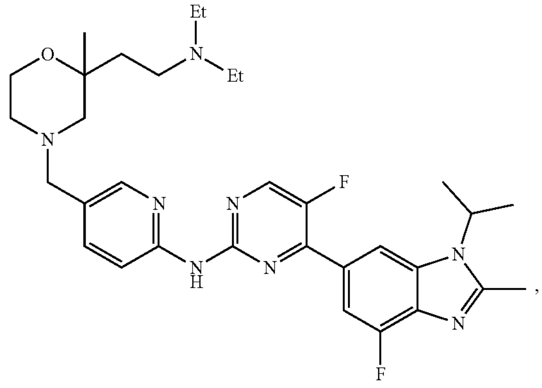 [SMILES: CCN(CC)CCC1(C)CN(Cc2ccc(Nc3ncc(F)c(-c4cc(F)c5nc(C)n(C(C)C)c5c4)n3)nc2)CCO1]
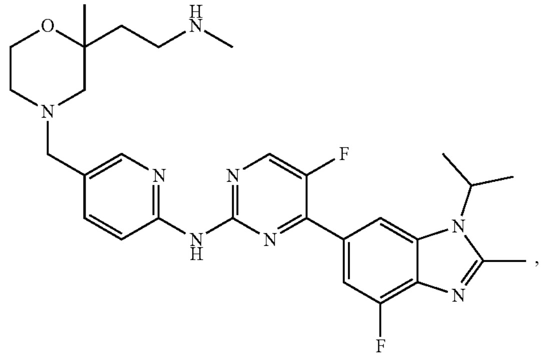
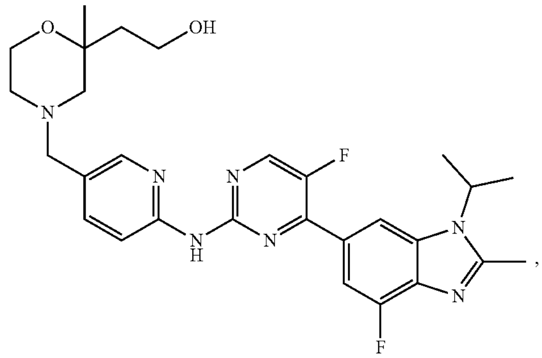

-continued
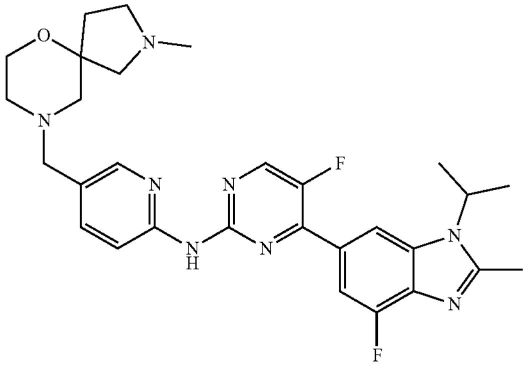
,
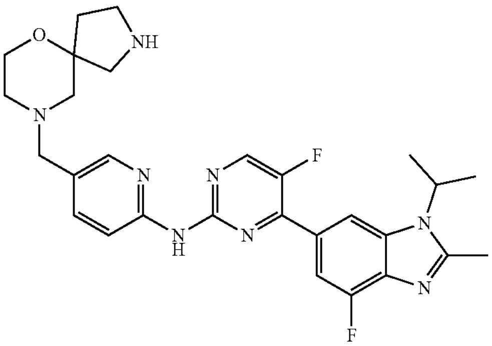
, and
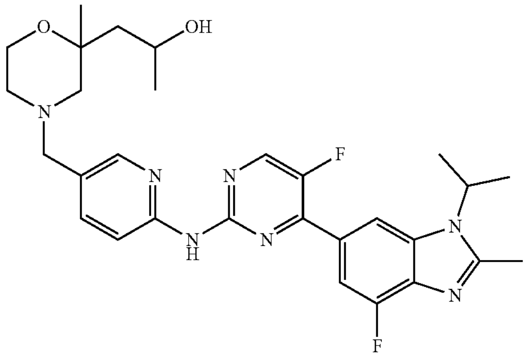
,
or a pharmaceutically acceptable salt thereof.
In still other preferred embodiments, the compound of Formula (I) is selected from:
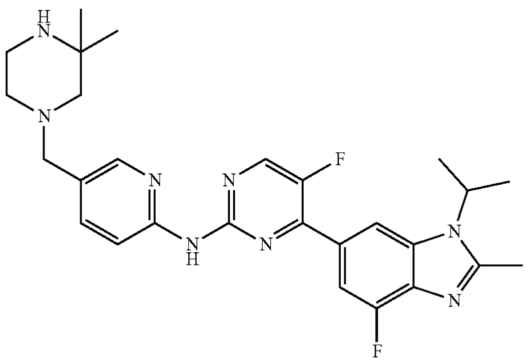
,
-continued
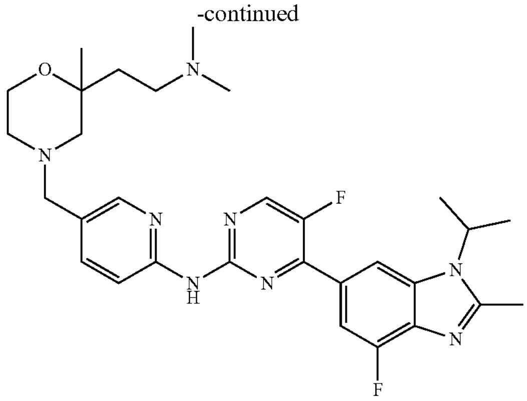
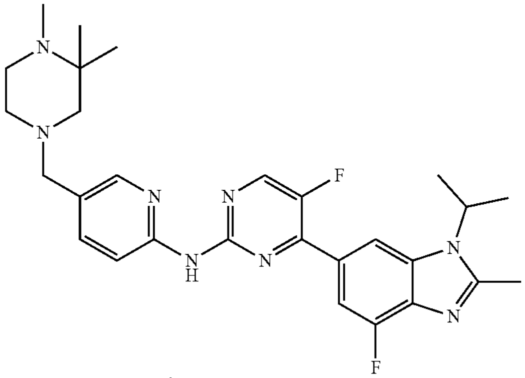
,
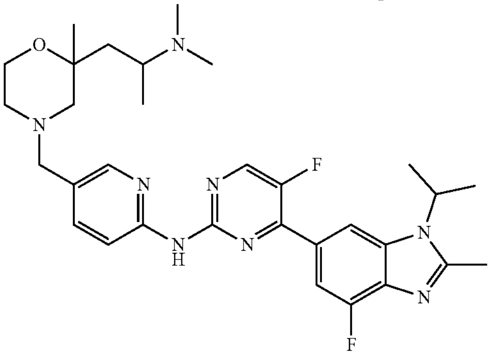
, and
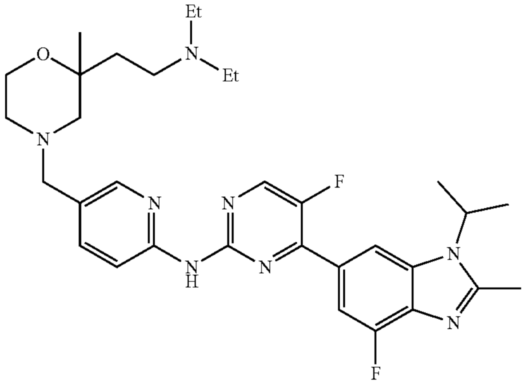
,
or a pharmaceutically acceptable salt thereof.
In other preferred embodiments, the compound of Formula (I) is selected from:

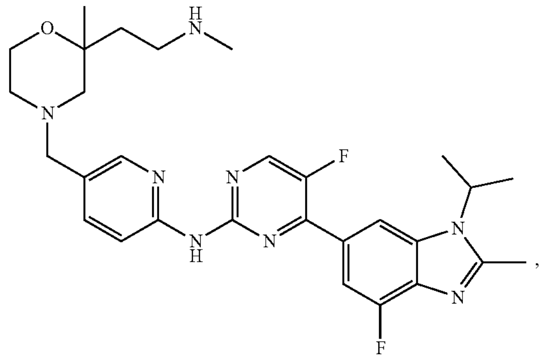
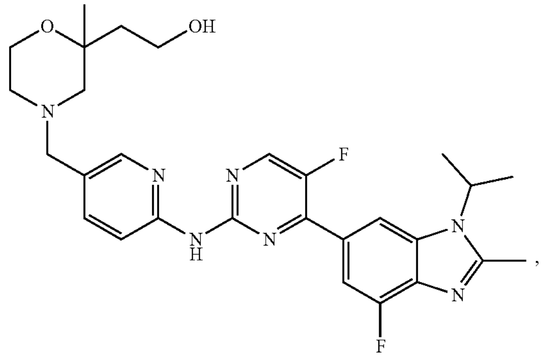
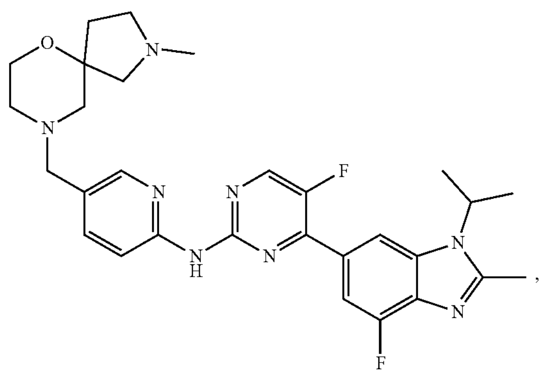
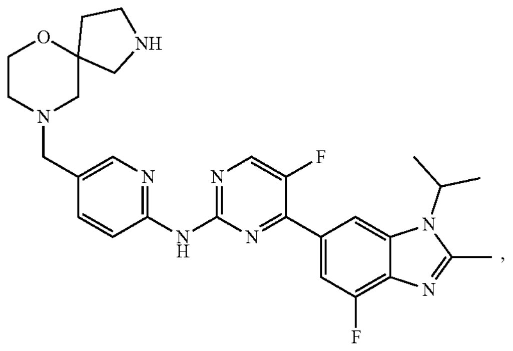
and
-continued
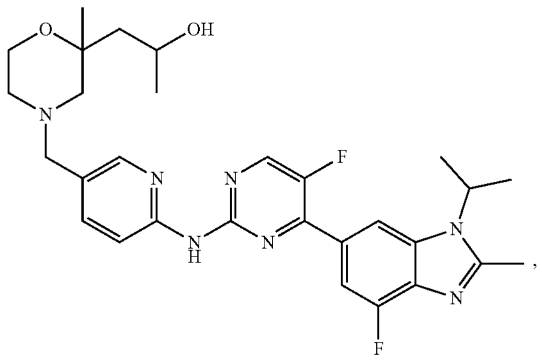 [SMILES: Cc1nc2c(F)cc(-c3nc(Nc4ccc(CN5CCOC(C)(CC(C)O)C5)cn4)ncc3F)cc2n1C(C)C]
or a pharmaceutically acceptable salt thereof.
In yet other preferred embodiments, the compound of Formula (I) is selected from:
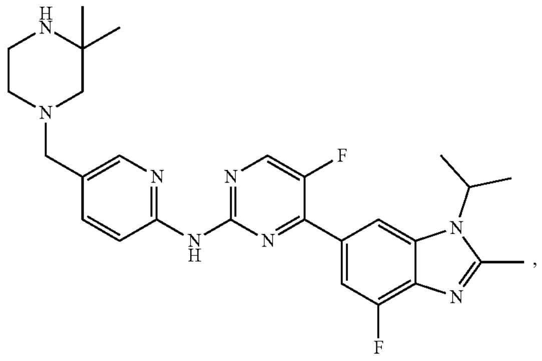
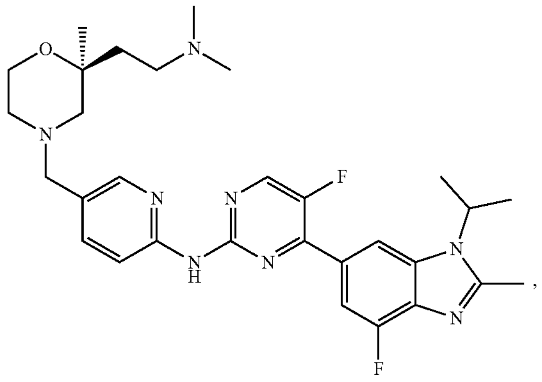
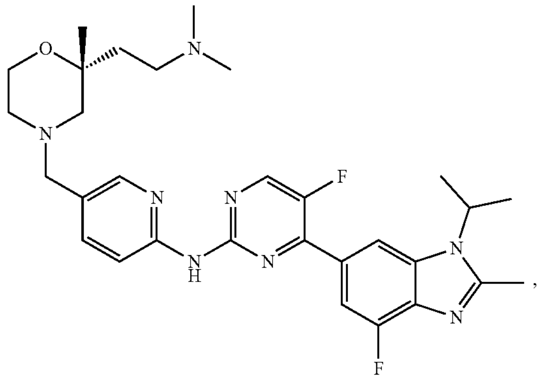

-continued
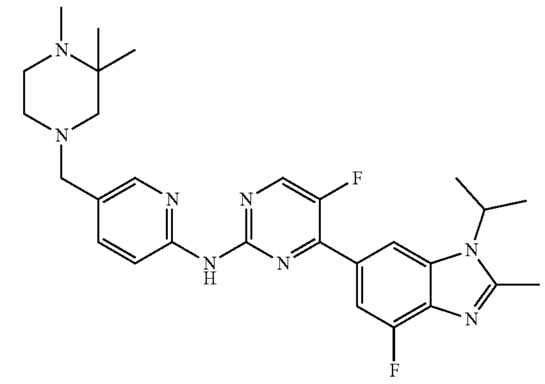
,
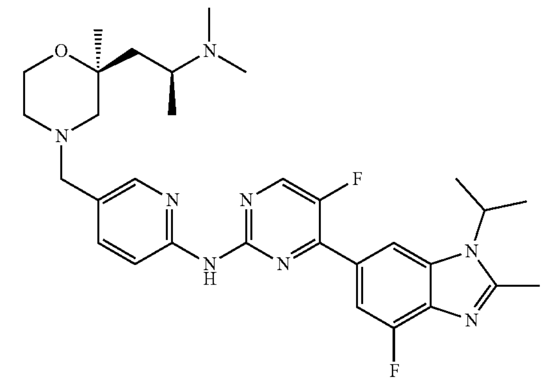
,
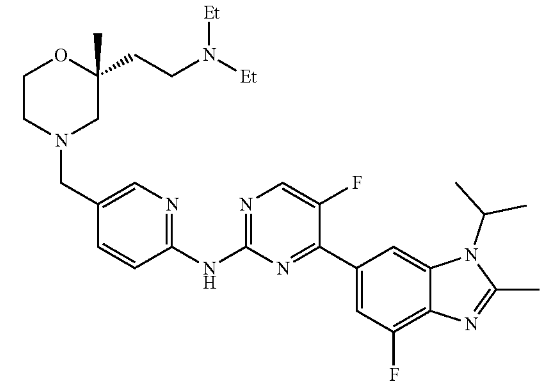
,
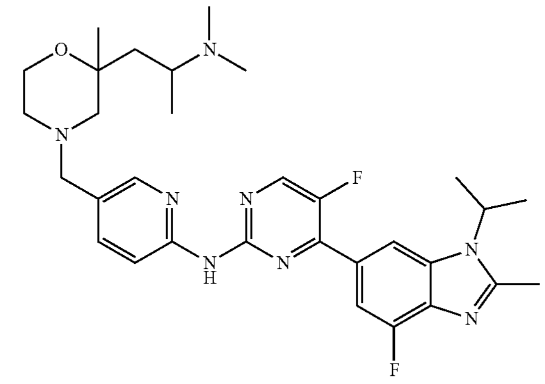
,
-continued
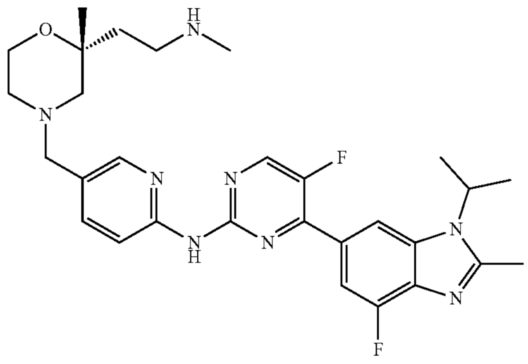
,
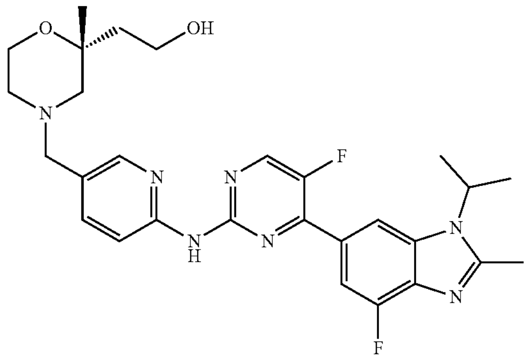
,
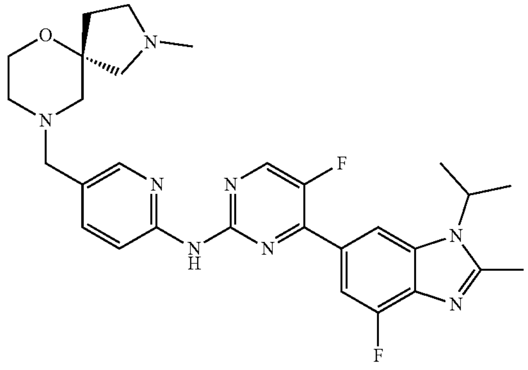
,
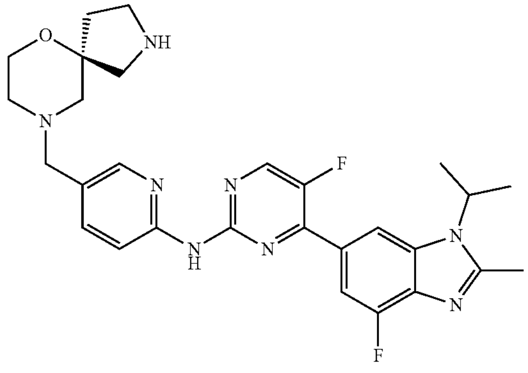
, -continued
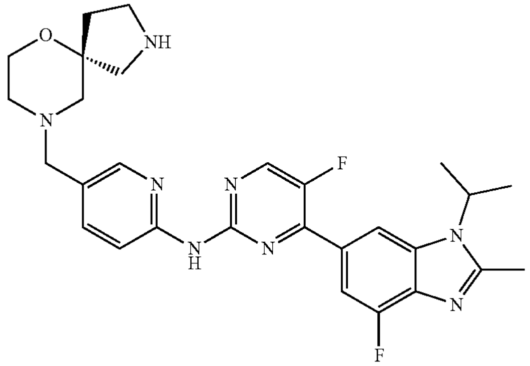
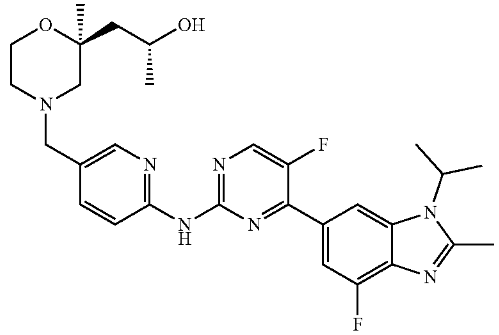
, and
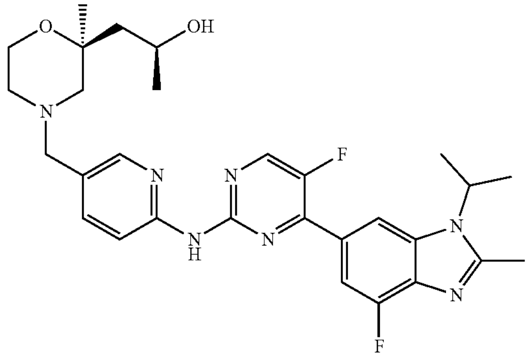
,
or a pharmaceutically acceptable salt thereof.
In still other preferred embodiments, the compound of Formula (I) is selected from:
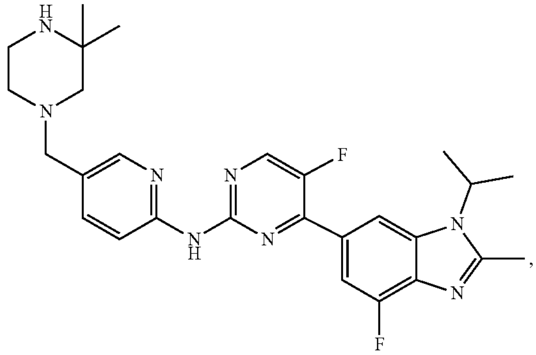
,
-continued
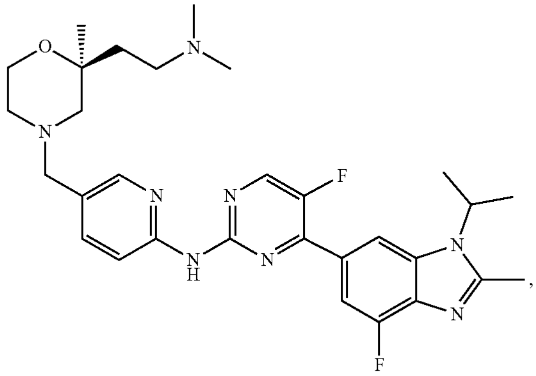
,
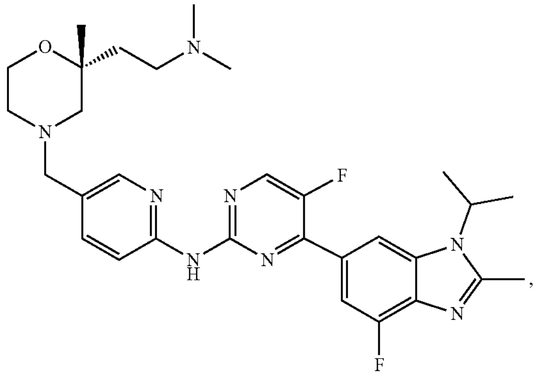
,
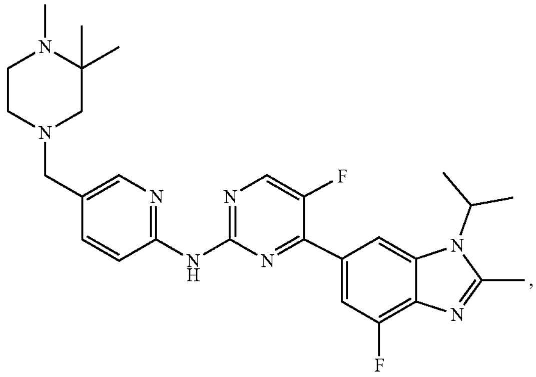
,
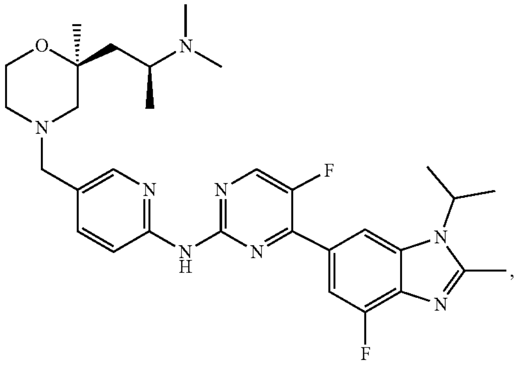
, and -continued
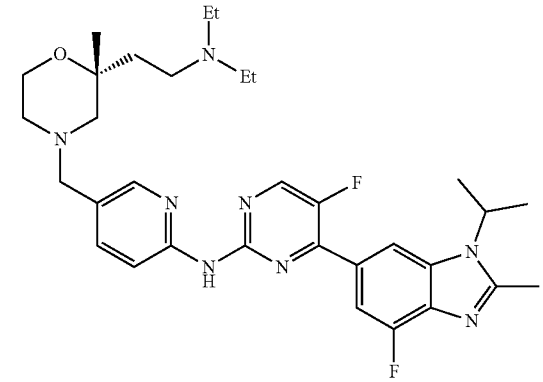
,
or a pharmaceutically acceptable salt thereof.
In other preferred embodiments, the compound of Formula (I) is selected from:
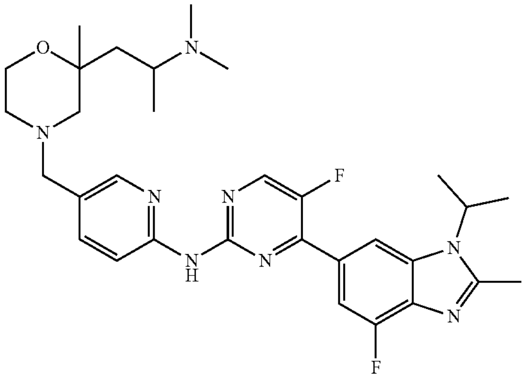
,
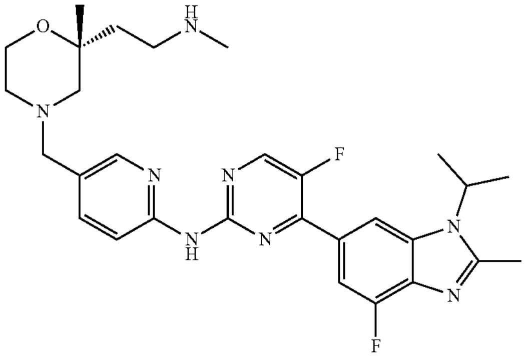
,
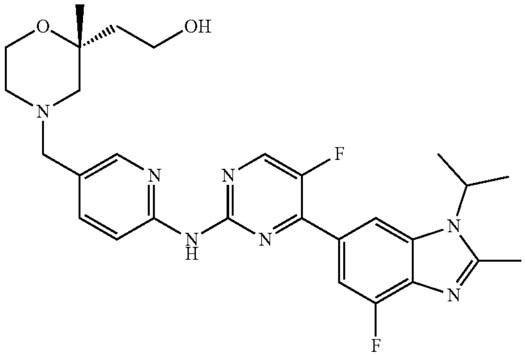
,
-continued
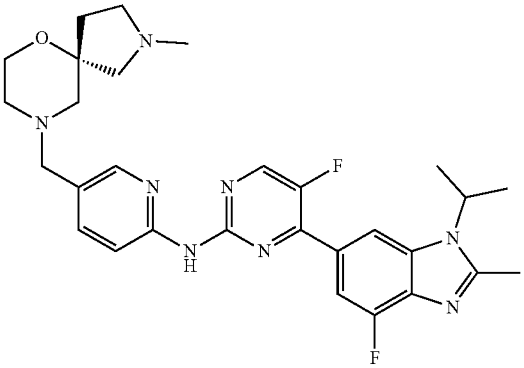
,
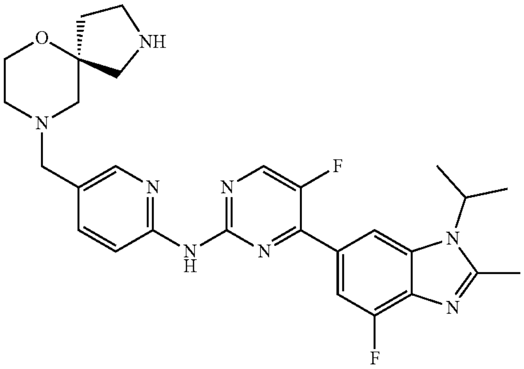
,
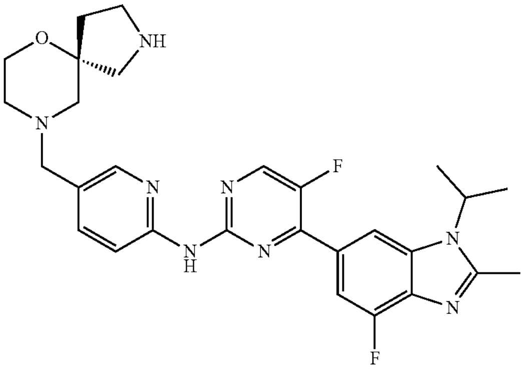
,
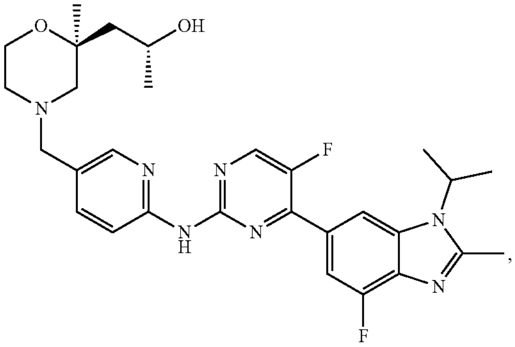
, and -continued
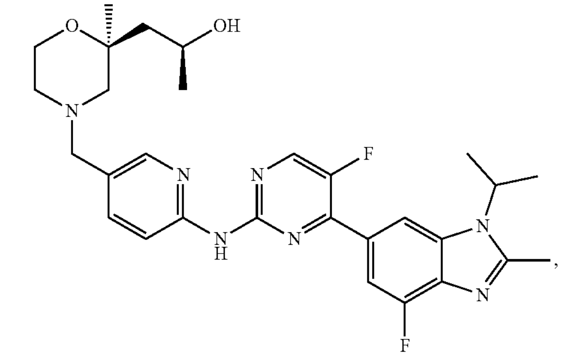
,
or a pharmaceutically acceptable salt thereof.
In some embodiments, the compound of Formula (I) is selected from:
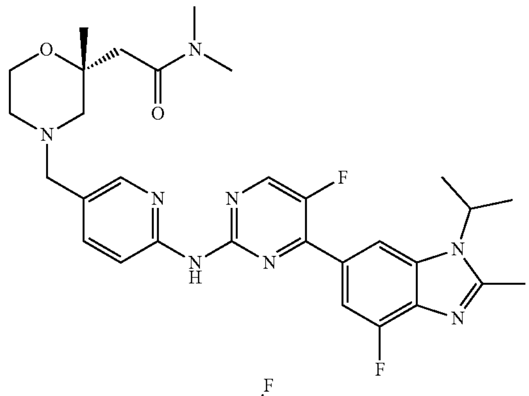
,
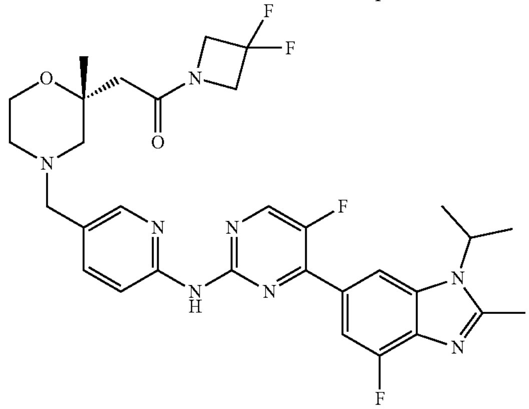
,
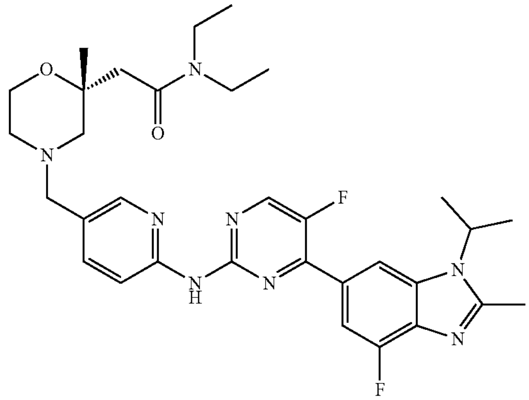
,
-continued
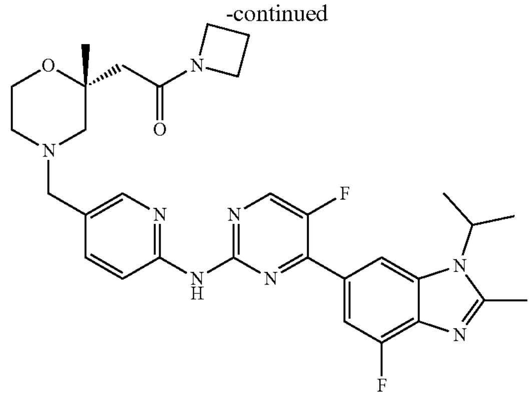
,
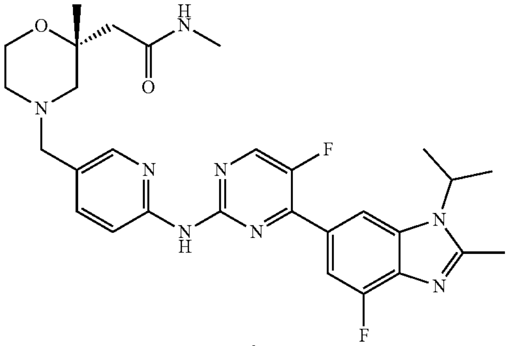
, and
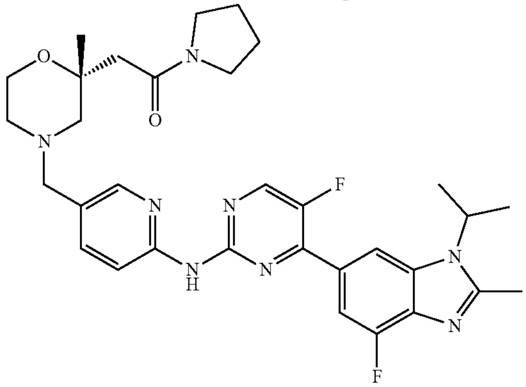
,
or a pharmaceutically acceptable salt thereof.
In some embodiments, the compound is a mesylate salt.
In certain embodiments, the invention relates to a compound having the structure of Formula (IVa) or (IVb):
(IVa)
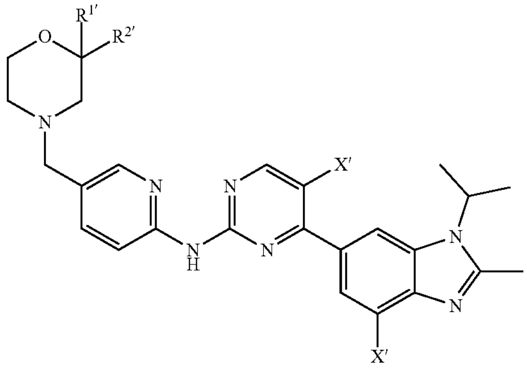

-continued (IVb)

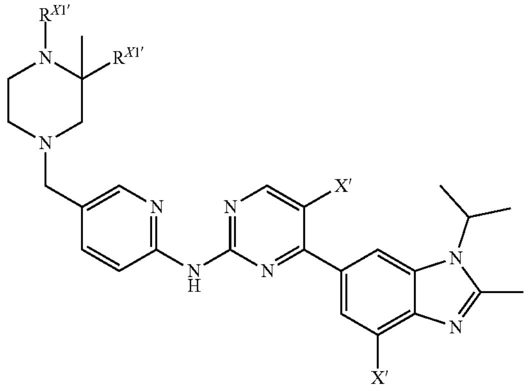

or a pharmaceutically acceptable salt thereof, wherein:

X' in each instance is independently halo, preferably F;

$R^{X1'}$ in each instance is independently H or lower alkyl;

$R^{1'}$ is $C_1$-$C_3$alkyl;

$R^{2'}$ is hydroxy alkyl or $(CR^{2c'}{}_2)_{n}NR^{2a'}R^{2b'}$;

$R^{2a'}$ is H, lower alkyl, acyl or haloalkyl;

$R^{2b'}$ is H, lower alkyl, acyl or haloalkyl; or $R^{2a'}$ and $R^{2b'}$ together through the N atom through which they are joined, form a 4-, 5- or 6-membered heterocyclic ring optionally substituted with $R^{ab'}{}_{z'}$; or $R^{1'}$ and $R^{2'}$ together through the C atom through which they are joined, form a 5- or 6-membered heterocyclic ring optionally substituted with acyloxy;

$R^{ab'}$, when present, in each instance is independently halo, hydroxy, lower alkyl or alkoxy;

each $R^{2c'}$ is independently H or alkyl, preferably methyl;

n' is an integer having a value of 1 or 2;

z' is an integer having a value of 0, 1 or 2; and wherein the compound has a CDK4 $K_i$ of about 0.960 nM or lower.

In some embodiments, the compound of Formula (IVa) or (IVb) has an average $IC_{50}$ of 150 nM or lower for the drug-sensitive cell lines of Table 2.

In certain embodiments, the average $IC_{50}$ of the compound of Formula (IVa) or (IVb) for the drug-sensitive cell lines of Table 2 is at least about 5-fold more potent than the average $IC_{50}$ of the same compound of Formula (IVa) or (IVb) for the drug-resistant cell lines of Table 2.

In certain embodiments, the compound of Formula (IVa) or (IVb) has a $P_{app}$ A-to-B score of about 0.07 or greater.

In certain embodiments, the compound of Formula (IVa) or (IVb) has a half-life of about 25 minutes or greater.

In some embodiments, the compound of Formula (IVa) or (IVb) is selected from:

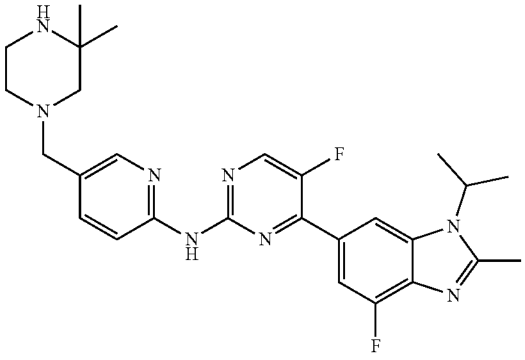

,

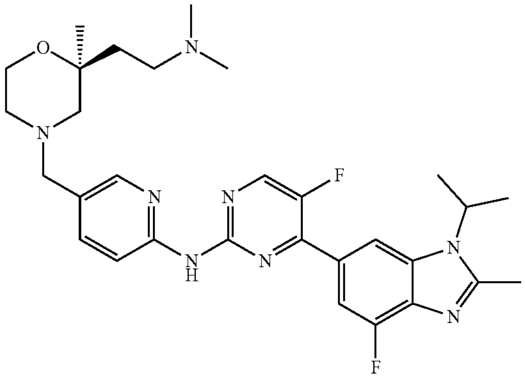

,

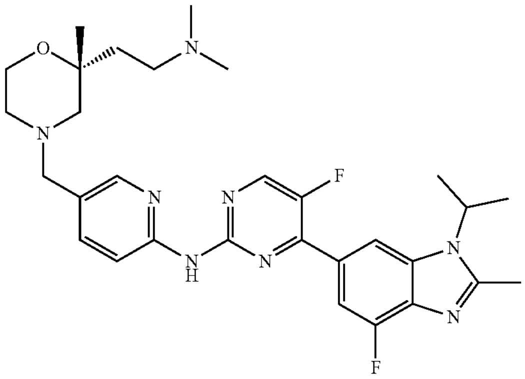

,

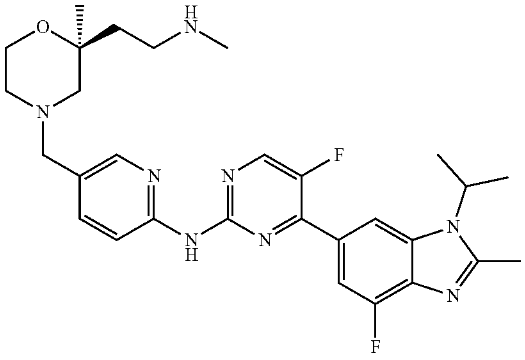

,

-continued
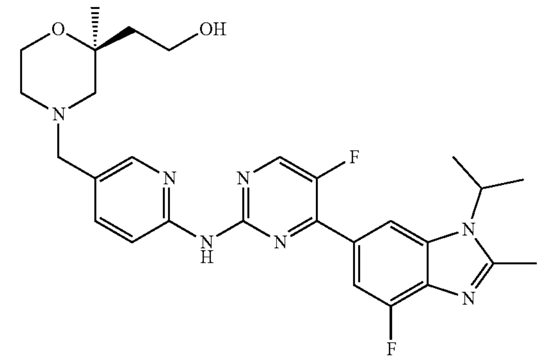
,
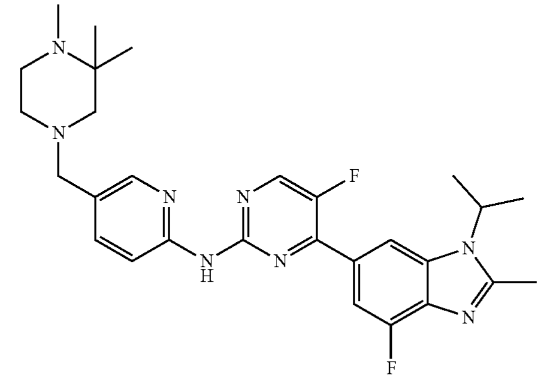
,
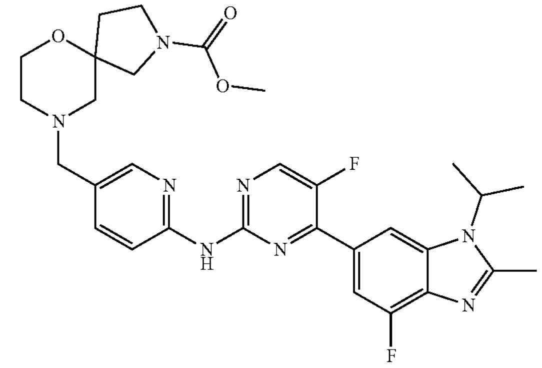
,
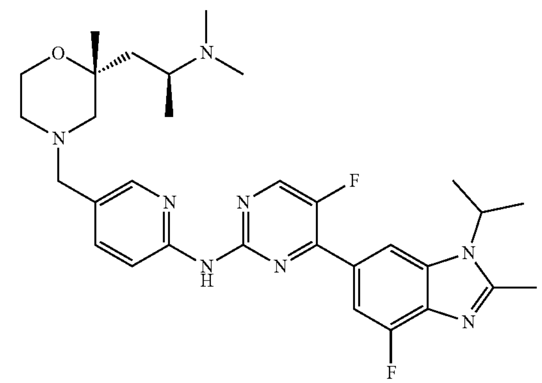
,
-continued
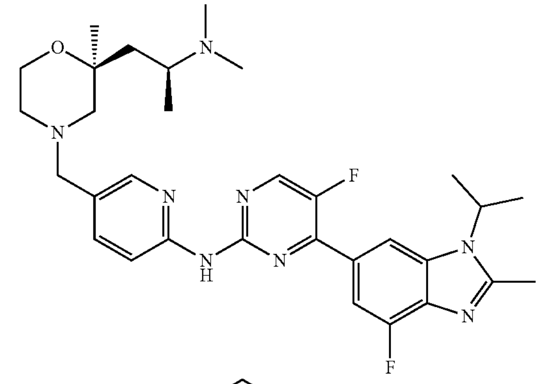
,
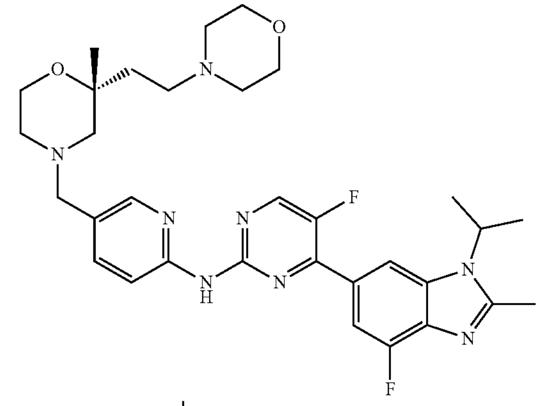
,
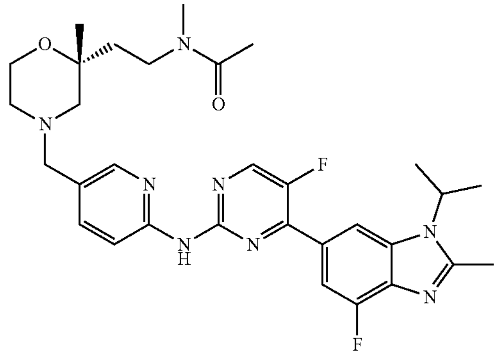
, and
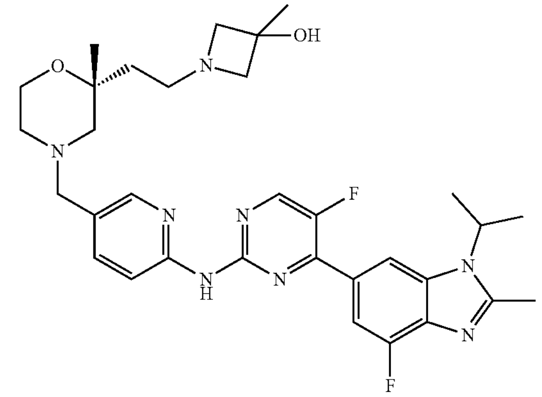
,
pharmaceutically salt thereof.
In some embodiments, the invention relates to a compound having the structure of Formula (V):

(V)

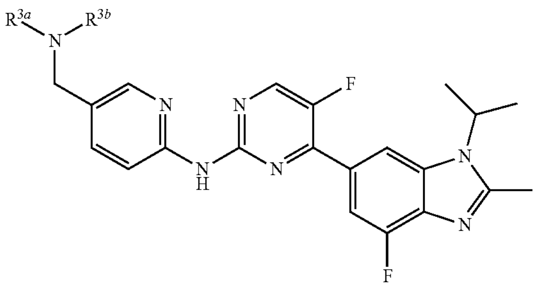

or a pharmaceutically acceptable salt thereof, wherein:

$R^{3a}$ and $R^{3b}$, taken together with the nitrogen atom to which they are attached, form an optionally substituted [3.3] spirocyclic moiety, wherein the optionally substituted [3.3] spirocyclic moiety optionally comprises at least one additional heteroatom selected from O, S, and SO2, provided that the compound is not

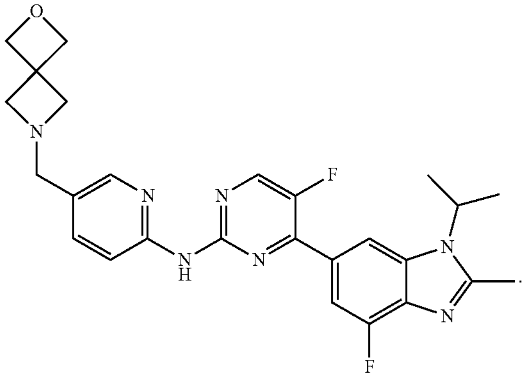 [SMILES: Cc1nc2c(F)cc(-c3nc(Nc4ccc(CN5CC6(COC6)C5)cn4)ncc3F)cc2n1C(C)C]

In some embodiments, the compound has the structure of Formula (Va):

(Va)

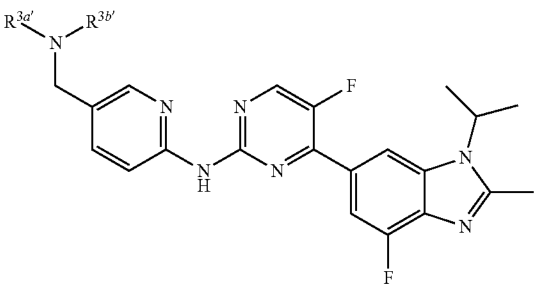

or a pharmaceutically acceptable salt thereof, wherein:

$R^{3a}$ and $R^{3b}$, taken together with the nitrogen atom to which they are attached, form a structure selected from:

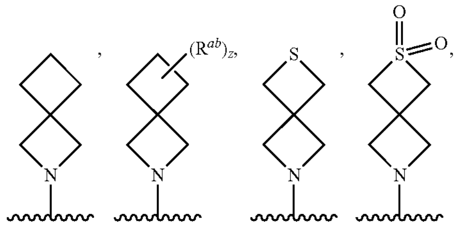

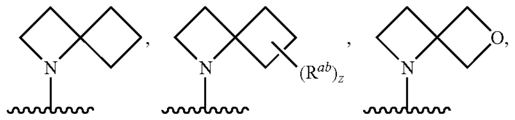

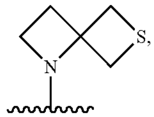

and

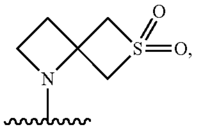

wherein each $R^{ab}$ is independently halo, hydroxyl, alkyl, haloalkyl, or alkoxy; and z is 0, 1, or 2.

In certain embodiments, $R^{3a}$ and $R^{3b}$, taken together with the nitrogen atom to which they are attached, form

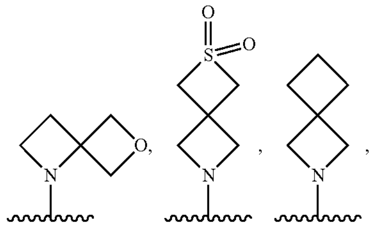

or

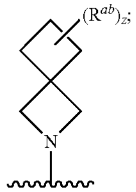

each $R^{ab}$ is independently halo; and z is 2.

In some embodiments, $R^{3a}$ and $R^{3b}$, taken together with the nitrogen atom to which they are attached, form

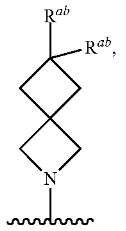

wherein $R^{ab}$ is fluoro.

In certain embodiments, the compound is selected from:

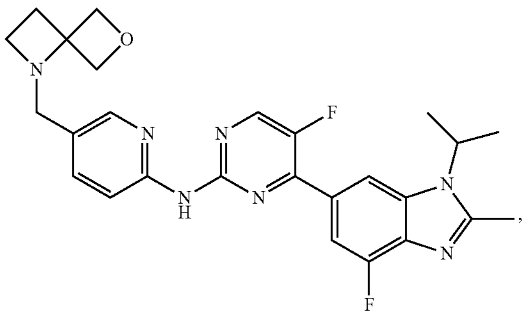

,

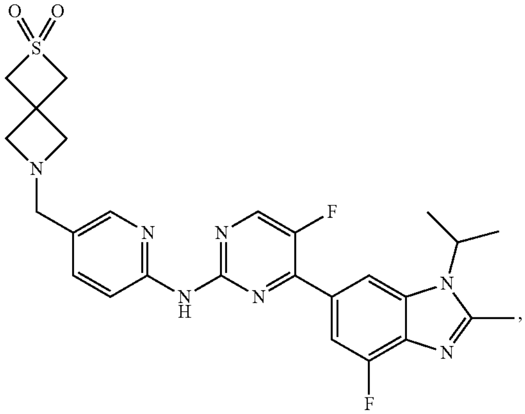

,

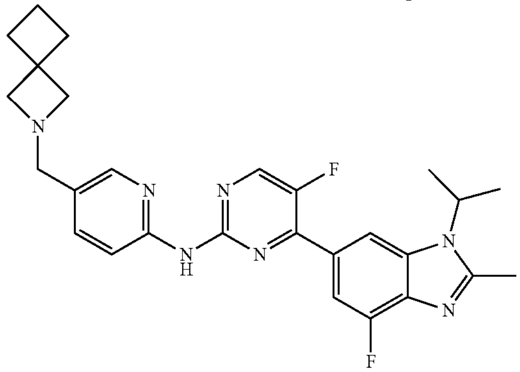

, and

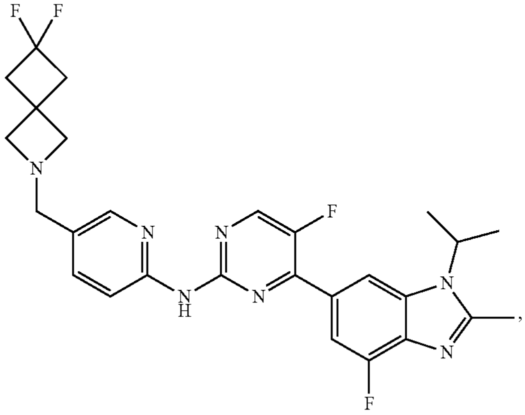

, or a pharmaceutically acceptable salt thereof.

Methods of Treatment

The compounds of the present invention are inhibitors of CDK4/6 and therefore may be useful for treating diseases wherein the underlying pathology is (at least in part) mediated by CDK4/6. Such diseases include cancer and other diseases in which there is a disorder of cell proliferation, apoptosis, or differentiation.

Examples of cancers which may be treated with a compound of the present invention include but are not limited to, carcinoma, for example a carcinoma of the bladder, breast, colon (e.g., colorectal carcinomas such as colon adenocarcinoma and colon adenoma), kidney, epidermis, liver, lung (e.g. adenocarcinoma, small cell lung cancer and non-small cell lung carcinomas), oesophagus, gall bladder, ovary, pancreas (e.g. exocrine pancreatic carcinoma), stomach, cervix, thyroid, nose, head and neck, prostate, and skin (e.g. squamous cell carcinoma) cancer. Other examples of cancers that may be treated with a compound of the present invention include hematopoietic tumours of lymphoid lineage (e.g. leukemia, acute lymphocytic leukemia, mantle cell lymphoma, chronic lymphocytic leukaemia, B-cell lymphoma (such as diffuse large B cell lymphoma), T-cell lymphoma, multiple myeloma, Hodgkin's lymphoma, non-Hodgkin's lymphoma, hairy cell lymphoma, and Burkett's lymphoma; hematopoietic tumours of myeloid lineage, for example acute and chronic myelogenous leukemias, myelodysplastic syndrome, and promyelocytic leukemia. Other cancers include thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; retinoblastoma; keratoctanthoma; thyroid follicular cancer; and Kaposi's sarcoma.

One group of cancers includes human breast cancers (e.g. primary breast tumours, node-negative breast cancer, invasive duct adenocarcinomas of the breast, non-endometrioid breast cancers); and endometrial cancers. Another subset of cancers wherein compounds having CDK4/6 inhibitory activity may be of particular therapeutic benefit include glioblastoma multiforme, T cell ALL, sarcomas, familial melanoma and melanoma. CDK4/6 inhibitors could also be useful in the treatment of viral infections, for example herpes virus, pox virus, Epstein-Barr virus, Sindbis virus, adenovirus, HIV, HPV, HCV, and HCMV; prevention of AIDS development in HIV-infected individuals; chronic inflammatory diseases, for example systemic lupus erythematosus, autoimmune mediated glomerulonephritis, rheumatoid arthritis, psoriasis, inflammatory bowel disease, and autoimmune diabetes mellitus; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplasia syndromes, ischemic injury associated myocardial infarctions, stroke and reperfusion injury, arrhythmia, atherosclerosis, toxin-induced or alcohol related liver diseases, hematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases, ophthalmic diseases including age related macular degeneration, uveitis, and cancer pain.

Moreover, the compounds of the present invention may be useful in the treatment of tumors with amplifications of CDK4 and CDK6 genes as well as tumors over-expressing cyclin partners of the cyclin-dependent kinases. In particular, the compounds of the present invention may be useful in the treatment of RB+ve (retinoblastoma protein positive)

tumors, including tumors harboring mutations in Ras, Raf, Growth Factor Receptors, or over-expression of Growth Factor Receptors. In addition, compounds of the present invention may also be useful in the treatment of RB−ve tumors.

The compounds of the present invention may also be useful in the treatment tumors with genetic aberrations that activate the CDK4/6 kinase activity. These include, but are not limited to, cancers with D-cyclin translocations such as mantle cell lymphoma and multiple myeloma, D-cyclin amplifications such as breast cancer and squamous cell esophageal cancer, CDK4 amplifications such as liposarcoma, CDK6 amplifications or over-expressions such as T-cell lymphoma, and p16 inactivation such as melanoma, non-small cell lung cancer and pancreatic cancer. The compounds of the present invention may be useful in the treatment of cancers that have genetic aberrations in the upstream regulators of D-cyclins, where the defect results in an increased D-cyclin abundance, can also be considered for treatment. These include, but are not limited to, acute myeloid leukemia with FLT3 activation, breast cancers with Her2/neu overexpression, ER dependency or triple negative phenotype, colon cancers with activating mutations of the MAPK, PI3K, or WNT pathway, melanomas with activating mutations of MAPK pathway, non small cell lung cancers with activating aberrations of EGFR pathway, and pancreatic cancers with activating aberrations of MAPK pathway including K-ras mutations.

The methods of treatment of the invention comprise administering a compound of the invention, or a pharmaceutically acceptable salt thereof, to a subject in need thereof. Individual embodiments of the invention include methods of treating any one of the above mentioned disorders or diseases by administering an effective amount of a compound of the invention, or a pharmaceutically acceptable salt thereof, to a subject in need thereof.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease. The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-9}$ molar and $10^{-3}$ molar concentrations. A therapeutically effective amount in vivo may range depending on the route of administration, between about 0.1-500 mg/kg, between about 1-100 mg/kg, or between about 100-300 mg/kg.

Certain embodiments of the present invention include a method of modulating CDK4/6 activity in a subject comprising administering to the subject a compound of the invention, or a pharmaceutically acceptable salt thereof. Additional embodiments of the present invention provide a method for the treatment of a disorder or a disease mediated by CDK4/6 in a subject in need thereof, comprising administering to the subject the compound of formula (I), (Ia), (Ib), (IVa), (IVb), (V), or (Va), or a pharmaceutically acceptable salt thereof. Other embodiments of the present invention provide a method of treating a disorder or a disease mediated by CDK4/6, in a subject in need of treatment thereof comprising administering a compound of the invention, or a pharmaceutically acceptable salt thereof, wherein the disorder or the disease is selected from carcinomas with genetic aberrations that activate the CDK4/6 kinase activity. These include, but are not limited to, cancers with D-cyclin translocations, such as mantle cell lymphoma and multiple myeloma, D-cyclin amplifications such as breast cancer and squamous cell esophageal cancer, CDK4 amplifications such as liposarcoma, CDK6 amplifications or over-expressions such as T-cell lymphoma and p16 inactivation such as melanoma, non-small cell lung cancer and pancreatic cancer.

The present invention also provides the use of a compound of the invention, or a pharmaceutically acceptable salt thereof, for the treatment of a disorder or disease mediated by CDK4.

In some embodiments, a compound of the invention, or a pharmaceutically acceptable salt thereof, is used for the treatment of a disorder or a disease mediated by CDK4, in a subject wherein the disorder or the disease is selected from carcinomas with genetic aberrations that activate the CDK4/6 kinase activity. These include, but are not limited to, cancers with D-cyclin translocations such as mantle cell lymphoma and multiple myeloma, D-cyclin amplifications such as breast cancer and squamous cell esophageal cancer, CDK4 amplifications such as liposarcoma, CDK6 amplifications or over-expressions such as T-cell lymphoma and p16 inactivation such as melanoma, non-small cell lung cancer and pancreatic cancer.

Yet other embodiments of the present invention provide a compound according to Formula (I), (Ia), (Ib), (IVa), (IVb), (V), or (Va), or a pharmaceutically acceptable salt thereof, for use as a medicament.

Still other embodiments of the present invention encompass the use of a compound of Formula (I), (Ia), (Ib), (IVa), (IVb), (V), or (Va), or a pharmaceutically acceptable salt thereof, in the manufacture of a medicament for the treatment of a disorder or disease mediated by CDK4/6 wherein the disorder or the disease is selected from carcinomas with genetic aberrations that activate the CDK4/6 kinase activity. These include, but are not limited to, cancers with D-cyclin translocations such as mantle cell lymphoma and multiple myeloma, D-cyclin amplifications such as breast cancer and squamous cell esophageal cancer, CDK4 amplifications such as liposarcoma, CDK6 amplifications or overexpressions such as T-cell lymphoma and p16 inactivation such as melanoma, non-small cell lung cancer and pancreatic cancer.

Combinations

The compounds of the present invention may be conjointly administered either simultaneously with, or before or after, one or more other therapeutic agents. The compounds of the present invention may be administered separately, by the same or different route of administration, or together in the same pharmaceutical composition as the other agents.

In some embodiments, the invention provides a product comprising a compound of the invention, or a pharmaceutically acceptable salt thereof, and at least one other therapeutic agent as a combined preparation for simultaneous, separate or sequential use in therapy. In some such embodiments, the therapy is the treatment of a disease or condition mediated by CDK4/6 inhibition. Products provided as a combined preparation include a composition comprising the compound of the present invention and the other therapeutic agent(s) together in the same pharmaceutical composition, or the compound of the present invention and the other therapeutic agent(s) in separate form, e.g., in the form of a kit. In certain embodiments, the invention provides a pharmaceutical composition comprising a compound of the invention, or a pharmaceutically acceptable salt thereof, and another therapeutic agent(s). Optionally, the pharmaceutical composition may comprise a pharmaceutically acceptable excipient, as described above.

In some embodiments, the invention provides a kit comprising two or more separate pharmaceutical compositions, at least one of which contains a compound of the invention, or a pharmaceutically acceptable salt thereof. In some such embodiments, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration. In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g., in the case of a kit comprising the compound of the invention and the other therapeutic agent); (ii) by the physician themselves (or under the guidance of the physician) shortly before administration; (iii) in the patient themselves, e.g., during sequential administration of the compound of the invention and the other therapeutic agent. Accordingly, the invention provides the use of a compound of the invention, or a pharmaceutically acceptable salt thereof, for treating a disease or condition mediated by inhibition of CDK4/6, wherein the medicament is prepared for administration with another therapeutic agent. The invention also provides the use of another therapeutic agent for treating a disease or condition mediated by inhibition of CDK4/6, wherein the medicament is administered with a compound of the present invention. The invention also provides a compound of the invention, or a pharmaceutically acceptable salt thereof, for use in a method of treating a disease or condition mediated by CDK4/6 inhibition, wherein the compound of the invention, or a pharmaceutically acceptable salt thereof, is prepared for administration with another therapeutic agent. The invention also provides another therapeutic agent for use in a method of treating a disease or condition mediated by CDK4/6 inhibition, wherein the other therapeutic agent is prepared for administration with a compound of the invention, or a pharmaceutically acceptable salt thereof. The invention also provides a compound of the invention, or a pharmaceutically acceptable salt thereof, for use in a method of treating a disease or condition mediated by CDK4/6 inhibition, wherein the compound of the invention, or a pharmaceutically acceptable salt thereof, is administered with another therapeutic agent. The invention also provides another therapeutic agent for use in a method of treating a disease or condition mediated by CDK4/6 inhibition, wherein the other therapeutic agent is administered with a compound of the invention, or a pharmaceutically acceptable salt thereof. The invention also provides the use of a compound of the invention, or a pharmaceutically acceptable salt thereof, for treating a disease or condition mediated by CDK4/6, wherein the patient has previously (e.g. within 24 hours) been treated with another therapeutic agent. The invention also provides the use of another therapeutic agent for treating a disease or condition mediated by CDK4/6, wherein the patient has previously (e.g., within 24 hours) been treated with a compound of the invention, or a pharmaceutically acceptable salt thereof.

In some embodiments, the other therapeutic agent is selected from an anti-inflammatory, anti-proliferative, chemotherapeutic agent, immunosuppressant, anti-cancer, cytotoxic agent or kinase inhibitor other than a compound of the present invention, or salt thereof. Further examples of agents that may be administered in combination with the compounds of the invention include, but are not limited to, a PTK inhibitor, cyclosporin A, CTLA4-lg, antibodies selected from anti-iCAM-3, anti-IL-2 receptor, anti-CD45RB, anti-CD2, anti-CD3, anti-CD4, anti-CD80, anti-CD86, and monoclonal antibody OKT3, agents blocking the interaction between CD40 and gp39, fusion proteins constructed from CD40 and gp39, inhibitors of NF-kappa B function, non-steroidal antiinflammatory drugs, steroids, gold compounds, antiproliferative agents, FK506, mycophenolate mofetil, cytotoxic drugs, TNF-a inhibitors, anti-TNF antibodies or soluble TNF receptor, rapamycin, mTOR inhibitors, leflunimide, cyclooxygenase-2 inhibitors, paclitaxel, cisplatin, carboplatin, doxorubicin, carminomycin, daunorubicin, aminopterin, methotrexate, methopterin, mitomycin C, ecteinascidin 743, porfiromycin, 5-fluororacii, 6-mercaptopurine, gemcitabine, cytosine arabinoside, podophyllotoxin, etoposide, etoposide phosphate, teniposide, melphalan, vinblastine, vincristine, leurosidine, epothilone, vindesine, leurosine, B-Raf inhibitor, MEK inhibitor, PI3K inhibitor, HSP90 inhibitor, CDK1 inhibitor, CDK2 inhibitor, CDK5 inhibitor, CDK7 inhibitor, CDK8 inhibitor, CDK9 inhibitor, EGFR inhibitor, FGFR inhibitor, PDGFR inhibitor, Her2 neu inhibitor, FLT3 inhibitor, Antagonists of androgen, glucocorticoid and prosterone receptors, S O inhibitor, WNT inhibitor, Bel inhibitor, IAP inhibitor, cl inhibitor, MD 2 inhibitor, p52 inhibitor, proteosome inhibitors (Velcade), or derivatives thereof.

Specific individual combinations that may provide particular treatment benefits include co-treatment of mantle cell lymphoma or pancreatic cancer patients with mTOR inhibitors, such as everolimus.

In some embodiments, a compound of the present invention may also be used in combination with other agents, e.g., an additional protein kinase inhibitor that is or is not a compound of the invention, for treatment of a protein kinase-associated disorder in a subject. By the term "combination" is meant either a fixed combination in one dosage unit form, or a kit of parts for the combined administration where a compound of the present invention and a combination partner may be administered independently at the same time or separately within time intervals that especially allow that the combination partners show a cooperative, e.g., synergistic, effect, or any combination thereof.

The compounds of the invention may be administered, simultaneously or sequentially, with an anti-inflammatory, anti-proliferative, chemotherapeutic agent, immunosuppressant, anti-cancer, cytotoxic agent or kinase inhibitor other than a compound of the Formula I or pharmaceutically acceptable salt thereof. Further examples of agents that may be administered in combination with the compounds of the invention include, but are not limited to, a PTK inhibitor, cyclosporin A, CTLA4-lg, antibodies selected from anti-ICAM-3, anti-IL-2 receptor, anti-CD45RB, anti-CD2, anti-CD3, anti-CD4, anti-CD80, anti-CD86, and monoclonal antibody OKT3, agents blocking the interaction between CD40 and gp39, fusion proteins constructed from CD40 and gp39, inhibitors of NF-kappa B function, non-steroidal anti-inflammatory drugs, steroids, gold compounds, antiproliferative agents, FK506, mycophenolate mofetil, cytotoxic drugs, TNF-ct inhibitors, anti-TNF antibodies or soluble TNF receptor, rapamycin, leflunimide, cyclooxygenase-2 inhibitors, paclitaxel, cisplatin, carboplatin, doxorubicin, carminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin, etoposide, etoposide phosphate, teniposide, melphalan, vinblastine, vincristine, leurosidine, epothilone, vindesine, leurosine, or derivatives thereof.

A compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times.

Alternatively, a composition of this invention may comprise an additional agent as described herein. Each component may be present in individual compositions, combination compositions, or in a single composition.

Pharmaceutical Compositions and Administration Thereof

The compositions and methods disclosed herein may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a disclosed compound and a pharmaceutically acceptable carrier.

Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection, or the like. The composition can also be present in a transdermal delivery system, e.g., a skin patch. The composition can also be present in a solution suitable for topical administration, such as an ointment or cream.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary, or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups, and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697, and 2005/004074; and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1% to about 99.5% (more preferably, about 0.5% to about 90.0%) of active ingredient in combination with a pharmaceutically acceptable carrier.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

EXEMPLIFICATION
Synthetic Protocols
TABLE 1
| Cmpd No | STRUCTURE |
|---|---|
| Abemaciclib (Ref. Cmpd. 1) | 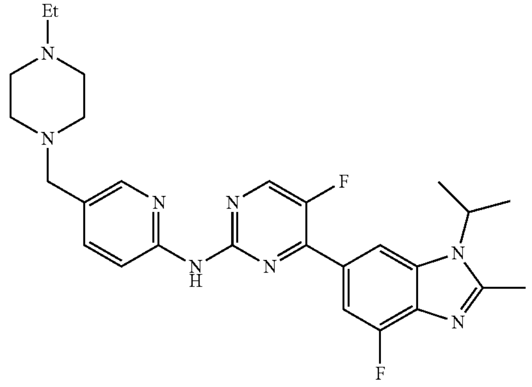 [SMILES: CCN1CCN(Cc2ccc(Nc3ncc(F)c(-c4cc(F)c5nc(C)n(C(C)C)c5c4)n3)nc2)CC1] |
| Palbociclib (Ref. Cmpd. 2) | 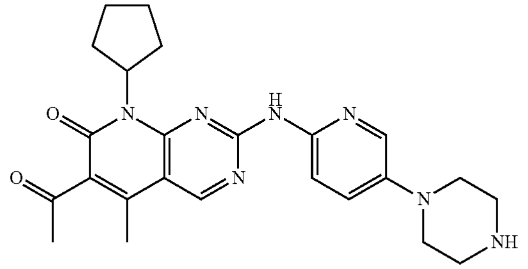 [SMILES: CC(=O)c1c(C)c2cnc(Nc3ccc(N4CCNCC4)cn3)nc2n(C2CCCC2)c1=O] |
| Ribociclib (Ref. Cmpd 3) | 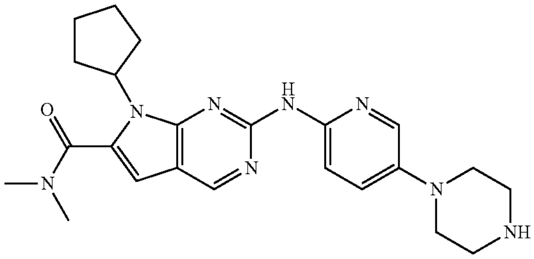 [SMILES: CN(C)C(=O)c1cc2cnc(Nc3ccc(N4CCNCC4)cn3)nc2n1C1CCCC1] |
| A45 | 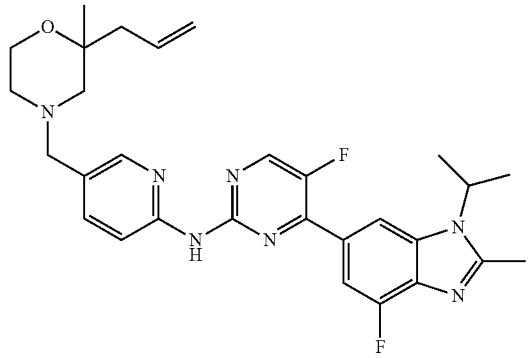 [SMILES: C=CCC1(C)CN(Cc2ccc(Nc3ncc(F)c(-c4cc(F)c5nc(C)n(C(C)C)c5c4)n3)nc2)CCO1] |

TABLE 1-continued
| Cmpd No | STRUCTURE |
|---|---|
| A46 | 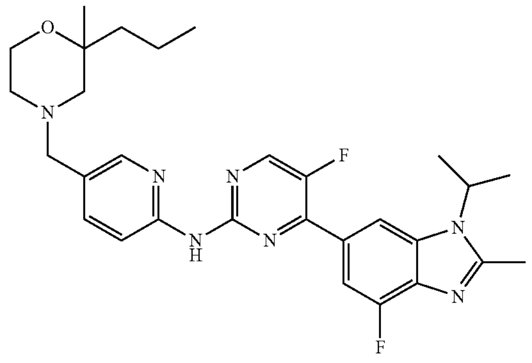 [SMILES: CCCC1(C)CN(Cc2ccc(Nc3ncc(F)c(-c4cc(F)c5nc(C)n(C(C)C)c5c4)n3)nc2)CCO1] |
| A40 | 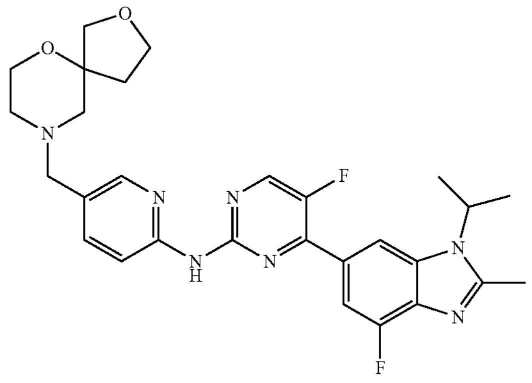 [SMILES: Cc1nc2c(F)cc(-c3nc(Nc4ccc(CN5CCOC6(CCOC6)C5)cn4)ncc3F)cc2n1C(C)C] |
| A48 | 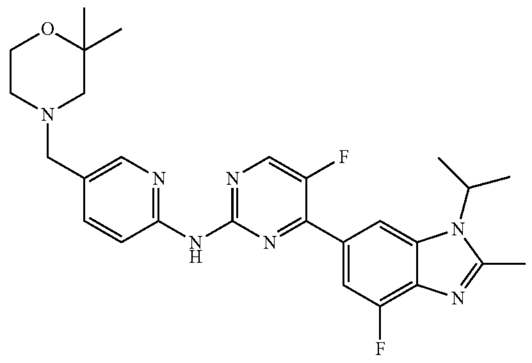 [SMILES: Cc1nc2c(F)cc(-c3nc(Nc4ccc(CN5CCOC(C)(C)C5)cn4)ncc3F)cc2n1C(C)C] |
| A4 | 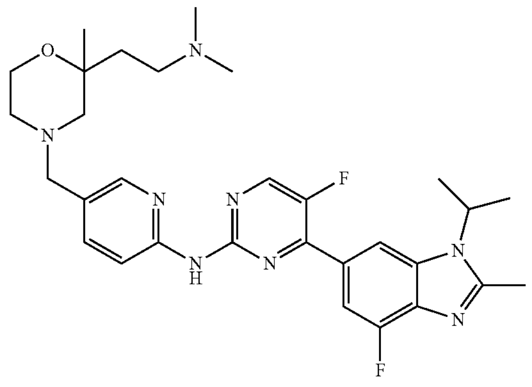 [SMILES: Cc1nc2c(F)cc(-c3nc(Nc4ccc(CN5CCOC(C)(CCN(C)C)C5)cn4)ncc3F)cc2n1C(C)C] |

TABLE 1-continued
| Cmpd No | STRUCTURE |
| --- | --- |
| A44 | 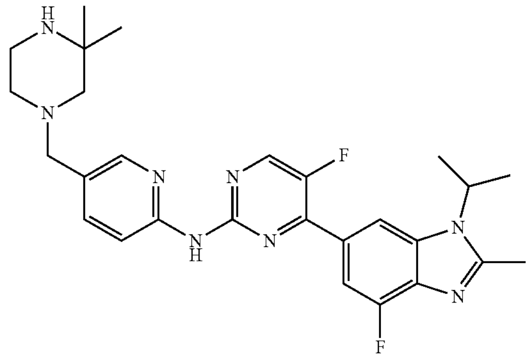 [SMILES: Cc1nc2c(F)cc(-c3nc(Nc4ccc(CN5CCNC(C)(C)C5)cn4)ncc3F)cc2n1C(C)C] |
| A1 | 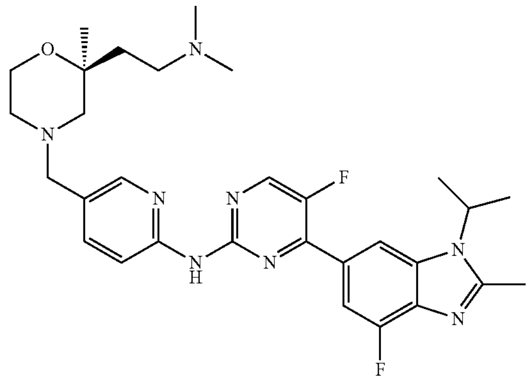 [SMILES: Cc1nc2c(F)cc(-c3nc(Nc4ccc(CN5CCO[C@@](C)(CCN(C)C)C5)cn4)ncc3F)cc2n1C(C)C] |
| A2 | 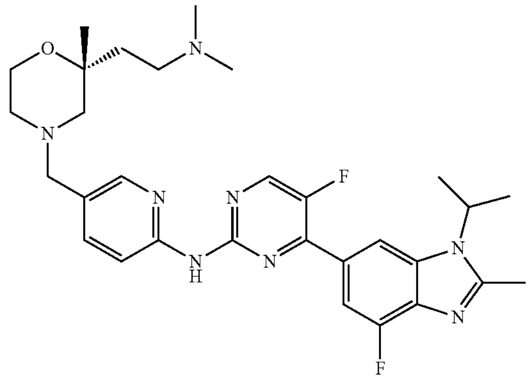 [SMILES: Cc1nc2c(F)cc(-c3nc(Nc4ccc(CN5CCO[C@](C)(CCN(C)C)C5)cn4)ncc3F)cc2n1C(C)C] |
| A25 | 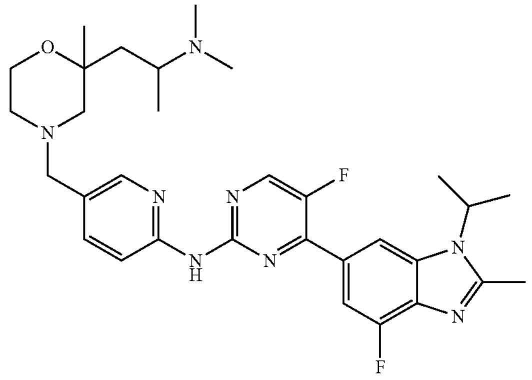 [SMILES: Cc1nc2c(F)cc(-c3nc(Nc4ccc(CN5CCOC(C)(CC(C)N(C)C)C5)cn4)ncc3F)cc2n1C(C)C] |

TABLE 1-continued
| Cmpd No | STRUCTURE |
|---|---|
| A24 | 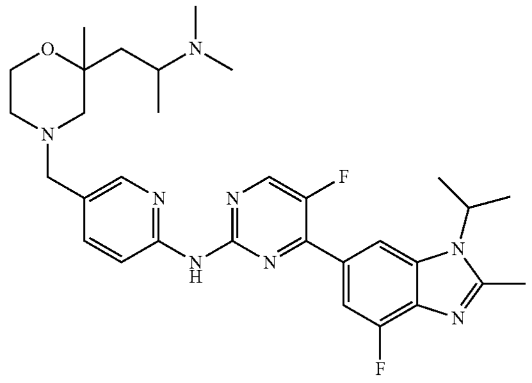 [SMILES: Cc1nc2c(F)cc(-c3nc(Nc4ccc(CN5CCOC(C)(CC(C)N(C)C)C5)cn4)ncc3F)cc2n1C(C)C] |
| A5 | 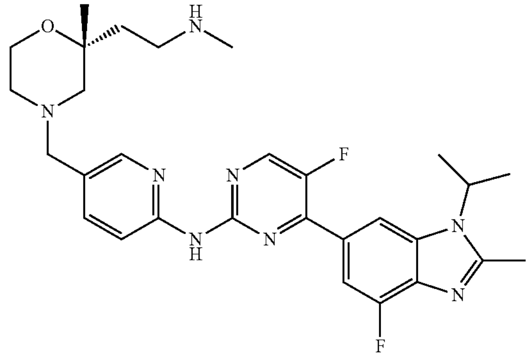 [SMILES: CNCC[C@]1(C)CN(Cc2ccc(Nc3ncc(F)c(-c4cc(F)c5nc(C)n(C(C)C)c5c4)n3)nc2)CCO1] |
| A22 | 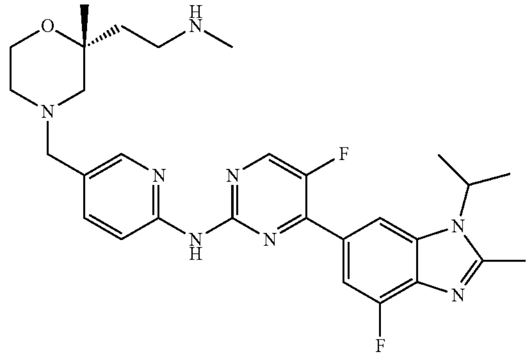 [SMILES: CNCC[C@]1(C)CN(Cc2ccc(Nc3ncc(F)c(-c4cc(F)c5nc(C)n(C(C)C)c5c4)n3)nc2)CCO1] |
| A49 | 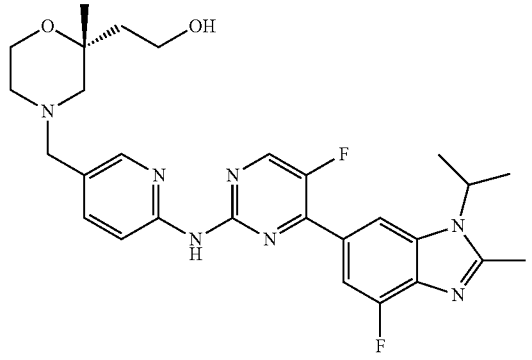 [SMILES: Cc1nc2c(F)cc(-c3nc(Nc4ccc(CN5CCO[C@](C)(CCO)C5)cn4)ncc3F)cc2n1C(C)C] |

TABLE 1-continued
| Cmpd No | STRUCTURE |
|---|---|
| A50 | 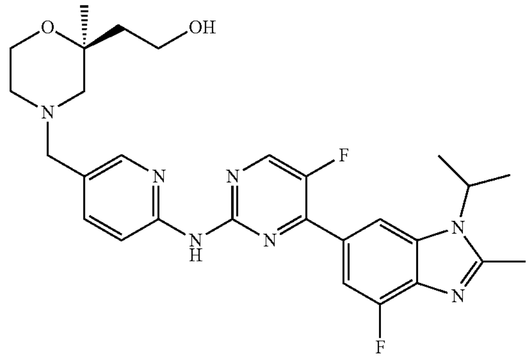 [SMILES: Cc1nc2c(F)cc(-c3nc(Nc4ccc(CN5CCO[C@@](C)(CCO)C5)cn4)ncc3F)cc2n1C(C)C] |
| A43 | 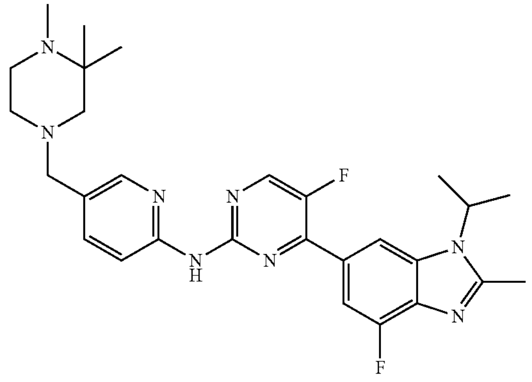 [SMILES: Cc1nc2c(F)cc(-c3nc(Nc4ccc(CN5CCN(C)C(C)(C)C5)cn4)ncc3F)cc2n1C(C)C] |
| A41 | 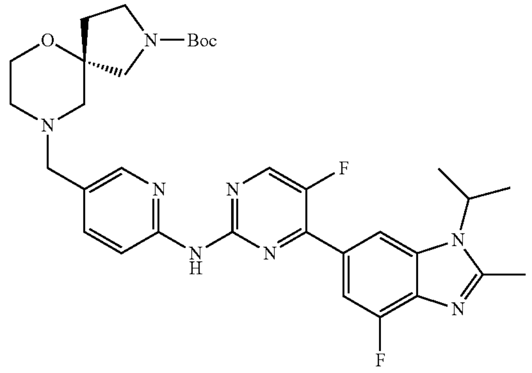 [SMILES: Cc1nc2c(F)cc(-c3nc(Nc4ccc(CN5CCO[C@@]6(CCN(C(=O)OC(C)(C)C)C6)C5)cn4)ncc3F)cc2n1C(C)C] |
| A42 | 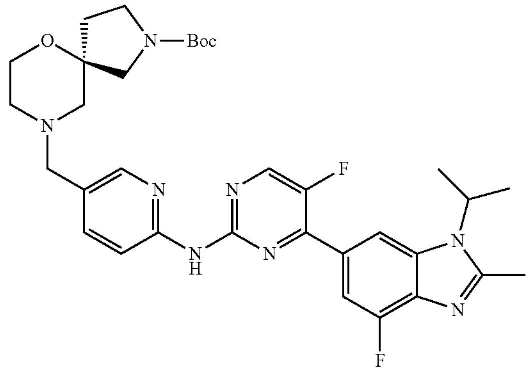 [SMILES: Cc1nc2c(F)cc(-c3nc(Nc4ccc(CN5CCO[C@]6(CCN(C(=O)OC(C)(C)C)C6)C5)cn4)ncc3F)cc2n1C(C)C] |

TABLE 1-continued
| Cmpd No | STRUCTURE |
|---|---|
| A39 | 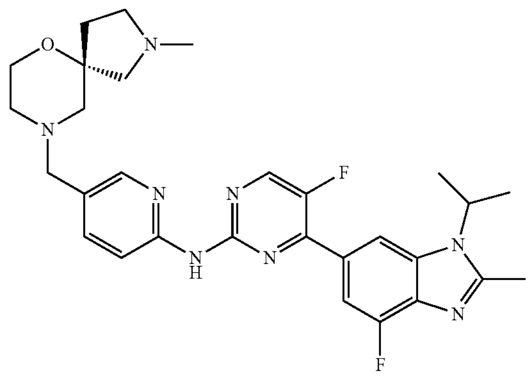 [SMILES: Cc1nc2c(F)cc(-c3nc(Nc4ccc(CN5CCO[C@@]6(CCN(C)C6)C5)cn4)ncc3F)cc2n1C(C)C] |
| A38 | 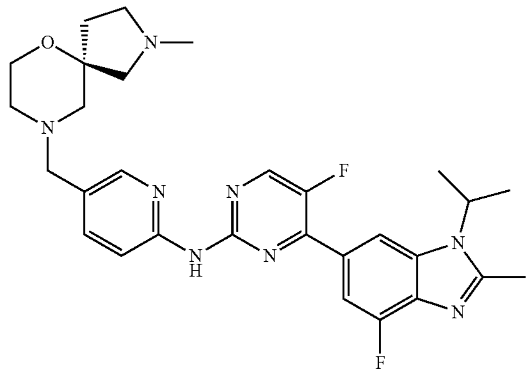 [SMILES: Cc1nc2c(F)cc(-c3nc(Nc4ccc(CN5CCO[C@]6(CCN(C)C6)C5)cn4)ncc3F)cc2n1C(C)C] |
| A37 | 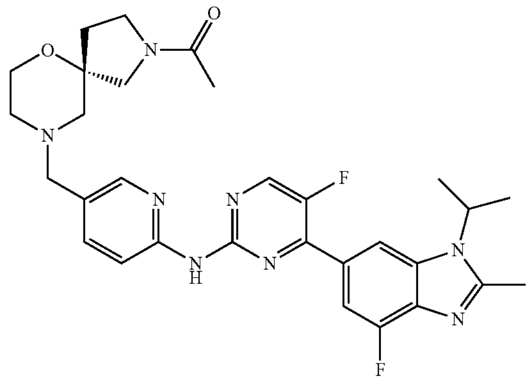 [SMILES: CC(=O)N1CC[C@]2(CN(Cc3ccc(Nc4ncc(F)c(-c5cc(F)c6nc(C)n(C(C)C)c6c5)n4)nc3)CCO2)C1] |
| A36 | 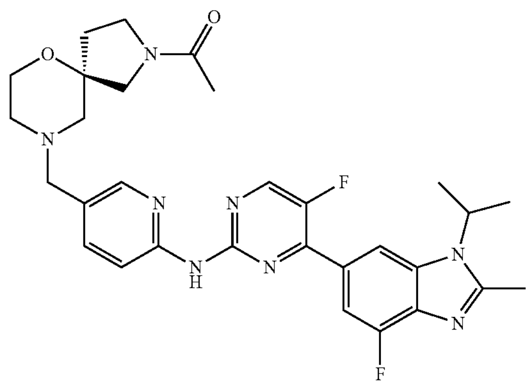 [SMILES: CC(=O)N1CC[C@@]2(CN(Cc3ccc(Nc4ncc(F)c(-c5cc(F)c6nc(C)n(C(C)C)c6c5)n4)nc3)CCO2)C1] |

TABLE 1-continued
| Cmpd No | STRUCTURE |
|---|---|
| A31 | 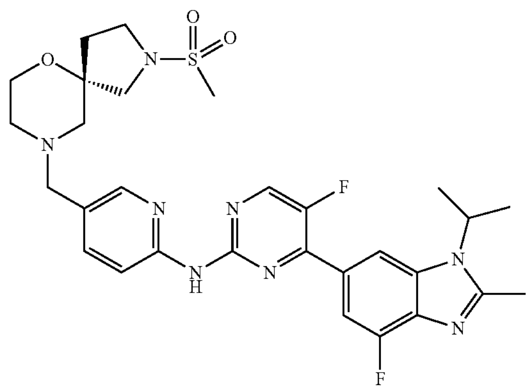 [SMILES: Cc1nc2c(F)cc(-c3nc(Nc4ccc(CN5CCO[C@@]6(CCN(S(C)(=O)=O)C6)C5)cn4)ncc3F)cc2n1C(C)C] |
| A32 | 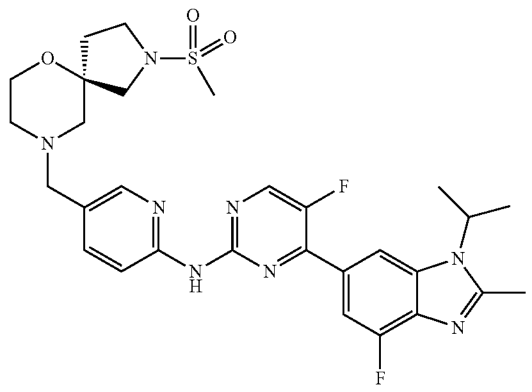 [SMILES: Cc1nc2c(F)cc(-c3nc(Nc4ccc(CN5CCO[C@]6(CCN(S(C)(=O)=O)C6)C5)cn4)ncc3F)cc2n1C(C)C] |
| A30 | 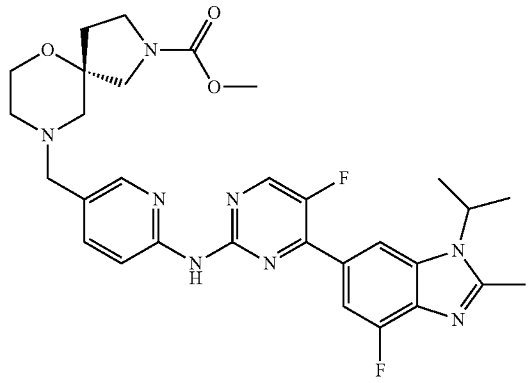 [SMILES: COC(=O)N1CC[C@]2(CN(Cc3ccc(Nc4ncc(F)c(-c5cc(F)c6nc(C)n(C(C)C)c6c5)n4)nc3)CCO2)C1] |
| A33 | 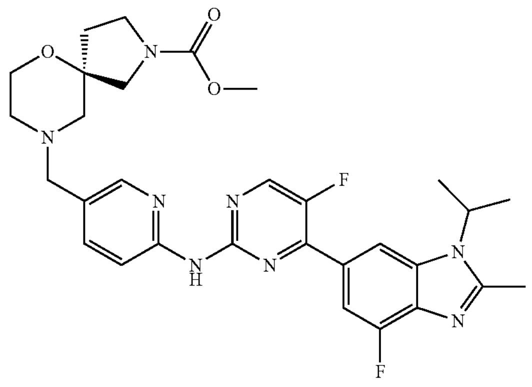 [SMILES: COC(=O)N1CC[C@@]2(CN(Cc3ccc(Nc4ncc(F)c(-c5cc(F)c6nc(C)n(C(C)C)c6c5)n4)nc3)CCO2)C1] |

TABLE 1-continued
| Cmpd No | STRUCTURE |
|---|---|
| A34 | 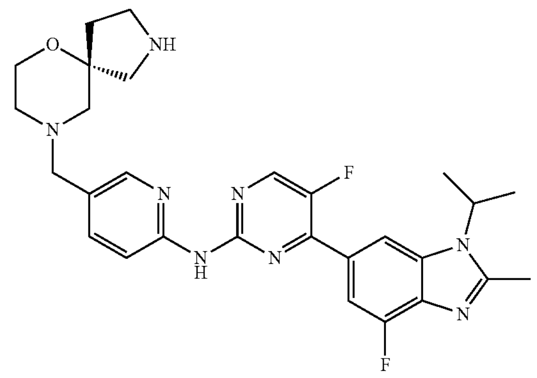 [SMILES: Cc1nc2c(F)cc(-c3nc(Nc4ccc(CN5CCO[C@@]6(CCNC6)C5)cn4)ncc3F)cc2n1C(C)C] |
| A35 | 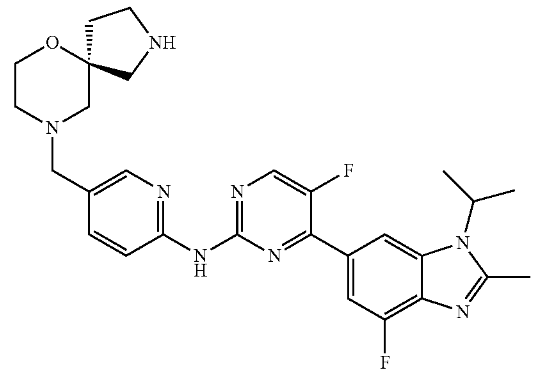 [SMILES: Cc1nc2c(F)cc(-c3nc(Nc4ccc(CN5CCO[C@]6(CCNC6)C5)cn4)ncc3F)cc2n1C(C)C] |
| A26 | 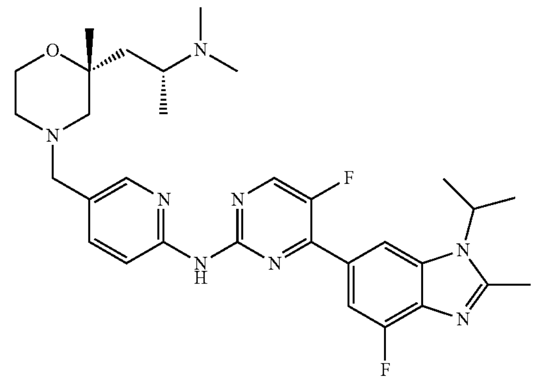 [SMILES: Cc1nc2c(F)cc(-c3nc(Nc4ccc(CN5CCO[C@](C)(C[C@@H](C)N(C)C)C5)cn4)ncc3F)cc2n1C(C)C] |
| A27 | 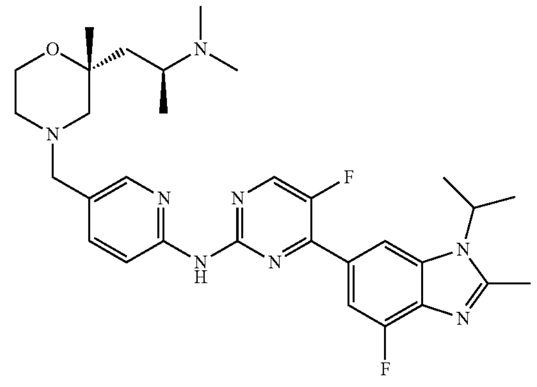 [SMILES: Cc1nc2c(F)cc(-c3nc(Nc4ccc(CN5CCO[C@](C)(C[C@H](C)N(C)C)C5)cn4)ncc3F)cc2n1C(C)C] |

TABLE 1-continued
| Cmpd No | STRUCTURE |
|---|---|
| A51 | 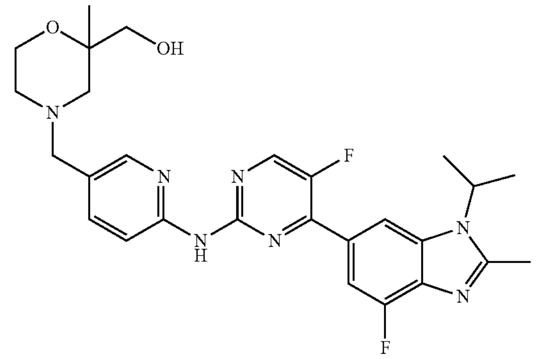 [SMILES: Cc1nc2c(F)cc(-c3nc(Nc4ccc(CN5CCOC(C)(CO)C5)cn4)ncc3F)cc2n1C(C)C] |
| A23 | 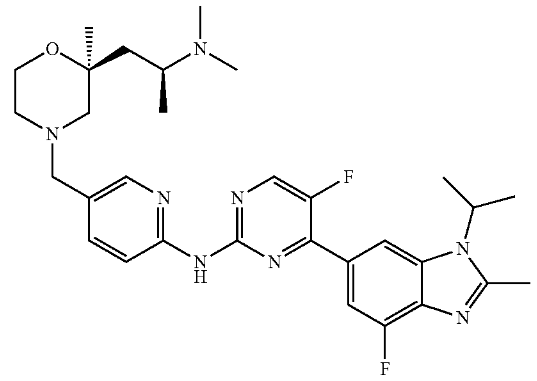 [SMILES: Cc1nc2c(F)cc(-c3nc(Nc4ccc(CN5CCO[C@@](C)(C[C@H](C)N(C)C)C5)cn4)ncc3F)cc2n1C(C)C] |
| A28 | 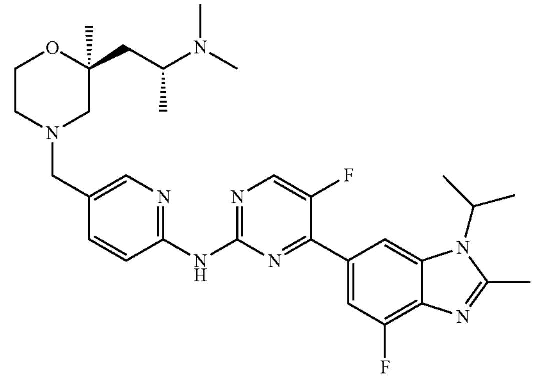 [SMILES: Cc1nc2c(F)cc(-c3nc(Nc4ccc(CN5CCO[C@@](C)(C[C@@H](C)N(C)C)C5)cn4)ncc3F)cc2n1C(C)C] |
| A52 | 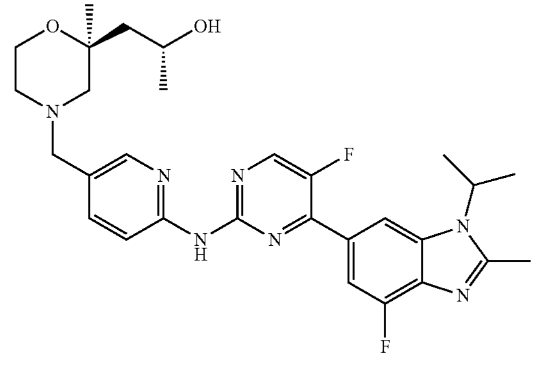 [SMILES: Cc1nc2c(F)cc(-c3nc(Nc4ccc(CN5CCO[C@@](C)(C[C@@H](C)O)C5)cn4)ncc3F)cc2n1C(C)C] |

TABLE 1-continued
| Cmpd No | STRUCTURE |
| --- | --- |
| A53 | 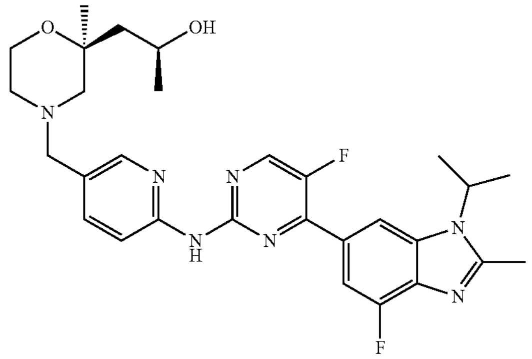 [SMILES: Cc1nc2c(F)cc(-c3nc(Nc4ccc(CN5CCO[C@@](C)(C[C@H](C)O)C5)cn4)ncc3F)cc2n1C(C)C] |
| A47 | 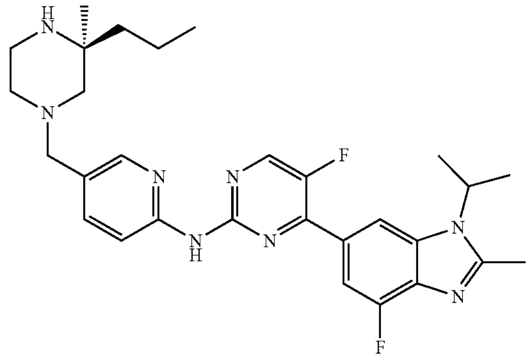 [SMILES: CCC[C@@]1(C)CN(Cc2ccc(Nc3ncc(F)c(-c4cc(F)c5nc(C)n(C(C)C)c5c4)n3)nc2)CCN1] |
| A19 | 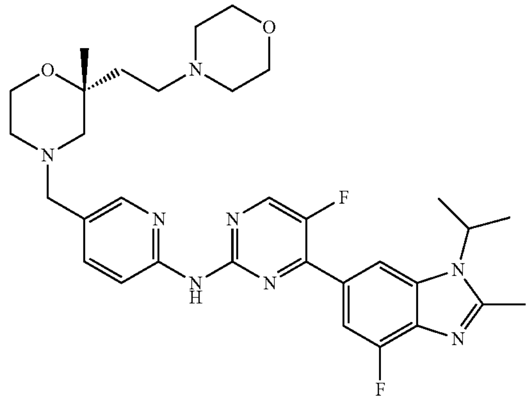 [SMILES: Cc1nc2c(F)cc(-c3nc(Nc4ccc(CN5CCO[C@](C)(CCN6CCOCC6)C5)cn4)ncc3F)cc2n1C(C)C] |
| A7 | 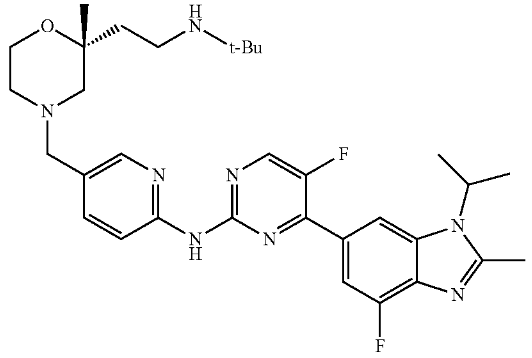 [SMILES: Cc1nc2c(F)cc(-c3nc(Nc4ccc(CN5CCO[C@](C)(CCNC(C)(C)C)C5)cn4)ncc3F)cc2n1C(C)C] |

TABLE 1-continued
| Cmpd No | STRUCTURE |
| --- | --- |
| A8 | 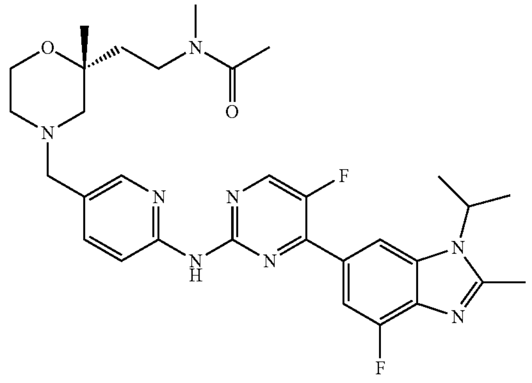 [SMILES: CC(=O)N(C)CC[C@]1(C)CN(Cc2ccc(Nc3ncc(F)c(-c4cc(F)c5nc(C)n(C(C)C)c5c4)n3)nc2)CCO1] |
| A54 | 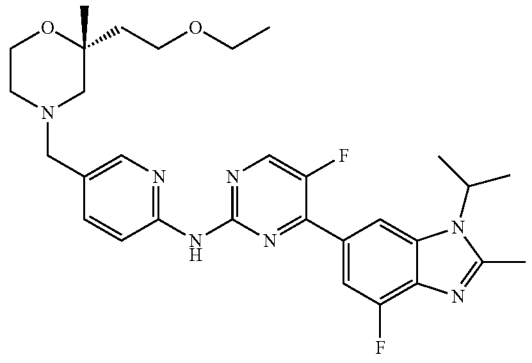 [SMILES: CCOCC[C@]1(C)CN(Cc2ccc(Nc3ncc(F)c(-c4cc(F)c5nc(C)n(C(C)C)c5c4)n3)nc2)CCO1] |
| A12 | 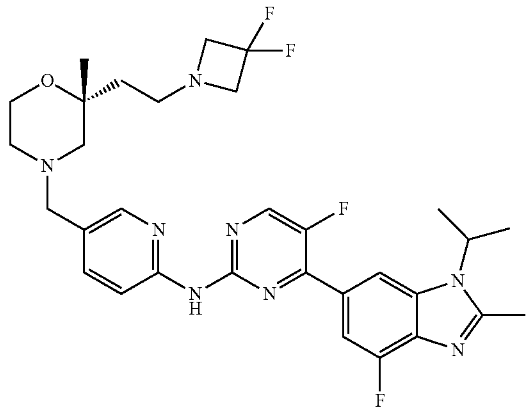 [SMILES: Cc1nc2c(F)cc(-c3nc(Nc4ccc(CN5CCO[C@](C)(CCN6CC(F)(F)C6)C5)cn4)ncc3F)cc2n1C(C)C] |
| A9 | 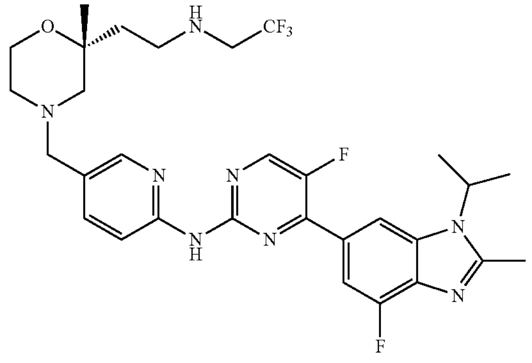 [SMILES: Cc1nc2c(F)cc(-c3nc(Nc4ccc(CN5CCO[C@](C)(CCNCC(F)(F)F)C5)cn4)ncc3F)cc2n1C(C)C] |

TABLE 1-continued
| Cmpd No | STRUCTURE |
|---|---|
| A10 | 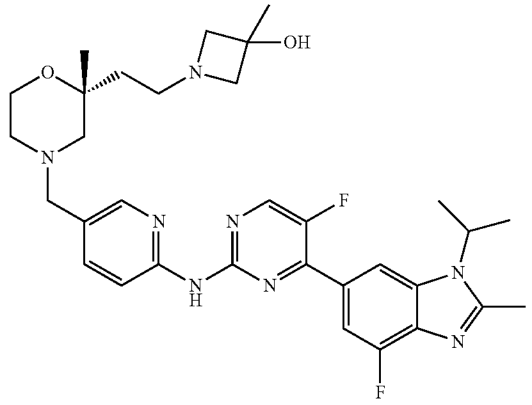 [SMILES: Cc1nc2c(F)cc(-c3nc(Nc4ccc(CN5CCO[C@](C)(CCN6CC(C)(O)C6)C5)cn4)ncc3F)cc2n1C(C)C] |
| A21 | 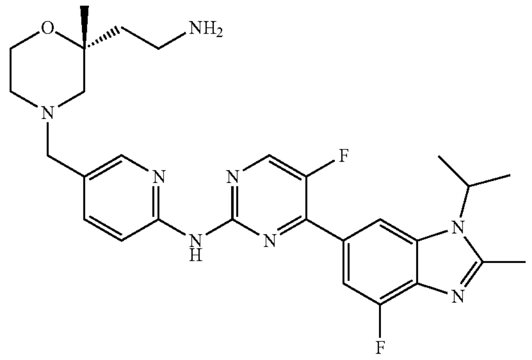 [SMILES: Cc1nc2c(F)cc(-c3nc(Nc4ccc(CN5CCO[C@](C)(CCN)C5)cn4)ncc3F)cc2n1C(C)C] |
| A13 | 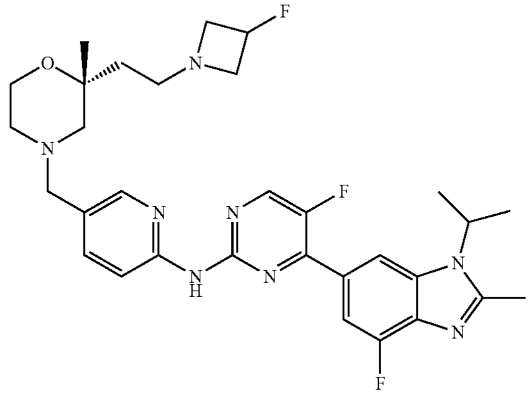 [SMILES: Cc1nc2c(F)cc(-c3nc(Nc4ccc(CN5CCO[C@](C)(CCN6CC(F)C6)C5)cn4)ncc3F)cc2n1C(C)C] |
| A15 | 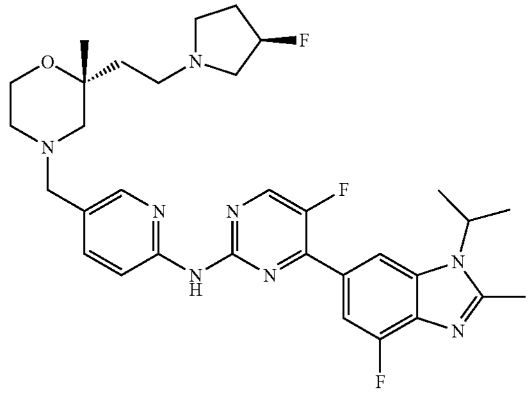 [SMILES: Cc1nc2c(F)cc(-c3nc(Nc4ccc(CN5CCO[C@](C)(CCN6CC[C@@H](F)C6)C5)cn4)ncc3F)cc2n1C(C)C] |

TABLE 1-continued
| Cmpd No | STRUCTURE |
|---|---|
| A14 | 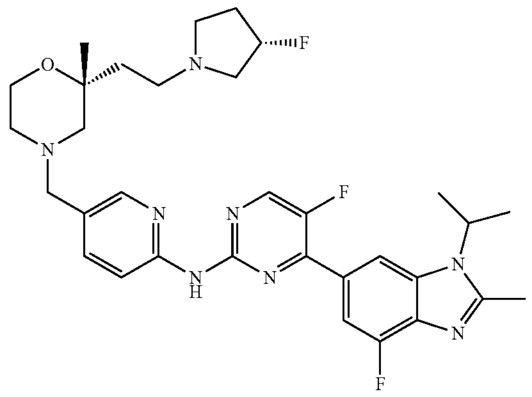 [SMILES: Cc1nc2c(F)cc(-c3nc(Nc4ccc(CN5CCO[C@](C)(CCN6CC[C@H](F)C6)C5)cn4)ncc3F)cc2n1C(C)C] |
| A6 | 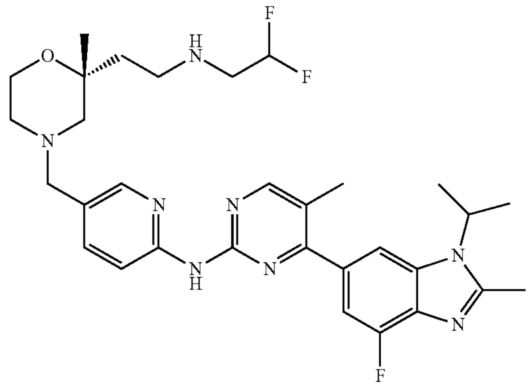 [SMILES: Cc1cnc(Nc2ccc(CN3CCO[C@](C)(CCNCC(F)F)C3)cn2)nc1-c1cc(F)c2nc(C)n(C(C)C)c2c1] |
| A29 | 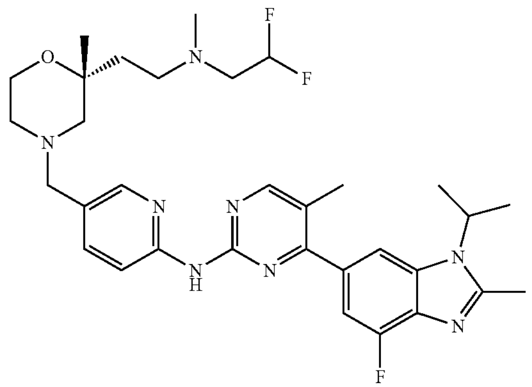 [SMILES: Cc1cnc(Nc2ccc(CN3CCO[C@](C)(CCN(C)CC(F)F)C3)cn2)nc1-c1cc(F)c2nc(C)n(C(C)C)c2c1] |
| A20 | 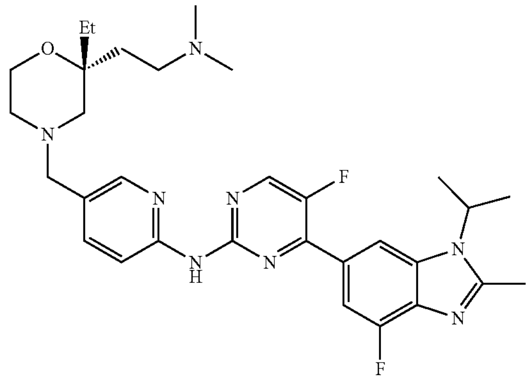 [SMILES: CC[C@@]1(CCN(C)C)CN(Cc2ccc(Nc3ncc(F)c(-c4cc(F)c5nc(C)n(C(C)C)c5c4)n3)nc2)CCO1] |

TABLE 1-continued
| Cmpd No | STRUCTURE |
|---|---|
| A3 | 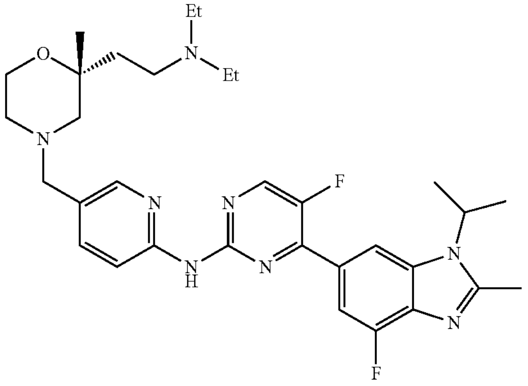 [SMILES: CCN(CC)CC[C@]1(C)CN(Cc2ccc(Nc3ncc(F)c(-c4cc(F)c5nc(C)n(C(C)C)c5c4)n3)nc2)CCO1] |
| A16 | 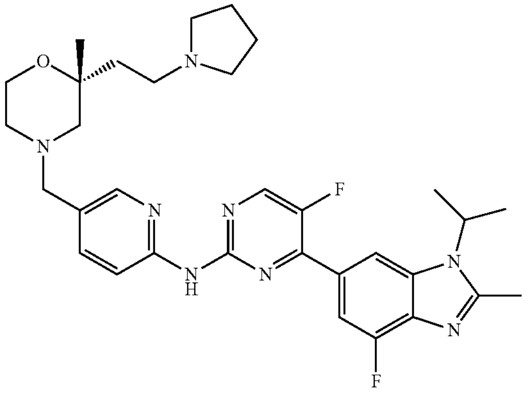 [SMILES: Cc1nc2c(F)cc(-c3nc(Nc4ccc(CN5CCO[C@](C)(CCN6CCCC6)C5)cn4)ncc3F)cc2n1C(C)C] |
| A11 | 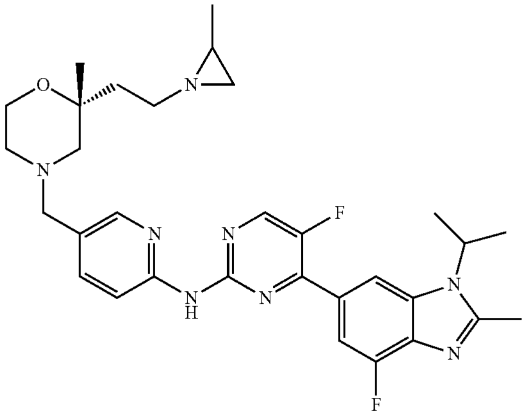 [SMILES: Cc1nc2c(F)cc(-c3nc(Nc4ccc(CN5CCO[C@](C)(CCN6CC6C)C5)cn4)ncc3F)cc2n1C(C)C] |
| A17 | 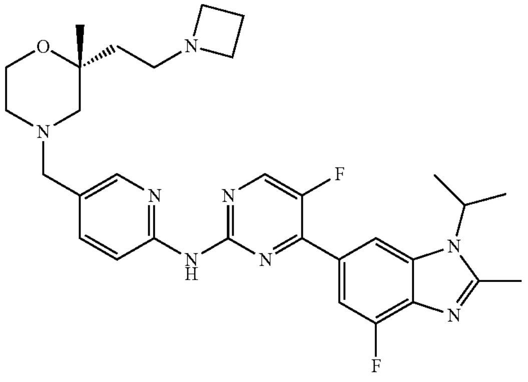 [SMILES: Cc1nc2c(F)cc(-c3nc(Nc4ccc(CN5CCO[C@](C)(CCN6CCC6)C5)cn4)ncc3F)cc2n1C(C)C] |

TABLE 1-continued
| Cmpd No | STRUCTURE |
|---|---|
| A18 | 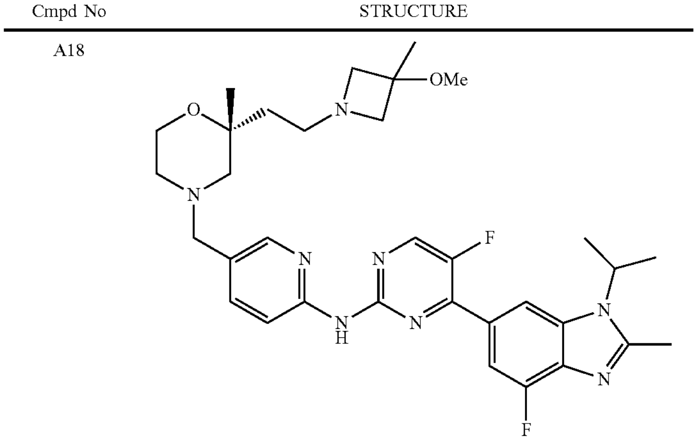 |
| A55 | 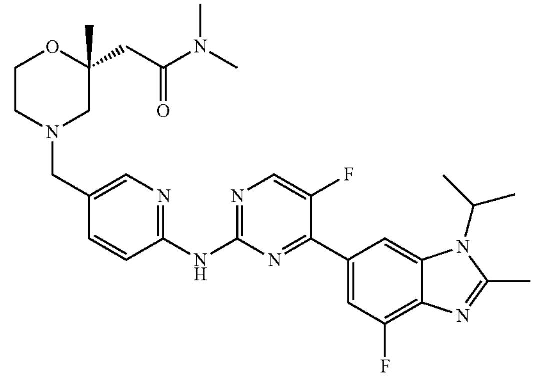 [SMILES: Cc1nc2c(F)cc(-c3nc(Nc4ccc(CN5CCO[C@](C)(CC(=O)N(C)C)C5)cn4)ncc3F)cc2n1C(C)C] |
| A56 | 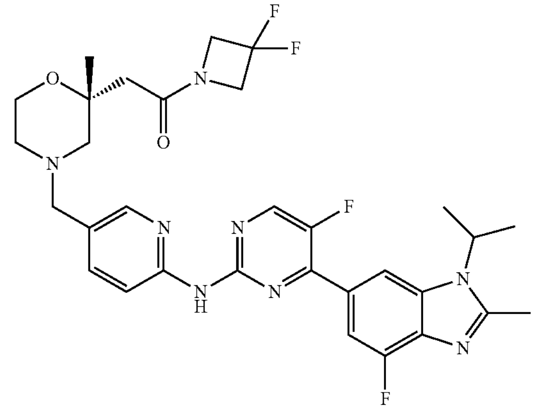 [SMILES: Cc1nc2c(F)cc(-c3nc(Nc4ccc(CN5CCO[C@](C)(CC(=O)N6CC(F)(F)C6)C5)cn4)ncc3F)cc2n1C(C)C] |
| A57 | 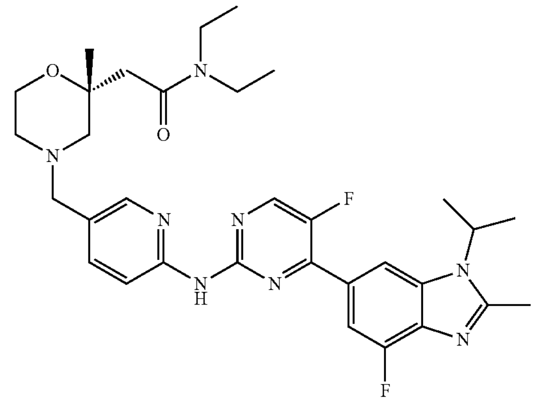 [SMILES: CCN(CC)C(=O)C[C@]1(C)CN(Cc2ccc(Nc3ncc(F)c(-c4cc(F)c5nc(C)n(C(C)C)c5c4)n3)nc2)CCO1] |

TABLE 1-continued
| Cmpd No | STRUCTURE |
|---|---|
| A58 | 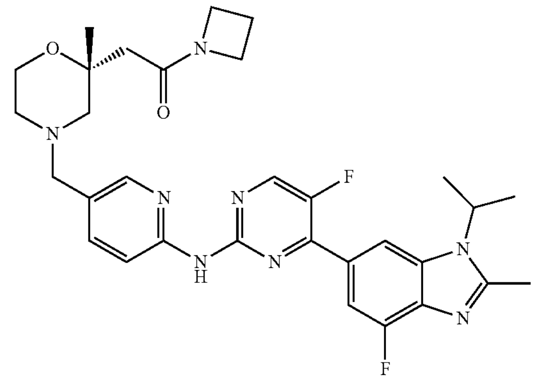 [SMILES: Cc1nc2c(F)cc(-c3nc(Nc4ccc(CN5CCO[C@](C)(CC(=O)N6CCC6)C5)cn4)ncc3F)cc2n1C(C)C] |
| A59 | 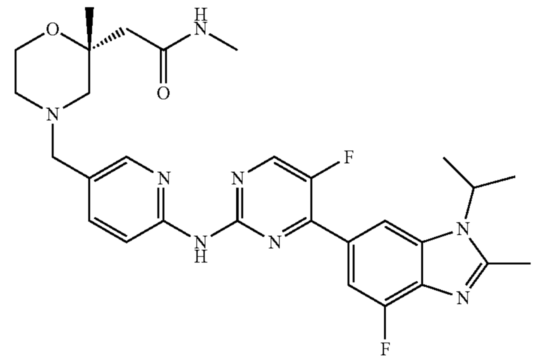 [SMILES: CNC(=O)C[C@]1(C)CN(Cc2ccc(Nc3ncc(F)c(-c4cc(F)c5nc(C)n(C(C)C)c5c4)n3)nc2)CCO1] |
| A60 | 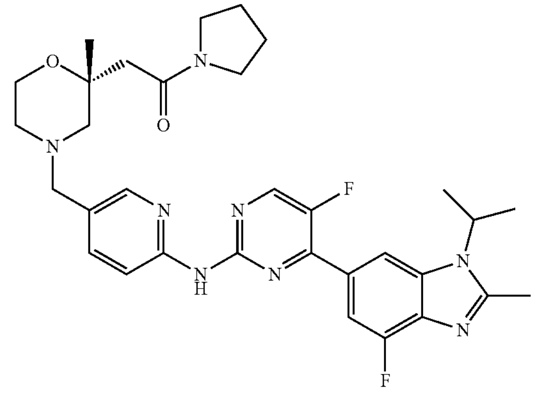 [SMILES: Cc1nc2c(F)cc(-c3nc(Nc4ccc(CN5CCO[C@](C)(CC(=O)N6CCCC6)C5)cn4)ncc3F)cc2n1C(C)C] |
| A61 | 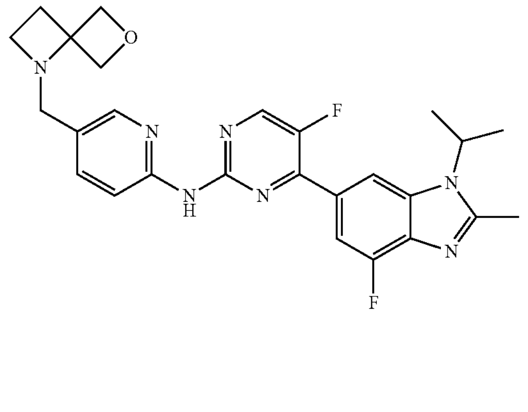 [SMILES: Cc1nc2c(F)cc(-c3nc(Nc4ccc(CN5CCC56COC6)cn4)ncc3F)cc2n1C(C)C] |

TABLE 1-continued
| Cmpd No | STRUCTURE |
| --- | --- |
| A62 | 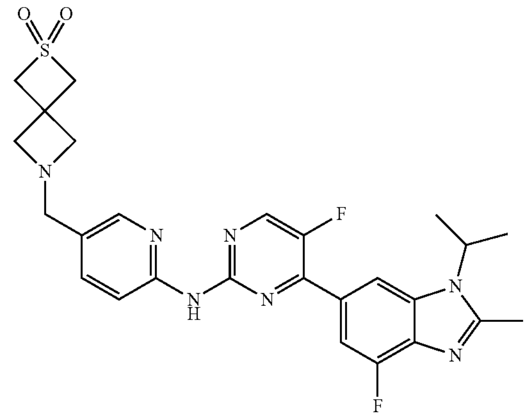 [SMILES: Cc1nc2c(F)cc(-c3nc(Nc4ccc(CN5CC6(C5)CS(=O)(=O)C6)cn4)ncc3F)cc2n1C(C)C] |
| A63 | 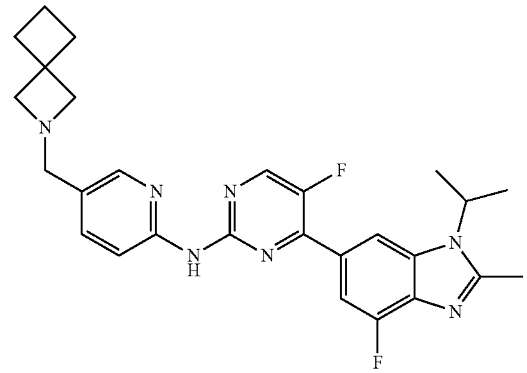 [SMILES: Cc1nc2c(F)cc(-c3nc(Nc4ccc(CN5CC6(CCC6)C5)cn4)ncc3F)cc2n1C(C)C] |
| A64 | 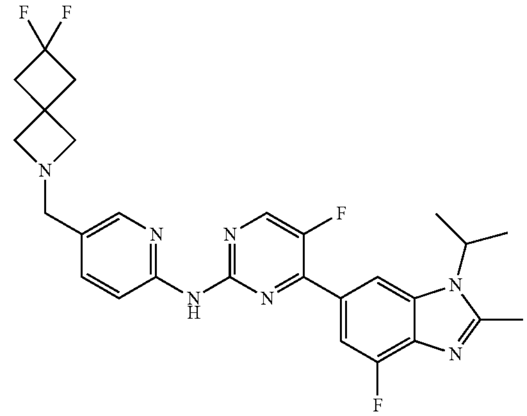 [SMILES: Cc1nc2c(F)cc(-c3nc(Nc4ccc(CN5CC6(C5)CC(F)(F)C6)cn4)ncc3F)cc2n1C(C)C] |

Example 1: Synthesis of Compounds A1, A2, A3, A5, A6, A7, A8, A9, A10, A11, A12, A13, A14, A15, A16, A17, A18, A19, A20, A21, A22, A29, A45, A47, A49, A50, A52, A53, A54, A55, A56, A57, A58, A59, A60

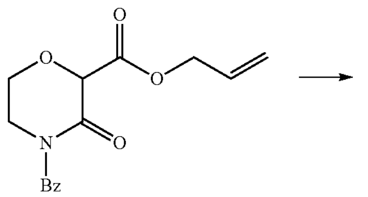

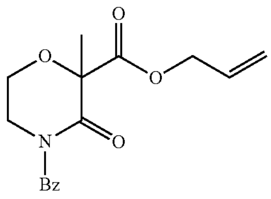

To a cooled (0° C.) solution of allyl 4-benzoyl-3-oxomorpholine-2-carboxylate (17.5 g, 60.5 mmol) in DMF (60 mL) was added iodomethane (7.5 mL, 121 mmol), followed by cesium carbonate (29.6 g, 90.8 mmol). The reaction was stirred for 2 hours, at which point saturated ammonium chloride (aq., 300 mL) and water (200 mL) were added. The mixture was extracted with $Et_2O$ (3×300 mL) and the combined organic layers were dried with $MgSO_4$ and concentrated in vacuo. The crude compound was purified using flash chromatography on $SiO_2$ (elution gradient of hexanes with EtOAc=0-50%) to afford allyl 4-benzoyl-2-methyl-3-oxomorpholine-2-carboxylate (14.6 g, 80% yield) as a white solid.

MS: $[M+H]^+$ m/z 304.1.

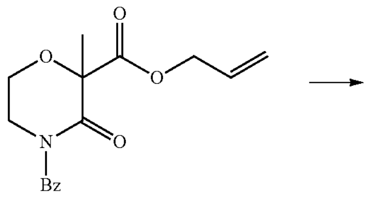

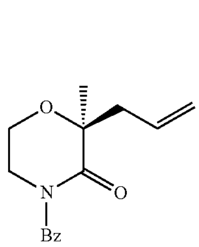

-continued

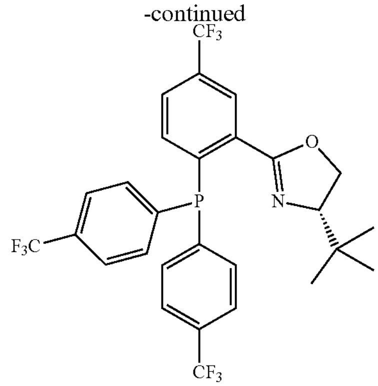

(S)-(p-CF₃)₃-t-BuPHOX

To a schlenk flask equipped with a stir bar was added $Pd_2(dba)_3$ (440 mg, 0.48 mmol), (S)-(p-$CF_3$)$_3$-t-BuPHOX (710 mg, 1.2 mmol), and MTBE (100 mL). the mixture was stirred for 30 min, after which allyl 4-benzoyl-2-methyl-3-oxomorpholine-2-carboxylate (14.6 g, 48 mmol) was added as a solution in MTBE (220 mL). The flask was sealed and heated to 50° C. for two days. Once complete, the reaction was cooled to room temperature and vented to release the evolved $CO_2$. The mixture was filtered through celite, washing with EtOAc, and concentrated in vacuo. The crude compound was purified using flash chromatography on $SiO_2$ (elution gradient of hexanes with EtOAc=0-20%) to afford (S)-2-allyl-4-benzoyl-2-methylmorpholin-3-one (12.1 g, 98% yield, 98% ee) as a white solid.

MS: $[M+H]^+$ m/z 260.1.

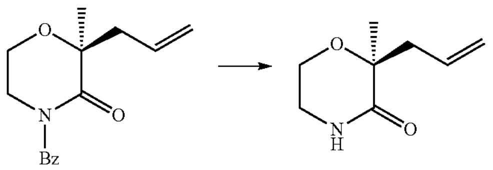

To a mixture of (S)-2-allyl-4-benzoyl-2-methyl morpholin-3-one (12.1 g, 47 mmol) in THF/MeOH (2:1, 24 mL) was added potassium carbonate (647 mg, 4.7 mmol). The flask was fitted with a reflux condenser and the reaction was heated to reflux for 3 h. Once complete, the mixture was cooled, filtered through celite, washing with $CH_2Cl_2$, and concentrated in vacuo. The crude compound was purified using flash chromatography on $SiO_2$ (elution gradient of $CH_2Cl_2$ with MeOH+2% $NH_3$=0-20%) to afford (S)-2-allyl-2-methylmorpholin-3-one (6.45 g, 89% yield) as a colorless oil.

MS: $[M+H]^+$ m/z 156.1.

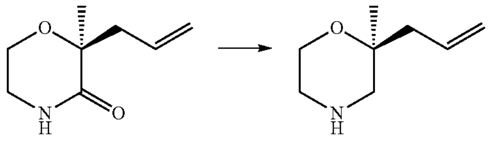

To a cooled (0° C.) solution of (S)-2-allyl-1-methylmorpholin-S-one (6.45 g, 42 mmol) in THF (210 mL) was added lithium aluminum hydride (4.73 g, 125 mmol). The mixture was warmed to room temperature and heated to 60° C. for 3 h. Once complete, the mixture was cooled to 0° C. and $Et_2O$ (300 mL) was added. Water (5.7 mL) was slowly added, followed by sodium hydroxide solution (1M aq., 5.7 mL), and the mixture was warmed to room temperature and stirred for 15 min. The mixture was dried with $MgSO_4$, filtered through celite, and concentrated in vacuo to afford (S)-2-allyl-2-methylmorpholine (5.29 g) as a colorless oil. The compound was used immediately without further purification.

Mass [M+H] 142.1.

Compound A45

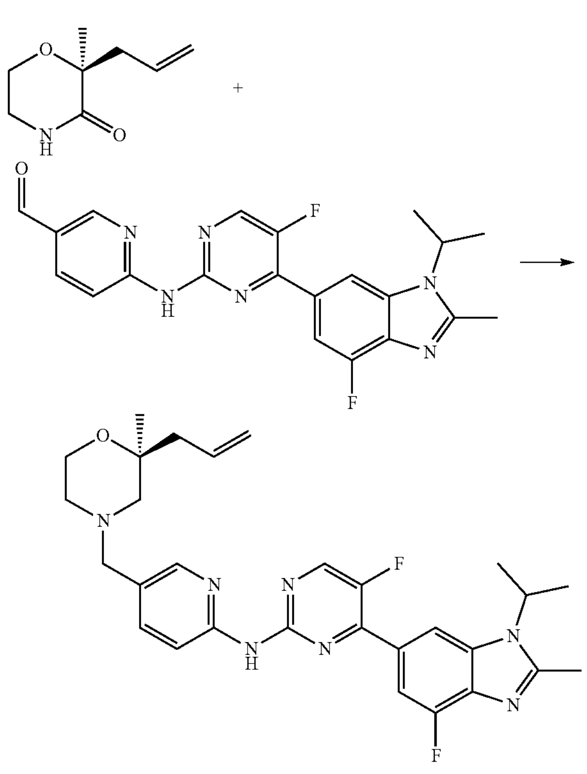

To a solution of (S)-2-allyl-2-methylmorpholine (5.29 g, 38 mmol) and 6-((5-fluoro-4-(4-fluoro-1-isopropyl-2-methyl-1H-benzo[d]imidazol-6-yl)pyrimidin-2-yl)amino) nicotinaldehyde (12.75 g, 31 mmol) in DMSO (315 mL) was added sodium triacetoxyborohydride (13.23 g, 62 mmol), followed by acetic acid (18 mL, 312 mmol). The reaction was heated to 60° C. and stirred for 24 h. Once complete, the mixture was cooled to 0° C. and sodium hydroxide solution (1 M aq., 630 mL) was added, followed by water (200 mL). The resulting heterogeneous mixture was stirred for 1 h, then filtered to collect the solid, rinsing with cold water, and finally lyophilized to yield (S)—N-(5-((2-allyl-2-methylmorpholino)methyl)pyridin-2-yl)-5-fluoro-4-(4-fluoro-1-isopropyl-2-methyl-1H-benzo[d]imidazol-6-yl)pyrimidin-2-amine (15.82 g) as a grey solid. The compound was used without further purification.

MS: $[M+H]^+$ m/z 534.3.

Compound B1

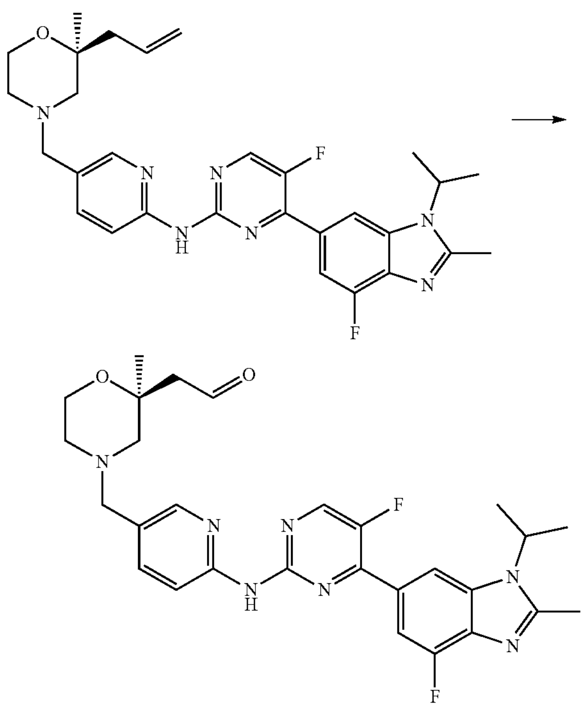

To a solution of (S)—N-(5-((2-allyl-2-methylmorpholino) methyl)pyridin-2-yl)-5-fluoro-4-(4-fluoro-1-isopropyl-2-methyl-1H-benzo[d]imidazol-6-yl)pyrimidin-2-amine (15.82 g, 30 mmol) in THF/$H_2O$ (2:1, 750 mL) was added osmium tetroxide (4% in $H_2O$, 9.4 mL, 1.48 mmol), followed by sodium periodate (19.02 g, 90 mmol). The reaction sonicated for 2.5 h, then stirred for 4.5 h. Once complete, saturated sodium thiosulfate (aq., 600 mL) was added, followed by sodium hydroxide solution (1 M aq., 400 mL), and the mixture was extracted with $CHCl_3$ (3×800 mL). The organic layers were combined, dried with $Na_2SO_4$, and concentrated in vacuo to afford (S)-2-(4-((6-((5-fluoro-4-(4-fluoro-1-isopropyl-2-methyl-1H-benzo[d]imidazol-6-yl)pyrimidin-2-yl)amino)pyridin-3-yl)methyl)-2-methylmorpholin-2-yl)acetaldehyde (15.94 g) as a brown solid. The compound was used without further purification.

MS: $[M+H]^+$ m/z 536.3.

Compound A1

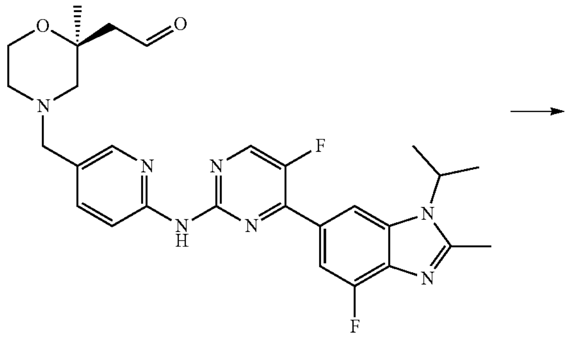

-continued

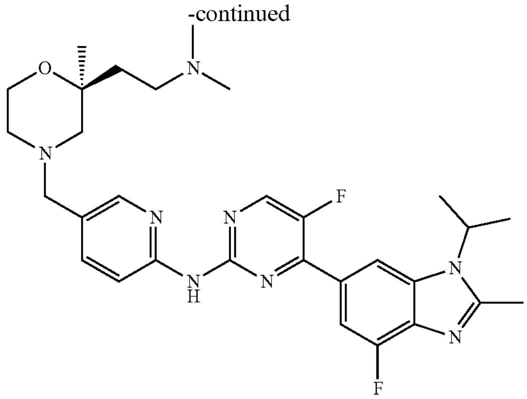

To a cooled (0° C.) solution of (S)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)acetaldehyde (15.94 g, 30 mmol) in $CHCl_3$/MeOH (2:1, 300 mL) was added dimethylamine (2 M in THF, 75 mL, 150 mmol). After 15 min of stirring, sodium triacetoxyborohydride (12.63 g, 60 mmol) was added and the reaction was warmed to room temperature and stirred for 2 h. Once complete, sodium hydroxide solution (0.5 M aq., 600 mL) was added and the mixture was extracted with $CHCl_3$ (3×500 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford (S)—N-(5-((2-(2-(dimethylamino)ethyl)-2-methylmorpholino)methyl)pyridin-2-yl)-5-fluoro-4-(4-fluoro-1-isopropyl-2-methyl-1H-benzo[d]imidazol-6-yl)pyrimidin-2-amine as a light orange oil. The oil was dissolved in water containing methanesulfonic acid (1.05 equiv.), and the solution was lyophilized to yield 12.6 g of the mesylate salt as a tan solid.

Spectra of Mesylate Salt $^1$H NMR (400 MHz, DMSO-$d_6$) δ 8.70 (d, J=3.8 Hz, 1H), 8.30 (d, J=1.3 Hz, 1H), 8.24 (dd, J=8.5, 0.8 Hz, 1H), 8.22-8.18 (m, 1H), 7.75-7.64 (m, 2H), 4.85 (hept, J=7.0 Hz, 1H), 3.59 (t, J=4.8 Hz, 2H), 2.64 (s, 3H), 2.42-2.01 (m, 17H), 1.87-1.76 (m, 1H), 1.63 (d, J=6.9 Hz, 6H), 1.53 (ddd, J=13.2, 10.4, 5.9 Hz, 1H), 1.11 (s, 3H). MS: $[M+H]^{+m/z}$ 565.3.

Compound B2

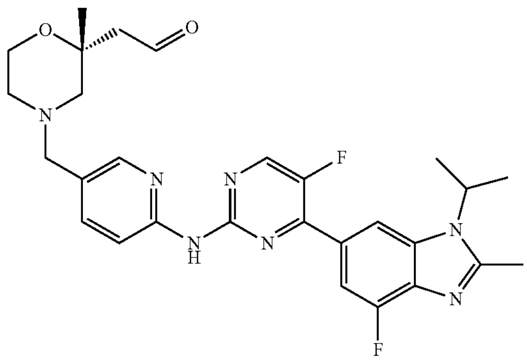

(R)-2-(4-((6-((5-fluoro-4-(4-fluoro-1-isopropyl-2-methyl-1H-benzo[d]imidazol-6-yl)pyrimidin-2-yl)amino) pyridin-3-yl)methyl)-2-methylmorpholin-2-yl)acetaldehyde was prepared in the same manner as compound B1 (above) using (R)-(p-$CF_3$)$_3$-t-BuPHOX as the chiral catalyst. MS: $[M+H]^+$ m/z 536.3.

Compound A2

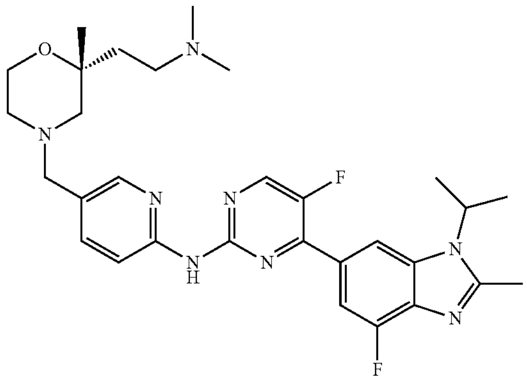

(S)—N-(5-((2-(2-(dimethylamino)ethyl)-2-methylmorpholino)methyl)pyridin-2-yl)-5-fluoro-4-(4-fluoro-1-isopropyl-2-methyl-1H-benzo[d]imidazol-6-yl)pyrimidin-2-amine and its mesylate salt from compound B1 in the same manner as described for compound A1 (above).

Compound A5

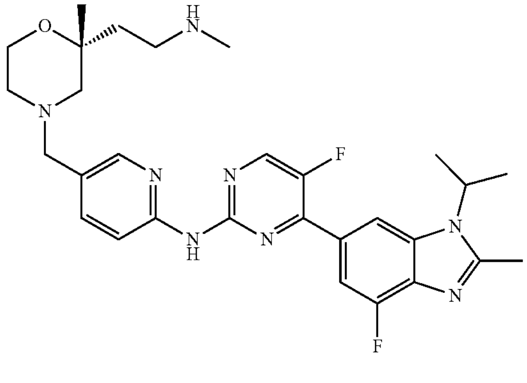

To a cooled (0° C.) solution of (R)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)acetaldehyde (90 mg, 0.17 mmol) in $CHCl_3$ (2.1 mL) was added $MgSO_4$ (120 mg) followed by methylamine (2 M in MeOH, 0.84 mL, 1.7 mmol). After warming to room temperature and stirring for 20 h, sodium borohydride (13 mg, 0.34 mmol) was added and the reaction was stirred for 4 h. Once complete, water (6 mL) and brine (2 mL) were added and the mixture was extracted with $CHCl_3$ (3×4 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford (R)-5-fluoro-4-(4-fluoro-1-isopropyl-2-methyl-1H-benzo[d]imidazol-6-yl)-N-(5-((2-methyl-2-(2-(methylamino)ethyl)morpholino)methyl)pyridin-2-yl)pyrimidin-2-amine as a light orange oil. The oil was dissolved in water containing methanesulfonic acid (1.05 equiv.), and the solution was lyophilized to yield 28.3 mg of the mesylate salt as a tan solid.

Spectra of Mesylate Salt

$^1$H NMR (400 MHz, DMSO-$d_6$) δ 8.70 (d, J=3.8 Hz, 1H), 8.29 (d, J=1.3 Hz, 1H), 8.26-8.20 (m, 2H), 7.72-7.67 (m, 2H), 4.85 (hept, J=6.8 Hz, 1H), 3.61 (t, J=4.9 Hz, 2H), 2.64 (s, 3H), 2.60-2.53 (m, 4H), 2.37-2.27 (m, 9H), 2.20 (d, J=11.1 Hz, 1H), 2.11 (d, J=11.1 Hz, 1H), 2.05-1.91 (m, 1H), 1.63 (d, J=7.0 Hz, 6H), 1.58-1.45 (m, 1H), 1.12 (s, 3H).

MS: $[M+H]^+$ m/z 551.3.

Compound A22

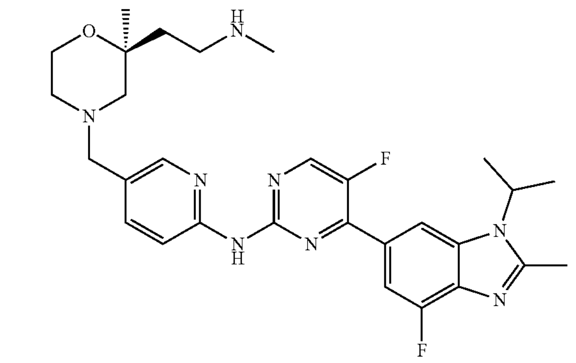 [SMILES: CNCC[C@@]1(C)CN(Cc2ccc(Nc3ncc(F)c(-c4cc(F)c5nc(C)n(C(C)C)c5c4)n3)nc2)CCO1]

(S)-5-fluoro-4-(4-fluoro-1-isopropyl-2-methyl-1H-benzo[d]imidazol-6-yl)-N-(5-((2-methyl-2-(2-(methylamino)ethyl)morpholino)methyl)pyridin-2-yl)pyrimidin-2-amine and its mesylate salt from compound B1 in the same manner as described for compound A5 (above).

Compound A49

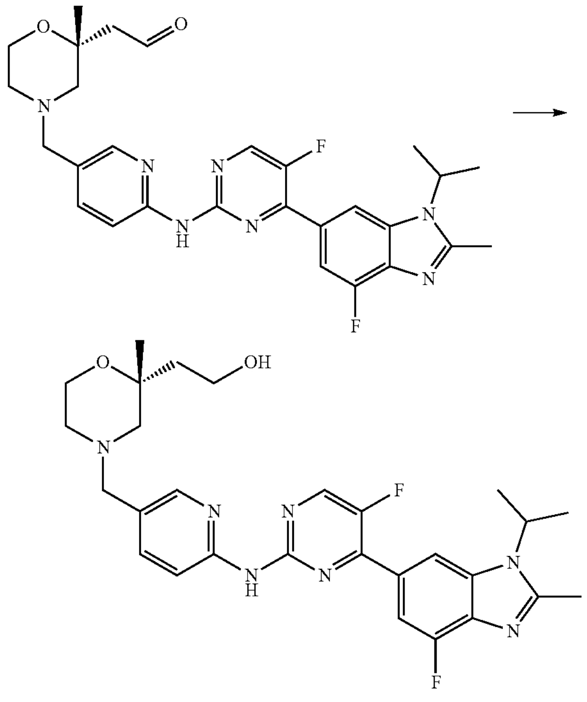

To a cooled (0° C.) solution of (R)-2-(4-((6-((5-fluoro-4-(4-fluoro-1-isopropyl-2-methyl-1H-benzo[d]imidazol-6-yl)pyrimidin-2-yl)amino)pyridin-3-yl)methyl)-2-methylmorpholin-2-yl)acetaldehyde (1.37 g, 2.13 mmol) in $CHCl_3$/MeOH (2:1, 30 mL) was added sodium borohydride (121 mg, 3.2 mmol) and the reaction was stirred for 2 h. Once complete, aqueous hydrochloric acid (1 M, 20 mL) was added and the mixture was stirred for an additional 15 min. Sodium hydroxide solution (0.5 M, 200 mL) was added and the mixture was extracted with $CHCl_3$ (3×150 mL). The organic layers were combined, dried with $Na_2SO_4$, and concentrated in vacuo. The crude compound was purified using flash chromatography on C18 reversed-phase $SiO_2$ (elution gradient of H2O+0.1% AcOH with MeCN=5-50%) to afford (R)-2-(4-((6-((5-fluoro-4-(4-fluoro-1-isopropyl-2-methyl-1H-benzo[d]imidazol-6-yl)pyrimidin-2-yl)amino)pyridin-3-yl)methyl)-2-methylmorpholin-2-yl)ethan-1-ol as a light orange oil. The oil was dissolved in water containing methanesulfonic acid (1.05 equiv.), and the solution was lyophilized to yield 400 mg of the mesylate salt as a tan solid.

Spectra of Mesylate Salt

$^1$H NMR (400 MHz, DMSO-$d_6$) δ 8.70 (d, J=2.8 Hz, 1H), 8.33-8.17 (m, 3H), 7.75-7.64 (m, 2H), 4.84 (p, J=7.0 Hz, 1H), 3.65-3.55 (m, 2H), 3.49-3.39 (m, 2H), 2.65 (s, 3H), 2.39-2.25 (m, 6H), 2.24-2.07 (m, 2H), 1.97-1.83 (m, 1H), 1.69-1.52 (m, 8H), 1.14 (s, 3H). MS: $[M+H]^+$ m/z 538.2.

Compound A50

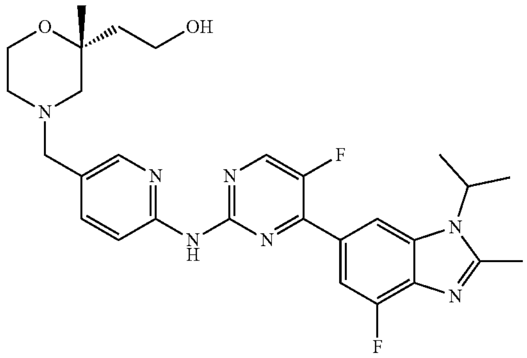 [SMILES: Cc1nc2c(F)cc(-c3nc(Nc4ccc(CN5CCO[C@](C)(CCO)C5)cn4)ncc3F)cc2n1C(C)C]

(S)-2-(4-((6-((5-fluoro-4-(4-fluoro-1-isopropyl-2-methyl-1H-benzo[d]imidazol-6-yl)pyrimidin-2-yl)amino)pyridin-3-yl)methyl)-2-methylmorpholin-2-yl)ethan-1-ol and its mesylate salt from compound B1 in the same manner as described for compound A49 (above).

Compound A19

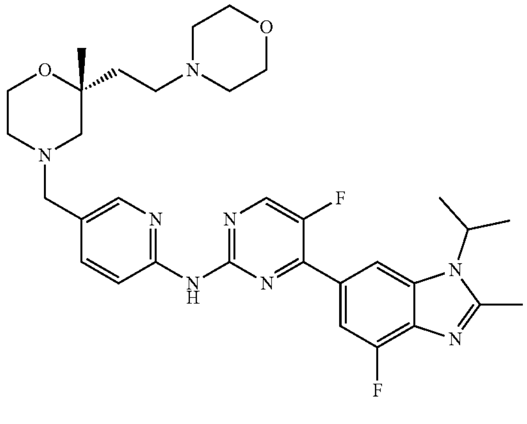 [SMILES: Cc1nc2c(F)cc(-c3nc(Nc4ccc(CN5CCO[C@](C)(CCN6CCOCC6)C5)cn4)ncc3F)cc2n1C(C)C]

To a cooled (0° C.) solution of (R)-2-(4-((6-((5-fluoro-4-(4-fluoro-1-isopropyl-2-methyl-1H-benzo[d]imidazol-6-yl)

pyrimidin-2-yl)amino)pyridin-3-yl)methyl)-2-methylmorpholin-2-yl)acetaldehyde (30 mg, 0.056 mmol) in $CHCl_3$/MeOH (2:1, 1 mL) was added morpholine (50 μL, 0.56 mmol). After 15 min of stirring, sodium triacetoxyborohydride (24 mg, 0.11 mmol) was added and the reaction was warmed to room temperature and stirred for 2 h. Once complete, sodium hydroxide solution (0.5 M aq., 3 mL) was added and the mixture was extracted with $CHCl_3$ (3×2 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford (R)-5-fluoro-4-(4-fluoro-1-isopropyl-2-methyl-1H-benzo[d]imidazol-6-yl)-N-(5-((2-methyl-2-(2-morpholinoethyl)morpholino)methyl)pyridin-2-yl)pyrimidin-2-amine as a light orange oil. The oil was dissolved in water containing methanesulfonic acid (1.05 equiv.), and the solution was lyophilized to yield 17.8 mg of the mesylate salt as a tan solid.

Spectra of Mesylate Salt $^1$H NMR (400 MHz, DMSO-$d_6$) δ 8.70 (d, J=3.8 Hz, 1H), 8.30 (d, J=1.3 Hz, 1H), 8.28-8.19 (m, 2H), 7.75-7.65 (m, 2H), 4.85 (hept, J=6.9 Hz, 1H), 3.60 (t, J=4.8 Hz, 2H), 3.52 (t, J=4.7 Hz, 4H), 2.65 (s, 3H), 2.44-2.17 (m, 13H), 2.10 (d, J=11.1 Hz, 1H), 1.85 (q, J=13.3, 10.7 Hz, 1H), 1.71-1.51 (m, 8H), 1.12 (s, 3H). MS: $[M+H]^+$ m/z 607.3.

Compound A7

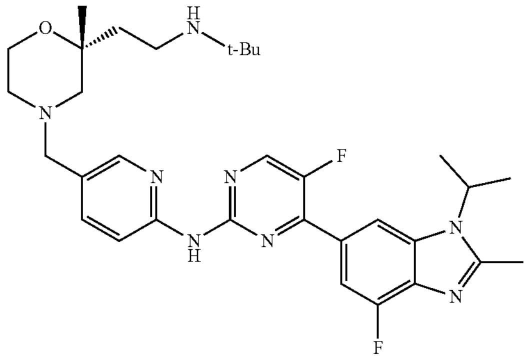 [SMILES: Cc1nc2c(F)cc(-c3nc(Nc4ccc(CN5CCO[C@](C)(CCNC(C)(C)C)C5)cn4)ncc3F)cc2n1C(C)C]

To a cooled (0° C.) solution of (R)-2-(4-((6-((5-fluoro-4-(4-fluoro-1-isopropyl-2-methyl-1H-benzo[d]imidazol-6-yl)pyrimidin-2-yl)amino)pyridin-3-yl)methyl)-2-methylmorpholin-2-yl)acetaldehyde (30 mg, 0.056 mmol) in $CHCl_3$/MeOH (2:1, 1 mL) was added $MgSO_4$ (40 mg) followed by t-butylamine (60 μL, 0.56 mmol). After warming to room temperature and stirring for 18 h, sodium borohydride (5 mg, 0.11 mmol) was added and the reaction was stirred for 4 h. Once complete, water (3 mL) and brine (1 mL) were added and the mixture was extracted with $CHCl_3$ (3×2 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford (R)—N-(5-((2-(2-(tert-butylamino)ethyl)-2-methylmorpholino)methyl)pyridin-2-yl)-5-fluoro-4-(4-fluoro-1-isopropyl-2-methyl-1H-benzo[d]imidazol-6-yl)pyrimidin-2-amine as a light orange oil. The oil was dissolved in water containing methanesulfonic acid (1.05 equiv.), and the solution was lyophilized to yield 14.2 mg of the mesylate salt as a tan solid.

Spectra of Mesylate Salt $^1$H NMR (400 MHz, DMSO-$d_6$) δ 8.70 (d, J=3.8 Hz, 1H), 8.29 (d, J=1.4 Hz, 1H), 8.27-8.20 (m, 2H), 7.73-7.66 (m, 2H), 4.84 (p, J=6.9 Hz, 1H), 3.64-3.59 (m, 2H), 2.64 (s, 3H), 2.60-2.53 (m, 2H), 2.43-2.28 (m, 7H), 2.23 (d, J=11.1 Hz, 1H), 2.10 (d, J=11.1 Hz, 1H), 1.95 (d, J=8.3 Hz, 1H), 1.63 (dd, J=6.9, 1.3 Hz, 6H), 1.59-1.42 (m, 1H), 1.14 (s, 3H), 1.07 (s, 9H). MS: $[M+H]^+$ m/z 593.3.

Compound A8

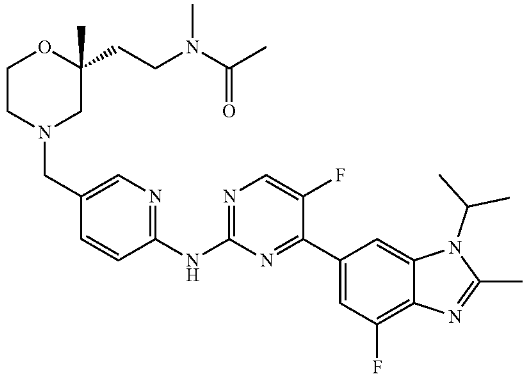 [SMILES: CC(=O)N(C)CC[C@]1(C)CN(Cc2ccc(Nc3ncc(F)c(-c4cc(F)c5nc(C)n(C(C)C)c5c4)n3)nc2)CCO1]

To a solution of (R)-5-fluoro-4-(4-fluoro-1-isopropyl-2-methyl-1H-benzo[d]imidazol-6-yl)-N-(5-((2-methyl-2-(2-(methylamino)ethyl)morpholino)methyl)pyridin-2-yl)pyrimidin-2-amine (17 mg, 0.031 mmol) in $CHCl_3$ (1.5 mL) was added acetyl chloride (4.5 μL, 0.062 mmol) followed by triethylamine (20 μL, 0.12 mmol). After stirring for 2 h, sodium hydroxide solution (1 M aq., 3 mL) was added and the mixture was stirred for 1 h. Once complete, water (3 mL) was added and the mixture was extracted with $CHCl_3$ (3×1.5 mL). The organic layers were combined, dried with $Na_2SO_4$, and concentrated in vacuo. The crude compound was stirred with lithium hydroxide solution (1 M aq., 2 mL) in DMF/MeOH (2 mL) for 2 h, before water (3 mL) was added and the mixture was extracted with $CHCl_3$ (3×1.5 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford (R)—N-(2-(4-((6-((5-fluoro-4-(4-fluoro-1-isopropyl-2-methyl-1H-benzo[d]imidazol-6-yl)pyrimidin-2-yl)amino)pyridin-3-yl)methyl)-2-methylmorpholin-2-yl)ethyl)-N-methylacetamide as a light orange oil. The oil was dissolved in water containing methanesulfonic acid (1.05 equiv.), and the solution was lyophilized to yield 17.2 mg of the mesylate salt as a tan solid.

Spectra of Mesylate Salt

Reported as a mixture of amide rotamers $^1$H NMR (400 MHz, DMSO-$d_6$) δ 8.70 (d, J=3.8 Hz, 1H), 8.30 (s, 1H), 8.28-8.20 (m, 2H), 7.73-7.65 (m, 2H), 4.85 (pd, J=6.8, 2.2 Hz, 1H), 3.74-3.75 (m, 2H), 3.39-3.12 (m, 4H), 2.91 (s, 1.5H), 2.76 (s, 1.5H), 2.65 (s, 253H), 2.44-2.19 (m, 7H), 2.16-2.04 (m, 1H), 1.97 (s, 1.5H), 1.94 (s, 1.5H), 1.63 (d, J=6.9 Hz, 6H), 1.55-1.43 (m, 1H), 1.15 (s, 1.5H), 1.12 (s, 1.5H). MS: $[M+H]^+$ m/z 593.3.

Compound A54

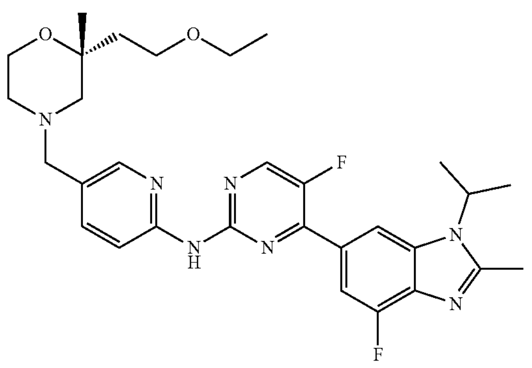 [SMILES: CCOCC[C@]1(C)CN(Cc2ccc(Nc3ncc(F)c(-c4cc(F)c5nc(C)n(C(C)C)c5c4)n3)nc2)CCO1]

To a cooled (0° C.) solution of (R)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)ethan-1-ol (30 mg, 0.056 mmol) in DMF (0.6 mL) was added sodium hydride (5 mg, 0.11 mmol). After stirring for 30 min, the mixture was cooled to 0° C. and iodoethane (7 μL, 0.084 mmol) was added. The mixture was warmed to room temperature and stirred for 15 h. Once complete, water (3 mL) was added and the mixture was extracted with $CHCl_3$ (3×2 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford (R)—N-((2-(2-ethoxyethyl)-2-methylmorpholino)methyl)pyridin-2-yl)-5-fluoro-4-(4-fluoro-1-isopropyl-2-methyl-1H-benzo[d]imidazol-6-yl)pyrimidin-2-amine as a light orange oil. The oil was dissolved in water containing methanesulfonic acid (1.05 equiv.), and the solution was lyophilized to yield 15.0 mg of the mesylate salt as a tan solid.

Spectra of Mesylate Salt $^1$H NMR (400 MHz, DMSO-$d_6$) δ 8.65 (s, 1H), 8.41-8.29 (m, 1H), 8.15 (s, 1H), 7.96-7.52 (m, 3H), 4.81 (p, J=7.0 Hz, 1H), 4.48-4.17 (m, 3H), 3.71-3.51 (m, 2H), 2.63 (s, 3H), 2.44-2.12 (m, 8H), 2.03-1.87 (m, 1H), 1.76-1.43 (m, 8H), 1.42-1.06 (m, 7H). MS: $[M+H]^+$ m/z 566.3.

Compound A12

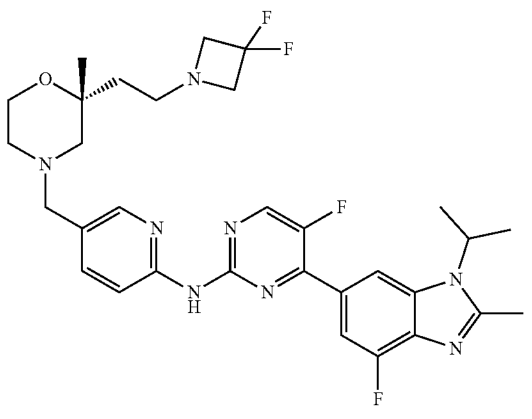 [SMILES: Cc1nc2c(F)cc(-c3nc(Nc4ccc(CN5CCO[C@](C)(CCN6CC(F)(F)C6)C5)cn4)ncc3F)cc2n1C(C)C]

To a cooled (0° C.) solution of (R)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)acetaldehyde (30 mg, 0.056 mmol) in $CHCl_3$/MeOH (2:1, 1 mL) was added 3,3-difluoroazetidine·HCl (37 mg, 0.28 mmol). After 15 min of stirring, sodium triacetoxyborohydride (24 mg, 0.11 mmol) was added and the reaction was warmed to room temperature and stirred for 4 h. Once complete, sodium hydroxide solution (0.5 M aq., 3 mL) was added and the mixture was extracted with $CHCl_3$ (3×2 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford (R)—N-(5-((2-(2-(3,3-difluoroazetidin-1-yl)ethyl)-2-methylmorpholino)methyl)pyridin-2-yl)-5-fluoro-4-(4-fluoro-1-isopropyl-2-methyl-1H-benzo[d]imidazol-6-yl)pyrimidin-2-amine as a light orange oil. The oil was dissolved in water containing methanesulfonic acid (1.05 equiv.), and the solution was lyophilized to yield 21.8 mg of the mesylate salt as a white solid.

Spectra of Mesylate Salt $^1$H NMR (400 MHz, DMSO-$d_6$) δ 8.70 (d, J=3.8 Hz, 1H), 8.31 (d, J=1.4 Hz, 1H), 8.25 (d, J=8.5 Hz, 1H), 8.22 (d, J=2.2 Hz, 1H), 7.70 (m, 2H), 4.86 (p, J=6.9 Hz, 1H), 3.59 (t, J=5.0 Hz, 2H), 3.54-3.45 (m, 7H), 2.65 (s, 3H), 2.40-2.25 (m, 6H), 2.21 (d, J=11.2 Hz, 1H), 2.10 (d, 7=11.2 Hz, 1H), 1.85-1.69 (m, 1H), 1.64 (d, 7=6.8 Hz, 6H), 1.45-1.35 (m, 1H), 1.12 (s, 3H). MS: $[M+H]^+$ m/z 613.3.

Compound A9

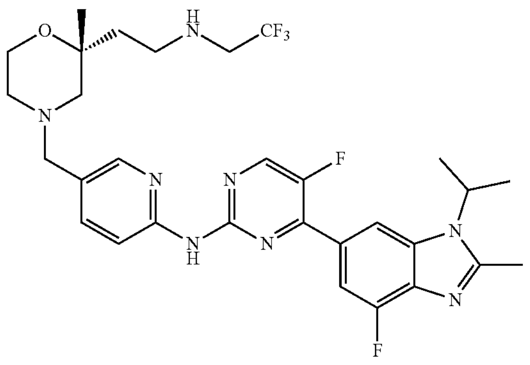 [SMILES: Cc1nc2c(F)cc(-c3nc(Nc4ccc(CN5CCO[C@](C)(CCNCC(F)(F)F)C5)cn4)ncc3F)cc2n1C(C)C]

To a cooled (0° C.) solution of (R)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)acetaldehyde (30 mg, 0.056 mmol) in $CHCl_3$/MeOH (2:1, 1 mL) was added $MgSO_4$ (40 mg) followed by 2,2,2-trifluoroethylamine (28 mg, 0.28 mmol). After warming to room temperature and stirring for 15 h, sodium borohydride (5 mg, 0.11 mmol) was added and the reaction was stirred for 1 h. Once complete, water (3 mL) and brine (1 mL) were added and the mixture was extracted with $CHCl_3$ (3×2 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford (R)-5-fluoro-4-(4-fluoro-1-isopropyl-2-methyl-1H-benzo[d]imidazol-6-yl)-N-(5-((2-methyl-2-(2-((2,2,2-trifluoroethyl)amino)ethyl)morpholino)methyl)pyridin-2-yl)pyrimidin-2-amine as a light orange oil. The oil was dissolved in water containing methanesulfonic acid (1.05 equiv.), and the solution was lyophilized to yield 15.0 mg of the mesylate salt as a tan solid.

Spectra of Mesylate Salt $^1$H NMR (400 MHz, DMSO-$d_6$) δ 8.70 (d, J=3.8 Hz, 1H), 8.30 (d, J=1.3 Hz, 1H), 8.28-8.19 (m, 2H), 7.73-7.66 (m, 2H), 4.85 (p, J=6.8 Hz, 1H), 3.60 (t, J=4.8 Hz, 2H), 3.16 (q, J=10.3 Hz, 2H), 2.66-2.54 (m, 6H), 2.37-2.29 (m, 6H), 2.19 (d, J=11.1 Hz, 1H), 2.11 (d, J=11.1 Hz, 1H), 1.95-1.78 (m, 1H), 1.63 (d, J=6.8 Hz, 6H), 1.48 (ddd, J=13.5, 9.7, 6.1 Hz, 1H), 1.12 (s, 3H). MS: $[M+H]^+$ m/z 619.3.

Compound A10

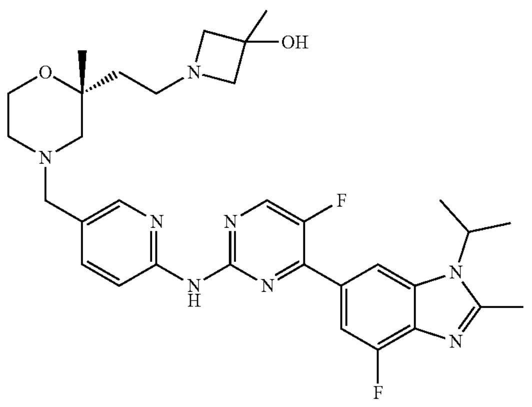 [SMILES: Cc1nc2c(F)cc(-c3nc(Nc4ccc(CN5CCO[C@](C)(CCN6CC(C)(O)C6)C5)cn4)ncc3F)cc2n1C(C)C]

To a cooled (0° C.) solution of (R)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)acetaldehyde (30 mg, 0.056 mmol) in $CHCl_3$/MeOH (2:1, 1 mL) was added 3-hydroxyl-3-methylazetidine·HCl (35 mg, 0.28 mmol). After 15 min of stirring, sodium triacetoxyborohydride (24 mg, 0.11 mmol) was added and the reaction was warmed to room temperature and stirred for 4 h. Once complete, sodium hydroxide solution (0.5 M aq., 3 mL) was added and the mixture was extracted with $CHCl_3$ (3×2 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford (R)-1-(2-(4-((6-((5-fluoro-4-(4-fluoro-1-isopropyl-2-methyl-1H-benzo[d]imidazol-6-yl)pyrimidin-2-yl)amino)pyridin-3-yl)methyl)-2-methylmorpholin-2-yl)ethyl)-3-methylazetidin-3-ol as a light orange oil. The oil was dissolved in water containing methanesulfonic acid (1.05 equiv.), and the solution was lyophilized to yield 15.9 mg of the mesylate salt as a tan solid.

Spectra of Mesylate Salt $^1$H NMR (400 MHz, DMSO-$d_6$) δ 8.70 (d, J=3.8 Hz, 1H), 8.29 (d, J=1.3 Hz, 1H), 8.27-8.19 (m, 2H), 7.74-7.65 (m, 2H), 4.85 (hept, J=6.8 Hz, 1H), 3.65-3.38 (m, 4H), 3.35-3.10 (m, 2H), 2.86-2.59 (m, 5H), 2.40-2.25 (s, 7H), 2.21 (d, J=11.2 Hz, 1H), 2.13 (d, 7=11.2 Hz, 1H), 1.94-1.78 (m, 1H), 1.63 (dd, J=6.8, 6H), 1.46-1.30 (m, 4H), 1.12 (s, 3H). MS: $[M+H]^+$ m/z 607.3.

Compound A21

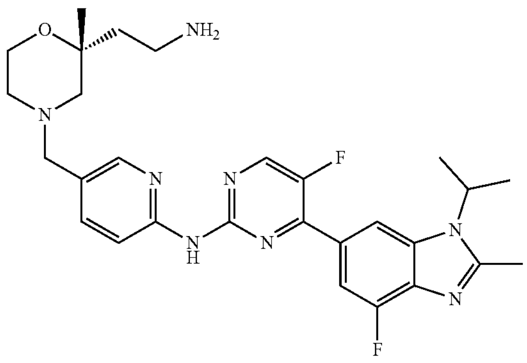 [SMILES: Cc1nc2c(F)cc(-c3nc(Nc4ccc(CN5CCO[C@](C)(CCN)C5)cn4)ncc3F)cc2n1C(C)C]

To a cooled (0° C.) solution of (R)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)acetaldehyde (30 mg, 0.056 mmol) in $CHCl_3$ (0.7 mL) was added $MgSO_4$ (20 mg) followed by ammonia (7 M in MeOH, 0.16 mL, 1.12 mmol). After warming to room temperature and stirring for 15 h, sodium borohydride (5 mg, 0.11 mmol) was added and the reaction was stirred for 4 h. Once complete, water (3 mL) and brine (1 mL) were added and the mixture was extracted with $CHCl_3$ (3×2 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford (R)—N-(5-((2-(2-aminoethyl)-2-methylmorpholino)methyl)pyridin-2-yl)-5-fluoro-4-(4-fluoro-1-isopropyl-2-methyl-1H-benzo [d]imidazol-6-yl)pyrimidin-2-amine as a light orange oil. The oil was dissolved in water containing methanesulfonic acid (1.05 equiv.), and the solution was lyophilized to yield 3.9 mg of the mesylate salt as a tan solid.

Spectra of Mesylate Salt $^1$H NMR (400 MHz, DMSO-$d_6$) δ 8.70 (d, J=3.8 Hz, 1H), 8.29 (d, J=1.4 Hz, 1H), 8.26-8.19 (m, 2H), 7.74-7.65 (m, 2H), 4.85 (p, J=6.9 Hz, 1H), 3.61 (t, J=5.0 Hz, 2H), 2.66-2.57 (m, 5H), 2.39-2.26 (m, 7H), 2.18 (d, J=11.2 Hz, 1H), 2.10 (d, J=11.2 Hz, 1H), 2.03-1.87 (m, 1H), 1.63 (d, J=6.9 Hz, 6H), 1.47 (dt, J=13.5, 8.0 Hz, 1H), 1.12 (s, 3H). MS: $[M+H]^+$ m/z 537.2.

Compound A13

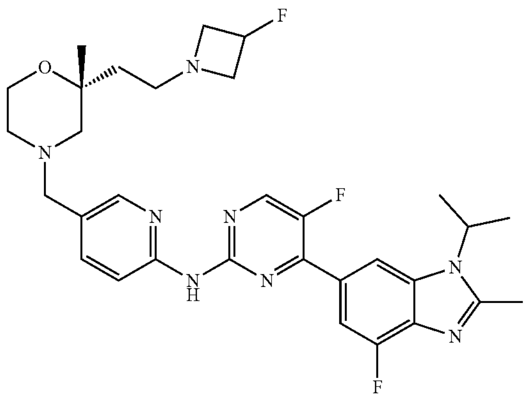 [SMILES: Cc1nc2c(F)cc(-c3nc(Nc4ccc(CN5CCO[C@](C)(CCN6CC(F)C6)C5)cn4)ncc3F)cc2n1C(C)C]

To a cooled (0° C.) solution of (R)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)acetaldehyde (60 mg, 0.11 mmol) in $CHCl_3$/

MeOH (2:1.2 mL) was added 3-fluoroazetidine·HCl (63 mg, 0.56 mmol). After 15 min of stirring, sodium triacetoxyborohydride (48 mg, 0.22 mmol) was added and the reaction was warmed to room temperature and stirred for 3 h. Once complete, sodium hydroxide solution (0.5 M aq., 6 mL) was added and the mixture was extracted with $CHCl_3$ (3×4 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford (R)-1-(2-(4-((6-((5-fluoro-4-(4-fluoro-1-isopropyl-2-methyl-1H-benzo[d]imidazol-6-yl)pyrimidin-2-yl)amino)pyridin-3-yl)methyl)-2-methylmorpholin-2-yl)ethyl)-3-methylazetidin-3-ol as a light orange oil. The oil was dissolved in water containing methanesulfonic acid (1.05 equiv.), and the solution was lyophilized to yield 44.8 mg of the mesylate salt as a white solid.

Spectra of Mesylate Salt $^1$H NMR (400 MHz, DMSO-$d_6$) δ 8.69 (d, 3.9 Hz, 1H), 8.30 (d, J=1.3 Hz, 1H), 8.24 (dd, J=8.5, 0.8 Hz, 1H), 8.22-8.17 (m, 1H), 7.74-7.65 (m, 2H), 5.09 (dddd, J=57.7, 10.3, 5.7, 4.7 Hz, 1H), 4.85 (p, J=6.9 Hz, 1H), 3.58 (t, J=5.1 Hz, 2H), 3.48-3.32 (m, 2H), 3.04-2.89 (m, 2H), 2.64 (s, 3H), 2.42-2.25 (s, 8H), 2.20 (d, J=11.1 Hz, 1H), 2.08 (d, J=11.1 Hz, 1H), 1.77-1.60 (m, 8H), 1.44-1.31 (m, 1H), 1.10 (s, 3H). MS: $[M+H]^{+m/z}$ 595.3.

Compound A15

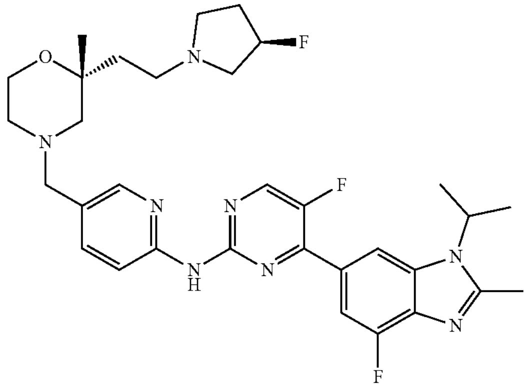 [SMILES: Cc1nc2c(F)cc(-c3nc(Nc4ccc(CN5CCO[C@](C)(CCN6CC[C@@H](F)C6)C5)cn4)ncc3F)cc2n1C(C)C]

To a cooled (0° C.) solution of (R)-2-(4-((6-((5-fluoro-4-(4-fluoro-1-isopropyl-2-methyl-1H-benzo[d]imidazol-6-yl)pyrimidin-2-yl)amino)pyridin-3-yl)methyl)-2-methylmorpholin-2-yl)acetaldehyde (45 mg, 0.084 mmol) in $CHCl_3$/MeOH (2:1, 1.5 mL) was added (R)-(−)-3-fluoropyrrolidine ·HCl (53 mg, 0.42 mmol). After 15 min of stirring, sodium triacetoxyborohydride (36 mg, 0.17 mmol) was added and the reaction was warmed to room temperature and stirred for 3 h. Once complete, sodium hydroxide solution (0.5 M aq., 5 mL) was added and the mixture was extracted with $CHCl_3$ (3×3 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford 5-fluoro-4-(4-fluoro-1-isopropyl-2-methyl-1H-benzo[d]imidazol-6-yl)-N-(5-(((R)-2-(2-((R)-3-fluoropyrrolidin-1-yl)ethyl)-2-methylmorpholino)methyl)pyridin-2-yl)pyrimidin-2-amine as a light orange oil. The oil was dissolved in water containing methanesulfonic acid (1.05 equiv.), and the solution was lyophilized to yield 32.3 mg of the mesylate salt as a tan solid.

Spectra of Mesylate Salt $^1$H NMR (400 MHz, DMSO-$d_6$) δ 8.73-8.67 (m, 1H), 8.30 (d, J=1.3 Hz, 1H), 8.25 (d, J=8.6 Hz, 1H), 8.22 (d, J=2.1 Hz, 1H), 7.74-7.66 (m, 2H), 5.30-5.03 (m, 1H), 4.85 (hept, J=6.9 Hz, 1H), 3.59 (d, J=5.1 Hz, 2H), 2.98-2.59 (m, 6H), 2.55-2.00 (m, 13H), 1.99-1.72 (m, 2H), 1.69-1.49 (m, 7H), 1.12 (s, 3H). MS: $[M+H]^+$ m/z 609.3.

Compound A14

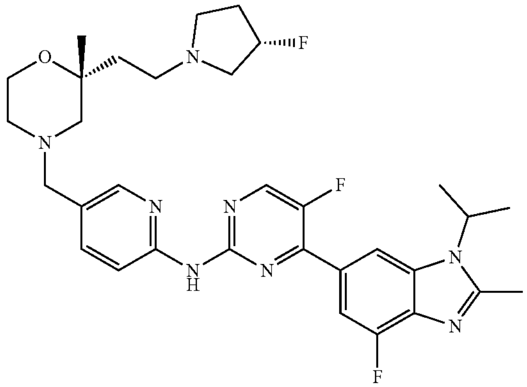 [SMILES: Cc1nc2c(F)cc(-c3nc(Nc4ccc(CN5CCO[C@](C)(CCN6CC[C@H](F)C6)C5)cn4)ncc3F)cc2n1C(C)C]

To a cooled (0° C.) solution of (R)-2-(4-((6-((5-fluoro-4-(4-fluoro-1-isopropyl-2-methyl-1H-benzo[d]imidazol-6-yl)pyrimidin-2-yl)amino)pyridin-3-yl)methyl)-2-methylmorpholin-2-yl)acetaldehyde (45 mg, 0.084 mmol) in $CHCl_3$/MeOH (2:1, 1.5 mL) was added (S)-(+)-3-fluoropyrrolidine ·HCl (53 mg, 0.42 mmol). After 15 min of stirring, sodium triacetoxyborohydride (36 mg, 0.17 mmol) was added and the reaction was warmed to room temperature and stirred for 3 h. Once complete, sodium hydroxide solution (0.5 M aq., 5 mL) was added and the mixture was extracted with $CHCl_3$ (3×3 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford 5-fluoro-4-(4-fluoro-1-isopropyl-2-methyl-1H-benzo[d]imidazol-6-yl)-N-(5-(((R)-2-(2-((S)-3-fluoropyrrolidin-1-yl)ethyl)-2-methylmorpholino)methyl)pyridin-2-yl)pyrimidin-2-amine as a light orange oil. The oil was dissolved in water containing methanesulfonic acid (1.05 equiv.), and the solution was lyophilized to yield 33.7 mg of the mesylate salt as a tan solid.

Spectra of Mesylate Salt $^1$H NMR (400 MHz, DMSO-$d_6$) δ 8.70 (d, 7=3.8 Hz, 1H), 8.31 (d, J=1.3 Hz, 1H), 8.25 (dt, J=8.5, 0.8 Hz, 1H), 8.22 (d, J=2.2 Hz, 1H), 7.74-7.66 (m, 2H), 5.15 (dt, J=55.9, 5.9 Hz, 1H), 4.85 (hept, J=6.9 Hz, 1H), 3.60 (t, J=4.8 Hz, 2H), 2.86-2.71 (m, 2H), 2.65 (s, 3H), 2.53-2.17 (m, 11H), 2.17-1.98 (m, 2H), 1.97-1.71 (m, 2H), 1.71-1.51 (m, 8H), 1.12 (s, 3H). MS: $[M+H]^+$ m/z 609.3.

Compound A6

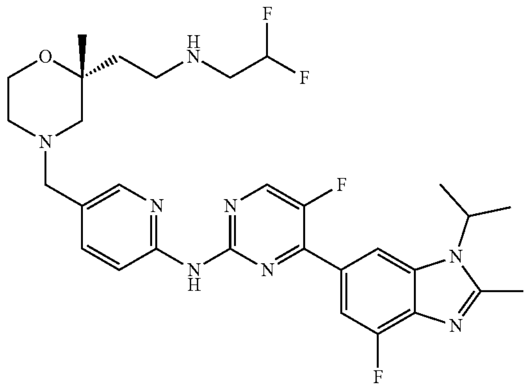 [SMILES: Cc1nc2c(F)cc(-c3nc(Nc4ccc(CN5CCO[C@](C)(CCNCC(F)F)C5)cn4)ncc3F)cc2n1C(C)C]

To a solution of (R)-2-(4-((6-((5-fluoro-4-(4-fluoro-1-isopropyl-2-methyl-1H-benzo[d]imidazol-6-yl)pyrimidin-2-yl)amino)pyridin-3-yl)methyl)-2-methylmorpholin-2-yl)acetaldehyde (45 mg, 0.084 mmol) in $CHCl_3$ (1 mL) was added 2,2-difluoroethylamine (30 μL, 0.42 mmol), followed by acetic acid (24 μL, 0.84 mmol). After 10 min of stirring, sodium triacetoxyborohydride (36 mg, 0.17 mmol) was added and the reaction was stirred for 18 h. Once complete, sodium bicarbonate solution (sat. aq., 5 mL) was added and the mixture was extracted with $CHCl_3$ (3×3 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-25%) to afford (R)—N-(5-((2-(2-((2,2-difluoroethyl)amino)ethyl)-2-methylmorpholino)methyl)pyridin-2-yl)-5-fluoro-4-(4-fluoro-1-isopropyl-2-methyl-1H-benzo[d]imidazol-6-yl)pyrimidin-2-amine as a light orange oil. The oil was dissolved in water containing methanesulfonic acid (1.05 equiv.), and the solution was lyophilized to yield 35.5 mg of the mesylate salt as a tan solid.

Spectra of Mesylate Salt $^1H$ NMR (400 MHz, DMSO-$d_6$) δ 8.70 (d, 7=3.8 Hz, 1H), 8.30 (d, J=1.3 Hz, 1H), 8.27-8.19 (m, 2H), 7.73-7.66 (m, 2H), 6.01 (tt, J=56.0, 4.1 Hz, 1H), 4.86 (p, J=6.9 Hz, 1H), 3.60 (t, J=4.8 Hz, 2H), 2.93 (t, J=16.2 Hz, 2H), 2.67-2.57 (m, 5H), 2.32 (s, 6H), 2.20 (d, J=11.2 Hz, 1H), 2.11 (d, J=11.2 Hz, 1H), 2.01-1.86 (m, 1H), 1.63 (d, 0.7=6.9 Hz, 6H), 1.56-1.44 (m, 1H), 1.12 (s, 3H). MS: $[M+H]^+$ m/z 601.3.

Compound A29

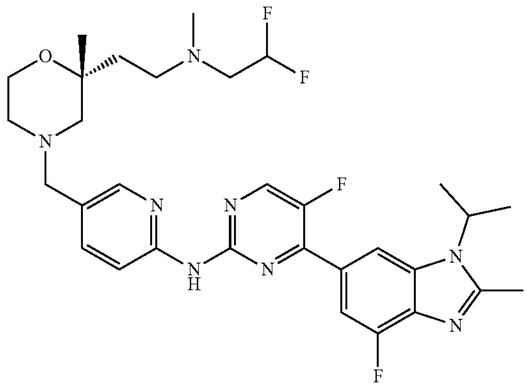 [SMILES: Cc1nc2c(F)cc(-c3nc(Nc4ccc(CN5CCO[C@](C)(CCN(C)CC(F)F)C5)cn4)ncc3F)cc2n1C(C)C]

To a solution of 5-fluoro-4-(4-fluoro-1-isopropyl-2-methyl-1H-benzo[d]imidazol-6-yl)-N-(5-(((R)-2-(2-((R)-3-fluoropyrrolidin-1-yl)ethyl)-2-methylmorpholino)methyl)pyridin-2-yl)pyrimidin-2-(30 mg, 0.05 mmol) in $CHCl_3$/MeOH (2:1, 1 mL) was added formaldehyde (37% in $H_2O$, 5 μL, 0.06 mmol). After 5 min of stirring, sodium triacetoxyborohydride (22 mg, 0.10 mmol) was added and the reaction was stirred for 2 h. Once complete, sodium bicarbonate solution (sat. aq., 5 mL) was added and the mixture was extracted with $CHCl_3$ (3×3 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-10%) to afford (R)—N-(5-((2-(2-((2,2-difluoroethyl)(methyl)amino)ethyl)-2-methylmorpholino)methyl)pyridin-2-yl)-5-fluoro-4-(4-fluoro-1-isopropyl-2-methyl-1H-benzo[d]imidazol-6-yl)pyrimidin-2-amine as a light orange oil. The oil was dissolved in water containing methanesulfonic acid (1.05 equiv.), and the solution was lyophilized to yield 25.2 mg of the mesylate salt as a tan solid.

Spectra of Mesylate Salt $^1H$ NMR (400 MHz, DMSO-$d_6$) δ 8.70 (d, J=3.8 Hz, 1H), 8.30 (d, J=1.4 Hz, 1H), 8.27-8.20 (m, 2H), 7.74-7.65 (m, 2H), 6.06 (t, J=55.8 Hz, 1H), 4.85 (hept, J=6.8 Hz, 1H), 3.67-3.54 (m, 2H), 2.83-2.60 (s, 6H), 2.49-2.17 (m, 12H), 2.17-2.03 (m, 1H), 1.95-1.77 (m, 1H), 1.63 (d, J=6.9 Hz, 6H), 1.61-1.50 (m, 1H), 1.12 (s, 3H). MS: $[M+H]^+$ m/z 615.3.

Compound A20

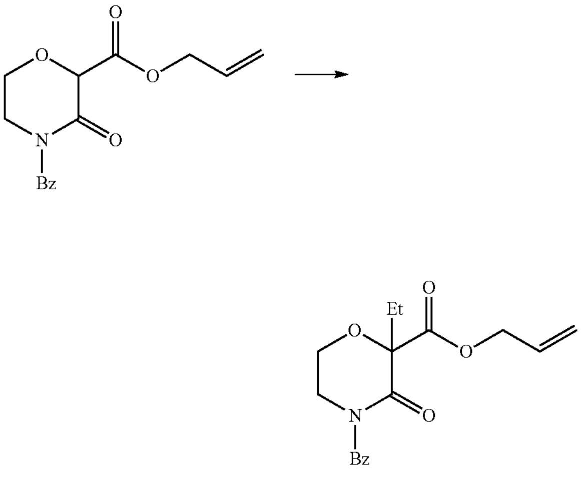

To a cooled (0° C.) solution of allyl 4-benzoyl-3-oxomorpholine-2-carboxylate (2.0 g, 6.9 mmol) in DMF (7 mL) was added iodoethane (1.45 mL, 13.8 mmol), followed by cesium carbonate (4.5 g, 13.8 mmol). The reaction was stirred for 2 hours, at which point saturated ammonium chloride (aq., 20 mL) and water (20 mL) was added. The mixture was extracted with $Et_2O$ (3×20 mL) and the combine organic layers were dried with $Na_2SO_4$ and concentrated in vacuo. The crude compound was purified using flash chromatography on $SiO_2$ (elution gradient of hexanes with EtOAc=0-50%) to afford allyl 4-benzoyl-2-ethyl-3-oxomorpholine-2-carboxylate (1.7 g, 78% yield) as a white solid.

MS: $[M+H]^+$ m/z 317.1.

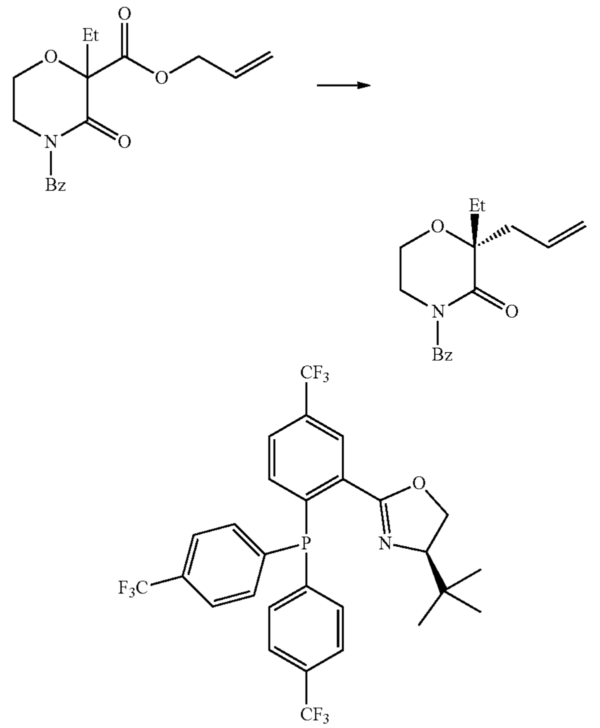

(R)-(p-$CF_3$)$_3$-t-BuPHOX

To a schlenk flask equipped with a stir bar was added $Pd(OAc)_2$ (6 mg, 0.027 mmol), (R)-(p-$CF_3$)$_3$-t-BuPHOX (80 mg, 0.134 mmol), and MTBE (40 mL). the mixture was stirred for 30 min, after which allyl 4-benzoyl-2-ethyl-3-oxomorpholine-2-carboxylate (1.7 g, 5.4 mmol) was added as a solution in MTBE (15 mL). The flask was sealed and heated to 55° C. for 4 days. Once complete, the reaction was cooled to room temperature and vented to release the evolved $CO_2$. The mixture was filtered through celite, washing with EtOAc, and concentrated in vacuo. The crude compound was purified using flash chromatography on $SiO_2$ (elution gradient of hexanes with EtOAc=0-20%) to afford (R)-2-allyl-4-benzoyl-2-ethylmorpholin-3-one (1.3 g, 90% yield, 98% ee) as a white solid.

MS: $[M+H]^+$ m/z 274.1.

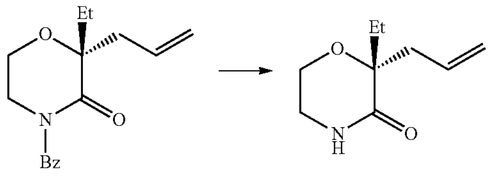

To a cooled (0° C.) solution of (R)-2-allyl-4-benzoyl-2-ethylmorpholin-3-one (1.3 g, 4.8 mmol) in iPrOH (100 mL) was added lithium hydroxide (4 M in $H_2O$, 1.8 mL, 7.1 mmol). The reaction was warmed to room temperature and stirred for 8 h. Once complete, $MgSO_4$ was added, and the mixture was filtered through celite, washing with $CH_2Cl_2$, and concentrated in vacuo. The crude compound was purified using flash chromatography on $SiO_2$ (elution gradient of $CH_2Cl_2$ with MeOH+2% $NH_3$=0-30%) to afford (R)-2-allyl-2-ethylmorpholin-3-one (367 mg, 45% yield) as a colorless oil.

MS: $[M+H]^+$ m/z 170.1.

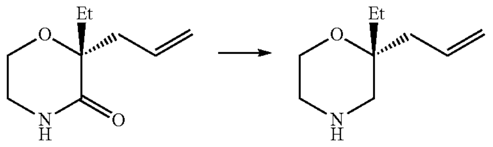

To a cooled (0° C.) solution of (R)-2-allyl-2-ethylmorpholin-3-one (367 mg, 2.2 mmol) in THF (11 mL) was added lithium aluminum hydride (250 mg, 6.5 mmol). The mixture was warmed to room temperature and heated to 60° C. for 2 h. Once complete, the mixture was cooled to 0° C. and $Et_2O$ (11 mL) was added. Water (0.3 mL) was slowly added, followed by sodium hydroxide solution (1M aq., 0.3 mL), and the mixture was warmed to room temperature and stirred for 15 min. The mixture was dried with $MgSO_4$, filtered through celite, and concentrated in vacuo to afford (R)-2-allyl-2-ethylmorpholine (336 mg) as a colorless oil. The compound was used immediately without further purification.

MS: $[M+H]^+$ m/z 156.2.

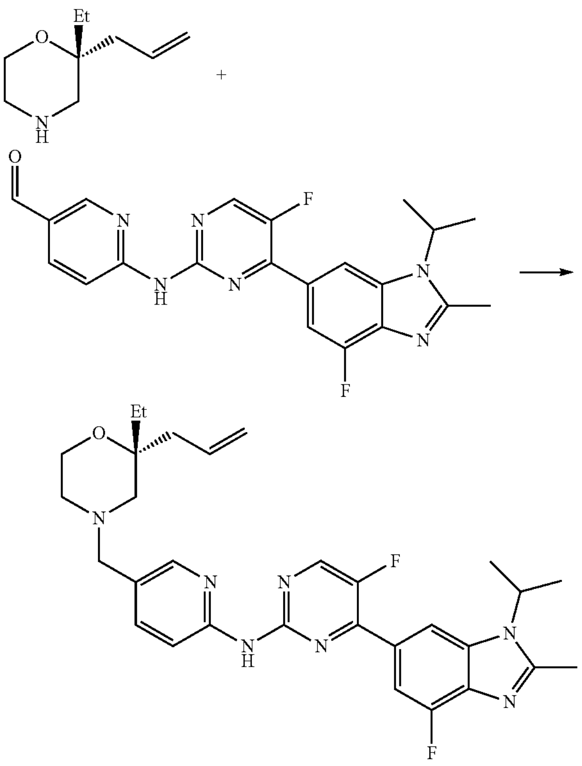

To a solution of (R)-2-allyl-2-ethylmorpholine (336 mg, 2.2 mmol) and 6-((5-fluoro-4-(4-fluoro-1-isopropyl-2-methyl-1H-benzo[d]imidazol-6-yl)pyrimidin-2-yl)amino)nicotinaldehyde (739 mg, 1.8 mmol) in DMSO (18 mL) was added sodium triacetoxyborohydride (770 mg, 3.6 mmol), followed by acetic acid (1.1 mL, 18 mmol). The reaction was heated to 60° C. and stirred for 24 h. Once complete, the mixture was cooled to 0° C. and sodium hydroxide solution (1 M aq., 40 mL) was added, followed by water (15 mL). The resulting heterogeneous mixture was stirred for 1 h, then filtered to collect the solid, rinsing with cold water, and finally lyophilized to yield (R)—N-(5-((2-allyl-2-ethylmorpholino)methyl)pyridin-2-yl)-5-fluoro-4-(4-fluoro-1-isopropyl-2-methyl-1H-benzo[d]imidazol-6-yl)pyrimidin-2-amine (862 mg) as a grey solid. The compound was used without further purification.

MS: $[M+H]^+$ m/z 548.3.

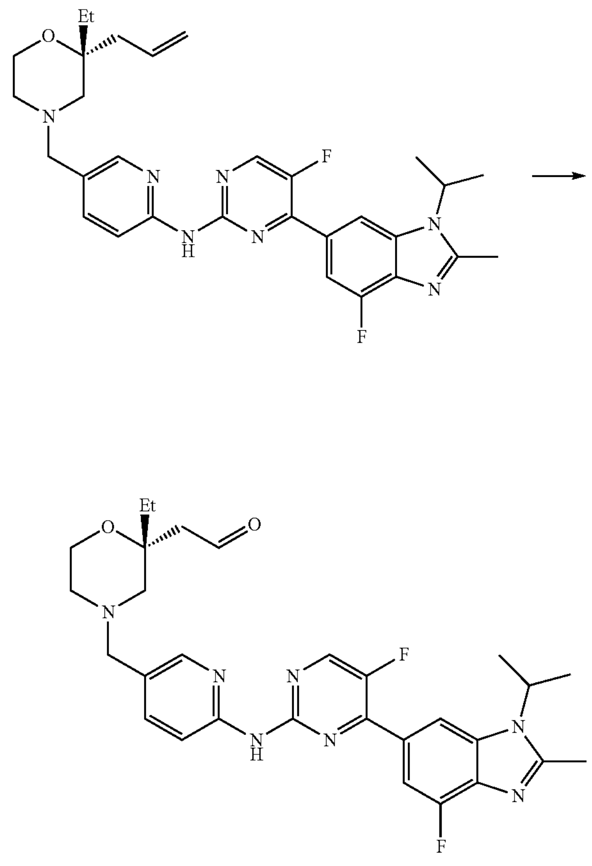

To a solution of (R)—N-(5-((2-allyl-2-ethylmorpholino)methyl)pyridin-2-yl)-5-fluoro-4-(4-fluoro-1-isopropyl-2-methyl-1H-benzo[d]imidazol-6-yl)pyrimidin-2-amine (862 mg, 1.6 mmol) in THF/$H_2O$ (2:1, 39 mL) was added osmium tetroxide (4% in $H_2O$, 0.5 mL, 0.08 mmol), followed by sodium periodate (1.00 g, 4.7 mmol). The reaction sonicated for 2.5 h, then stirred for 4.5 h. Once complete, saturated sodium thiosulfate (aq., 80 mL) was added, followed by sodium hydroxide solution (1 M aq., 50 mL), and the mixture was extracted with $CHCl_3$ (3x50 mL). The organic layers were combined, dried with $Na_2SO_4$, and concentrated in vacuo to afford (R)-2-(2-ethyl-4-((6-((5-fluoro-4-(4-fluoro-1-isopropyl-2-methyl-1H-benzo[d]imidazol-6-yl)pyrimidin-2-yl)amino)pyridin-3-yl)methyl)morpholin-2-yl)acetaldehyde (815 mg) as a black solid. The compound was used without further purification.

MS: $[M+H]^+$ m/z 550.3.

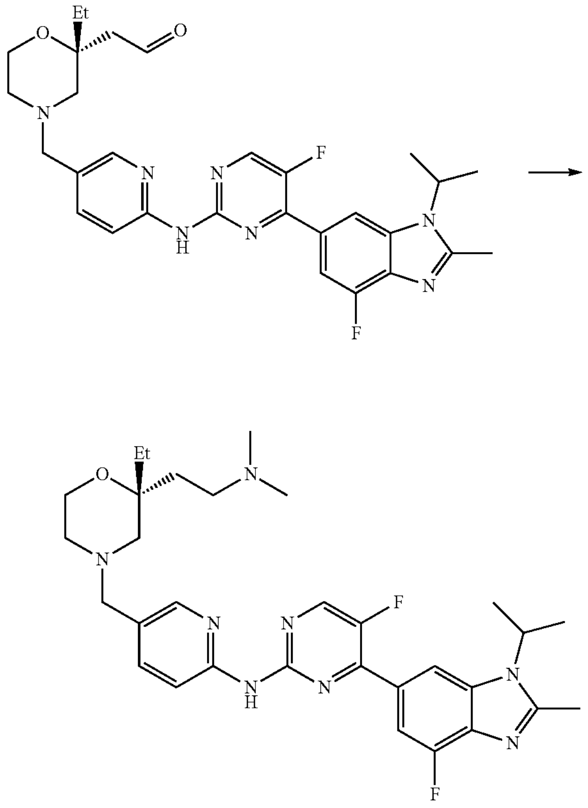 [SMILES: CC[C@@]1(CC=O)CN(Cc2ccc(Nc3ncc(F)c(-c4cc(F)c5nc(C)n(C(C)C)c5c4)n3)nc2)CCO1 ; CC[C@@]1(CCN(C)C)CN(Cc2ccc(Nc3ncc(F)c(-c4cc(F)c5nc(C)n(C(C)C)c5c4)n3)nc2)CCO1]

To a cooled (0° C.) solution of (R)-2-(2-ethyl-4-((6-((5-fluoro-4-(4-fluoro-1-isopropyl-2-methyl-1H-benzo[d]imidazol-6-yl)pyrimidin-2-yl)amino)pyridin-3-yl)methyl)morpholin-2-yl)acetaldehyde (70 mg, 0.13 mmol) in $CHCl_3$/MeOH (2:1, 2 mL) was added dimethylamine (2 M in THF, 0.64 mL, 1.3 mmol). After 15 min of stirring, sodium triacetoxyborohydride (55 mg, 0.25 mmol) was added and the reaction was warmed to room temperature and stirred for 2 h. Once complete, sodium hydroxide solution (0.5 M aq., 6 mL) was added and the mixture was extracted with $CHCl_3$ (3x3 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford (R)—N-(5-((2-(2-(dimethylamino)ethyl)-2-ethylmorpholino)methyl)pyridin-2-yl)-5-fluoro-4-(4-fluoro-1-isopropyl-2-methyl-1H-benzo[d]imidazol-6-yl)pyrimidin-2-amine as a fight orange oil. The oil was dissolved in water containing methanesulfonic acid (1.05 equiv.), and the solution was lyophilized to yield 25.3 mg of the mesylate salt as a tan solid.

Spectra of Mesylate Salt $^1$H NMR (400 MHz, DMSO-$d_6$) δ 8.70 (d, J=3.8 Hz, 1H), 8.30 (d, J=1.3 Hz, 1H), 8.27-8.19 (m, 2H), 7.73-7.65 (m, 2H), 4.85 (hept, J=6.9 Hz, 1H), 3.59 (m, 2H), 2.65 (s, 203H), 2.42-2.03 (m, 17H), 1.85-1.71 (m, 1H), 1.70-1.51 (m, 8H), 1.49-1.36 (m, 1H), 0.74 (t, J=7.5 Hz, 3H). MS: $[M+H]^+$ m/z 579.3.

Compound A3

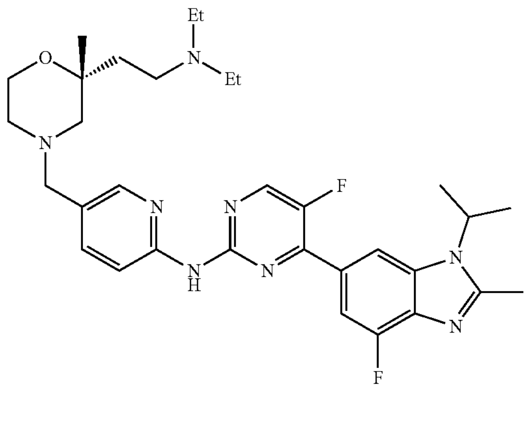 [SMILES: CCN(CC)CC[C@]1(C)CN(Cc2ccc(Nc3ncc(F)c(-c4cc(F)c5nc(C)n(C(C)C)c5c4)n3)nc2)CCO1]

To a cooled (0° C.) solution of (R)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)acetaldehyde (303 mg, 0.57 mmol) in $CHCl_3$/MeOH (2:1, 7 mL) was added diethylamine (0.3 mL, 2.83 mmol). After 15 min of stirring, sodium triacetoxyborohydride (242 mg, 1.14 mmol) was added and the reaction was warmed to room temperature and stirred for 2 h. Once complete, sodium hydroxide solution (0.5 M aq., 14 mL) was added and the mixture was extracted with $CHCl_3$ (3×10 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford (S)—N-(5-((2-(2-(diethylamino)ethyl)-2-methylmorpholino)methyl) pyridin-2-yl)-5-fluoro-4-(4-fluoro-1-isopropyl-2-methyl-1H-benzo[d]imidazol-6-yl)pyrimidin-2-amine as a light orange oil. The oil was dissolved in water containing methanesulfonic acid (1.05 equiv.), and the solution was lyophilized to yield 230 mg of the mesylate salt as a white solid.

Spectra of Mesylate Salt $^1H$ NMR (400 MHz, DMSO-$d_6$) δ 8.70 (d, J=3.9 Hz, 1H), 8.30 (d, J=1.3 Hz, 1H), 8.24 (dd, J=8.5, 0.8 Hz, 1H), 8.21 (dd, J=2.4, 0.8 Hz, 1H), 7.74-7.65 (m, 2H), 4.86 (p, J=6.8 Hz, 1H), 3.60 (t, J=4.8 Hz, 2H), 2.71-2.51 (m, 4H), 2.47-2.26 (m, 12H), 2.23 (d, J=11.0 Hz, 1H), 2.08 (d, J=11.2 Hz, 1H), 1.87-1.72 (m, 1H), 1.63 (d, J=6.9 Hz, 6H), 1.53 (ddd, J=13.3, 10.3, 5.9 Hz, 1H), 1.11 (s, 3H), 0.90 (t, J=7.1 Hz, 6H). MS: $[M+H]^+$ m/z 593.3.

Compound A16

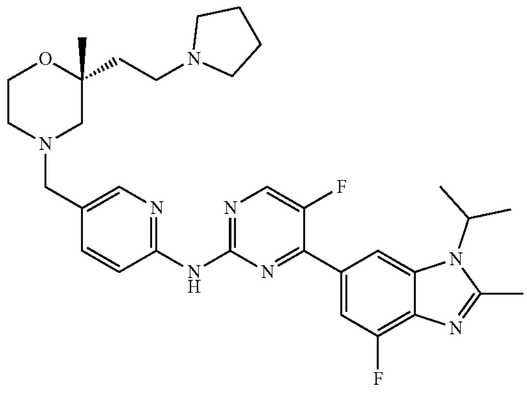 [SMILES: Cc1nc2c(F)cc(-c3nc(Nc4ccc(CN5CCO[C@](C)(CCN6CCCC6)C5)cn4)ncc3F)cc2n1C(C)C]

To a cooled (0° C.) solution of (R)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)acetaldehyde (45 mg, 0.084 mmol) in $CHCl_3$/MeOH (2:1, 1.5 mL) was added pyrrolidine (35 µL, 0.42 mmol). After 15 min of stirring, sodium triacetoxyborohydride (36 mg, 0.17 mmol) was added and the reaction was warmed to room temperature and stirred for 2 h. Once complete, sodium hydroxide solution (0.5 M aq., 5 mL) was added and the mixture was extracted with $CHCl_3$ (3×3 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford (R)-5-fluoro-4-(4-fluoro-1-isopropyl-2-methyl-1H-benzo[d]imidazol-6-yl)-N-(5-((2-methyl-2-(2-(pyrrolidin-1-yl)ethyl) morpholino)methyl)pyridin-2-yl)pyrimidin-2-amine as a light orange oil. The oil was dissolved in water containing methanesulfonic acid (1.05 equiv.), and the solution was lyophilized to yield 29.7 mg of the mesylate salt as a white solid.

Spectra of Mesylate Salt $^1H$ NMR (400 MHz, DMSO-$d_6$) δ 8.70 (d, 7=3.8 Hz, 1H), 8.30 (d, J=1.3 Hz, 1H), 8.24 (dd, J=8.5, 0.8 Hz, 1H), 8.21 (d, J=2.2 Hz, 1H), 7.74-7.65 (m, 2H), 4.85 (p, J=6.9 Hz, 1H), 3.59 (t, J=4.8 Hz, 2H), 2.64 (s, 4H), 2.47-2.26 (m, 12H), 2.23 (d, J=11.1 Hz, 1H), 2.09 (d, J=11.1 Hz, 1H), 1.99-1.78 (m, 1H), 1.69-1.53 (m, 11H), 1.11 (s, 3H).

MS: $[M+H]^+$ m/z 591.3.

Compound A11

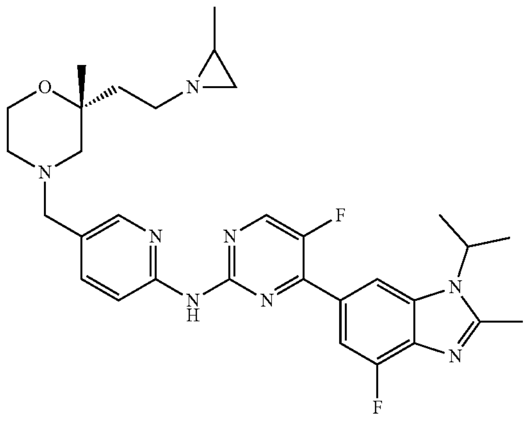 [SMILES: Cc1nc2c(F)cc(-c3nc(Nc4ccc(CN5CCO[C@](C)(CCN6CC6C)C5)cn4)ncc3F)cc2n1C(C)C]

To a cooled (0° C.) solution of (R)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)acetaldehyde (45 mg, 0.084 mmol) in $CHCl_3$/MeOH (2:1, 1.5 mL) was added 2-methylaziridine (30 µL, 0.42 mmol). After 15 min of stirring, sodium triacetoxyborohydride (36 mg, 0.17 mmol) was added and the reaction was warmed to room temperature and stirred for 2 h. Once complete, sodium hydroxide solution (0.5 M aq., 5 mL) was added and the mixture was extracted with $CHCl_3$ (3×3 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford 5-fluoro-4-(4-fluoro-1-isopropyl-2-methyl-1H-benzo[d]imidazol-6-yl)-N-(5-(((2R)-2-methyl-2-(2-(2-methylaziridin-1-yl) ethyl)morpholino)methyl)pyridin-2-yl)pyrimidin-2-amine as a light orange oil. The oil was dissolved in water containing methanesulfonic acid (1.05 equiv.), and the solution was lyophilized to yield 15.1 mg of the mesylate salt as a tan solid.

Spectra of Mesylate Salt

$^1$H NMR (400 MHz, DMSO-$d_6$) δ 8.70 (d, J=3.8 Hz, 1H), 8.30 (d, J=1.3 Hz, 1H), 8.28-8.14 (m, 2H), 7.81-7.60 (m, 2H), 5.80 (ddt, J=17.3, 10.3, 5.8 Hz, 1H), 5.13 (dq, J=17.2, 1.7 Hz, 1H), 5.02 (ddt, J=10.2, 2.4, 1.3 Hz, 1H), 4.85 (hept, J=6.9 Hz, 1H), 3.60 (t, J=5.0 Hz, 2H), 3.12 (dt, J=5.9, 1.5 Hz, 2H), 2.70-2.60 (m, 4H), 2.47 (m, 2H), 2.38-2.27 (m, 7H), 2.19 (d, J=11.0 Hz, 1H), 2.10 (d, J=11.0 Hz, 1H), 1.98-1.77 (m, 1H), 1.63 (d, J=6.9 Hz, 6H), 1.50 (ddd, J=13.6, 9.9, 6.1 Hz, 1H), 1.11 (s, 3H). MS: $[M+H]^+$ m/z 577.3.

Compound A17

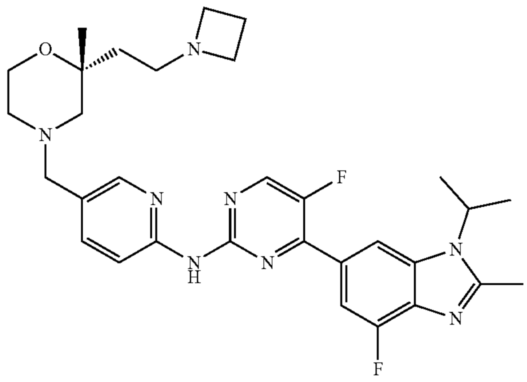 [SMILES: Cc1nc2c(F)cc(-c3nc(Nc4ccc(CN5CCO[C@](C)(CCN6CCC6)C5)cn4)ncc3F)cc2n1C(C)C]

To a cooled (0° C.) solution of (R)-2-(4-((6-((5-fluoro-4-(4-fluoro-1-isopropyl-2-methyl-1H-benzo[d]imidazol-6-yl)pyrimidin-2-yl)amino)pyridin-3-yl)methyl)-2-methylmorpholin-2-yl)acetaldehyde (45 mg, 0.084 mmol) in $CHCl_3$/MeOH (2:1, 1.5 mL) was added azetidine·HCl (40 mg, 0.42 mmol). After 15 min of stirring, sodium triacetoxyborohydride (36 mg, 0.17 mmol) was added and the reaction was warmed to room temperature and stirred for 2 h. Once complete, sodium hydroxide solution (0.5 M aq., 5 mL) was added and the mixture was extracted with $CHCl_3$ (3×3 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford (R)—N-(5-((2-(2-(azetidin-1-yl)ethyl)-2-methyl morpholino)methyl)pyridin-2-yl)-5-fluoro-4-(4-fluoro-1-isopropyl-2-methyl-1H-benzo[d]imidazol-6-yl)pyrimidin-2-amine as a light orange oil. The oil was dissolved in water containing methanesulfonic acid (1.05 equiv.), and the solution was lyophilized to yield 29.7 mg of the mesylate salt as a white solid.

Spectra of Mesylate Salt

$^1$H NMR (400 MHz, DMSO-$d_6$) δ 8.70 (d, J=3.8 Hz, 1H), 8.30 (d, J=1.3 Hz, 1H), 8.24 (dd, J=8.6, 0.9 Hz, 1H), 8.22-8.19 (m, 1H), 7.73-7.65 (m, 2H), 4.86 (p, J=6.9 Hz, 1H), 3.58 (t, J=4.9 Hz, 2H), 3.15-3.02 (m, 4H), 2.65 (s, 3H), 2.32 (s, 8H), 2.20 (d, J=11.1 Hz, 1H), 2.08 (d, J=11.3 Hz, 1H), 1.92 (p, J=6.9 Hz, 2H), 1.75-1.57 (m, 8H), 1.40-1.29 (m, 1H), 1.09 (s, 3H). MS: $[M+H]^+$ m/z 577.3.

Compound A18

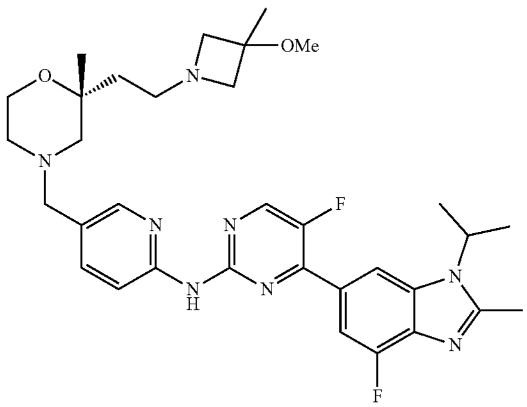 [SMILES: COC1(C)CN(CC[C@]2(C)CN(Cc3ccc(Nc4ncc(F)c(-c5cc(F)c6nc(C)n(C(C)C)c6c5)n4)nc3)CCO2)C1]

To a cooled (0° C.) solution of (R)-2-(4-((6-((5-fluoro-4-(4-fluoro-1-isopropyl-2-methyl-1H-benzo[d]imidazol-6-yl)pyrimidin-2-yl)amino)pyridin-3-yl)methyl)-2-methylmorpholin-2-yl)acetaldehyde (45 mg, 0.084 mmol) in $CHCl_3$/MeOH (2:1, 1.5 mL) was added 3-methoxy-3-methylazetidine·HCl (58 mg, 0.42 mmol). After 15 min of stirring, sodium triacetoxyborohydride (36 mg, 0.17 mmol) was added and the reaction was warmed to room temperature and stirred for 2 h. Once complete, sodium hydroxide solution (0.5 M aq., 5 mL) was added and the mixture was extracted with $CHCl_3$ (3×3 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-40%) to afford (R)-5-fluoro-4-(4-fluoro-1-isopropyl-2-methyl-1H-benzo[d]imidazol-6-yl)-N-(5-((2-(2-(3-methoxy-3-methylazetidin-1-yl)ethyl)-2-methylmorpholino)methyl)pyridin-2-yl)pyrimidin-2-amine as a light orange oil. The oil was dissolved in water containing methanesulfonic acid (1.05 equiv.), and the solution was lyophilized to yield 32.8 mg of the mesylate salt as a tan solid.

Spectra of Mesylate Salt

$^1$H NMR (400 MHz, DMSO-$d_6$) δ 8.70 (d, J=3.8 Hz, 1H), 8.30 (d, J=1.3 Hz, 1H), 8.25 (dd, J=8.5, 0.8 Hz, 1H), 8.22-8.19 (m, 1H), 7.74-7.65 (m, 2H), 4.85 (p, J=6.9 Hz, 1H), 3.58 (t, J=4.9 Hz, 2H), 3.11-3.04 (m, 5H), 2.83 (d, J=7.1 Hz, 2H), 2.64 (s, 3H), 2.43-2.25 (m, 8H), 2.21 (d, J=11.1 Hz, 1H), 2.07 (d, J=11.1 Hz, 1H), 1.77-1.58 (m, 7H), 1.44-1.26 (m, 5H), 1.10 (s, 3H). MS: $[M+H]^+$ m/z 621.3.

Compounds A52 and A53

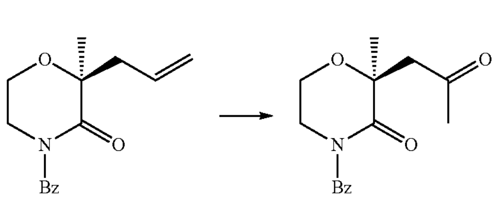

To a flask containing (S)-2-allyl-4-benzoyl-2-methylmorpholin-3-one (1.13 g, 4.4 mmol) was added $PdCl_2(CH_3CN)_3$ (34 mg, 0.13 mmol) and p-benzoquinone (0.71 g, 6.5 mmol). The flask was evacuated and backfilled with nitrogen gas 3 times before the t-BuOH/MeOH (1:1, 22 mL) and $H_2O$ (0.2 mL) were added. The reaction was heated to 50° C. and stirred for 4 h. Upon completion, the mixture was cooled to room temperature and the solvent was removed in vacuo. Sodium carbonate solution (1M aq., 100 mL) was then added and the mixture was extracted using EtOAc (3×100 mL). the combined organic layers were dried with $Na_2SO_4$ and concentrated in vacuo. The crude compound was purified using flash chromatography on $SiO_2$ (elution gradient of hexanes with EtOAc=0-30%) to afford (S)-4-benzoyl-2-methyl-2-(2-oxopropyl)morpholin-3-one (820 mg, 68% yield) as a colorless oil.

MS: $[M+H]^+$ m/z 276.1.

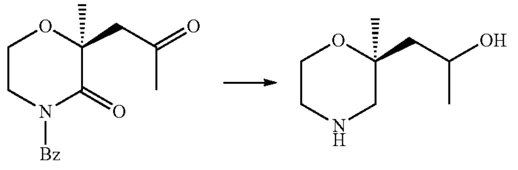

To a cooled (0° C.) solution of (S)-4-benzoyl-2-methyl-2-(2-oxopropyl)morpholin-3-one (43 mg, 0.16 mmol) in THF (1.6 mL) was added lithium aluminum hydride (59 mg, 1.6 mmol). The mixture was warmed to room temperature and heated to 50° C. for 22 h. Once complete, the mixture was cooled to 0° C. and $Et_2O$ (2 mL) was added. Water (0.071 mL) was slowly added, followed by sodium hydroxide solution (1M aq., 0.071 mL), and the mixture was warmed to room temperature and stirred for 15 min. The mixture was dried with $MgSO_4$, filtered through celite, and concentrated in vacuo to afford 1-((S)-2-methylmorpholin-2-yl)propan-2-ol (25 mg) as a colorless oil and mixture of diasteriomers at the alcohol. The compound was used immediately without further purification.

MS: $[M+H]^+$ m/z 160.1.

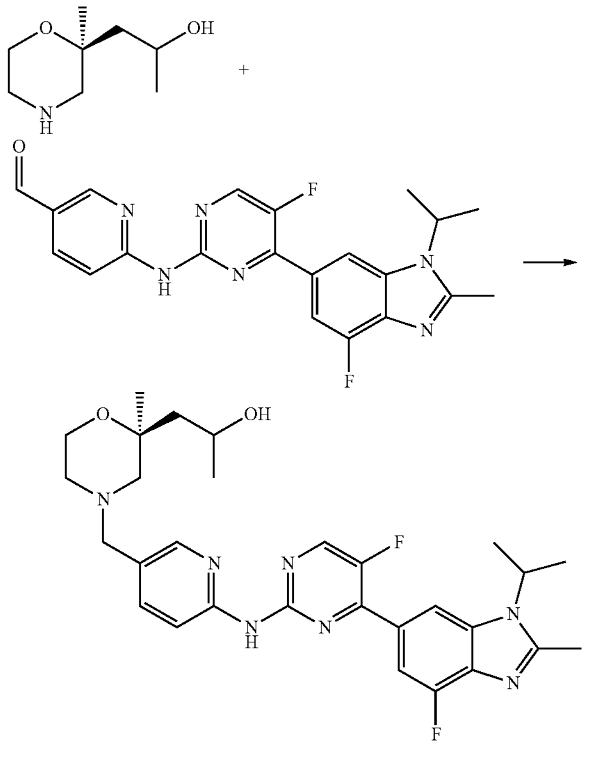

To a solution of 1-((S)-2-methylmorpholin-2-yl)propan-2-ol (25 mg, 0.16 mmol) and 6-((5-fluoro-4-(4-fluoro-1-isopropyl-2-methyl-1H-benzo[d]imidazol-6-yl)pyrimidin-2-yl)amino)nicotinaldehyde (26 mg, 0.06 mmol) in DMSO (1.7 mL) was added sodium triacetoxyborohydride (41 mg, 0.19 mmol), followed by acetic acid (37 μL, 0.64 mmol). The reaction was heated to 60° C. and stirred for 16 h. Once complete, the mixture was filtered and purified using preparative HPLC (elution gradient of $H_2O$+0.25% TFA with MeCN=10-24%) to yield 1-((S)-4-((6-((5-fluoro-4-(4-fluoro-1-isopropyl-2-methyl-1H-benzo[d]imidazol-6-yl)pyrimidin-2-yl)amino)pyridin-3-yl)methyl)-2-methylmorpholin-2-yl)propan-2-ol (8 mg of major diastereomer, 6 mg of minor diastereomer) as light brown solids.

Spectra of Freebase

Compound A52: Peak 1, Minor Diastereomer

15 $^1$H NMR (400 MHz, Chloroform-d) δ 8.47 (d, J=3.7 Hz, 1H), 8.44 (dd, J=8.6, 0.8 Hz, 1H), 8.36 (s, 1H), 8.31-8.26 (m, 1H), 8.21 (d, J=1.3 Hz, 1H), 7.82 (dd, J=11.6, 1.4 Hz, 1H), 7.72 (dd, J=8.6, 2.3 Hz, 1H), 4.76 (hept, J=7.0 Hz, 1H), 4.25 (dtt, J=12.8, 6.6, 3.2 Hz, 1H), 4.09 (s, 1H), 3.86-3.77 (m, 2H), 3.45 (q, J=12.2 Hz, 2H), 2.72 (s, 3H), 2.55 (dt, J=10.6, 3.9 Hz, 1H), 2.41-2.29 (m, 2H), 2.15 (d, J=11.2 Hz, 1H), 1.90 (dd, J=14.7, 10.5 Hz, 1H), 1.74 (d, J=7.0 Hz, 6H), 1.40 (s, 3H), 1.32 (dd, J=14.5, 1.4 Hz, 1H), 1.17 (d, J=6.1 Hz, 3H). MS: $[M+H]^+$ m/z 552.3.

Compound A53: Peak 1, Major Diastereomer $^1$H NMR (400 MHz, Chloroform-d) δ 8.71-8.14 (m, 5H), 7.82 (dd, J=11.5, 1.2 Hz, 1H), 7.73 (d, J=8.6 Hz, 1H), 4.76 (hept, J=6.9 Hz, 1H), 4.23-4.10 (m, 1H), 3.88 (ddd, J=12.2, 9.4, 2.8 Hz, 1H), 3.75 (dt, J=11.9, 3.4 Hz, 1H), 3.56 (d, J=13.1 Hz, 1H), 3.39 (d, J=13.2 Hz, 1H), 2.72 (s, 3H), 2.59 (d, J=11.3 Hz, 1H), 2.44 (d, J=11.4 Hz, 1H), 2.38-2.22 (m, 2H), 1.86-1.68 (m, 8H), 1.52 (dd, J=14.9, 1.6 Hz, 1H), 1.35 (s, 3H), 1.16 (d, 7=6.2 Hz, 3H). MS: $[M+H]^+$ m/z 552.3.

Compound A47

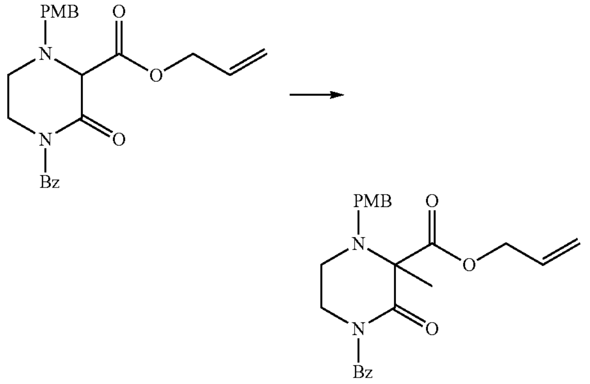

To a cooled (0° C.) solution of allyl 4-benzoyl-1-(4-methoxybenzyl)-3-oxopiperazine-2-carboxylate (1.2 g, 3.0 mmol) in THF (30 mL) was added sodium hydride (60% mineral oil dispersion, 0.14 g, 3.5 mmol). After 45 min of stirring, iodomethane (0.3 mL, 4.4 mmol) was added and the reaction was warmed to room temperature, stirring for 20 h. Once complete, saturated ammonium chloride (aq., 30 mL) and saturated sodium bicarbonate (aq., 30 mL) was added. The mixture was extracted with $CH_2Cl_2$ (2×50 mL) and the combine organic layers were dried with $Na_2SO_4$ and concentrated in vacuo. The crude compound was purified using flash chromatography on $SiO_2$ (elution gradient of hexanes with EtOAc=0-50%) to afford allyl 4-benzoyl-1-(4-methoxybenzyl)-2-methyl-3-oxopiperazine-2-carboxylate (141 mg, 11% yield) as a colorless oil.

MS: $[M+H]^+$ m/z 423.2.

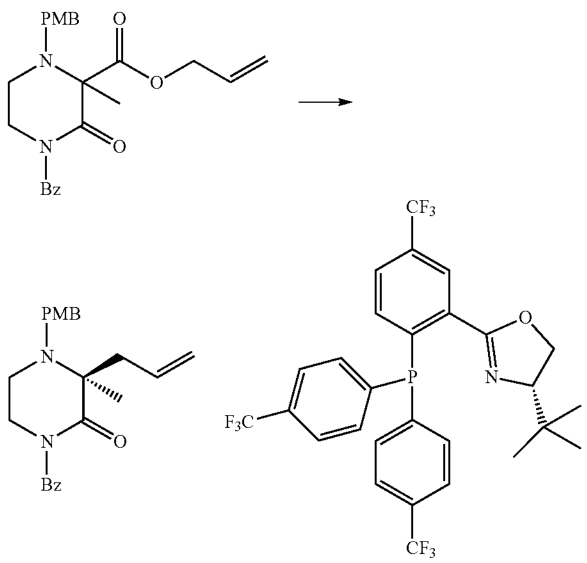

(S)-(p-$CF_3$)$_3$-t-BuPHOX

To a schlenk flask equipped with a stir bar was added $Pd(OAc)_2$ (3.7 mg, 0.017 mmol), (S)-(p-$CF_3$)$_3$-t-BuPHOX (25 mg, 0.041 mmol), and THF (7 mL). the mixture was stirred for 30 min, after which allyl 4-benzoyl-1-(4-methoxybenzyl)-2-methyl-3-oxopiperazine-2-carboxylate (141 mg, 0.33 mmol) was added as a solution in THF (4 mL). The flask was sealed and heated to 50° C. for 3 days. Once complete, the reaction was cooled to room temperature and vented to release the evolved $CO_2$. The mixture was filtered through celite, washing with EtOAc, and concentrated in vacuo. The crude compound was purified using flash chromatography on $SiO_2$ (elution gradient of hexanes with EtOAc=0-30%) to afford (S)-3-allyl-1-benzoyl-4-(4-methoxybenzyl)-3-methylpiperazin-2-one (78 mg, 62% yield, 90% ee) as a colorless oil.

MS: $[M+H]^+$ m/z 379.2.

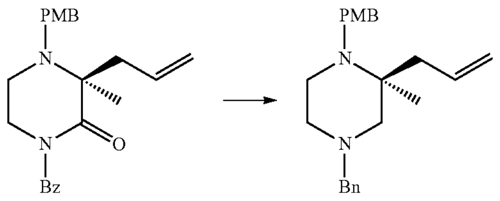

To a cooled (0° C.) solution of (S)-3-allyl-1-benzoyl-4-(4-methoxybenzyl)-3-methylpiperazin-2-one (78 mg, 0.21 mmol) in THF (2.2 mL) was added lithium aluminum hydride (78 mg, 2.1 mmol). The mixture was warmed to room temperature and heated to 50° C. for 18 h. Once complete, the mixture was cooled to 0° C. and $Et_2O$ (3 mL) was added. Water (0.1 mL) was slowly added, followed by sodium hydroxide solution (1M aq., 0.1 mL), and the mixture was warmed to room temperature and stirred for 15 min. The mixture was dried with $MgSO_4$, filtered through celite, and concentrated in vacuo to afford (S)-2-allyl-4-benzyl-1-(4-methoxybenzyl)-2-methylpiperazine (18 mg) as a colorless oil. The compound was used immediately without further purification.

MS: $[M+H]^+$ m/z 351.2.

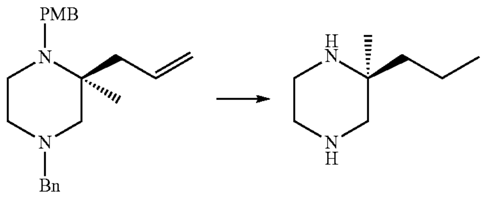

To a solution of (S)-2-allyl-4-benzyl-1-(4-methoxybenzyl)-2-methylpiperazine (18 mg, 0.051 mmol) in EtOH/$CH_2C_{1-2}$ (4:1, 1.25 mL) was added 10% palladium on carbon (10 mg). The reaction vessel was placed in a pressure bomb and charged with 1000 psi of hydrogen gas. The system was heated to 60° C. for 2 days. Once complete, the mixture was filtered through celite, washing with $CH_2Cl_2$/MeOH (1:1) and concentrated in vacuo to afford (S)-2-methyl-2-propyl piperazine (7 mg) as a colorless oil. The compound was used immediately without further purification.

MS: $[M+H]^+$ m/z 143.2.

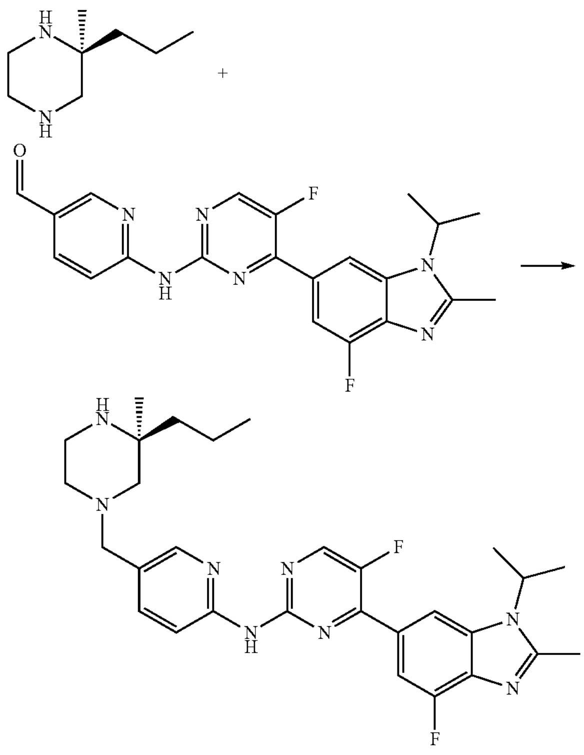

To a solution of (S)-2-methyl-2-propylpiperazine (7 mg, 0.05 mmol) and 6-((5-fluoro-4-(4-fluoro-1-isopropyl-2-methyl-1H-benzo[d]imidazol-6-yl)pyrimidin-2-yl)amino) nicotinaldehyde (10 mg, 0.025 mmol) in DMSO (0.5 mL) was added sodium triacetoxyborohydride (16 mg, 0.075 mmol), followed by acetic acid (14 μL, 0.25 mmol). The reaction was heated to 60° C. and stirred for 24 h. Once complete, the mixture was filtered and purified using preparative HPLC (elution gradient of $H_2O$+0.1% AcOH with MeCN=10-50%) to yield (S)-5-fluoro-4-(4-fluoro-1-isopropyl-2-methyl-1H-benzo[d]imidazol-6-yl)-N-(5-((3-methyl-3-propylpiperazin-1-yl)methyl)pyridin-2-yl)pyrimidin-2-amine (10 mg) as a white solid.

Spectra of Freebase

$^1$H NMR (400 MHz, Chloroform-<f) δ8.46 (d, J=3.7 Hz, 1H), 8.42 (dd, J=8.6, 0.8 Hz, 1H), 8.31-8.24 (m, 2H), 8.23 (d, J=1.3 Hz, 1H), 7.85-7.78 (m, 1H), 7.72 (dd, J=8.6, 2.3 Hz, 1H), 4.76 (hept, J=7.0 Hz, 1H), 3.45 (s, 2H), 2.95 (d, J=5.4 Hz, 2H), 2.72 (s, 3H), 2.52-2.33 (m, 2H), 2.28-2.10 (m, 2H), 1.74 (d, J=6.9 Hz, 6H), 1.68-1.49 (m, 1H), 1.47-1.19 (m, 4H), 1.13 (s, 3H), 0.93 (t, J=6.9 Hz, 3H). MS: $[M+H]^+$ m/z 535.3.

Compound B3

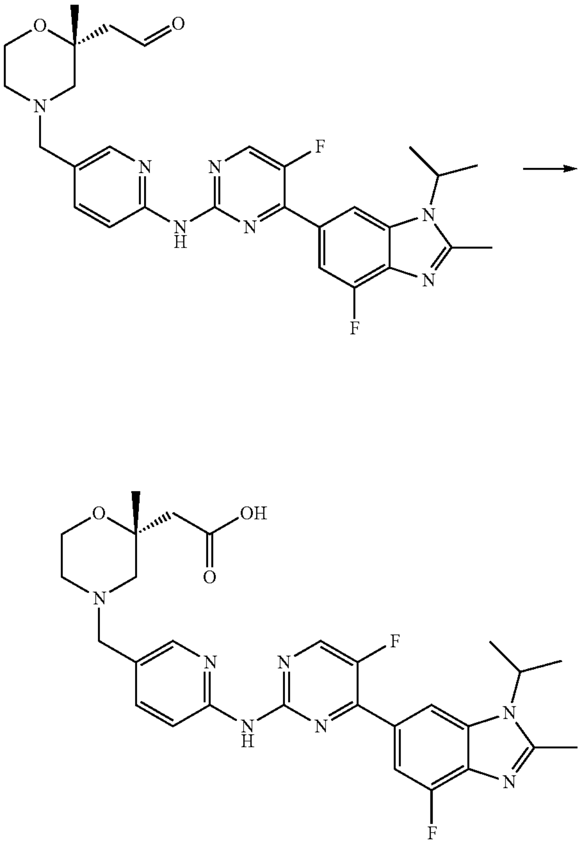

To a cooled (0° C.) solution of (R)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)acetaldehyde (B2) (30 mg, 0.056 mmol) in tBuOH/MeCN (1:1, 1 mL) was added 2-methyl-2-butene (0.12 mL, 1.12 mmol), followed by dropwise addition of a solution of sodium chlorite (50 mg, 0.56 mmol) and sodium phosphate monobasic (87 mg, 0.56 mmol) in water (1 mL). the reaction was warmed to room temperature and stirred for 5 h. Once complete, water (1 mL) was added and the mixture was extracted with $CHCl_3$ (3×2 mL). The organic layers were combined, dried with $Na_2SO_4$, and concentrated in vacuo to afford (R)-2-(4-((6-((5-fluoro-4-(4-fluoro-1-isopropyl-2-methyl-1H-benzo[d]imidazol-6-yl)pyrimidin-2-yl) amino)pyridin-3-yl)methyl)-2-methylmorpholin-2-yl)acetic acid (31 mg) as a brown solid. The compound was used without further purification.

MS: $[M+H]^+$ m/z 552.3.

Compound A55

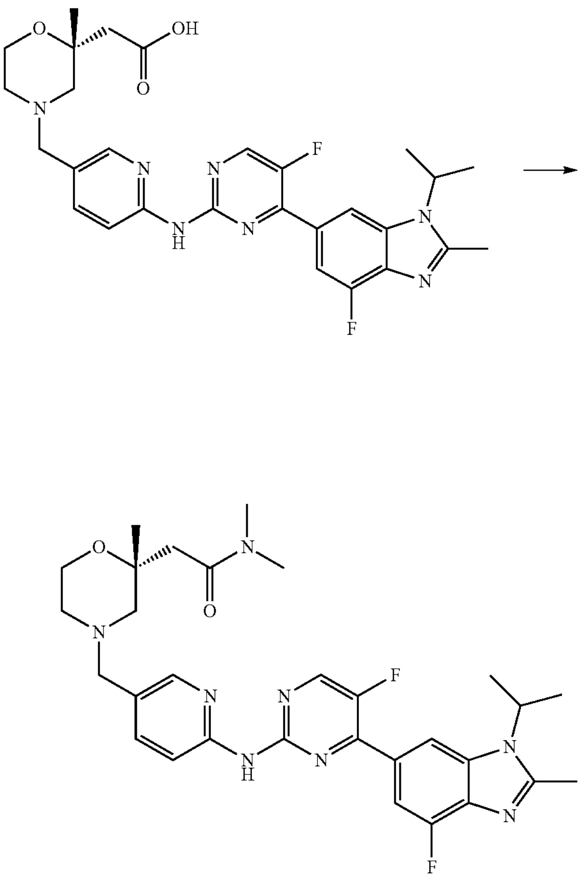

To a cooled (0° C.) solution of (R)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)acetic acid (31 mg, 0.056 mmol) in DMF (2.5 mL) was added N,N-diisopropylethylamine (50 μL, 0.28 mmol), followed by HATU (32 mg, 0.084 mmol). After 15 min of stirring, dimethylamine (2 M in THF, 84 μL, 0.17 mmol) was added and the reaction was stirred for 1.5 h. Once complete, saturated sodium bicarbonate (aq., 5 mL) was added and the mixture was extracted with $CHCl_3$ (3×2 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-20%) to afford (R)-2-(4-((6-((5-fluoro-4-(4-fluoro-1-isopropyl-2-methyl-1H-benzo [d]imidazol-6-yl)pyrimidin-2-yl)amino)pyridin-3-yl) methyl)-2-methylmorpholin-2-yl)-N,N-dimethylacetamide as a light orange oil. The oil was dissolved in water containing methanesulfonic acid (1.05 equiv.), and the solution was lyophilized to yield 7.2 mg of the mesylate salt as a tan solid.

Spectra of Mesylate Salt (Signals Broadened by Amide Rotamers)

$^1$H NMR (400 MHz, DMSO-d6) δ 10.42 (s, 1H), 8.70 (d, J=3.6 Hz, 1H), 8.36 (s, 1H), 8.29 (d, J=8.8 Hz, 1H), 8.23 (s, 1H), 7.86 (d, J=8.9 Hz, 1H), 7.66 (d, J=12.0 Hz, 1H), 4.80 (hept, J=6.9 Hz, 1H), 4.31 (d, J=22.5 Hz, 2H), 3.85-3.74 (m, 2H), 3.20-3.04 (m, 2H) 2.96-2.89 (m, 3H), 2.77-2.69 (m, 3H), 2.63-2.52 (m, 5H), 2.23 (s, 3H), 1.57 (d, J=6.8 Hz, 6H), 1.36 (s, 2H), 1.28-1.06 (m, 3H). MS: $[M+H]^+$ m/z 579.3.

Compound A56

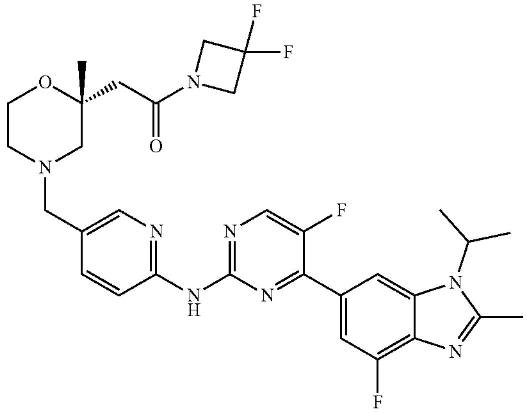 [SMILES: Cc1nc2c(F)cc(-c3nc(Nc4ccc(CN5CCO[C@](C)(CC(=O)N6CC(F)(F)C6)C5)cn4)ncc3F)cc2n1C(C)C]

To a cooled (0° C.) solution of (R)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)acetic acid (31 mg, 0.056 mmol) in DMF (2.5 mL) was added N,N-diisopropylethylamine (50 μL, 0.28 mmol), followed by HATU (32 mg, 0.084 mmol). After 15 min of stirring, 3,3-difluoroazetidine·HCl (22 mg, 0.17 mmol) was added and the reaction was stirred for 1.5 h. Once complete, saturated sodium bicarbonate (aq., 5 mL) was added and the mixture was extracted with $CHCl_3$ (3×2 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-20%) to afford (R)-1-(3,3-difluoroazetidin-1-yl)-2-(4-((6-((5-fluoro-4-(4-fluoro-1-isopropyl-2-methyl-1H-benzo[d]imidazol-6-yl)pyrimidin-2-yl)amino)pyridin-3-yl)methyl)-2-methylmorpholin-2-yl) ethan-1-one as a light orange oil. The oil was dissolved in water containing methanesulfonic acid (1.05 equiv.), and the solution was lyophilized to yield 7.2 mg of the mesylate salt as a tan solid.

Spectra of Mesylate Salt (Signals Broadened by Amide Rotamers)

$^1$H NMR (400 MHz, DMSO-$d_6$) δ 10.43 (s, 1H), 8.70 (d, J=3.7 Hz, 1H), 8.36 (s, 1H), 8.28 (d, J=8.8 Hz, 1H), 8.23 (d, J=1.3 Hz, 1H), 7.92-7.82 (m, 1H), 7.72-7.62 (m, 1H), 4.80 (p, J=6.9 Hz, 1H), 4.65-4.45 (m, 2H), 4.43-4.12 (m, 4H), 3.88-3.71 (m, 2H), 3.25-3.08 (m, 2H), 3.08-2.74 (m, 2H), 2.60 (s, 3H), 2.49-2.36 (m, 2H), 2.23 (s, 3H), 1.57 (d, J=6.9 Hz, 6H), 1.17 (d, J=6.1 Hz, 3H). MS: $[M+H]^+$ m/z 627.3.

Compound A57

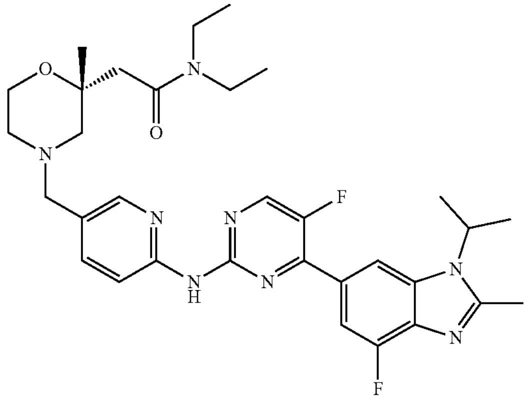 [SMILES: CCN(CC)C(=O)C[C@]1(C)CN(Cc2ccc(Nc3ncc(F)c(-c4cc(F)c5nc(C)n(C(C)C)c5c4)n3)nc2)CCO1]

To a cooled (0° C.) solution of (R)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)acetic acid (31 mg, 0.056 mmol) in DMF (2.5 mL) was added N,N-diisopropylethylamine (50 μL, 0.28 mmol), followed by HATU (32 mg, 0.084 mmol). After 15 min of stirring, diethylamine (18 μL, 0.17 mmol) was added and the reaction was stirred for 1 h. Once complete, saturated sodium bicarbonate (aq., 5 mL) was added and the mixture was extracted with $CHCl_3$ (3×2 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-20%) to afford (R)-2-(4-((6-((5-fluoro-4-(4-fluoro-1-isopropyl-2-methyl-1H-benzo[d]imidazol-6-yl)pyrimidin-2-yl)amino)pyridin-3-yl)methyl)-2-methyl-morpholin-2-yl)-N,N-diethylacetamide as a tan oil. The oil was dissolved in water containing methanesulfonic acid (1.05 equiv.), and the solution was lyophilized to yield 10.4 mg of the mesylate salt as a tan solid.

Spectra of Mesylate Salt (Signals Broadened by Amide Rotamers)

$^1$H NMR (400 MHz, DMSO-d6) δ 10.45 (s, 1H), 8.70 (d, J=3.7 Hz, 1H), 8.37 (s, 1H), 8.33-8.18 (m, 2H), 7.93-7.82 (m, 1H), 7.67 (d, J=11.9 Hz, 1H), 4.80 (p, J=7.0 Hz, 1H), 4.44-4.18 (m, 2H), 3.89-3.70 (m, 2H), 3.68-3.58 (m, 2H), 3.23-3.09 (m, 4H), 3.06-2.77 (m, 2H), 2.60 (s, 3H), 2.56-2.43 (m, 2H), 2.23 (s, 3H), 1.57 (d, J=6.9, 6H), 1.16 (d, J=6.6 Hz, 3H), 1.06-0.98 (m, 3H), 0.96-0.86 (m, 3H). MS: $[M+H]^+$ m/z 10579.3.

Compound A58

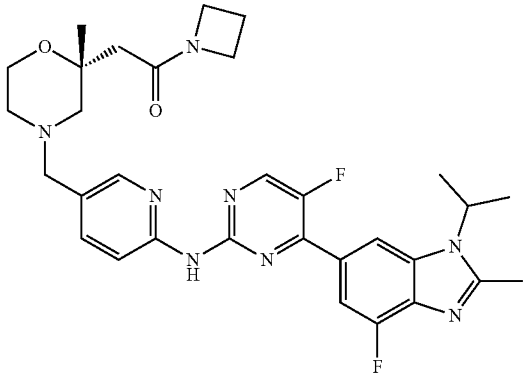 [SMILES: Cc1nc2c(F)cc(-c3nc(Nc4ccc(CN5CCO[C@](C)(CC(=O)N6CCC6)C5)cn4)ncc3F)cc2n1C(C)C]

To a cooled (0° C.) solution of (R)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)acetic acid (31 mg, 0.056 mmol) in DMF (2.5 mL) was added N,N-diisopropylethylamine (50 μL, 0.28 mmol), followed by HATU (32 mg, 0.084 mmol). After 15 min of stirring, azetidine·HCl (16, 0.17 mmol) was added and the reaction was stirred for 1 h. Once complete, saturated sodium bicarbonate (aq., 5 mL) was added and the mixture was extracted with $CHCl_3$ (3×2 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-20%) to afford (R)-1-(azetidin-1-yl)-2-(4-((6-((5-fluoro-4-(4-fluoro-1-isopropyl-2-methyl-1H-benzo[d]imidazol-6-yl)pyrimidin-2-yl)amino)pyridin-3-yl) methyl)-2-methylmorpholin-2-yl)ethan-1-one as a pale orange oil. The oil was dissolved in water containing methanesulfonic acid (1.05 equiv.), and the solution was lyophilized to yield 6.7 mg of the mesylate salt as a tan solid.

Spectra of Mesylate Salt (Signals Broadened by Amide Rotamers)

$^1$H NMR (400 MHz, DMSO-d6) δ 10.46 (s, 1H), 8.71 (d, J=3.7 Hz, 1H), 8.43-8.16 (m, 3H), 7.87 (d, J=8.8 Hz, 1H), 7.68 (d, J=12.0 Hz, 1H), 4.81 (p, J=6.8 Hz, 1H), 4.45-4.18 (m, 2H), 4.13-4.01 (m, 2H), 3.86-3.70 (m, 4H), 3.49-3.33 (m, 2H), 3.25-3.12 (m, 2H), 3.05-2.77 (m, 2H), 2.60 (s, 3H), 2.24 (s, 3H), 2.14-2.03 (m, 2H), 1.57 (d, J=6.7 Hz, 6H), 1.16 (d, J=6.0 Hz, 3H). MS: $[M+H]^+$ m/z 591.3.

Compound A59

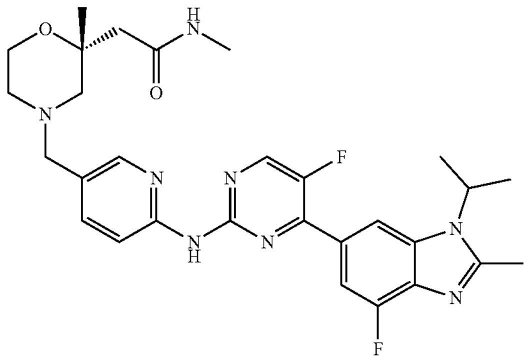 [SMILES: CNC(=O)C[C@]1(C)CN(Cc2ccc(Nc3ncc(F)c(-c4cc(F)c5nc(C)n(C(C)C)c5c4)n3)nc2)CCO1]

To a cooled (0° C.) solution of (R)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)acetic acid (31 mg, 0.056 mmol) in DMF (2.5 mL) was added N,N-diisopropylethylamine (50 μL, 0.28 mmol), followed by HATU (32 mg, 0.084 mmol). After 15 min of stirring, methylamine (2 M in MeOH, 84 μL, 0.17 mmol) was added and the reaction was stirred for 1 h. Once complete, saturated sodium bicarbonate (aq., 5 mL) was added and the mixture was extracted with $CHCl_3$ (3x2 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-20%) to afford (R)-2-(4-((6-((5-fluoro-4-(4-fluoro-1-isopropyl-2-methyl-1H-benzo [d]imidazol-6-yl)pyrimidin-2-yl)amino)pyridin-3-yl) methyl)-2-methylmorpholin-2-yl)-A-methylacetamide as a light orange oil. The oil was dissolved in water containing methanesulfonic acid (1.05 equiv.), and the solution was lyophilized to yield 8.9 mg of the mesylate salt as a tan solid.

Spectra of Mesylate Salt (Signals Broadened by Amide Rotamers)

$^1$H NMR (400 MHz, DMSO-$d_6$) δ 10.41 (s, 1H), 8.70 (d, J=3.7 Hz, 1H), 8.36 (s, 1H), 8.29 (d, J=8.5 Hz, 1H), 8.23 (d, J=1.3 Hz, 1H), 7.86 (d, J=9.2 Hz, 1H), 7.66 (dd, J=11.9, 1.3 Hz, 1H), 4.80 (p, J=6.9 Hz, 1H), 4.42-4.20 (m, 2H), 3.86-3.70 (m, 2H), 3.69-3.51 (m, 2H), 3.07-2.43 (m, 2H), 2.59 (s, 3H), 2.54-2.43 (m, 4H), 2.34-2.19 (m, 6H), 1.57 (d, J=6.8 Hz, 6H), 1.14 (d, J=22.9 Hz, 3H). MS: $[M+H]^+$ m/z 565.3.

Compound A60

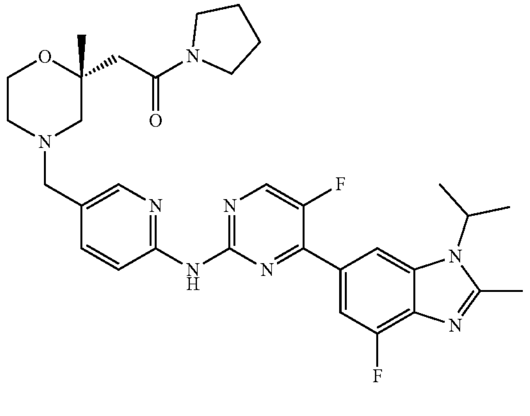 [SMILES: Cc1nc2c(F)cc(-c3nc(Nc4ccc(CN5CCO[C@](C)(CC(=O)N6CCCC6)C5)cn4)ncc3F)cc2n1C(C)C]

To a cooled (0° C.) solution of (R)-2-(4-((6-((5-fluoro-4-(4-fluoro-1-isopropyl-2-methyl-1H-benzo[d]imidazol-6-yl) pyrimidin-2-yl)amino)pyridin-3-yl)methyl)-2-methylmorpholin-2-yl)acetic acid (31 mg, 0.056 mmol) in DMF (2.5 mL) was added N,N-diisopropylethylamine (50 μL, 0.28 mmol), followed by HATU (32 mg, 0.084 mmol). After 15 min of stirring, pyrrolidine (15 μL, 0.17 mmol) was added and the reaction was stirred for 1 h. Once complete, saturated sodium bicarbonate (aq., 5 mL) was added and the mixture was extracted with $CHCl_3$ (3x2 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-20%) to afford (R)-2-(4-((6-((5-fluoro-4-(4-fluoro-1-isopropyl-2-methyl-1H-benzo[d]imidazol-6-yl)pyrimidin-2-yl)amino)pyridin-3-yl)methyl)-2-methylmorpholin-2-yl)-1-(pyrrolidin-1-yl)ethan-1-one as a light orange oil. The oil was dissolved in water containing methanesulfonic acid (1.05 equiv.), and the solution was lyophilized to yield 7.9 mg of the mesylate salt as a tan solid.

Spectra of Mesylate Salt (Signals Broadened by Amide Rotamers)

$^1$H NMR (400 MHz, DMSO-$d_6$) δ 10.39 (s, 1H), 8.69 (d, J=3.7 Hz, 1H), 8.36 (s, 1H), 8.29 (d, J=8.6 Hz, 1H), 8.22 (d, J=1.3 Hz, 1H), 7.85 (d, J=8.9 Hz, 1H), 7.65 (d, J=11.9 Hz, 1H), 4.79 (p, J=6.9 Hz, 1H), 4.41-4.20 (m, 2H), 3.87-3.72 (m, 2H), 3.69-3.55 (m, 2H), 3.23-3.08 (m, 4H), 3.04-2.76 (m, 2H), 2.59 (s, 3H), 2.52-2.46 (m, 2H), 2.23 (s, 3H), 1.86-1.74 (m, 2H), 1.74-1.63 (m, 2H), 1.57 (d, J=6.9 Hz, 6H), 1.17 (s, 3H). MS: $[M+H]^+$ m/z 605.3.

Example 2: Synthesis of Compound A43 and A44

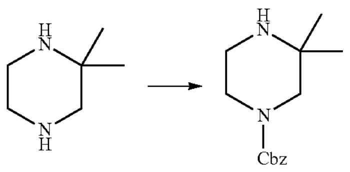

A dry round-bottomed flask was charged with 2,2-dimethylpiperazine (896 mg, 7.8 mmol) followed by dichloromethane (40 mL) and triethylamine (1.63 mL, 11.8 mmol). The reaction flask was cooled to −78° C. and benzyl chloroformate was injected (1.23 mL, 8.6 mmol), the reaction was allowed to warm to ambient temperature for three hours. Solvent was removed in vacuo and the reaction was purified by silica gel chromatography (0-10% methanol/dichloromethane). The major fraction was collected to yield after removal of solvent benzyl 3,3-dimethylpiperazine-1-carboxylate (1.96 g, quant.). MS: $[M+H]^+$ m/z 249.

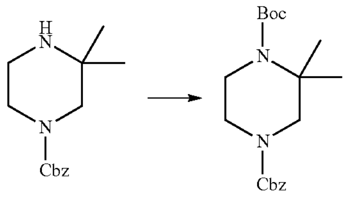 [SMILES: CC1(C)CN(C(=O)OCc2ccccc2)CCN1 ; CC(C)(C)OC(=O)N1CCN(C(=O)OCc2ccccc2)CC1(C)C]

Benzyl 3,3-dimethylpiperazine-1-carboxylate (3.77 g, 15.0 mmol) was dissolved in dichloromethane (75 mL) under nitrogen and triethylamine (6.2 mL, 45.0 mmol) was injected, followed by di-tert-butyl dicarbonate (3.98 g, 18.2 mmol). After two hours conversion was incomplete by TLC analysis and a second portion of di-tert-butyl dicarbonate (2.00 g, 9.1 mmol) was added and the reaction was stirred for 16 hours. The reaction was concentrated in vacuo and purified by silica gel chromatography (ethyl acetate/hexanes 0-100%) to yield 4-benzyl 1-(tert-butyl) 2,2-dimethylpiperazine-1,4-dicarboxylate as a clear oil (4.95 g, 95%). MS: $[M+H]^+$ m/z 349.

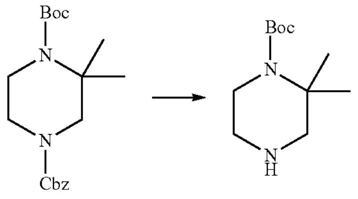 [SMILES: CC(C)(C)OC(=O)N1CCN(C(=O)OCc2ccccc2)CC1(C)C ; CC(C)(C)OC(=O)N1CCNCC1(C)C]

A flask containing 4-benzyl 1-(tert-butyl) 2,2-dimethylpiperazine-1,4-dicarboxylate (4.95 g, 14.2 mmol) was charged with ethyl acetate (100 mL), followed by palladium on carbon (10%, 376 mg). Hydrogen gas was bubbled through the reaction mixture for 10 minutes and stirring was continued under an atmosphere of hydrogen for 5 hours. At this time TLC analysis indicated the reaction was complete (10% dichloromethane/methanol). The reaction was filtered through celite and the filtrate was concentrated in vacuo to yield tert-butyl 2,2-dimethylpiperazine-1-carboxylate (3.01 g, 1099%) as a slightly yellow oil. MS: $[M+H]^+$ m/z 215.

Compound A44

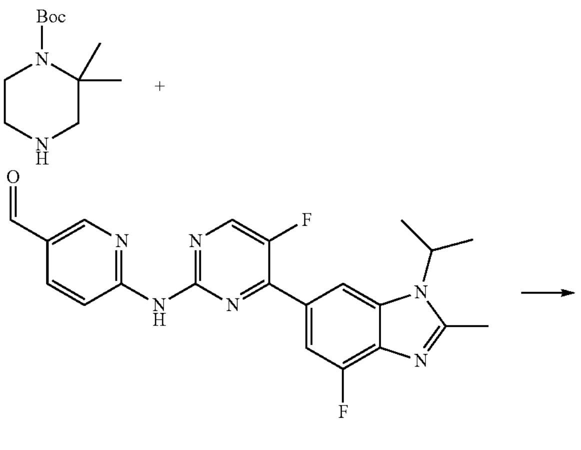

-continued

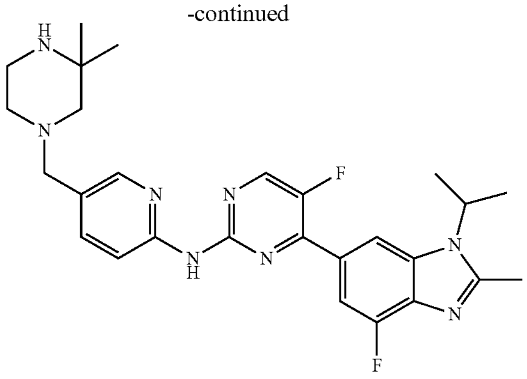

tert-butyl 2,2-dimethylpiperazine-1-carboxylate (352 mg, 1.6 mmol) was dissolved in dimethylsulfoxide (16.5 mL) and acetic acid (0.45 mL). 6-((5-fluoro-4-(4-fluoro-1-isopropyl-2-methyl-1H-benzo[d]imidazol-6-yl)pyrimidin-2-yl)amino)nicotinaldehyde was added (336 mg, 0.8 mmol) and the reaction was stirred for 30 minutes followed by addition of sodium triacetoxyborohydride (694 mg, 3.3 mmol). The reaction was warmed to 60° C. and heated for 17 hours before cooling to ambient temperature and pouring into a mixture of chloroform and 1N sodium hydroxide (100 mL portions). The organic phase was separated, dried over sodium sulfate, filtered and concentrated to dryness. The crude product was dissolved in dichloromethane and trifluoroacetic acid (5 mL portions) and stirred for 2 hours. The reaction was concentrated in vacuo and dissolved in dimethylsulfoxide. After filtration, the filtrate was purified by reversed phase HPLC (10-60% acetonitrile/water+0.25% trifluoroacetic acid over 15 minutes). The active fractions were pooled and concentrated on the Genevac to yield a white solid that was partitioned between ethyl acetate and saturated sodium bicarbonate to yield after concentration of the organic phase 7V-(5-((3,3-dimethylpiperazin-1-yl)methyl)pyridin-2-yl)-5-fluoro-4-(4-fluoro-1-isopropyl-2-methyl-1H-benzo[d]imidazol-6-yl)pyrimidin-2-amine (241 mg, 58%) as a white solid. The mesylate salt was prepared via treating an acetonitrile solution of the compound with aqueous methanesulfonic acid and then freezing the solution and concentrating to a white solid on the lyophilizer.

$^1H$ NMR (500 MHz, Methanol-$d_4$) δ 8.60 (d, J=3.8 Hz, 1H), 8.40 (dd, J=8.6, 0.8 Hz, 1H), 8.37 (d, J=1.3 Hz, 1H), 8.28 (dd, J=2.4, 0.8 Hz, 1H), 7.89-7.82 (m, 2H), 5.01-4.96 (m, 1H), 3.65 (s, 2H), 3.32 (t, J=5.2 Hz, 2H), 2.76 (s, 5H), 2.52 (s, 2H), 1.78 (d, J=6.9 Hz, 6H), 1.46 (s, 6H). MS: $[M+H]^+$ m/z 507.

Compound A43

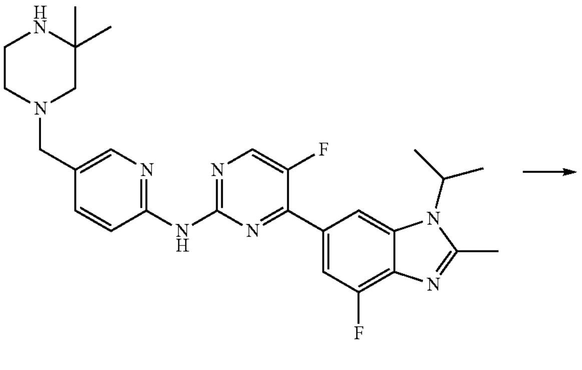

-continued

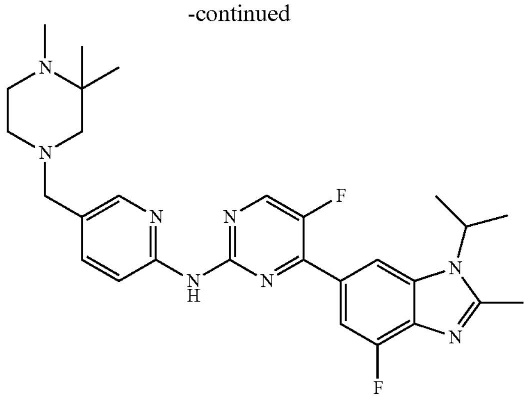

A flask containing the freebase N-(5-((3,3-dimethylpiperazin-1-yl)methyl)pyridin-2-yl)-5-fluoro-4-(4-fluoro-1-isopropyl-2-methyl-1H-benzo[d]imidazol-6-yl)pyrimidin-2-amine (63 mg, 0.1 mmol) was dissolved in chloroform: methanol (9:1, 1 mL) and 37% formaldehyde was added (0.014 mL, 0.2 mmol) followed by sodium triacetoxyborohydride (87.3 mg, 0.4 mmol). After two hours the complete reaction was poured into dichloromethane and sodium hydroxide (50 mL portions, 1N). The organic phase was separated and concentrated in vacuo. The residue was purified by reversed phase HPLC (10-50% acetonitrile/water+ 0.25% acetic acid over 15 minutes). The active fractions were pooled and concentrated on the Genevac and the residue was dissolved in acetonitrile and treated with methanesulfonic acid (1.05 equiv.). The resulting solution was frozen and concentrated on the lyophilizer to yield 5-fluoro-4-(4-fluoro-1-isopropyl-2-methyl-1H-benzo[d]imidazol-6-yl)-N-(5-((3,3,4-trimethylpiperazin-1-yl)methyl)pyridin-2-yl)pyrimidin-2-amine (23 mg, 42%) as the corresponding mesylate salt.

$^1$H NMR (500 MHz, Methanol-$d_4$) δ 8.68 (d, J=3.7 Hz, 1H), 8.38 (d, J=1.3 Hz, 1H), 8.31 (d, J=2.1 Hz, 1H), 8.25-8.15 (s, 1H), 8.00 (s, 1H), 7.93-7.84 (m, 1H), 4.99 (q, J=6.9 Hz, 1H), 3.68 (q, J=13.5 Hz, 2H), 3.50-3.40 (m, 2H), 3.15 (d, J=12.7 Hz, 1H), 2.92 (t, J=14.0 Hz, 1H), 2.87 (s, 3H), 2.76 (s, 3H), 2.75 (s, 3H), 2.51 (s, 1H), 2.35 (d, J=512.8 Hz, 1H), 1.78 (d, J=6.9 Hz, 6H), 1.51 (s, 3H), 1.44 (s, 3H). MS: $[M+H]^+$ m/z 521.

Example 3: Synthesis of Compounds A30, A31, A34, A37, A39, and A41

A solution of tert-butyl-8-oxo-6-oxa-2,9-diazaspiro[4.5] decane-2-carboxylate (450 mg) in methanol was purified by SFC. The separation returned tert-butyl (S)-8-oxo-6-oxa-2,9-diazaspiro[4.5]decane-2-carboxylate (160.5 mg) and tert-butyl (R)-8-oxo-6-oxa-2,9-diazaspiro[4.5]decane-2-carboxylate (209.3 mg) as white solids. The below reactions were conducted on both enantiomers, but the yield and exact procedure from the first peak is reported.

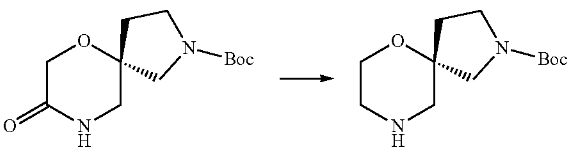 [SMILES: CC(C)(C)OC(=O)N1CC[C@]2(CNC(=O)CO2)C1 ; CC(C)(C)OC(=O)N1CC[C@]2(CNCCO2)C1]

A round bottomed flask was charged with tert-butyl (S)-8-oxo-6-oxa-2,9-diazaspiro[4.5]decane-2-carboxylate (160.5 mg, 0.63 mmol) and tetrahydrofuran was injected to yield a clear solution (4 mL). Borane in tetrahydrofuran was injected under an atmosphere of nitrogen (1 M, 1.9 mL, 1.9 mmol) and the reaction was stirred at ambient temperature for three hours. Solvent was removed under reduced pressure and the residue was dissolved in methanol (5 mL). To the resulting solution was added palladium on carbon (10%, 10 mg) and the suspension was stirred for one hour and filtered through celite. The filter cake was washed with dichloromethane. Concentration in vacuo gave tert-butyl (S)-6-oxa-2,9-diazaspiro[4.5]decane-2-carboxylate (112 mg, 73%). MS: $[M+H]^+$ m/z 243.

Compound A41

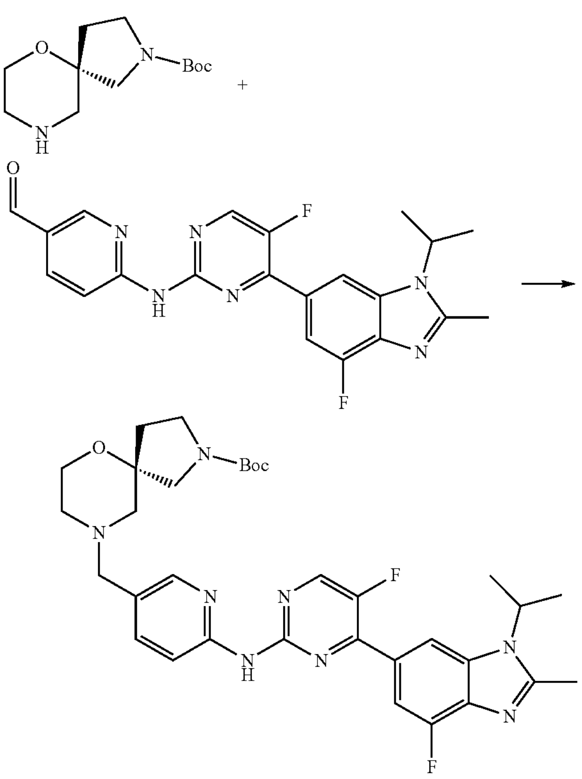

A round-bottomed flask was charged with tert-butyl (S)-6-oxa-2,9-diazaspiro[4.5]decane-2-carboxylate (112 mg, 0.45 mmol) and 6-((5-fluoro-4-(4-fluoro-1-isopropyl-2-methyl-1H-benzo[d]imidazol-6-yl)pyrimidin-2-yl)amino) nicotinaldehyde (226 mg, 0.55 mmol). Dimethylsulfoxide (10 mL) and acetic acid (1 mL) were injected under nitrogen and the reaction was warmed to 60° C. for a period of 18 hours. The reaction was allowed to cool and diluted with sodium hydroxide (1N aq., 20 mL) and water (100 mL). A cloudy white precipitate formed and was stirred for one hour and then filtered. The white solid was washed with several portions of water (5 mL each) and dried on the lyophilizer to yield tert-butyl (S)-9-((6-((5-fluoro-4-(4-fluoro-1-isopropyl-2-methyl-1H-benzo[d]imidazol-6-yl)pyrimidin-2-yl) amino)pyridin-3-yl)methyl)-6-oxa-2,9-diazaspiro[4.5]decane-2-carboxylate (265 mg, 90%).

$^1$H NMR (500 MHz, DMSO-$d_6$) δ 8.71 (d, J=3.7 Hz, 1H), 8.31 (s, 1H), 8.26 (d, J=8.5 Hz, 1H), 8.21 (d, J=2.2 Hz, 1H), 7.73-7.67 (m, 2H), 4.86 (p, J=7.0 Hz, 1H), 3.74-3.58 (m,

4H), 3.32-3.11 (m, 4H), 2.66 (s, 3H), 2.50-2.22 (m, 4H), 1.99 (d, J=11.8 Hz, 1H), 1.82 (s, 1H), 1.65 (dd, J=7.0, 3.1 Hz, 6H), 1.38 (s, 9H). MS: $[M+H]^+$ m/z 635.

Compound A34

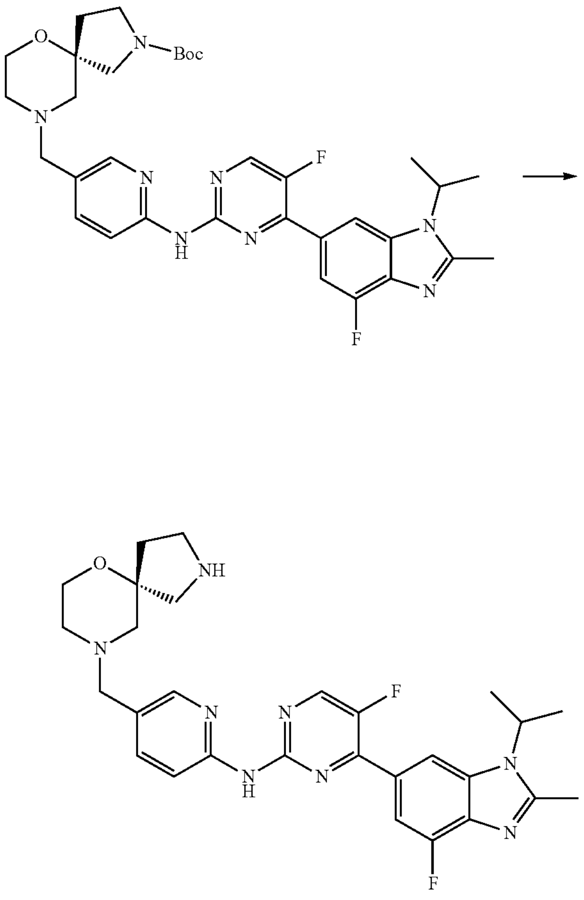

tert-butyl (S)-9-((6-((5-fluoro-4-(4-fluoro-1-isopropyl-2-methyl-1H-benzo[d]imidazol-6-yl)pyrimidin-2-yl)amino)pyridin-3-yl)methyl)-6-oxa-2,9-diazaspiro[4.5]decane-2-carboxylate (248 mg, 0.46 mmol) was dissolved in chloroform (6 mL) and trifluoroacetic acid was added via pipet (3 mL). The resulting orange solution was stirred for thirty minutes and concentrated to yield (R)—N-(5-((6-oxa-2,9-diazaspiro[4.5]decan-9-yl)methyl)pyridin-2-yl)-5-fluoro-4-(4-fluoro-1-isopropyl-2-methyl-1H-benzo[d]imidazol-6-yl)pyrimidin-2-amine as a trifluoroacetate salt that was used without further purification (301 mg, quant.). A portion of this sample was free-based with aqueous sodium bicarbonate and dichloromethane and purified by preparative HPLC (10-35% acetonitrile/water+0.25% acetic acid over 15 minutes). This yielded an analytical sample (3.9 mg) that was used for analysis by NMR and in biochemical and cell based assays.

$^1$H NMR (500 MHz, DMSO-$d_6$) δ 8.70 (d, J=3.7 Hz, 1H), 8.30 (d, J=1.3 Hz, 1H), 8.28-8.18 (m, 2H), 7.75-7.64 (m, 2H), 4.86 (p, J=6.9 Hz, 1H), 3.58-3.55 (m, 2H), 3.46 (m, 2H), 2.77 (d, J=11.2 Hz, 2H), 2.66-2.60 (m, 5H), 2.42-2.33 (m, 2H), 2.28 (d, J=12.8 Hz, 1H), 1.76 (s, 1H), 1.68-1.59 (m, 6H). MS: $[M+H]^+$ m/z 535.

Compound A39

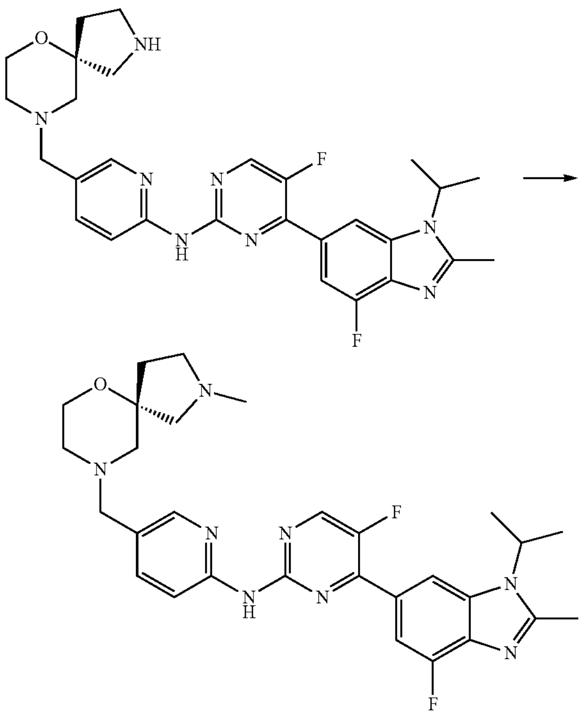

(R)—N-(5-((6-oxa-2,9-diazaspiro[4.5]decan-9-yl)methyl)pyridin-2-yl)-5-fluoro-4-(4-fluoro-1-isopropyl-2-methyl-1H-benzo[d]imidazol-6-yl)pyrimidin-2-amine 2,2,2-trifluoroacetate (32 mg, 0.049 mmol) was dissolved in dimethylformamide (3 mL) and treated with formaldehyde (0.10 mL, 37% in water, 1.68 mmol) followed by sodium triacetoxyborohydride (32 mg, 0.15 mmol). The reaction was stirred for three hours and filtered through celite. The filtrate was directly purified by HPLC (10-35% acetonitrile/water+0.25% acetic acid over 15 minutes). The active fractions were pooled and concentrated on the lyophilizer to yield (R)-5-fluoro-4-(4-fluoro-1-isopropyl-2-methyl-1H-benzo[d]imidazol-6-yl)-N-(5-((2-methyl-6-oxa-2,9-diazaspiro[4.5]decan-9-yl)methyl)pyridin-2-yl)pyrimidin-2-amine (4.7 mg, 18%) as a white solid.

$^1$H NMR (500 MHz, DMSO-$d_6$) δ 8.71 (d, J=3.7 Hz, 1H), 8.31 (d, J=1.2 Hz, 1H), 8.27-8.21 (m, 2H), 7.74-7.67 (m, 2H), 4.87 (p, J=6.9 Hz, 1H), 3.81-3.48 (m, 4H), 2.70-2.65 (m, 5H), 2.50-2.27 (m, 5H), 2.17 (s, 3H), 1.74 (q, J=7.0, 6.3 Hz, 1H), 1.65 (d, J=6.8 Hz, 6H). MS: $[M+H]^+$ m/z 549.

Compound A37

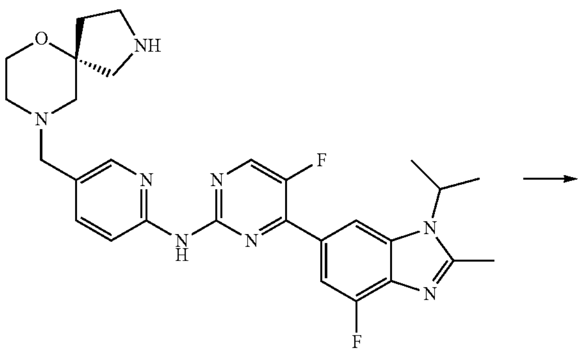

-continued

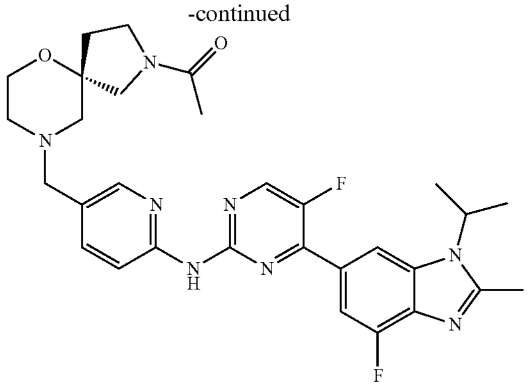

(R)—N-(5-((6-oxa-2,9-diazaspiro[4.5]decan-9-yl)methyl)pyridin-2-yl)-5-fluoro-4-(4-fluoro-1-isopropyl-2-methyl-1H-benzo[d]imidazol-6-yl)pyrimidin-2-amine 2,2,2-trifluoroacetate (32 mg, 0.049 mmol) was dissolved in dimethylformamide (3 mL) and treated with triethylamine (0.05 mL, 0.36 mmol) and acetyl chloride (10 μL, 0.18 mmol). The reaction was stirred for three hours and quenched with several drops of methanol. After filtration through celite the filtrate was purified by reversed phase HPLC (10-60% acetonitrile/water+0.25% acetic acid over 15 minutes). The active fractions were pooled and concentrated on the lyophilizer to yield (S)-1-(9-((6-((5-fluoro-4-(4-fluoro-1-isopropyl-2-methyl-1H-benzo[d]imidazol-6-yl)pyrimidin-2-yl)amino)pyridin-3-yl)methyl)-6-oxa-2,9-diazaspiro[4.5]decan-2-yl)ethan-1-one (4.0 mg, 14%) as a white solid.

$^1$H NMR (500 MHz, DMSO-$d_6$) δ 8.71 (d, J=3.7 Hz, 1H), 8.33-8.28 (m, 1H), 8.28-8.20 (m, 2H), 7.76-7.65 (m, 2H), 4.86 (p, J=6.9 Hz, 1H), 3.76-3.50 (m, 4H), 2.66 (s, 3H), 2.50-2.25 (m, 4H), 2.14-1.95 (m, 2H), 1.94-1.90 (m, 3H), 1.67-1.63 (m, 6H). MS: $[M+H]^+$ m/z 577.

Compound A31

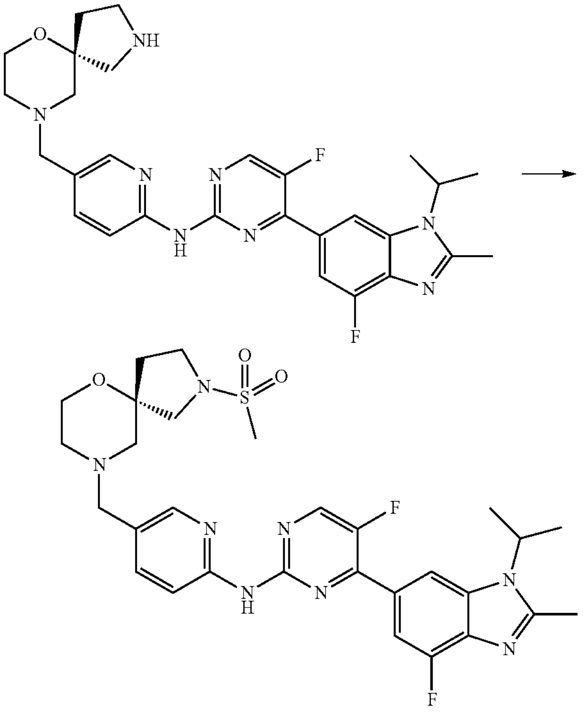

(R)—N-(5-((6-oxa-2,9-diazaspiro[4.5]decan-9-yl)methyl)pyridin-2-yl)-5-fluoro-4-(4-fluoro-1-isopropyl-2-methyl 1H-benzo[d]imidazol-6-yl)pyrimidin-2-amine 2,2,2-trifluoroacetate (32 mg, 0.049 mmol) was dissolved in dimethylformamide (3 mL) and treated with triethylamine (0.05 mL, 0.36 mmol) and mesyl chloride (10 μL). The reaction was stirred for three hours and quenched with several drops of methanol. After filtration through celite the filtrate was purified by reversed phase HPLC (10-60% acetonitrile/water+0.25% acetic acid over 15 minutes). The active fractions were pooled and concentrated on the lyophilizer to yield (S)-5-fluoro-4-(4-fluoro-1-isopropyl-2-methyl-1H-benzo[d]imidazol-6-yl)-N-(5-((2-(methylsulfonyl)-6-oxa-2,9-diazaspiro[4.5]decan-9-yl)methyl)pyridin-2-yl)pyrimidin-2-amine (3.8 mg, 13%) as a white solid.

$^1$H NMR (500 MHz, DMSO-$d_6$) δ 8.71 (d, J=3.8 Hz, 1H), 8.31 (d, J=1.2 Hz, 1H), 8.28-8.17 (m, 2H), 7.76-7.67 (m, 2H), 4.86 (p, J=6.9 Hz, 1H), 3.69 (t, J=4.8 Hz, 2H), 3.50-3.45 (m, 3H), 3.28 (dd, J=8.8, 5.3 Hz, 2H), 3.23-3.14 (m, 1H), 2.85 (s, 3H), 2.66 (s, 3H), 2.50-2.46 (m, 2H), 2.31 (d, J=11.4 Hz, 2H), 2.09-1.96 (m, 1H), 1.87 (dt, J=13.1, 8.8 Hz, 1H), 1.65 (d, J=6.8 Hz, 6H). MS: $[M+H]^+$ m/z 613.

Compound A30

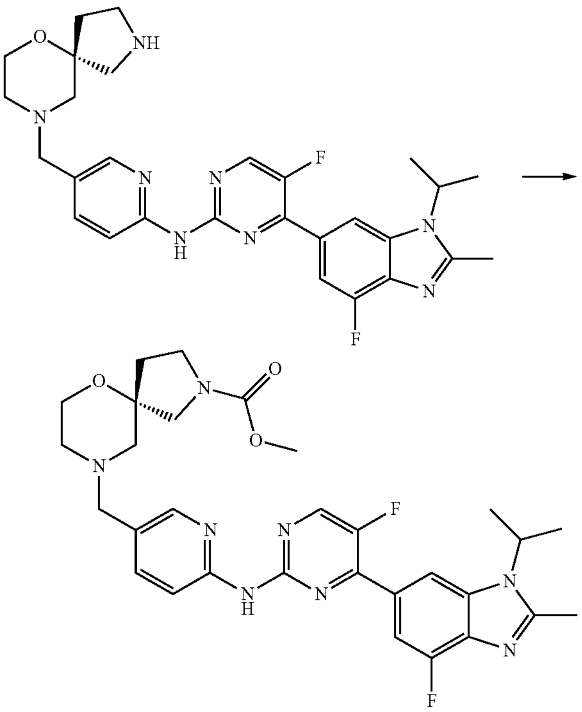

(R)—N-(5-((6-oxa-2,9-diazaspiro[4.5]decan-9-yl)methyl)pyridin-2-yl)-5-fluoro-4-(4-fluoro-1-isopropyl-2-methyl-1H-benzo[d]imidazol-6-yl)pyrimidin-2-amine 2,2,2-trifluoroacetate (32 mg, 0.049 mmol) was dissolved in dimethylformamide (3 mL) and treated with triethylamine (0.05 mL, 0.36 mmol) and methyl chloroformate (10 μL). The reaction was stirred for three hours and quenched with several drops of methanol. After filtration through celite the filtrate was purified by reversed phase HPLC (10-60% acetonitrile/water+0.25% acetic acid over 15 minutes). The active fractions were pooled and concentrated on the lyophilizer to yield methyl (S)-9-((6-((5-fluoro-4-(4-fluoro-1-isopropyl-2-methyl-1H-benzo[d]imidazol-6-yl)pyrimidin-2-yl)amino)pyridin-3-yl)methyl)-6-oxa-2,9-diazaspiro[4.5]

decane-2-carboxylate (5.0 mg, 18%) as a white solid. $^1H$ NMR (500 MHz, DMSO-$d_6$) δ 8.71 (d, J=3.7 Hz, 1H), 8.35-8.16 (m, 3H), 7.78-107.62 (m, 2H), 4.86 (p, J=6.8 Hz, 1H), 3.73-3.60 (m, 2H), 3.57 (s, 3H), 3.48 (s, 2H), 3.37-3.11 (m, 4H), 2.66 (s, 3H), 2.49-2.22 (m, 4H), 2.11-1.77 (m, 2H), 1.65 (d, J=6.9 Hz, 6H). MS: $[M+H]^+$ m/z 593.

Example 4: Synthesis of Compounds A23 and A28

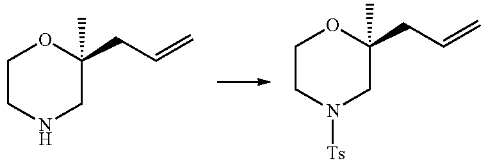

To a cooled solution of (S)-2-allyl-2-methylmorpholine (6.74 g, 47.8 mmol) in dichloromethane (120 mL, 0.4 M) under nitrogen was added triethylamine (9.80 mL, 71.7 mmol) and the mixture was cooled in an ice/water bath. 4-toluenesulfonyl chloride (10.03 g, 52.3 mmol) was added in several portions, the reaction was stirred for 30 minutes and allowed to warm to ambient temperature for a period of 90 minutes. Excess reagent was quenched by addition of water (50 mL) and saturated sodium bicarbonate (50 mL). The mixture was transferred to a separatory funnel. The organic phase was separated and the aqueous phase was washed with two additional portions of dichloromethane (30 mL). The combined organic washings were concentrated onto silica gel and the residue was dry loaded onto a silica flash column (gradient hexanes/dichloromethane+2% ethyl acetate: 0-100%). The active fractions were pooled and concentrated to yield (S)-2-allyl-2-methyl-4-tosylmorpholine (11.95 g, 85%) as an off-white solid. MS: $[M+H]^+$ m/z 296.

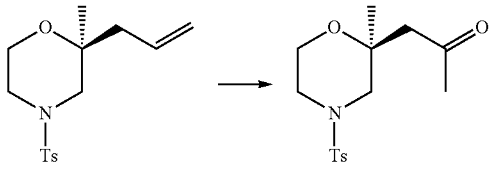 [SMILES: C=CC[C@@]1(C)CN(S(=O)(=O)c2ccc(C)cc2)CCO1 ; CC(=O)C[C@@]1(C)CN(S(=O)(=O)c2ccc(C)cc2)CCO1]

A flask containing (S)-2-allyl-2-methyl-4-tosylmorpholine (11.95 g, 40.48 mmoles) was charged with tert-butyl alcohol, methanol and water (125 mL: 75 mL: 2 mL) and purged with nitrogen. To the resulting solution was added 1,4-benzoquinone (6.56 g, 60.72 mmoles) and $PdCl_2(CH_3CN)_2$ (313 mg, 1.21 mmoles). The reaction was gently warmed to 50° C. and allowed to cool after three hours. The resulting solution was quenched with 1N hydrochloric acid (15 mL) and diluted after 30 minutes with ethyl acetate (300 mL). The aqueous phase was separated and the remaining organic portion was washed several times with sodium hydroxide solution (1N, 50 mL portions) and saturated sodium bicarbonate (50 mL). The organic portion was concentrated onto silica gel and dry loaded onto a silica flash column (gradient hexanes/ethyl acetate: 0-100%). The active fractions were pooled and concentrated to yield (S)-1-(2-methyl-4-tosylmorpholin-2-yl)propan-2-one (10.55 g, 85%) as an off-white solid. MS: $[M+H]^+$ m/z 312.

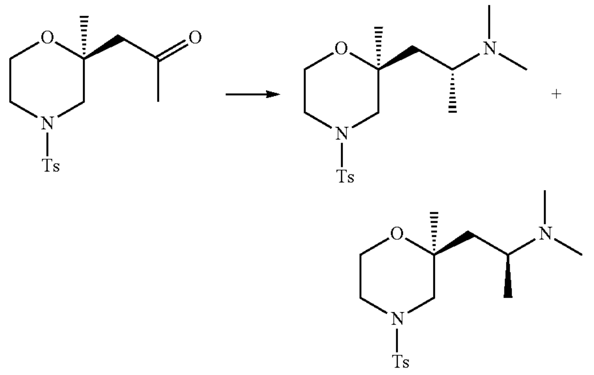

A glass bottle fitted to a bomb reactor was charged with palladium on carbon (10%, 4.11 g) and nitrogen gas was gently purged to blanket the catalyst bed. Under nitrogen tetrahydrofuran (50 mL) was added with a pipet and the mixture was stirred vigorously. Dimethylamine in tetrahydrofuran (100 mL, 2 M) was mixed with acetic acid (5.77 mL, 100 mmol) and the resulting solution was transferred into the catalyst solution via pipet. Finally, (N)-1-(2-methyl-4-tosylmorpholin-2-yl)propan-2-one (8.23 g, 26.4 mmol) was dissolved in tetrahydrofuran (50 mL) and transferred into the catalyst solution. The bomb reactor was sealed under an atmosphere of nitrogen and attached to a high-pressure hydrogen tank. The reactor was pressurized to 1000 psi and the pressure was bled out three times. The pressurized reaction was then sealed and warmed to 60° C. for a period of 38 hours. The reaction was allowed to cool and excess hydrogen gas was released. The catalyst solution was filtered through celite and the cake was washed with ethyl acetate without allowing the palladium to dry. Caution: the remaining palladium catalyst can be pyrophoric and was kept wet with ethyl acetate and then water before transfer to a waste container. After filtration, the filtrate was diluted with ethyl acetate (300 mL) and transferred to a separatory funnel. The organic phase was washed with sodium hydroxide solution (2 N, 200 mL) and saturated sodium bicarbonate. The combined organic washings were concentrated onto silica gel and the residue was dry loaded onto a silica flash column (gradient dichloromethane/methanol: 0-25%). Three fractions were collected, the first containing starting material, followed by (S)—N,N-dimethyl-1-((R)-2-methyl-4-tosylmorpholin-2-yl)propan-2-amine (2.33 g, 26%) and finally by the product (S)—N,N-dimethyl-1-((S)-2-methyl-4-tosylmorpholin-2-yl)propan-2-amine (3.25 g, 36%). MS: $[M+H]^+$ m/z 341.

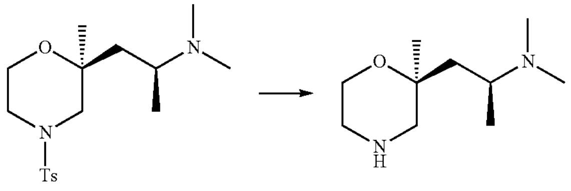 [SMILES: Cc1ccc(S(=O)(=O)N2CCO[C@@](C)(C[C@H](C)N(C)C)C2)cc1 ; C[C@@H](C[C@@]1(C)CNCCO1)N(C)C]

A round bottomed flask was charged with (S)—N,N-dimethyl-1-((S)-2-methyl-4-tosylmorpholin-2-yl)propan-2-amine (2.84 g, 8.35 mmol). Tetrahydrofuran was injected under nitrogen (42 mL) and the resulting solution was cooled to −78° C. Lithium aluminum hydride (2.14 g, 56.36 mmol) was added in a single portion and the reaction was allowed to warm to ambient temperature. The reaction was warmed to 60° C. for a period of 50.5 hours. At this time the reaction was cooled again in a dry ice/acetone bath, sodium hydroxide (1 N, 2.5 mL) and water (2.5 mL) were added dropwise with vigorous evolution of hydrogen gas. After warming for thirty minutes, magnesium sulfate was added (20.0 g) and the reaction was diluted with one volume of diethyl ether and stirred vigorously. After 30 minutes, the mixture was filtered through celite and the filter cake was washed with dichloromethane. The filtrate was concentrated to yield (S)—N,N-di methyl-1-((S)-2-methylmorpholin-2-yl)propan-2-amine (1.51 g, 97% crude) as a pure yellow oil. MS: $[M+H]^+$ m/z 187.

Compound A23

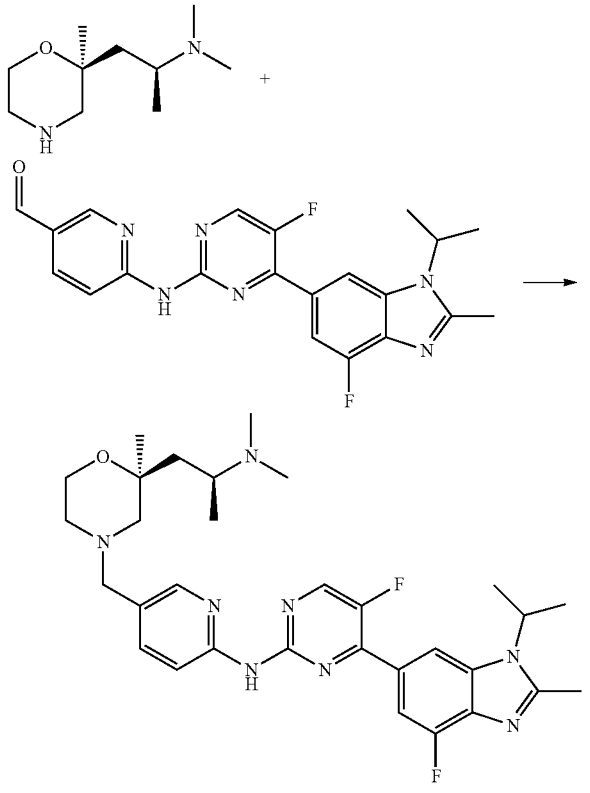

(S)—N,N-dimethyl-1-((S)-2-methylmorpholin-2-yl)propan-2-amine (1.51 g, 8.35 mmol) was transferred to a round bottomed flask and dissolved in DMSO (80 mL) and acetic acid (4.58 mL, 79.5 mmol). 6-((5-fluoro-4-(4-fluoro-1-isopropyl-2-methyl-1H-benzo[d]imidazol-6-yl)pyrimidin-2-yl)amino)nicotinaldehyde (3.24 g, 7.95 mmol) was added to yield a milky white suspension. After 30 minutes sodium triacetoxyborohydride (5.05 g, 23.85 mmol) was added and the reaction was warmed to 60° C. for 14.5 h. After cooling the resulting clear yellow solution was poured into sodium hydroxide (0.5 N, 1 L) and the aqueous phase was washed with three portions of chloroform (600 mL each). The combined organic washings were dried over sodium sulfate, filtered and concentrated onto silica gel. The residue was dry loaded onto a silica flash column (gradient dichloromethane/methanol with 3% 17 N methanol/ammonia: 0-50%—followed by changing the strong phase to methanol+4% ammonium hydroxide). The active fractions were pooled and concentrated to yield N-(5-(((S)-2-(S)-2-(dimethylamino)propyl)-2-methylmorpholino)methyl)pyridin-2-yl)-5-fluoro-4-(4-fluoro-1-isopropyl-2-methyl-1H-benzo[d]imidazol-6-yl)pyrimidin-2-amine (3.30 g, 67%). The free base was analyzed by proton NMR and LC/MS indicating the desired product. The entire portion was dissolved in acetonitrile and aqueous methansulfonic acid (0.23 M, 26 mL) was added. The salt solution was frozen in a dry ice acetone bath and concentrated on the lyophilizer over several days.

$^1$H NMR (500 MHz, Chloroform-d) δ 8.43 (d, J=3.7 Hz, 1H), 8.39 (dd, J=8.5, 0.8 Hz, 1H), 8.25 (dd, J=2.3, 0.8 Hz, 1H), 8.22 (s, 1H), 8.19 (d, J=1.3 Hz, 1H), 7.79 (dd, J=11.5, 1.3 Hz, 1H), 7.69 (dd, J=8.6, 2.3 Hz, 1H), 4.74 (p, J=7.0 Hz, 1H), 3.76 (t, J=4.9 Hz, 2H), 3.42 (s, 2H), 2.90-2.62 (m, 4H), 2.47-2.39 (m, 1H), 2.36 (q, J=5.3 Hz, 1H), 2.33-2.25 (m, 1H), 2.25-2.18 (m, 1H), 2.18 (s, 6H), 1.90 (dd, J=14.1, 3.8 Hz, 1H), 1.72 (d, J=7.0 Hz, 6H), 1.39 (dd, J=14.1, 6.9 Hz, 1H), 1.27 (s, 3H), 0.99 (d, J=6.5 Hz, 3H). MS: $[M+H]^+$ m/z 579.

Compound A28

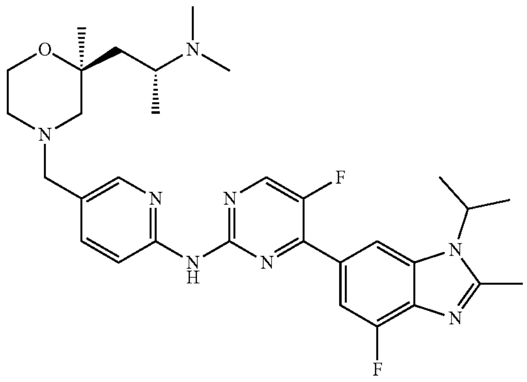 [SMILES: Cc1nc2c(F)cc(-c3nc(Nc4ccc(CN5CCO[C@@](C)(C[C@@H](C)N(C)C)C5)cn4)ncc3F)cc2n1C(C)C]

(S)—N,N-dimethyl-1-((R)-2-methyl-4-tosylmorpholin-2-yl)propan-2-amine participated in the final two step sequence in an identical manner to yield N-(5-(((S)-2-((R)-2-(dimethylamino)propyl)-2-methylmorpholino)methyl)pyridin-2-yl)-5-fluoro-4-(4-fluoro-1-isopropyl-2-methyl-1H-benzo[d]imidazol-6-yl)pyrimidin-2-amine methanesulfonate.

$^1$H NMR (500 MHz, Chloroform-d) δ 8.44 (d, J=3.8 Hz, 1H), 8.40 (dd, J=8.5, 0.8 Hz, 1H), 8.30 (s, 1H), 8.25 (dd, J=2.3, 0.8 Hz, 1H), 8.19 (d, J=1.3 Hz, 1H), 7.82-7.77 (m, 1H), 7.69 (dd, J=8.6, 2.3 Hz, 1H), 4.73 (td, J=14.0, 7.1 Hz, 1H), 3.71 (t, J=4.9 Hz, 2H), 3.51-3.31 (m, 2H), 2.83 (q, J=6.3, 5.7 Hz, 1H), 2.69 (s, 3H), 2.38-2.34 (m, 2H), 2.24 (d, 7=11.1 Hz, 1H), 2.19 (s, 6H), 1.71 (d, J=7.0 Hz, 6H), 1.60 (dd, J=14.2, 7.1 Hz, 1H), 1.25 (s, 3H), 1.02 (d, J=6.6 Hz, 3H). MS: $[M+H]^+$ m/z 579.

Example 5: Synthesis of Compounds A61-A64

Compound A61

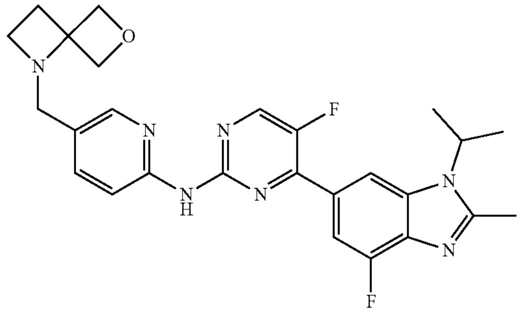 [SMILES: Cc1nc2c(F)cc(-c3nc(Nc4ccc(CN5CCC56COC6)cn4)ncc3F)cc2n1C(C)C]

To a solution of 6-oxa-1-azaspiro[3.3]heptane hemioxalate (22 mg, 0.073 mmol) and 6-((5-fluoro-4-(4-fluoro-1-isopropyl-2-methyl-1H-benzo[d]imidazol-6-yl)pyrimidin-2-yl)amino)nicotinaldehyde (50 mg, 0.12 mmol) in DMSO (1.5 mL) was added acetic acid (70 μL, 1.2 mmol), followed by sodium triacetoxyborohydride (52 mg, 0.25 mmol). The reaction was heated to 60° C. and stirred for 24 h. Once complete, the mixture was cooled to room temperature and sodium hydroxide solution (1 M aq., 2 mL) was added, followed by water (2 mL). The mixture was extracted with $CHCl_3$ (3×3 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-20%) to afford N-(5-((6-oxa-1-azaspiro[3.3]heptan-1-yl)methyl)pyridin-2-yl)-5-fluoro-4-(4-fluoro-1-isopropyl-2-methyl-1H-benzo[d]imidazol-6-yl)pyrimidin-2-amine as a clear oil. The oil was dissolved in water containing methanesulfonic acid (1.05 equiv.), and the solution was lyophilized to yield 42 mg of the mesylate salt as a white solid.

Spectra of Mesylate Salt $^1H$ NMR (400 MHz, DMSO-$d_6$) δ 10.35 (s, 1H), 10.28 (bs, 1H), 8.68 (d, J=3.7 Hz, 1H), 8.38 (s, 1H), 8.27 (d, J=8.7 Hz, 1H), 8.22 (d, J=1.3 Hz, 1H), 7.86 (dd, J=8.8, 2.4 Hz, 151H), 7.65 (dd, J=11.9, 1.2 Hz, 1H), 5.28 (d, J=9.3 Hz, 1H), 4.93-4.58 (m, 5H), 4.39-4.27 (m, 1H), 3.96-3.81 (m, 1H), 3.68-3.54 (m, 1H), 2.70-2.55 (m, 5H), 2.23 (s, 3H), 1.57 (d, J=6.9 Hz, 6H). MS: $[M+H]^+$ m/z 492.2.

Compound A62

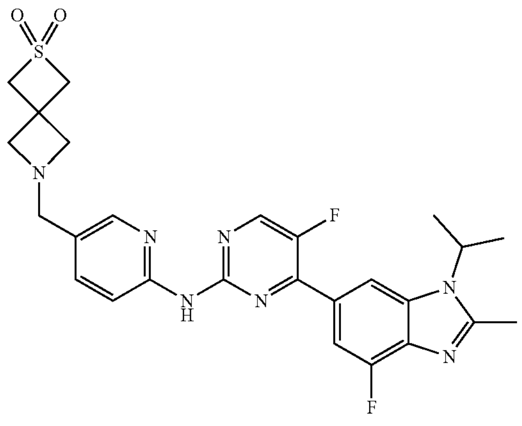 [SMILES: Cc1nc2c(F)cc(-c3nc(Nc4ccc(CN5CC6(C5)CS(=O)(=O)C6)cn4)ncc3F)cc2n1C(C)C]

To a solution of 2-Thia-6-azaspiro[3.3]heptane-2,2-dioxide hydrochloride (27 mg, 0.15 mmol) and 6-((5-fluoro-4-(4-fluoro-1-isopropyl-2-methyl-1H-benzo[d]imidazol-6-yl)pyrimidin-2-yl)amino)nicotinaldehyde (50 mg, 0.12 mmol) in DMSO (1.5 mL) was added acetic acid (70 μL, 1.2 mmol), followed by sodium triacetoxyborohydride (52 mg, 0.25 mmol). The reaction was heated to 60° C. and stirred for 24 h. Once complete, the mixture was cooled to room temperature and sodium hydroxide solution (1 M aq., 2 mL) was added, followed by water (2 mL). The mixture was extracted with $CHCl_3$ (3×3 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-20%) to afford 6-((6-((5-fluoro-4-(4-fluoro-1-isopropyl-2-methyl-1H-benzo[d]imidazol-6-yl)pyrimidin-2-yl)amino)pyridin-3-yl)methyl)-2-thia-6-azaspiro[3.3]heptane 2,2-dioxide as a clear oil. The oil was dissolved in water containing methanesulfonic acid (1.05 equiv.), and the solution was lyophilized to yield 8.5 mg of the mesylate salt as a white solid.

Spectra of Mesylate salt $^1H$ NMR (400 MHz, DMSO-$d_6$) δ 10.36 (s, 1H), 10.13 (bs, 1H), 8.68 (d, J=3.7 Hz, 1H), 8.32 (d, J=2.4 Hz, 1H), 8.26 (d, J=8.7 Hz, 1H), 8.22 (d, J=1.3 Hz, 1H), 7.78 (dd, J=8.7, 2.4 Hz, 1H), 7.65 (dd, J=11.9, 1.3 Hz, 1H), 4.79 (p, J=6.9 Hz, 1H), 4.53-4.37 (m, 6H), 4.31 (d, J=5.6 Hz, 2H), 4.27-4.16 (m, 2H), 2.59 (s, 3H), 2.23 (s, 3H), 1.57 (d, J=6.9 Hz, 6H). MS: $[M+H]^+$ m/z 540.2.

Compound A63

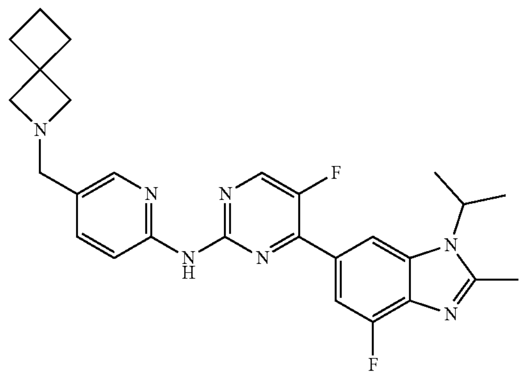 [SMILES: Cc1nc2c(F)cc(-c3nc(Nc4ccc(CN5CC6(CCC6)C5)cn4)ncc3F)cc2n1C(C)C]

To a solution of 2-Azaspiro[3.3]heptane hemioxalate (21 mg, 0.075 mmol) and 6-((5-fluoro-4-(4-fluoro-1-isopropyl-2-methyl-1H-benzo[d]imidazol-6-yl)pyrimidin-2-yl)amino)nicotinaldehyde (50 mg, 0.12 mmol) in DMSO (1.5 mL) was added acetic acid (70 μL, 1.2 mmol), followed by sodium triacetoxyborohydride (52 mg, 0.25 mmol). The reaction was heated to 60° C. and stirred for 24 h. Once complete, the mixture was cooled to room temperature and sodium hydroxide solution (1 M aq., 2 mL) was added, followed by water (2 mL). The mixture was extracted with $CHCl_3$ (3×3 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-20%) to afford N-(5-((2-azaspiro[3.3]heptan-2-yl)methyl)pyridin-2-yl)-5-fluoro-4-(4-fluoro-1-isopropyl-2-methyl-1H-benzo[d]imidazol-6-yl)pyrimidin-2-amine as a clear oil. The oil was dissolved in water containing methanesulfonic acid (1.05 equiv.), and the solution was lyophilized to yield 42 mg of the mesylate salt as a white solid.

Spectra of Mesylate Salt $^1H$ NMR (400 MHz, DMSO-d6) δ 10.35 (s, 1H), 9.85 (bs, 1H), 8.68 (d, J=3.7 Hz, 1H), 8.31 (d, J=2.3 Hz, 1H), 8.28-8.17 (m, 2H), 7.79 (dd, J=8.7, 2.4 Hz, 1H), 7.65 (dd, J=11.9, 1.3 Hz, 1H), 4.80 (p, J=6.9 Hz, 1H), 4.23 (d, J=6.0 Hz, 2H), 4.12-4.00 (m, 2H), 4.00-3.90 (m, 2H), 2.59 (s, 3H), 2.23 (s, 3H), 2.15 (dd, J=8.8, 6.6 Hz, 2H), 2.12-2.04 (m, 2H), 1.76-1.63 (m, 2H), 1.57 (d, J=6.9 Hz, 6H). MS: $[M+H]^+$ m/z 490.3.

Compound A64

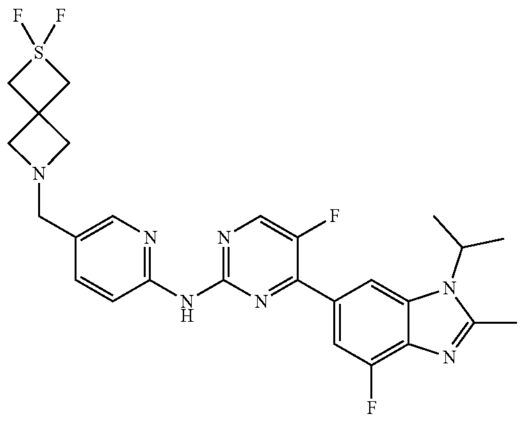 [SMILES: Cc1nc2c(F)cc(-c3nc(Nc4ccc(CN5CC6(C5)CS(F)(F)C6)cn4)ncc3F)cc2n1C(C)C]

To a solution of 6,6-Difluoro-2-aza-spiro[3.3]heptane trifluoroacetate (37 mg, 0.15 mmol) and 6-((5-fluoro-4-(4-fluoro-1-isopropyl-2-methyl-1H-benzo[d]imidazol-6-yl)pyrimidin-2-yl)amino)nicotinaldehyde (50 mg, 0.12 mmol) in DMSO (1.5 mL) was added acetic acid (70 μL, 1.2 mmol), followed by sodium triacetoxyborohydride (52 mg, 0.25 mmol). The reaction was heated to 60° C. and stirred for 24 h. Once complete, the mixture was cooled to room temperature and sodium hydroxide solution (1 M aq., 2 mL) was added, followed by water (2 mL). The mixture was extracted with $CHCl_3$ (3×3 mL). The organic layers were combined, dried with $Na_2SO_4$, and concentrated in vacuo. The crude compound was purified using flash chromatography on $SiO_2$ (elution gradient of $CH_2Cl_2$ with MeOH+2% $NH_3$=0-20%) to afford N-(5-((6,6-difluoro-2-azaspiro[3.3]heptan-2-yl)methyl)pyridin-2-yl)-5-fluoro-4-(4-fluoro-1-isopropyl-2-methyl-1H-benzo[d]imidazol-6-yl)pyrimidin-2-amine as a clear oil. The oil was dissolved in water containing methanesulfonic acid (1.05 equiv.), and the solution was lyophilized to yield 45 mg of the mesylate salt as a white solid.

Spectra of Mesylate Salt $^1$H NMR (400 MHz, DMSO-$d_6$) δ 10.36 (s, 1H), 9.99 (bs, 1H), 8.68 (d, J=3.7 Hz, 1H), 8.32 (d, J=2.3 Hz, 1H), 8.28-8.19 (m, 2H), 7.79 (dd, J=8.7, 2.4 Hz, 1H), 7.65 (dd, J=11.9, 1.3 Hz, 1H), 4.80 (p, J=6.9 Hz, 1H), 4.32-4.21 (m, 4H), 4.14-4.02 (m, 2H), 2.92-2.77 (m, 4H), 2.59 (s, 3H), 2.23 (s, 3H), 1.57 (d, J=6.9 Hz, 6H). MS: $[M+H]^+$ m/z 492.2.

Biological Experiments

General Methods

Cell Line Growth Retardation Assay

Cells were seeded at densities of 1,000-5,000 cells per well in 48-well tissue culture plates. After a 24 hours rest period, cells were treated with compound at 10 μM, 2 μM, 0.4 μM, 0.08 μM, 0.016 μM, and 0.0032 μM. A group of cells were treated with the vehicle in which the compound was prepared and served as a control. The cells were grown in the presence of compounds for 6 days and were counted on day 0 and day 6. All cell counting was performed using a Synentec Cellavista plate imager. Cells that did not receive compound were counted on day 1 and this count was used as a baseline for the calculation of growth inhibition. Growth inhibition was calculated as a ratio of cell population doublings in the presence of compound versus the absence of compound. If treatment resulted in a net loss of cells from baseline, percent lethality was defined as the decrease in cell numbers in treated wells compared with counts on day 1 of non-treated wells post-seeding. $IC_{50}$ values for each compound (see Table 3; reported in μM) were calculated by fitting curves to data points from each dose-response assay using the Proc NLIN function in SAS for Windows version 9.2 (SAS Institute, Inc.).

Cdk4 and 6 Enzymatic Inhibition Assay

For the $K_i$ determination assay, 200 μM stock solutions of compounds were subjected to a serial, semi-logarithmic dilution using 100% DMSO as a solvent. 10 distinct concentrations were prepared, with a dilution endpoint of $6×10^{-9}$ M in 100% DMSO. 100% DMSO was used as a control. 10 μL from each of the serial dilutions were aliquoted into separate wells of a 96-well plate and 90 μL of water were added to each of those wells. The plate was shaken thoroughly, and 5 μL from each of the plate's wells were transferred into wells of the assay plate. The final volume of wells in the assay plate was 50 μL. All compounds were tested at 10 assay concentrations in the range from $2×10^{-6}$ M to $6×10^{-11}$ M. The final DMSO concentration in the wells of the assay plate was 1% in all cases. $K_i$s for compounds are presented in Table 3 in nM.

A radiometric protein kinase assay (33PanQinase® Activity Assay) was used for measuring the kinase activity of six protein kinases. All kinase assays were performed in 96-well FlashPlates™ from PerkinElmer (Boston, MA, USA). The assay for all protein kinases contained 70 mM HEPES-NaOH pH 7.5, 3 mM $MgCl_2$, 3 mM $MnCl_2$, 3 μM Na-orthovanadate, 1.2 mM DTT, 50 μg/mL PEG20000, ATP [γ-33P]-ATP (approx. 9×1005 cpm per well), protein kinase and substrate. The reaction cocktails were incubated at 30° C. for 60 minutes. The reaction was stopped with 50 μL of 2% (v/v) $H_3PO_4$, and plates were aspirated and washed two times with 200 μL 0.9% (w/v) NaCl. Incorporation of $^{33}$Pi was determined with a microplate scintillation counter (Microbeta, Wallac).

Caco-2 Assay ($P_{app}$ A to B)

The degree of bi-directional human intestinal permeability for compounds was estimated using a Caco-2 cell permeability assay. Caco-2 cells were seeded onto polyethylene membranes in 96-well plates. The growth medium was refreshed every 4 to 5 days until cells formed a confluent cell monolayer. HBSS with 10 mM HEPES at pH 7.4 was used as the transport buffer. Compounds were tested at 2 μM bi-directionally in duplicate. Digoxin, nadolol and metoprolol were included as standards. Digoxin was tested at 10 μM bi-directionally in duplicate, while nadolol and metoprolol were tested at 2 μM in the A to B direction in duplicate. The final DMSO concentration was adjusted to less than 1% for all experiments. The plate was incubated for 2 hours in a $CO_2$ incubator at 37° C., with 5% $CO_2$ at saturated humidity. After incubation, all wells were mixed with acetonitrile containing an internal standard, and the plate was centrifuged at 4,000 rpm for 10 minutes. 100 μL supernatant was collected from each well and diluted with 100 μL distilled water for LC/MS/MS analysis. Concentrations of test and control compounds in starting solution, donor solution, and receiver solution were quantified by LC/MS/MS, using peak area ratio of analyte/internal standard. The apparent permeability coefficient $P_{app}$ (cm/s) was calculated using the equation:

$$P_{app}=(dC_r/dt)\times V_r/(A\times C_0)$$

Where $dC_r/dt$ is the cumulative concentration of compound in the receiver chamber as a function of time (μM/s); $V_r$ is the solution volume in the receiver chamber (0.075 mL on the apical side, 0.25 mL on the basolateral side); A is the surface area for the transport, which is 0.0804 $cm^2$ for the area of the monolayer; $C_0$ is the initial concentration in the donor chamber (μM). $P_{app}$ scores are presented in Table 3 for compounds.

The efflux ratio was calculated using the equation:

$$\text{Efflux Ratio}=P_{app}(BA)/P_{app}(AB)$$

Percent recovery was calculated using the equation:

$$\%\ \text{Recovery}=100\times[(V_r\times C_r)+(V_d\times C_d)]/(V_d\times C_0)$$

Where Vd is the volume in the donor chambers, which are 0.075 mL on the apical side and 0.25 mL on the basolateral side; $C_d$ and $C_r$ are the final concentrations of transport compound in donor and receiver chambers, respectively.

CYP Enzymatic Inhibition Assay

Inhibition of various CYP isozymes was measured for each compound using a CYP enzyme inhibition assay in human liver microsomes (HLM). Compounds and standard inhibitors were prepared at a 100× working solutions. Substrates or PBS were added to the corresponding wells followed by addition of compounds, solvent or positive control working solution to corresponding wells. HLMs were added to the pre-warmed (37° C.) plate and mixed with NADPH cofactor for 10 minutes at 37° C. The reaction was terminated by adding 400 μL cold stop solution (200 ng/mL Tolbutamide and 200 ng/mL Labetalol in ACN). The plate was centrifuged at 4,000 rpm for 20 minutes, and supernatant was transferred to 100 μL HPLC water followed by LC/MS/MS analysis. The $IC_{50}$s of the CYP isozymes were averaged for each compound and are presented in Table 3 in μM.

Measurement of Compound Metabolic Stability

The metabolic stability of compounds was determined in hepatocytes from mice and rats. Compound half-lives are presented in Table 3 in minutes. Compounds were diluted to 5 μM in Williams' Medium E from 10 mM stock solutions. 10 μL of each compound was aliquoted into a well of a 96-well plate and reactions were started by aliquoting 40 μL of a 625,000 cells/mL suspension into each well. The plate was incubated at 37° C. with 5% $CO_2$. At each corresponding time point, the reaction was stopped by quenching with ACN containing internal standards (IS) at a 1:3. Plates were shaken at 500 rpm for 10 min, and then centrifuged at 3,220×g for 20 minutes. Supernatants were transferred to another 96-well plate containing a dilution solution. Supernatants were analyzed by LC/MS/MS. Compound half-life was estimated using the following equation:

$$\%\ \text{Remaining Compound} = \frac{\text{Peak Area Ratios of Tested Compound vs. Internal Standard at End Point}}{\text{Peak Area Ratios of Tested Compound vs. Internal Standard at Start Point}}$$

hERG Inhibition Assay

Effects of compounds on hERG potassium channel conductance was assessed using the automated patch clamp method QPatch$^{HTX}$. Compounds were prepared at 10 mM stocks. CHO cells stably expressing hERG potassium channels were used for this assay. Cells were cultured in a humidified and air-controlled 5% $CO_2$) incubator at 37° C. Compound stocks and the positive control Amitriptyline were dissolved in 100% DMSO to make various solution concentrations. These solutions were further diluted into extracellular solution to achieve final concentrations for testing. The final DMSO concentration in extracellular solution was 0.30%. The hERG QPatch$^{HTX}$ assay was conducted at room temperature.

The following voltage command protocol was used:

From the holding potential of −80 mV, the voltage was first stepped to −50 mV for 80 ms for leak subtraction, and then stepped to +20 mV for 4,800 ms to open hERG channels.

After which, the voltage was stepped back down to −50 mV for 5,000 ms, causing a "rebound" or tail current, which was measured and collected for data analysis.

Finally, the voltage was stepped back to the holding potential of −80 mV for 3,100 ms.

For each experiment, three additions of 5 μL of the vehicle were applied, followed by 30 runs of the voltage command protocol for a baseline period. Then, the ascending doses of each compound were added with three repetitions (5 μL of compound each time). Percent of control values were calculated for compounds by taking the ratio of the current response in the presence of the compound over the peak current in the presence of the vehicle control and multiplying by 100% (see Table 3).

Compound Solubility Assay

The relative kinetic solubility of each compound was determined at both low (1.2) and neutral (7.4) pH. Compounds were prepared at 10 mM stocks. Kinetic solubility was determined by UV and calibrated using a 3-standard curve (1, 20, and 200 μM). Compounds were allowed to shake at room temperature for 24 hours in 50 mM phosphate buffer pH 7.4, or in SGF buffer pH 1.2 at 37° C. for 24 hours. Compound solubilities are reported in Table 3 in μM.

Kinome Analysis

Recombinant kinases were produced in and purified from either BL21 strain *E. coli* or HEK-293 cells. Kinases were subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock with 1% BSA, 0.05% Tween 20, and 1 mM DTT) to remove unbound ligand and to reduce nonspecific phage binding. Binding reactions were assembled by combining kinases, liganded affinity beads, and compounds in binding buffer (20% SeaBlock, 0.17× PBS, 0.05% Tween 20, 6 mM DTT). Compounds were prepared as 40× stocks in 100% DMSO and directly diluted into the assay. A11 reactions were performed in polypropylene 384-well plates in a final volume of 0.02 mL. The assay plates were incubated at room temperature with shaking for 1 hour and the affinity beads were washed with wash buffer (1×PBS and 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR. Results for primary screen binding interactions are reported as "% of Ctrl", where lower numbers indicate stronger affinity for a tested compound.

Rodent Xenograft Studies

Xenograft models of human cancer cell lines were established in six-week-old CD-athymic nude mice by subcutaneous injection of 1.0-3.0×$10^7$ cells with or without 50% matrigel. When tumors reached an average size of 150-300 $mm^3$, mice (n=8) were randomized into treatment groups. Tumor xenografts were measured with calipers three times per week, and tumor volume (in $mm^3$) was determined by multiplying height×width×length. For ER+ studies, 17-ß-estradiol 60-day release pellets were implanted subcutaneously into the left flank seven days before tumor inoculation. Statistical differences between treatment arms at specific time points were performed using a two-tailed paired Student t-test. Differences between groups were considered statistically significant at $p<0.05$. Compounds were formulated in 1% HEC in 25 mM phosphate buffer (pH=2) and dosed by daily oral gavage (PO). Data were analyzed using StudyLog software from StudyDirector (San Francisco, CA).

Rodent Pharmacokinetic and Single-Dose Saturation Studies

For pharmacokinetic (PK) analysis of compounds, non-tumor bearing six-week-old CD-1 athymic nude mice received a single PO dose of compound followed by saphenous vein blood draw at the following time points post dosing: 15, 30, 60, 120, 240, 480 & 1,440 minutes. No mouse was bled more than twice within the 1,440 minutes period. Untreated samples were collected from vehicle control animals. For plasma preparation, whole blood was collected into EDTA-treated tubes. Cells were removed from plasma by centrifugation for 10 minutes at 1,000-2,000×g using a refrigerated centrifuge. The plasma fraction was removed and stored at −80° C.

In order to determine the concentration at which drug exposure saturates, mice were dosed as described above with increasing concentrations of compound covering a log-fold concentration range (100 mg/kg to 1,000 mg/kg). Triplicate mice were used for each collection time-point and dose.

In order to determine amount (ng/ml) of compound in peripheral circulation, plasma samples were analyzed by mass spectrometry (HPLC). For this analysis, 20 μL of plasma sample was mixed with two volumes of ice-cold internal standard solution (ISS), and centrifuged at 6,100 g for 30 minutes. ISS contained acetonitrile with 100 ng/mL compound, 50 ng/mL dextromethorphan and 50 ng/mL imipramine. Aliquots of the supernatant was transferred to an autosampler plate and diluted with two volumes of 0.2% formic acid in water. Specific analyte concentrations were determined against a standard curve (10,000-5 ng/ml), and mean concentrations+/−standard deviation were calculated.

Rodent Maximum Tolerated Dose Studies

For maximum tolerated dose (MTD) determination studies, non-tumor bearing CD-athymic nude mice were randomized into 5 treatment groups (5 mice per group) and treated with either 500, 400, 300, 200, or 100 mg/kg of compound by daily PO. Mice were weighed daily and % body weight loss was calculated relative to individual mouse body weights at the start of treatment. Studies were continued for 14 days or until >10% group mean body weight loss was observed in the animals. MTD was determined as the highest dose at which a mean body weight loss of <10% over 14 days of dosing was observed.

Designation of Sensitivity and Resistant Cohorts and Calculation of Average $IC_{50}$ Values Human cancer cell lines were grouped as "sensitive" or "resistant" to CDK4/6 inhibition based on whether their growth was retarded by ribociclib, palbociclib and abemaciclib (see Table 2). These sensitive and resistant cohorts were interrogated for response to each compound, and $IC_{50}$s were calculated for each cell line using the same technique described above. Average $IC_{50}$s for the sensitive and resistant cohorts were calculated as geometric means of the group. "Therapeutic Window" for each compound was calculated by dividing the average $IC_{50}$ for the drug-resistant group by the average $IC_{50}$ for the drug-sensitive group.

TABLE 2

Cell line cohorts

| Cell Line Name | Cohort |
|---|---|
| EFM-19 | Sensitive |
| MDA-MB-453 | Sensitive |
| T-47D | Sensitive |
| ZR-75-1 | Sensitive |
| NCI-H441 | Sensitive |
| OVTOKO | Sensitive |
| NCI-H1838 | Sensitive |
| NCI-H1437 | Resistant |
| OV207 | Resistant |
| HCC1806 | Resistant |
| NCI-H2172 | Resistant |

Example 6: Single Treatment PK to Identify Saturation Dose

Collected plasma at 6 time points (30 min, 60 min, 2 hrs, 4 hrs, 8 hrs & 24 hrs).

Determined AUC and dose for saturation of exposure.

3 mice were used per time point, bled same mice twice.
- 30 min & 4 hrs
- 60 min & 8 hrs
- 2 hrs & 24 hrs
- 9 mice per concentration
- 5 concentrations (1.78-fold dilution, 1000 mg/kg to 100)

Example 7: Dose De-Escalation 14 Day MTD

Started at 500 mg/kg, dose until >0.10% BWL then dropped to 400 mg/kg with 4 new nice, and so on Also defined abemaciclib MTD (250, 200, 150, 100 mg/kg).

Example 8—Activity-Guided Selection of Inhibitors

Subgenera of CDK4/6 inhibitors having desirable properties were identified using a combination of in vitro data.

In particular, the results from the assays described above (e.g., Cell Line Growth Retardation Assay, Cdk4 and 6 Enzymatic Inhibition Assay, Caco-2 Assay ($P_{app}$ A to B), Measurement of Compound Metabolic Stability, and Designation of Sensitivity and Resistant Cohorts and Calculation of Average $IC_{50}$ Valued) were used to select compounds having structural and functional features defined in the subgenera of Formula (IVa) and Formula (IVb).

Figure 37:
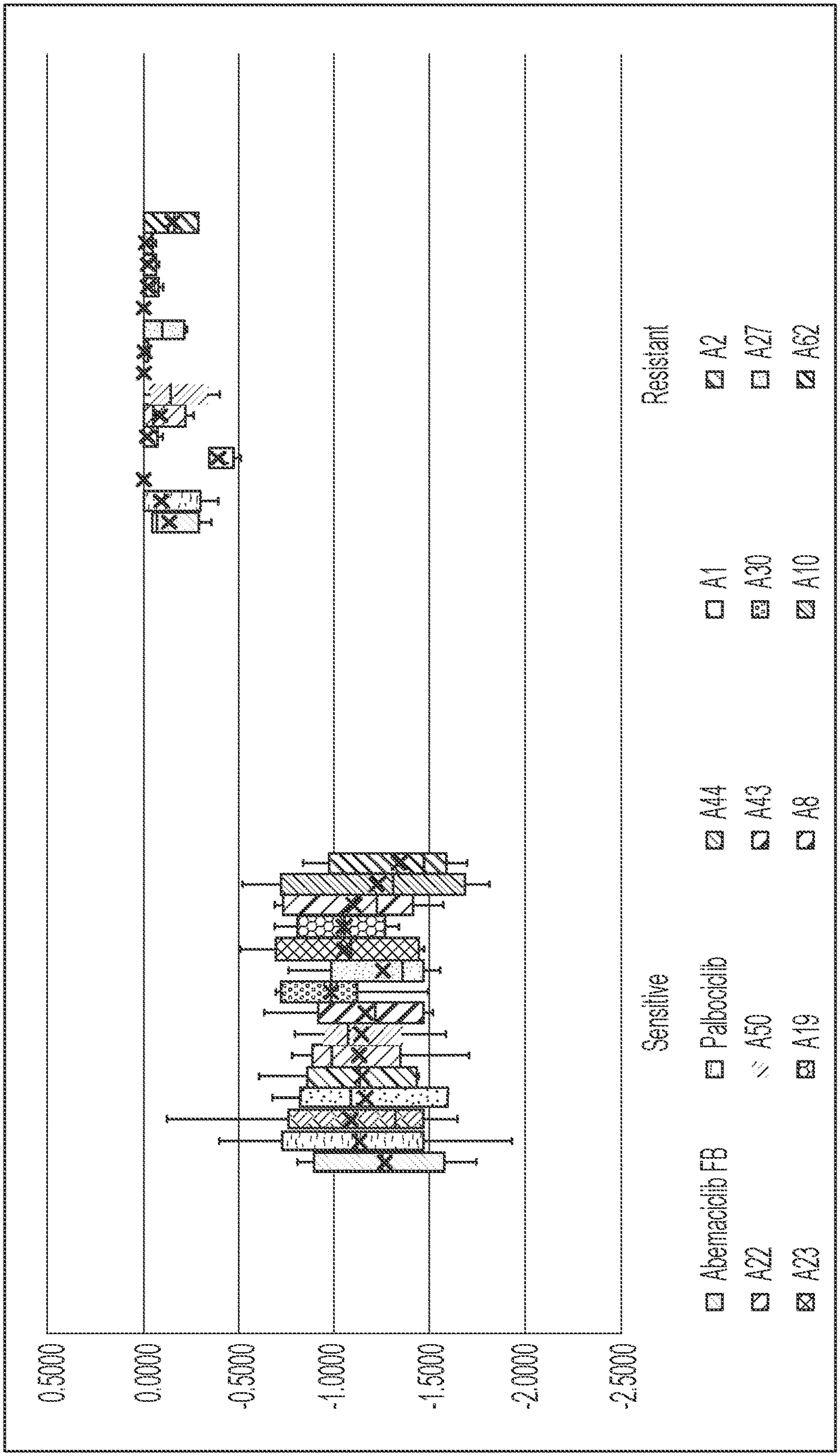
FIG. 37 shows a summary of the log differences in average $IC_{50}$ for certain compounds across resistant cell lines and sensitive cell lines.

In particular, selected compounds were examined in sensitive and resistant cell lines, as described above. Log differences between sensitive and resistant cohorts for selected compounds are depicted in FIG. 37.

In general, the $K_i$ for CDK4 correlated with the magnitude of the therapeutic window (i.e., potency difference between sensitive and resistance cell line cohorts), where a smaller $K_i$ for CDK4 is associated with a larger therapeutic window. This correlation ends when the CDK4 $K_i$ is about 0.960 nM or greater.

The skilled artisan would readily recognize that the results of additional assays (e.g., CYP Enzymatic Inhibition Assay, hERG Inhibition Assay, Compound Solubility Assay, Kinome Analysis, Rodent Xenograft Studies, Rodent Pharmacokinetic and Single-Dose Saturation Studies, Rodent Maximum Tolerated Dose Studies, and Oral Bioavailability assay) could be used to identify other subgenera of CDK4/6 inhibitors, or to narrow subgenera determined using other results, for example, the subgenera of Formulas IVa and IVb.

TABLE 3

DMPK Profiles for Compounds of the Invention and Comparator Compounds

| Compound | CDK4 $K_i$ | CDK6 $K_i$ | $AvgSensIC_{50}$ | $AvgResIC_{50}$ | Ther Window | Papp A2B | AvgCYP $IC_{50}$ | HalfLife (min) | hERG | KS1 | KS7 |
|---|---|---|---|---|---|---|---|---|---|---|---|
| Abemaciclib MS | | | 0.09 | 0.67 | 7.27 | 1.86 | 63.72 | 25.73 | 15.36 | 193.31 | 150.72 |
| Abemaciclib FB | 0.48 | 2.69 | 0.10 | 0.67 | 6.73 | | | | | | |
| Palbociclib | 2.19 | 1.44 | 0.10 | 0.89 | 9.37 | 0.27 | 97.66 | 54.88 | 43.15 | 195.66 | 29.56 |
| A45 | 3.43 | 1.43 | 0.78 | 1.00 | 1.29 | | | | | | |
| A46 | 5.08 | 1.95 | 0.79 | 1.00 | 1.26 | | | | | | |
| A40 | 2.27 | 7.99 | 0.45 | 0.98 | 2.18 | | | | | | |
| A48 | 1.77 | 1.08 | 0.64 | 1.00 | 1.56 | | | | | | |
| A4 | 1.16 | 5.09 | 0.16 | 0.96 | 5.80 | | | | | | |
| A44 | 0.70 | 3.04 | 0.09 | 0.96 | 10.25 | 0.01 | 64.21 | 81.23 | 10.84 | 200.00 | 6.30 |
| A1 | 0.65 | 2.90 | 0.09 | 0.40 | 4.25 | 0.08 | 38.02 | 151.71 | 18.98 | 200.00 | 42.48 |
| A2 | 0.72 | 3.38 | 0.10 | 0.97 | 9.95 | 0.11 | 40.21 | 78.48 | 26.05 | 200.00 | 31.41 |
| A25 | 0.80 | 3.47 | 0.12 | 0.79 | 6.52 | | | | | | |
| A24 | 0.04 | 0.16 | 0.04 | 0.13 | 3.02 | | | | | | |
| A5 | 1.21 | 6.26 | 0.18 | 0.96 | 5.33 | | | | 14.76 | | |
| A22 | 0.52 | 3.55 | 0.08 | 0.87 | 10.57 | 0.05 | 35.78 | 201.96 | 15.58 | 199.54 | 15.57 |
| A49 | 1.09 | 7.46 | 0.15 | 0.89 | 5.76 | | | | | | |
| A50 | 0.78 | 5.32 | 0.07 | 0.73 | 9.87 | 3.25 | 34.96 | 17.52 | 18.96 | 200.00 | 1.13 |
| A43 | 0.77 | 4.13 | 0.07 | 1.00 | 15.03 | 0.27 | 90.61 | 24.21 | 12.12 | 200.00 | 8.37 |
| A41 | 11.32 | 73.92 | | | | | | | | | |
| A42 | 6.47 | 34.87 | | | | | | | | | |
| A39 | 1.83 | 6.62 | 0.30 | 0.98 | 3.25 | | | | 14.81 | | |
| A38 | 1.47 | 7.23 | 0.22 | 0.84 | 3.81 | 0.17 | 80.16 | 38.21 | 10.65 | 200.00 | 40.50 |
| A37 | 1.60 | 6.86 | 0.26 | 0.81 | 3.10 | 0.39 | 43.34 | 26.97 | 15.08 | 197.04 | 109.06 |
| A36 | 1.91 | 10.81 | 0.25 | 0.91 | 3.57 | 0.59 | 23.42 | 30.77 | 21.60 | 200.00 | 3.28 |
| A31 | 1.71 | 10.23 | 0.14 | 0.96 | 6.72 | 0.85 | 12.75 | 5.65 | 21.67 | 200.00 | 3.09 |
| A32 | 3.07 | 17.41 | 0.16 | 1.00 | 6.24 | 1.08 | 31.49 | 4.24 | 14.35 | 200.00 | 1.60 |
| A30 | 2.95 | 16.54 | 0.11 | 0.99 | 9.41 | 4.60 | 30.03 | 4.99 | 15.21 | 200.00 | 2.52 |
| A33 | 3.42 | 20.06 | 0.15 | 1.00 | 6.51 | 3.94 | 18.68 | 4.73 | 18.72 | 200.00 | 2.02 |
| A34 | 1.57 | 7.21 | 0.20 | 1.00 | 5.02 | | | | | | |
| A35 | 1.31 | 7.16 | 0.19 | 1.00 | 5.36 | | | | | | |
| A26 | 1.73 | 8.63 | 0.13 | 0.77 | 6.10 | 0.03 | 51.49 | 89.39 | 39.08 | 200.00 | 140.39 |
| A27 | 1.21 | 6.57 | 0.08 | 0.90 | 11.50 | 0.06 | 25.79 | 71.23 | 24.78 | 200.00 | 106.96 |
| A51 | 8.00 | 38.40 | 0.62 | 1.00 | 1.62 | | | | | | |
| A23 | 1.09 | 6.47 | 0.12 | 0.99 | 8.44 | 0.32 | 64.67 | 76.39 | 15.77 | 197.65 | 133.17 |
| A28 | 0.46 | 2.60 | 0.07 | 0.39 | 5.23 | 0.09 | 94.00 | 55.16 | 6.78 | 200.00 | 15.85 |
| A52 | 3.55 | 15.40 | 0.35 | 1.00 | 2.82 | | | | | | |
| A53 | 2.49 | 11.90 | 0.21 | 1.00 | 4.85 | | | | | | |
| A47 | 1.01 | 5.17 | 0.09 | 0.46 | 4.96 | 0.04 | 29.96 | 125.80 | 21.76 | 192.92 | 1.00 |
| A19 | 1.37 | 7.07 | 0.19 | 0.97 | 5.12 | 0.91 | 29.04 | 16.78 | 18.14 | 200.00 | 138.82 |
| A7 | 1.00 | 4.24 | 0.16 | 0.92 | 5.75 | 0.04 | | 74.50 | | | |
| A8 | 1.76 | 11.30 | 0.17 | 0.97 | 5.64 | 2.35 | 30.89 | 4.24 | 11.87 | 200.00 | 128.44 |
| A54 | 26.90 | 108.00 | 1.00 | 1.00 | 1.00 | | | | | | |
| A12 | 2.18 | 12.80 | 0.11 | 0.86 | 8.17 | 2.62 | 21.62 | 13.10 | 19.54 | 200.00 | 1.00 |
| A9 | 2.54 | 14.50 | 0.12 | 1.00 | 8.59 | 2.14 | 26.07 | 15.26 | 21.86 | 200.00 | 1.00 |
| A10 | 0.96 | 5.52 | 0.07 | 0.97 | 14.08 | 0.01 | | 66.77 | | | |
| A21 | 0.73 | 4.90 | 0.15 | 1.00 | 6.58 | 0.00 | | 96.52 | | | |
| A13 | 0.92 | 4.79 | 0.07 | 0.71 | 10.82 | 1.02 | 15.25 | 8.90 | 23.72 | | |
| A15 | 0.78 | 4.04 | 0.08 | 0.59 | 7.07 | 0.80 | 17.12 | 19.29 | 17.46 | | |
| A14 | 0.92 | 4.99 | 0.08 | 0.98 | 11.53 | 0.69 | 16.94 | 10.69 | 23.34 | | |
| A6 | 0.83 | 5.35 | 0.10 | 1.00 | 10.42 | 1.12 | 14.63 | 14.24 | 32.76 | | |
| A29 | 1.80 | 10.50 | 0.17 | 0.89 | 5.36 | 1.95 | 16.43 | 5.84 | 25.45 | | |
| A20 | 0.55 | 3.69 | 0.08 | 1.00 | 12.21 | 0.07 | 24.81 | 100.58 | 32.36 | | |
| A3 | 2.04 | 7.39 | 0.07 | 1.00 | 13.77 | 0.05 | 37.22 | 130.38 | 26.68 | 200.00 | 162.95 |
| A16 | 1.42 | 5.81 | 0.06 | 0.87 | 15.20 | 0.01 | 47.88 | 216.80 | 18.09 | | |
| A11 | 1.35 | 5.90 | 0.08 | 1.00 | 12.62 | 0.02 | 29.21 | 102.62 | 19.86 | | |
| A17 | 1.03 | 5.25 | 0.05 | 0.85 | 15.41 | 0.02 | 51.72 | 216.80 | 20.47 | | |
| A18 | 1.55 | 7.62 | 0.09 | 0.92 | 10.77 | 0.11 | 26.80 | 67.71 | 21.45 | | |
| A55 | 1.60 | 11.90 | 0.21 | 0.90 | 4.33 | 0.11 | 20.06 | 5.402 | 26.03 | 195.58 | |
| A56 | 2.4 | 14.8 | 0.26 | 1.00 | 3.76 | | | | | | |
| A57 | 3.91 | 24.0 | 0.39 | 1.00 | 2.56 | | | | | | |
| A58 | 2.64 | 19.8 | 0.34 | 1.00 | 2.94 | | | | | | |
| A59 | 1.46 | 10.1 | 0.21 | 1.00 | 4.76 | 0.7 | 21.24 | 3.511 | 25.3 | 198.95 | |
| A60 | 2.14 | 14.5 | 0.27 | 1.00 | 3.70 | 1.0 | 18.11 | 3.319 | 28 | 186.4 | 3.12 |
| A61 | 1.53 | 9.53 | 0.22 | 0.94 | 4.27 | | | | | | |
| A62 | 0.59 | 3.80 | 0.09 | 0.73 | 8.11 | 0.15 | 33.91 | 33.89 | 40.8 | 190.47 | 1.0 |
| A63 | 0.75 | 3.14 | 0.10 | 0.50 | 5.03 | | | | | | |
| A64 | 0.9 | 4.53 | 0.15 | 0.73 | 4.87 | | | | | | |

TABLE 4

| Multi-dose Single Treatment PK | | | | | | |
|---|---|---|---|---|---|---|
| Molecule | Dose (mg/kg) | # of mice | mouse wt | # of doses | amount of molecule | Total |
| A1 | 100.0 | 9 | 0.03 | 1 | 27.00 | |
| A1 | 178.0 | 9 | 0.03 | 1 | 48.06 | |
| A1 | 316.8 | 9 | 0.03 | 1 | 85.55 | |
| A1 | 564.0 | 9 | 0.03 | 1 | 152.27 | |
| A1 | 1003.9 | 9 | 0.03 | 1 | 271.05 | 583.93 |
| A2 | 100.0 | 9 | 0.03 | 1 | 27.00 | |
| A2 | 178.0 | 9 | 0.03 | 1 | 48.06 | |
| A2 | 316.8 | 9 | 0.03 | 1 | 85.55 | |
| A2 | 564.0 | 9 | 0.03 | 1 | 152.27 | |
| A2 | 1003.9 | 9 | 0.03 | 1 | 271.05 | 583.93 |
| Molecule | Dose (mg/kg) | # mice | mouse wt | number of doses | amount of molecule | Total |
| A23 | 100.0 | 9 | 0.03 | 1 | 27.00 | |
| A23 | 178.0 | 9 | 0.03 | 1 | 48.06 | |
| A23 | 316.8 | 9 | 0.03 | 1 | 85.55 | |
| A23 | 564.0 | 9 | 0.03 | 1 | 152.27 | |
| A23 | 1003.9 | 9 | 0.03 | 1 | 271.05 | 583.93 |
| Abemaciclib | 100.0 | 9 | 0.03 | 1 | 27.00 | |
| Abemacilib | 178.0 | 9 | 0.03 | 1 | 48.06 | |
| Abemacilib | 316.8 | 9 | 0.03 | 1 | 85.55 | |
| Abemacilib | 564.0 | 9 | 0.03 | 1 | 152.27 | |
| Abemaciclib | 1003.9 | 9 | 0.03 | 1 | 271.05 | 583.93 |

We claim:

1. A compound having the structure of Formula (Ia)

(Ia)

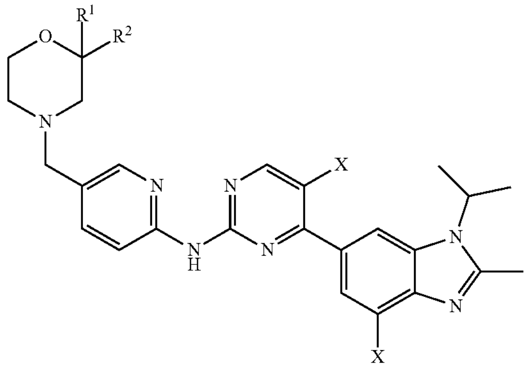

or a pharmaceutically acceptable salt thereof, wherein:

X is, independently for each occurrence, halo; and $R^1$ is alkyl; and $R^2$ is $(CH_2)_nC(O)NR^{2a}R^{2b}$ or $(CH_2)_nNR^{2a}R^{2b}$; wherein:

$R^{2a}$ and $R^{2b}$ are each independently H, alkyl, haloalkyl, alkenyl, $(CR^cR^d)_mOR^e$, or —C(O)alkyl;

$R^c$, $R^d$, and $R^e$ are each independently H or alkyl;

n is an integer having a value of 1 or 2; and m is an integer having a value of 2 to 5; or $R^{2a}$ and $R^{2b}$, together with the nitrogen atom through which they are joined, form an optionally substituted 3- to 6-membered heterocyclic ring; or $R^1$ is methyl; and $R^2$ is $(CR^{2c}_2)_nNR^{2a}R^{2b}$; wherein:

$R^{2a}$ is H, methyl, or ethyl;

$R^{2b}$ is H, methyl, or ethyl;

each $R^{2c}$ is independently H or alkyl; and n is an integer having a value of 1 to 4.

2. The compound of claim 1, having the structure of Formula (II):

(II)

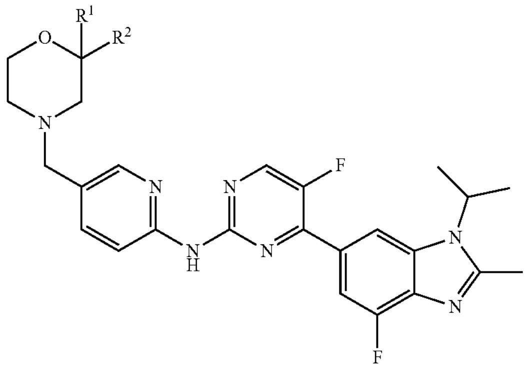

or a pharmaceutically acceptable salt thereof.

3. The compound of claim 2, having the structure of Formula (IIa):

(IIa)

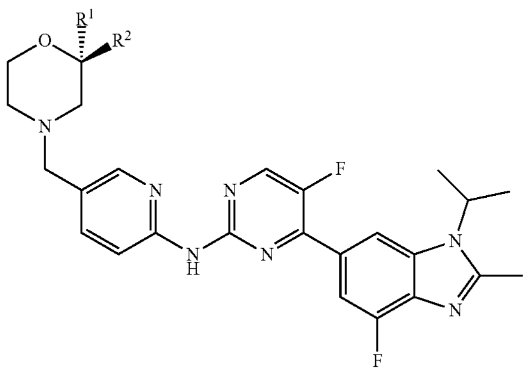

or a pharmaceutically acceptable salt thereof.

4. The compound of claim 2, having the structure of Formula (IIb):

(IIb)

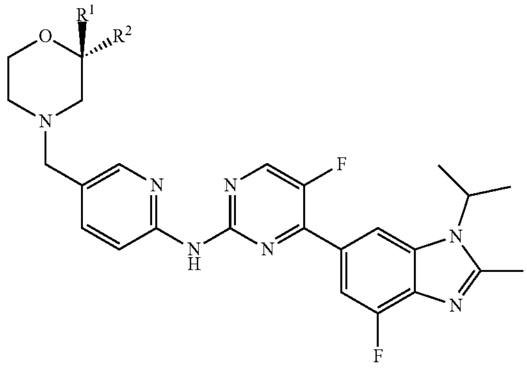

or a pharmaceutically acceptable salt thereof.

5. The compound of claim 1, wherein $R^1$ is $C_1$-$C_4$-alkyl.

6. The compound of claim 5, wherein $R^1$ is methyl or ethyl.

7. The compound of claim 1, wherein $R^1$ is methyl.

8. The compound of claim 1, wherein $R^2$ is $—(CH_2)_2N(H)(CH_3)$, $—(CH_2)_2N(H)(C(CH_3)_3)$, $—(CH_2)_2N(H)(C(O)CH_3)$, $—(CH_2)_2N(H)(CH_2CH_2F)$, $—(CH_2)_2N(CH_3)(CH_2CH_2F)$, $—(CH_2)_2N(CH_3)_2$, $—(CH_2)_2N(CH_2CH_3)_2$, or $—(CH_2CH(CH_3))N(CH_3)_2$.

9. The compound of claim 1, wherein $R^2$ is $(CH_2)_nC(O)NR^{2a}R^{2b}$ or $(CH_2)_nNR^{2a}R^{2b}$, wherein:

$R^{2a}$ and $R^{2b}$ are each independently H, alkyl, haloalkyl, alkenyl, $(CR^cR^d)_mOR^e$, or —C(O)alkyl;

$R^c$, $R^d$, and $R^e$ are each independently H or alkyl;

n is an integer having a value of 1 or 2; and m is an integer having a value of 2 to 5; or $R^{2a}$ and $R^{2b}$, together with the nitrogen atom through which they are joined, form an optionally substituted 3- to 6-membered heterocyclic ring.

10. The compound of claim 1, wherein:

$R^1$ is methyl;

$R^2$ is $(CR^{2c}{}_2)_nNR^{2a}R^{2b}$;

$R^{2a}$ is H, methyl, or ethyl;

$R^{2b}$ is H, methyl, or ethyl;

each $R^{2c}$ is independently H or alkyl; and n is an integer having a value of 1 to 4.

11. The compound of claim 10, wherein at least one $R^{2c}$ is methyl.

12. The compound of claim 11, wherein at least one $R^{2c}$ is methyl and the rest are H.

13. The compound of claim 10, wherein $R^{2a}$ and $R^{2b}$ are not both H.

14. The compound of claim 1, wherein:

$R^2$ is $(CR^{2c}{}_2)_nNR^{2a}R^{2b}$;

$R^{2a}$ is unsubstituted methyl or unsubstituted ethyl;

$R^{2b}$ is unsubstituted methyl or unsubstituted ethyl;

n is an integer having a value of 2 to 4.

15. The compound of claim 1, selected from:

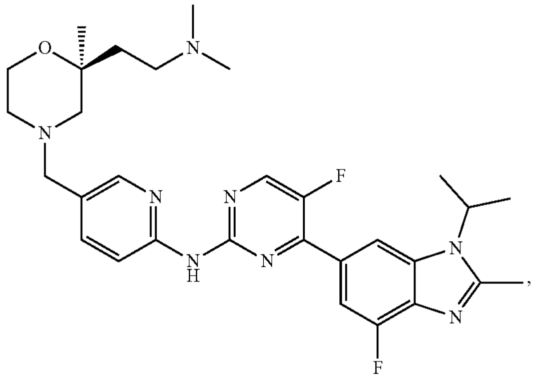

,

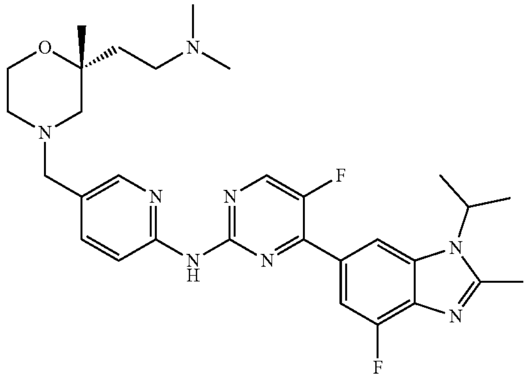

,

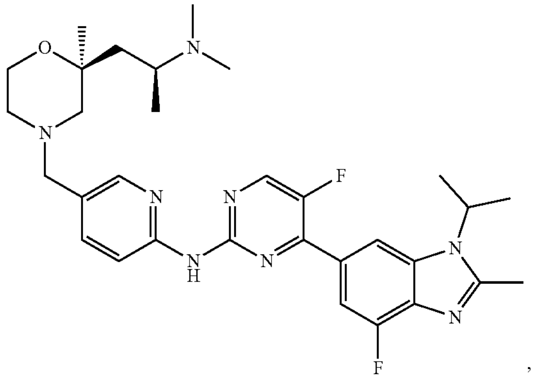

, and

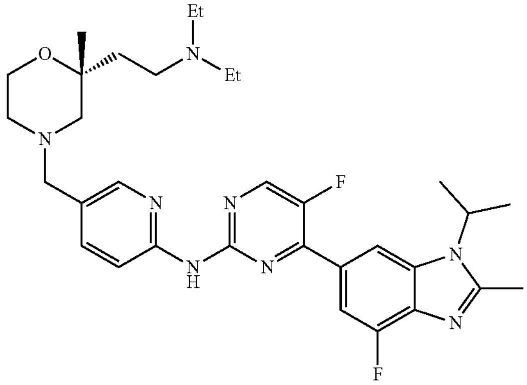

, or a pharmaceutically acceptable salt thereof.

16. A compound having the structure of Formula (Ia)

(Ia)

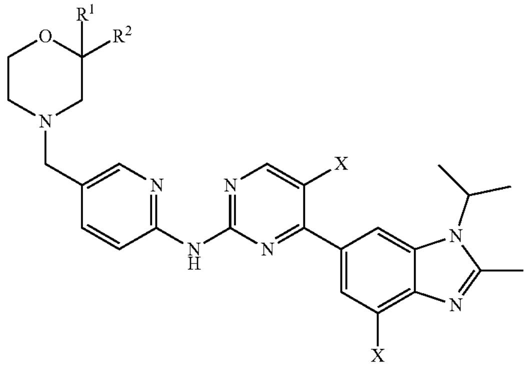

or a pharmaceutically acceptable salt thereof, wherein:

X is, independently for each occurrence, halo;

$R^1$ is $C_1$-$C_3$alkyl;

$R^2$ is $(CR^{2c}{}_2)_nNR^{2a}R^{2b}$;

$R^{2a}$ is H, lower alkyl, acyl or haloalkyl;

$R^{2b}$ is H, lower alkyl, acyl or haloalkyl; or $R^{2a}$ and $R^{2b}$ together through the N atom through which they are joined, form a 4-, 5- or 6-membered heterocyclic ring optionally substituted with $R^{ab}{}_z$; or $R^1$ and $R^2$ together through the C atom through which they are joined, form a 5- or 6-membered heterocyclic ring optionally substituted with acyloxy;

$R^{ab}$, when present, in each instance is independently halo, hydroxy, lower alkyl or alkoxy;

each $R^{2c}$ is independently H or alkyl;

n is an integer having a value of 1 or 2;

z is an integer having a value of 0, 1 or 2; and wherein the compound has a CDK4 $K_i$ of about 0.960 nM or lower.

17. The compound of claim 16, wherein the compound has an average $IC_{50}$ of 150 nM or lower for the drug-sensitive cell lines of the following table:

| |
|---|
| EFM-19 |
| MDA-MB-453 |
| T-47D |
| ZR-75-1 |
| NCI-H441 |
| OVTOKO |
| NCI-H1838. |

18. The compound of claim 16, wherein the average $IC_{50}$ of the compound for the drug-sensitive cell lines of the following table

| |
|---|
| EFM-19 |
| MDA-MB-453 |
| T-47D |
| ZR-75-1 |
| NCIH441 |
| OVTOKO |
| NCI-H1838 |

is at least about 5-fold more potent than the average $IC_{50}$ of the compound for the drug-resistant cell lines of the following table:

| |
|---|
| NCI-H1437 |
| OV207 |
| HCC1806 |
| NCI-H2172. |

19. The compound of claim 16, wherein the compound has a $P_{app}$ A-to-B score of about 0.07 or greater.

20. The compound of claim 16, wherein the compound has a half-life of about 25 minutes or greater.

21. The compound of claim 16, wherein the compound is selected from:

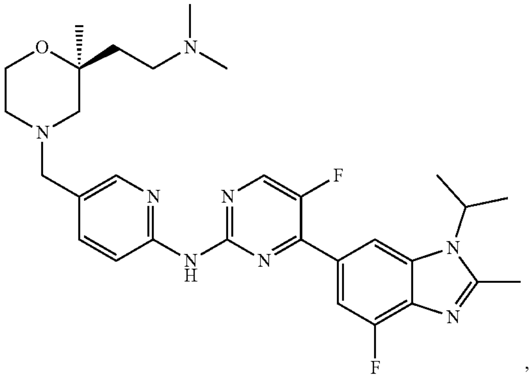

,

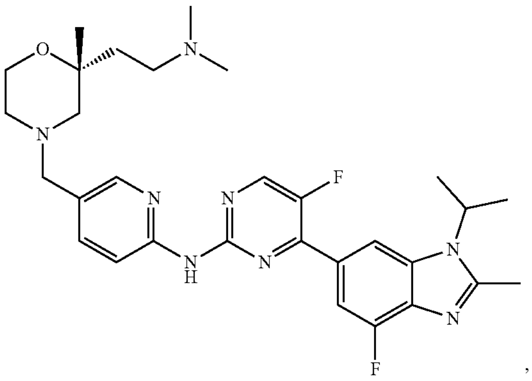

,

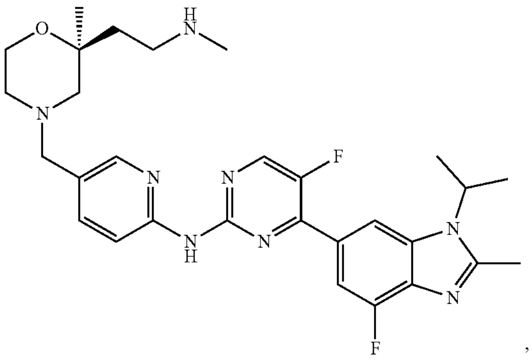

,

-continued
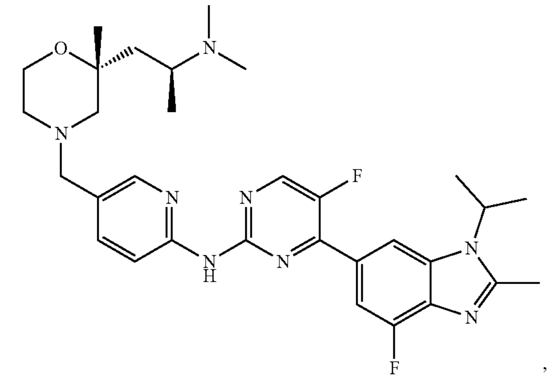
,
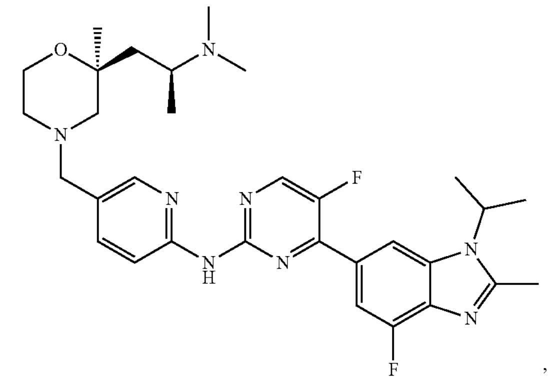
,
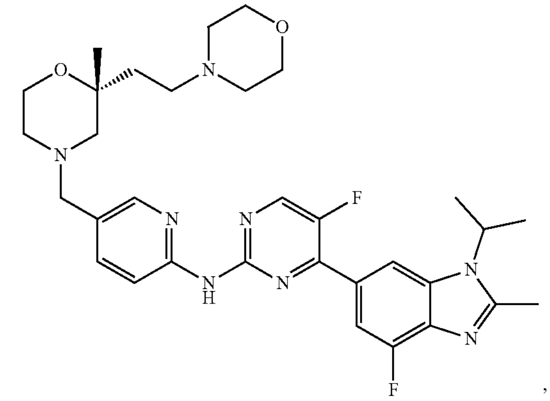
,
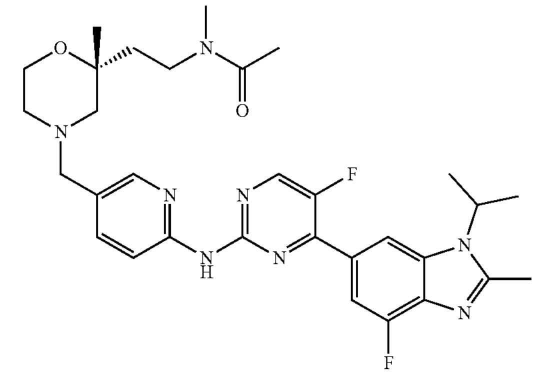
, and
-continued
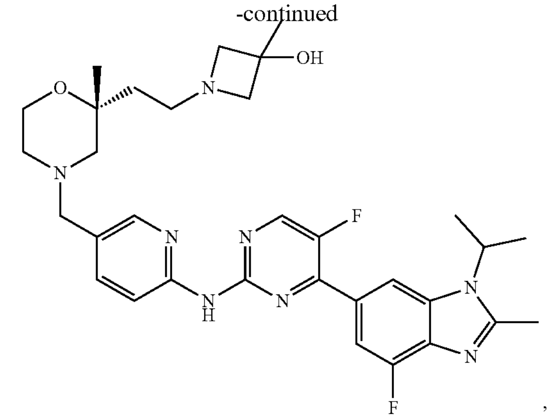
,
or a pharmaceutically salt thereof.
22. A pharmaceutical composition comprising a compound of claim 1 and a pharmaceutically acceptable diluent or excipient.
23. A compound selected from:
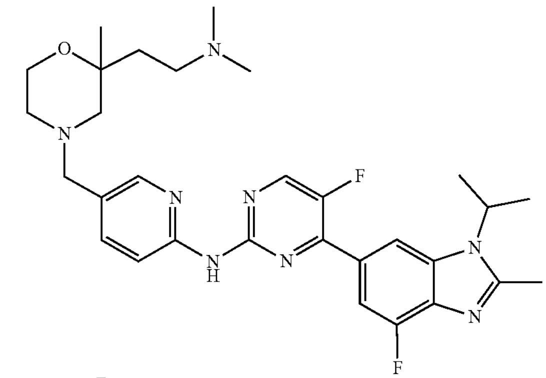
,
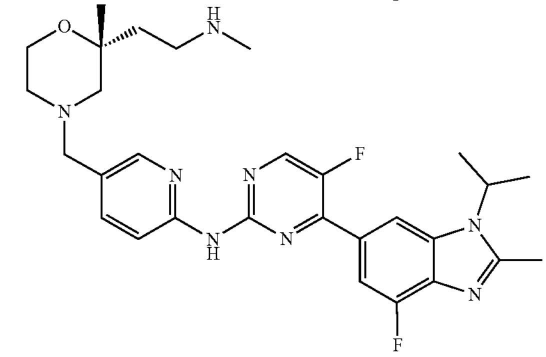
,
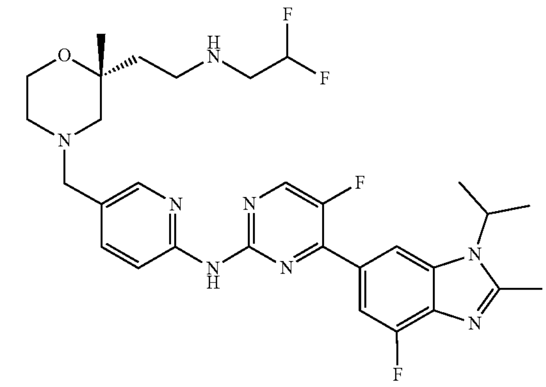
, -continued
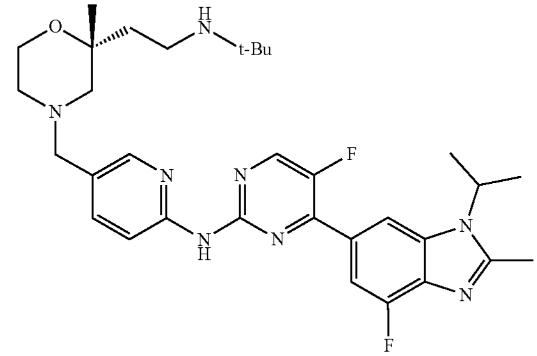
,
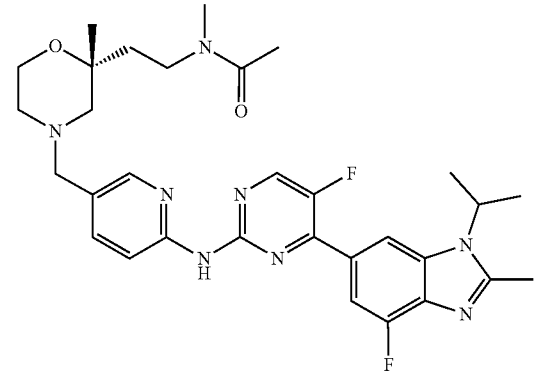
,
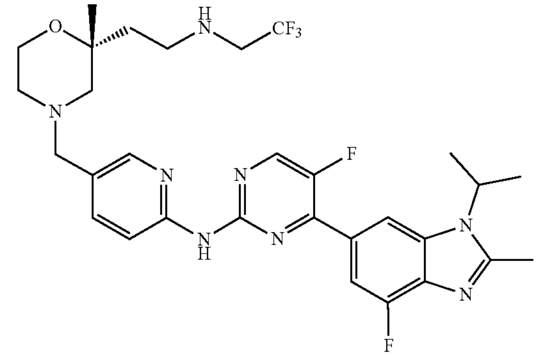
,
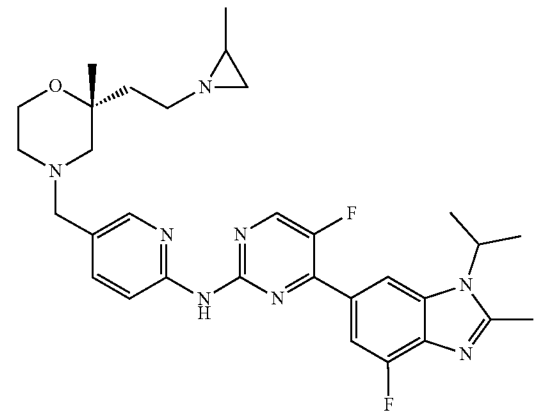
,
-continued
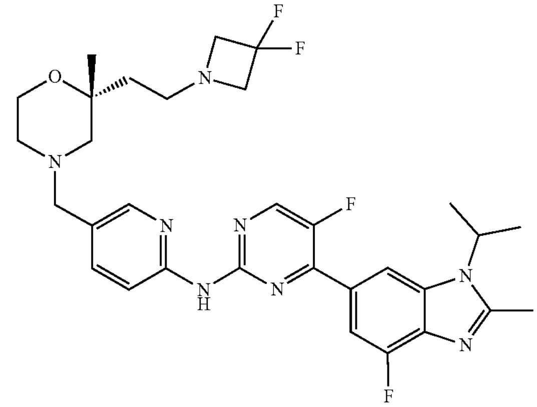
,
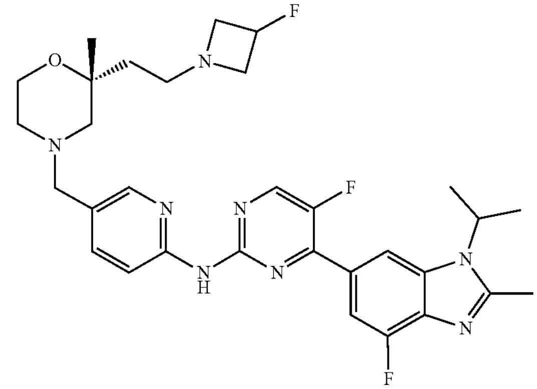
,
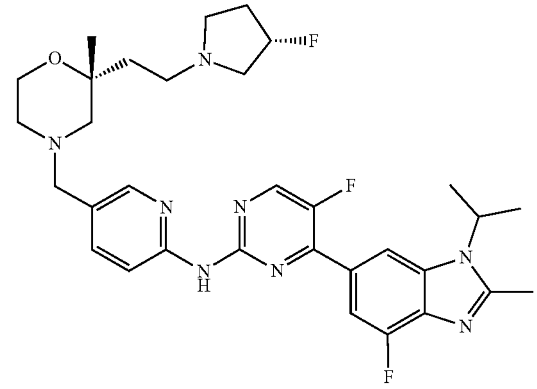
,
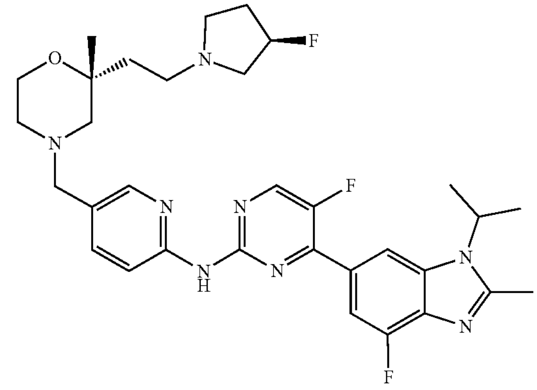
, -continued
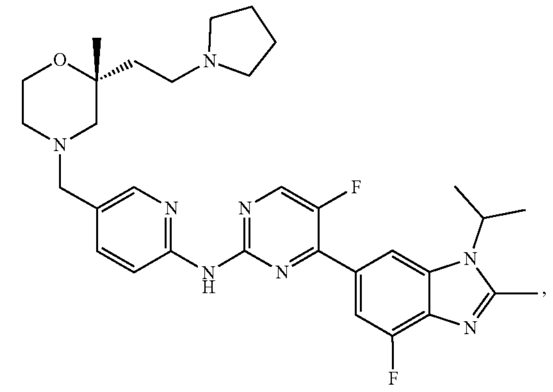
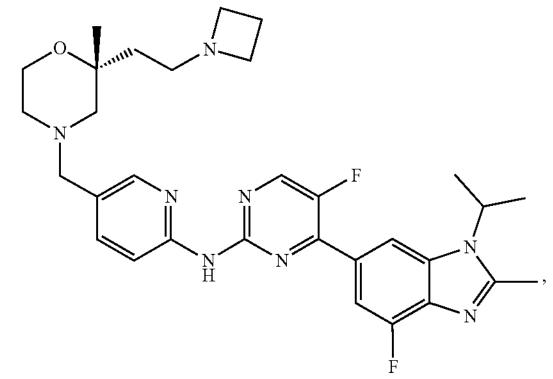
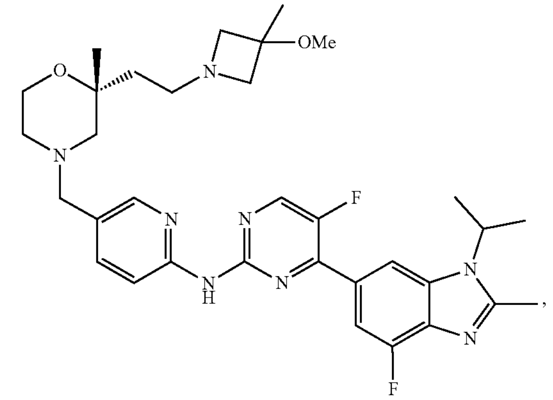
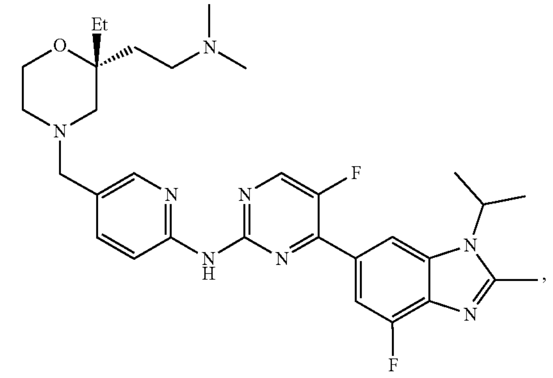
-continued
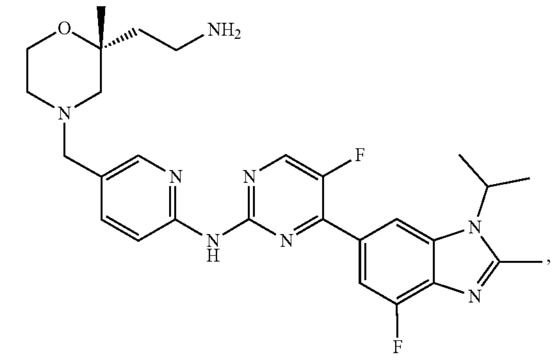
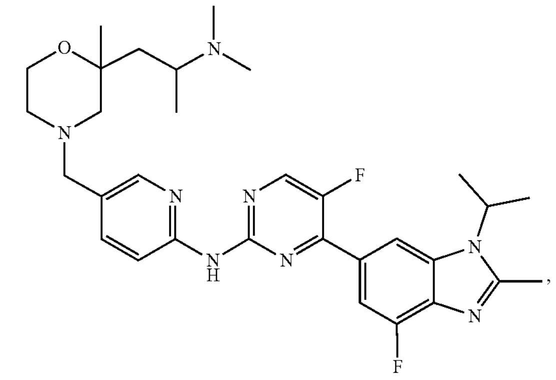
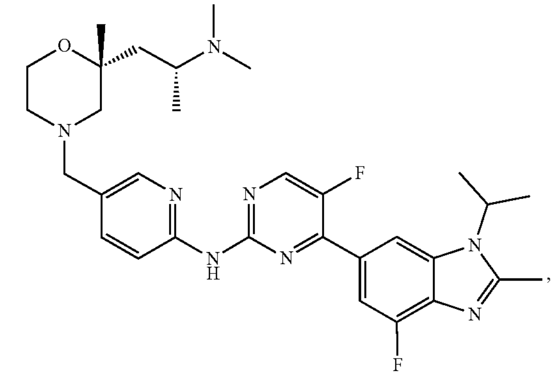
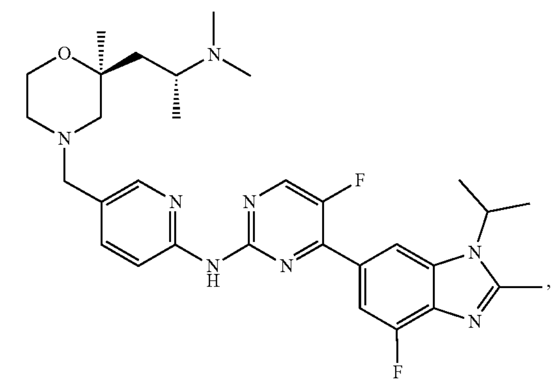

-continued
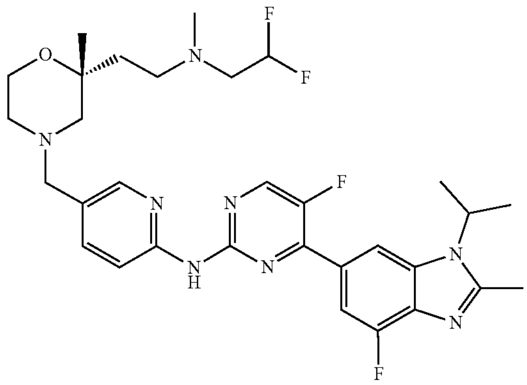
,
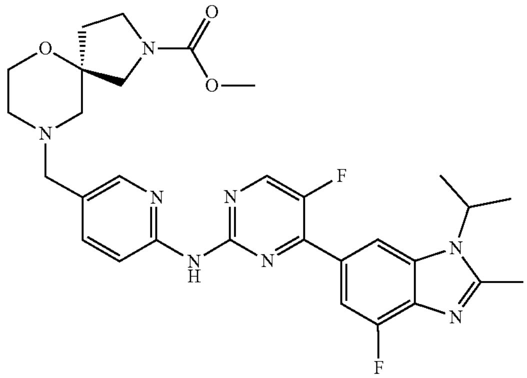
,
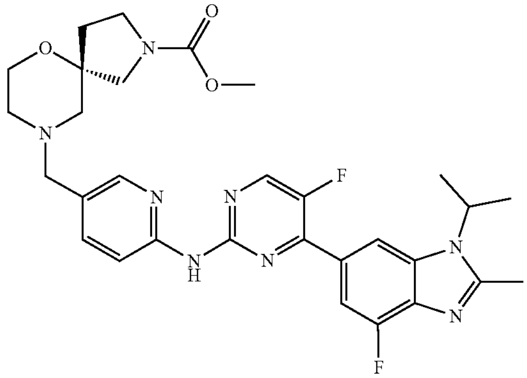
,
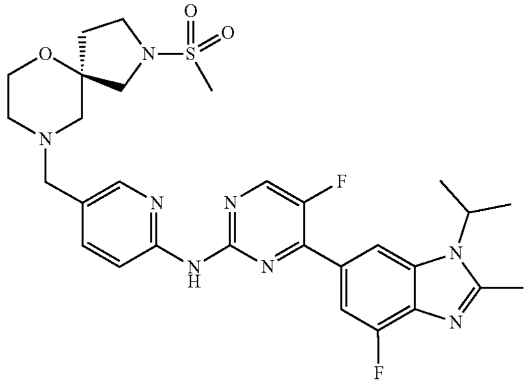
,
-continued
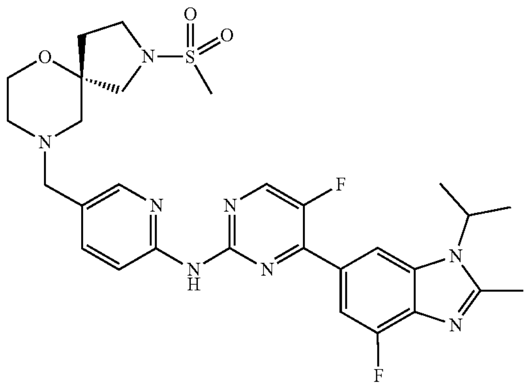
,
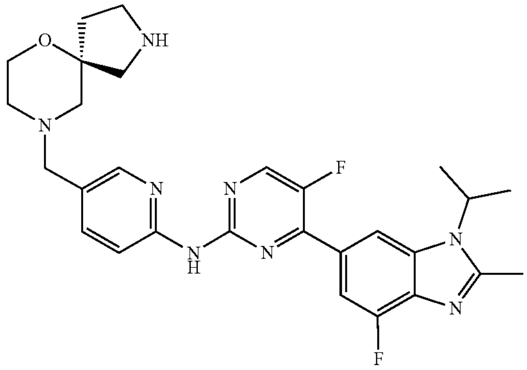
,
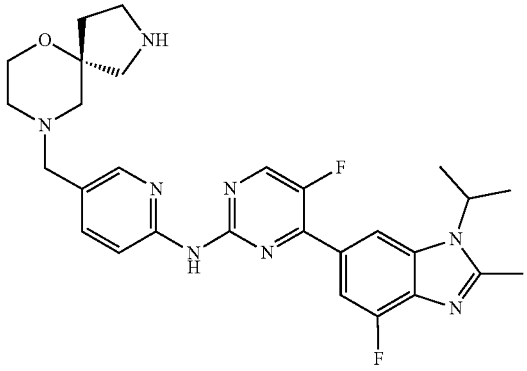
,
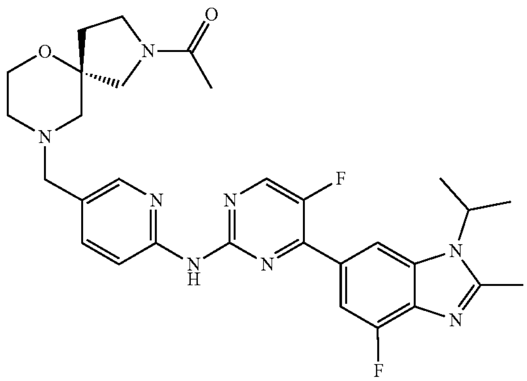
, -continued
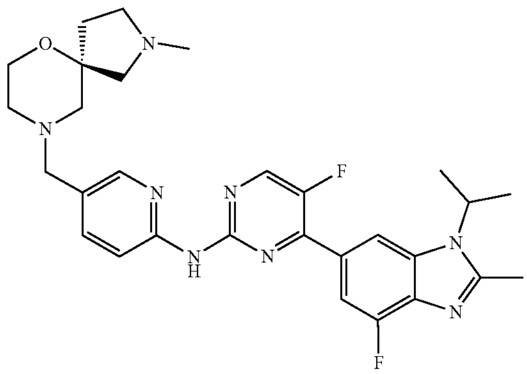
,
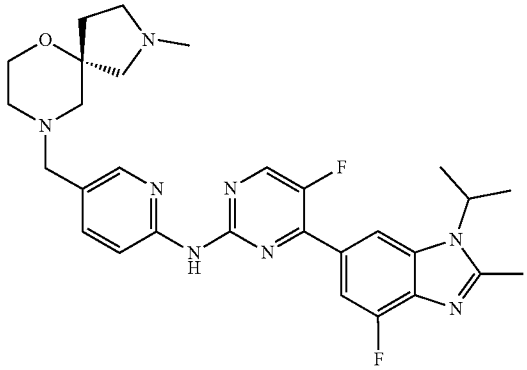
,
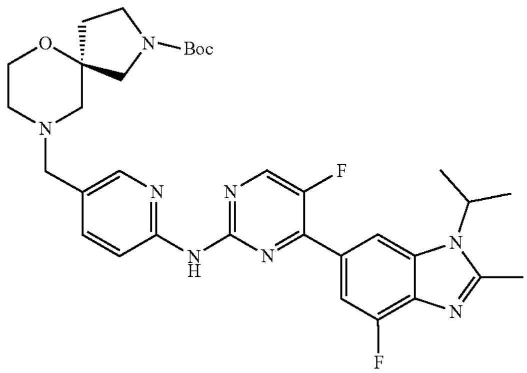
,
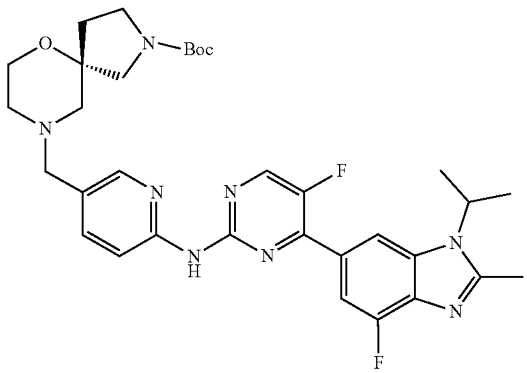
,
-continued
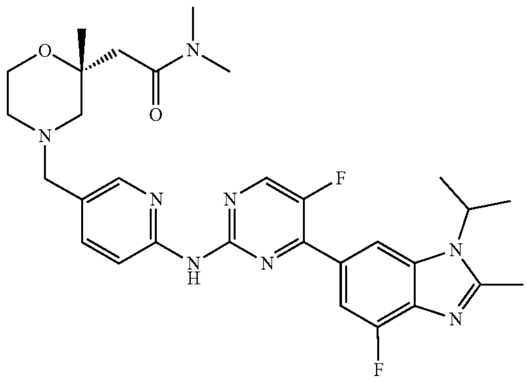
,
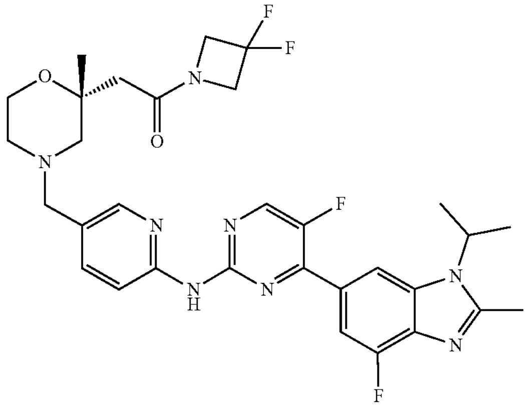
,
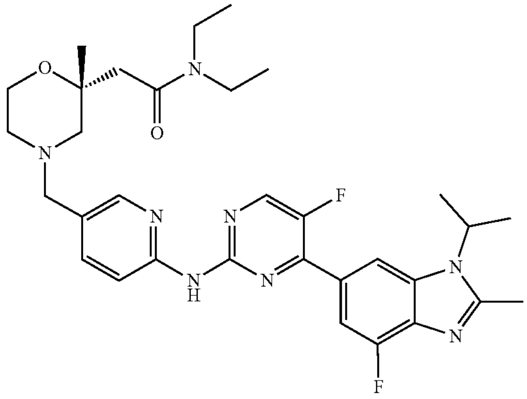
,
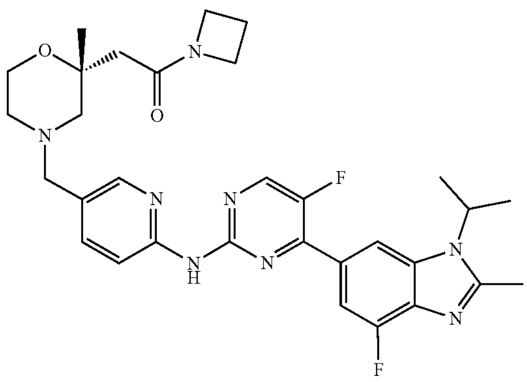
, -continued
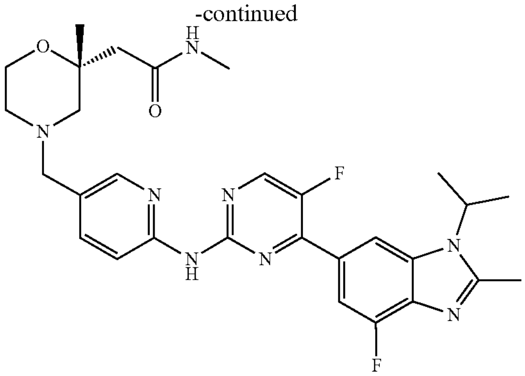
,
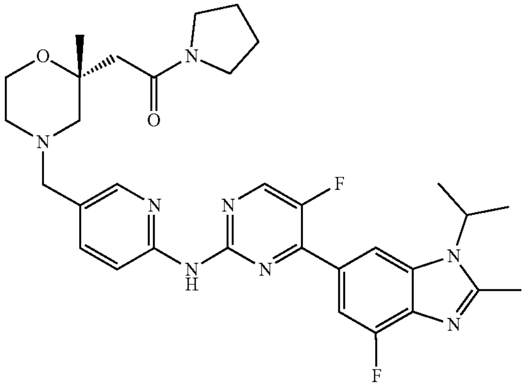
,
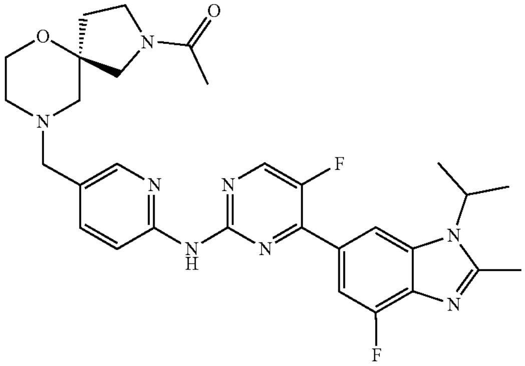
,
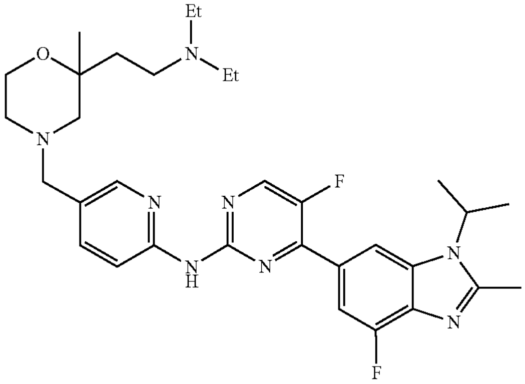
,
-continued
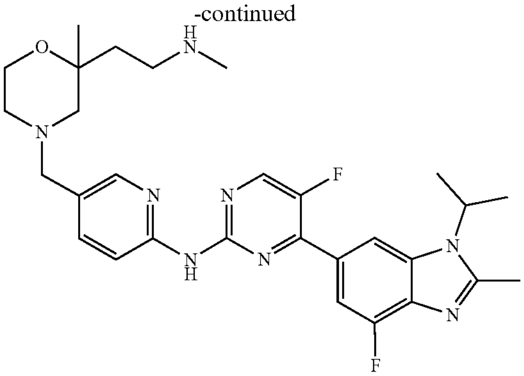
,
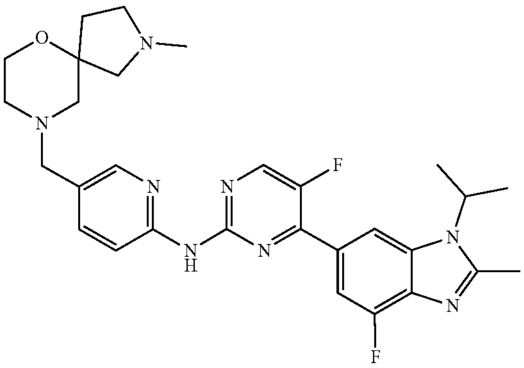
,
and
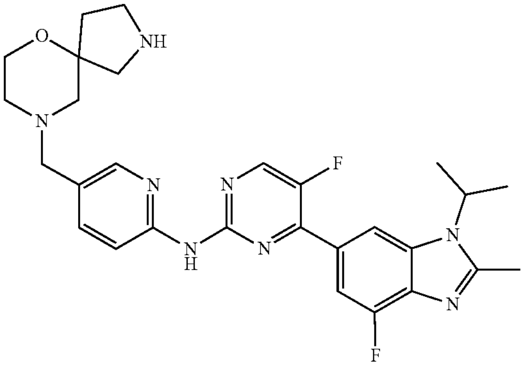
,
or a pharmaceutically acceptable salt thereof.
* * * * *